United States Patent
Tisdale et al.

(10) Patent No.: US 12,215,159 B2
(45) Date of Patent: Feb. 4, 2025

(54) ANTI-CD161 ANTIBODIES AND USES THEREOF

(71) Applicant: Immunitas Therapeutics, Inc., Waltham, MA (US)

(72) Inventors: Alison Tisdale, Belmont, MA (US); Uli Bialucha, Winchester, MA (US); George Punkosdy, Belmont, MA (US); Alexandria Fusco, Derry, NH (US); Frano Irvine, Medford, MA (US); Emily Rosentrater, Marlborough, MA (US); Elizabeth Scanlon, Allston, MA (US); Michael Battles, Lebanon, NH (US)

(73) Assignee: IMMUNITAS THERAPEUTICS, INC., Waltham, MA (US)

( * ) Notice: Subject to any disclaimer, the term of this patent is extended or adjusted under 35 U.S.C. 154(b) by 0 days.

(21) Appl. No.: 18/582,950

(22) Filed: Feb. 21, 2024

(65) Prior Publication Data
US 2024/0279346 A1   Aug. 22, 2024

Related U.S. Application Data

(63) Continuation of application No. PCT/US2022/075370, filed on Aug. 23, 2022.

(60) Provisional application No. 63/236,122, filed on Aug. 23, 2021.

(51) Int. Cl.
| | |
|---|---|
| *C07K 16/00* | (2006.01) |
| *A61P 35/00* | (2006.01) |
| *A61P 37/04* | (2006.01) |
| *C07K 16/28* | (2006.01) |
| *G01N 33/68* | (2006.01) |
| *A61K 39/00* | (2006.01) |

(52) U.S. Cl.
CPC .......... *C07K 16/2851* (2013.01); *A61P 35/00* (2018.01); *A61P 37/04* (2018.01); *G01N 33/6854* (2013.01); *A61K 2039/505* (2013.01); *C07K 2317/52* (2013.01); *C07K 2317/565* (2013.01); *G01N 2333/70596* (2013.01); *G01N 2800/52* (2013.01)

(58) Field of Classification Search
None
See application file for complete search history.

(56) References Cited

U.S. PATENT DOCUMENTS 11,459,389 B2 * 10/2022 Wittrup .............. C07K 16/2851

FOREIGN PATENT DOCUMENTS

| WO | WO2019/094983 A1 | 5/2019 |
| WO | WO2021/080682 A1 | 4/2021 |

OTHER PUBLICATIONS

Aldemir H, Prod'homme V, Dumaurier MJ, et al. Cutting edge: lectin-like transcript 1 is a ligand for the CD161 receptor. J Immunol. 2005;175(12):7791-7795. doi:10.4049/jimmunol.175.12.7791.

International Search Report and Written Opinion issued for International Patent Application No. PCT/US2022/075370 dated Dec. 7, 2022.

Rosen DB, Bettadapura J, Alsharifi M, Mathew PA, Warren HS, Lanier LL. Cutting edge: lectin-like transcript-1 is a ligand for the inhibitory human NKR-P1A receptor. J Immunol. 2005;175(12):7796-7799. doi:10.4049/jimmunol.175.12.7796.

* cited by examiner

*Primary Examiner* — Meera Natarajan
(74) *Attorney, Agent, or Firm* — Haynes and Boone, LLP

(57) ABSTRACT

The invention relates generally to anti-CD161 antibodies, pharmaceutical compositions comprising such antibodies, and methods of using such antibodies for treating disorders associated with or mediated by CD161, for example, certain cancers. In addition, the invention also relates to expression vectors and host cells for making these antibodies.

30 Claims, 32 Drawing Sheets
Specification includes a Sequence Listing.

FIG. 3

| | | | |
|---|---|---|---|
| Q12918 KLRB1_HUMAN | 1 | MDQQAIYAELNLPTDSGPESSSPSSLPRD----VCQGSPWHQFALKLSCAG-I----I | 49 |
| Q9NZS2 KLRF1_HUMAN | 1 | MQDEERYMTLNVQSKKRSSAQTSQLTFKD---YSVTLHWYKILLGISGTVNGILTLLIS | 57 |
| D3W0D1 KLRF2_HUMAN | 1 | MENEDGYMTLSFKNRCKSKQR------SKD--FSLYPQYCLLLIFGCI------V | 42 |
| Q2HXU8 CL12B_HUMAN | 1 | MSEEVTYATLTFQDSAGARNNRDGNNLRKRGHPAPSPIWRHAALGL------VTLCLML | 53 |
| | | * .: :* * | |
| Q12918 KLRB1_HUMAN | 50 | LLVLVTGLSVSVTSLLIQKSSIEKCS-------VDI------- | 78 |
| Q9NZS2 KLRF1_HUMAN | 58 | LILLVSQGVLLKC------QKGSCS------NATQYEDTGDLKVNGT---- | 93 |
| D3W0D1 KLRF2_HUMAN | 43 | ILIFIMTGIDLKF--------WHK------KMD---- | 61 |
| Q2HXU8 CL12B_HUMAN | 54 | LIGLVTLGMMFLQISNDINSDSEKLSQLQKTIQQQDNLSQLGNSNNLSMEEFLKSQI | 113 |
| | | *: :: . . : | |
| Q12918 KLRB1_HUMAN | 79 | ----QQSRNKTTERPGLLNCPIYWQQLREKCLLFS-HTVNPWNNSLADCS | 123 |
| Q9NZS2 KLRF1_HUMAN | 94 | ----RRNISNKDLCASRSADQTVLCQSEWLKYQGKCYWFS-NEMKSWDSYVYCL | 143 |
| D3W0D1 KLRF2_HUMAN | 62 | ----FSQNVNVSSLSGHNYLCPNDMLLNEGKCYWFS--TSFKTWKESQRDCT | 107 |
| Q2HXU8 CL12B_HUMAN | 114 | SSVLKRQEQMAIKLCQELIHTSDHERCNPCPRMWQYQNSCYYFTTNEEKTWANSRKDCI | 173 |
| | | * | |
| Q12918 KLRB1_HUMAN | 124 | TKESSLLIRDKDELIHTQNLIRDKAILFWIGLNFSLSEKNWKWINGSTLNSNDLEIRGD | 183 |
| Q9NZS2 KLRF1_HUMAN | 144 | ERKSHLLITHDQLEMARTQKNLRQL-NYWIGLNFTSLRKMTWTWVDGSPIDSKIFFIKGP | 202 |
| D3W0D1 KLRF2_HUMAN | 108 | QLQAHLLVIQNLDEHEFIQNSLKPG-HFGWIGLYVTFQGNLMWWIDEHFLVPELFSVIGP | 166 |
| Q2HXU8 CL12B_HUMAN | 174 | DKNSTLVKIDSLEEKEDFLMSQPLLMFSFFWLGLSWDSSGRSWFWEDGSVPSPSLFSTKEL | 233 |
| | | :* *: ::. * : : * | |
| Q12918 KLRB1_HUMAN | 184 | ---AKENSCISISQTSVYSEYCSTEIRWICQKELTPVRNKVYPDS | 225 |
| Q9NZS2 KLRF1_HUMAN | 203 | ---AKENSCAATKESKIFSETCSSVFKWICQY----- | 231 |
| D3W0D1 KLRF2_HUMAN | 167 | TDDRSCAVTGNWVYSEDCSSTFKGTCQRDAILTHNGTSGV- | 207 |
| Q2HXU8 CL12B_HUMAN | 234 | DQINGSKGCAYFQKGNIYISRCSAEITFWICEKTAAPVKTEDLD--- | 276 |
| | | . :* * . :** : | |

FIG. 4

| | | | |
|---|---|---|---|
| Q12918 KLRB1_HUMAN | 1 | MDQQAIYAELNLPTDSGPESSSPSSLPRD-VC------QGSPWHQFALKLSCAGIIL | 50 |
| Q9UHP7 CLC2D_HUMAN | 1 | MH-----DSNNV-----EKDITPSELPANPGCTHSKEHSIKATLIWRLFTL---IMP | 44 |
| | | * * *: : | |
| Q12918 KLRB1_HUMAN | 51 | LVLIVTGLSVSVTLLIQKSSIEKCSVDIQQSRNKTTERPGLLNCPIYWQQLREKCLLFSH | 110 |
| Q9UHP7 CLC2D_HUMAN | 45 | LTIIVCGMVAALSAIRA-----NC-------HQEPSVCLQAACPESWIGPQRKCFYFSD | 91 |
| | | * **: *** :: : * ** :: ::*:. * | |
| Q12918 KLRB1_HUMAN | 111 | TVNPWNNSLADCSTKESSLLIRDKDELIHTQNLIRDKAILFWIGLNFSLSEKNWKWING | 170 |
| Q9UHP7 CLC2D_HUMAN | 92 | DTKNWTSSQRFCDSDADLAQVESFQELNFL--LRVKGPSDHWIGLSRE--QGQPWKWING | 148 |
| | | . . * * :**. . * * ****** | |
| Q12918 KLRB1_HUMAN | 171 | SFLNSNDLEIRGDAKENSCISISQTSVYSEYCSTEIRWICQKELTPVRNKVYPDS | 225 |
| Q9UHP7 CLC2D_HUMAN | 149 | TEWTRQF-PILG---AGECAYLNDKGASSARHYTERKWICSKSDIHV------ | 191 |
| | | .:. *. ** ** *. . | |

|  | | CDR-H1 | | CDR-H2 | |
|---|---|---|---|---|---|
| Cons | 1 | EVQLLESGGGLVQPGGSLRLSCAASGF$X_1$F$X_2X_3X_4$AMSWVRQAPGKGLEWVSAIS$X_5X_6$GG$X_7$T$X_8$YAD | | | |
| Ab1 | 1 | .........................A.STY.................................AA..T.Y... | | | |
| Ab2 | 1 | .........................A.STY.................................GV..T.Y... | | | |
| Ab3 | 1 | .........................T.ERY.................................AA..T.Y... | | | |
| Ab4 | 1 | .........................T.ERY.................................AV..T.K... | | | |
| Ab5 | 1 | .........................T.GQY.................................AV..T.A... | | | |
| Ab6 | 1 | .........................T.GQY.................................AA..T.Y... | | | |
| Ab7 | 1 | .........................T.GQY.................................AA..T.Y... | | | |
| Ab8 | 1 | .........................T.GTF.................................GV..T.Y... | | | |
| Ab9 | 1 | .........................T.SPY.................................AS..T.Y... | | | |
| Ab10 | 1 | .........................T.SQY.................................AV..S.Y... | | | |
| Ab11 | 1 | .........................T.SQY.................................AA..T.Y... | | | |

FIG. 12A

|  | | CDR-H2 | CDR-H3 | |
|---|---|---|---|---|
| Cons | 63 | SVKGRFTISRDNSKNTLYLQMNSLRAEDTAVYYCAKPLDSS$X_9$WADF$X_{10}X_{11}$WGRGTLVTVSS | | |
| Ab1 | 63 | .................................................L...DL........ | | |
| Ab2 | 63 | .................................................L...DL........ | | |
| Ab3 | 63 | .................................................Q...DL........ | | |
| Ab4 | 63 | .................................................L...DA........ | | |
| Ab5 | 63 | .................................................L...QL........ | | |
| Ab6 | 63 | .................................................Q...DL........ | | |
| Ab7 | 63 | .................................................Q...DL........ | | |
| Ab8 | 63 | .................................................F...DL........ | | |
| Ab9 | 63 | .................................................F...DL........ | | |
| Ab10 | 63 | .................................................Q...DL........ | | |
| Ab11 | 63 | .................................................Q...DL........ | | |

FIG. 12A (Continued)

CDR-L1                                                                CDR-L2
Cons  1 DIQ$X_1$TQSPSSVSASVGDRVTITCRASQ$X_{12}$I$X_{13}$SWLAWYQQKPGKAPK$X_{14}$LIY$X_{15}$AS$X_5$LQ$X_{16}$GVPSRF
Ab1   1 ...M.........................  .G.D......................L.  .A..S..S
Ab2   1 ....L........................  .G.S......................L.  .Y..S..D
Ab3   1 ....L........................  .D.S......................F.  .A..A..S
Ab4   1 ....L........................  .G.S......................L.  .A..G..S
Ab5   1 ....L........................  .D.S......................L.  .F..S..S
Ab6   1 ....L........................  .G.S......................L.  .A..S..S
Ab7   1 ....L........................  .G.S......................L.  .A..F..S
Ab8   1 ....L........................  .T.S......................L.  .A..S..S
Ab9   1 ....L........................  .G.S......................L.  .A..S..S
Ab10  1 ....L........................  .D.S......................L.  .A..A..S
Ab11  1 ....L........................  .G.Y......................L.  .A..S..S

FIG. 12B

CDR-L3
Cons 63 SGSGSGTDFTLTI$X_C$SLQPEDFATYYCQQ$X_{17}$$X_{18}$$X_{19}$LPITFGGGTKVEIK
Ab1  63 .............S..................A S V
Ab2  63 .............S..................A S V
Ab3  63 .............S..................A L V
Ab4  63 .............S..................A S Y
Ab5  63 .............S..................A S K
Ab6  63 .............N..................A W V
Ab7  63 .............S..................A S V
Ab8  63 .............S..................Q S V
Ab9  63 .............S..................H S V
Ab10 63 .............S..................A D V
Ab11 63 .............S..................A S D FIG. 12B (Continued)

CDR-H1                                                                    CDR-H2
Cons  1 QVQLVESGGGLVX$_a$PGGSLRLSCAASGFTFX$_1$X$_2$YYMSWIRQAPGKGLEWVSYISPSGX$_3$TIX$_4$YAD
Ab12  1 ..............................AQ.........................S..A...
Ab13  1 .............K................AN.........................A..A...
Ab14  1 .............K................GQ.........................A..A...
Ab15  1 .............K................PQ.........................A..Y...
Ab16  1 .............K................SD.........................A..A...
Ab17  1 .............K................SD.........................A..Y...
Ab18  1 .............K................SQ.........................A..A...
Ab19  1 .............K................SQ.........................A..Y...
Ab20  1 .............Q................SQ.........................A..A...

FIG. 13A

CDR-H2                                                             CDR-H3
Cons  63 SVKGRFTISRDNX$_b$KNX$_c$LYLQMNSLRAEDTAVYYCARSLMX$_5$TGTHLYFDLWGRGTLVTVSS
Ab12  63 ...........................................A.....................
Ab13  63 .........A..S..............................A.....................
Ab14  63 .........A..S..............................S.....................
Ab15  63 .........A..S..............................S.....................
Ab16  63 .........S..T..............................S.....................
Ab17  63 .........A..S..............................A.....................
Ab18  63 .........A..S..............................S.....................
Ab19  63 .........A..S..............................A.....................
Ab20  63 .........A..S..............................S.....................

CDR-L1 — CDR-L2

| | DIQLTQSPSSVSASVGDRVTITCRAS x₆x₇ISx₈WLAWYQQKPGKAPKLLIYAA x₉x₁₀LQSGVPSRF |
|---|---|
| Cons | |
| Ab12 | . . . . . . . . . . . . . . . . . . . . . . . . . . . Q D . S . . . . . . . . . . . . . . . . . . . . . . . S S . . . . . . . . . . |
| Ab13 | . . . . . . . . . . . . . . . . . . . . . . . . . . . S G . S . . . . . . . . . . . . . . . . . . . . . . . S E . . . . . . . . . . |
| Ab14 | . . . . . . . . . . . . . . . . . . . . . . . . . . . Q G . D . . . . . . . . . . . . . . . . . . . . . . . S S . . . . . . . . . . |
| Ab15 | . . . . . . . . . . . . . . . . . . . . . . . . . . . Q G . S . . . . . . . . . . . . . . . . . . . . . . . S S . . . . . . . . . . |
| Ab16 | . . . . . . . . . . . . . . . . . . . . . . . . . . . Q G . S . . . . . . . . . . . . . . . . . . . . . . . S G . . . . . . . . . . |
| Ab17 | . . . . . . . . . . . . . . . . . . . . . . . . . . . Q G . S . . . . . . . . . . . . . . . . . . . . . . . S S . . . . . . . . . . |
| Ab18 | . . . . . . . . . . . . . . . . . . . . . . . . . . . Q G . S . . . . . . . . . . . . . . . . . . . . . . . E S . . . . . . . . . . |
| Ab19 | . . . . . . . . . . . . . . . . . . . . . . . . . . . Q G . S . . . . . . . . . . . . . . . . . . . . . . . S A . . . . . . . . . . |
| Ab20 | . . . . . . . . . . . . . . . . . . . . . . . . . . . Q G . S . . . . . . . . . . . . . . . . . . . . . . . S V . . . . . . . . . . |

CDR-L3

| | SGSGSGTDFTLTISSLQPEDFATYCQQ x₁₁TSx₁₂x₁₃PYTFGGGTKVEIK |
|---|---|
| Cons | |
| Ab12 | . . . . . . . . . . . . . . . . . . . . . . . . . . V . . F P . . . . . . . . . . . |
| Ab13 | . . . . . . . . . . . . . . . . . . . . . . . . . . A . . F P . . . . . . . . . . . |
| Ab14 | . . . . . . . . . . . . . . . . . . . . . . . . . . V . . F P . . . . . . . . . . . |
| Ab15 | . . . . . . . . . . . . . . . . . . . . . . . . . . V . . T P . . . . . . . . . . . |
| Ab16 | . . . . . . . . . . . . . . . . . . . . . . . . . . S . . F P . . . . . . . . . . . |
| Ab17 | . . . . . . . . . . . . . . . . . . . . . . . . . . V . . V P . . . . . . . . . . . |
| Ab18 | . . . . . . . . . . . . . . . . . . . . . . . . . . V . . Q P . . . . . . . . . . . |
| Ab19 | . . . . . . . . . . . . . . . . . . . . . . . . . . V . . A P . . . . . . . . . . . |
| Ab20 | . . . . . . . . . . . . . . . . . . . . . . . . . . V . . F L . . . . . . . . . . . |

FIG. 13B (Continued)

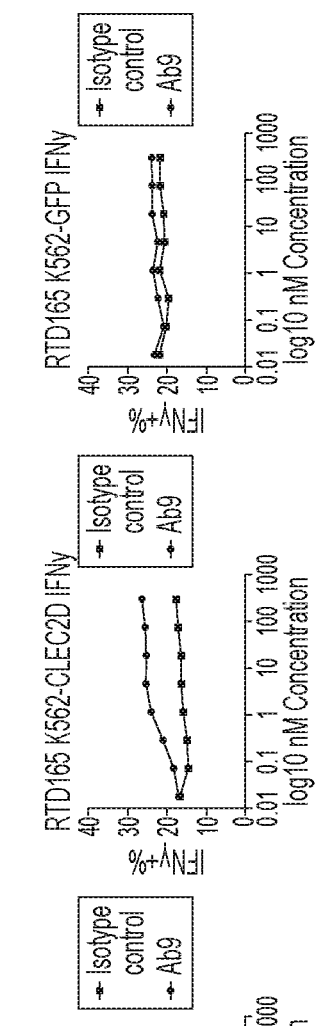
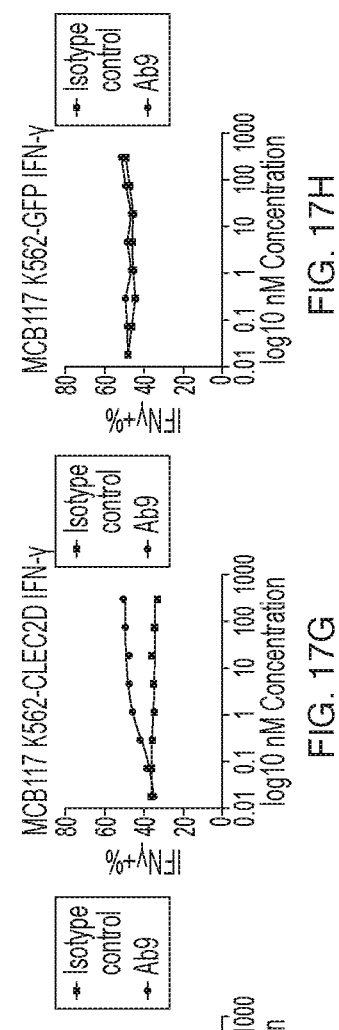
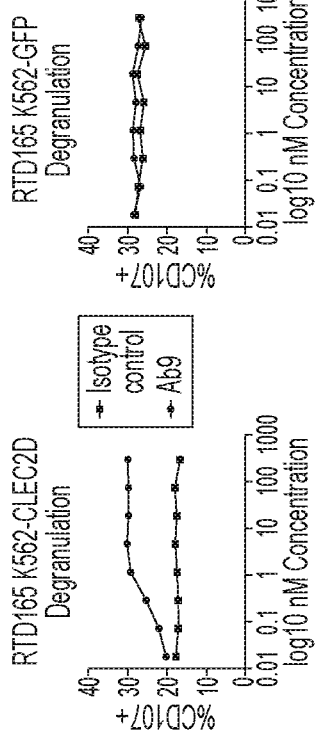
FIG. 17A  FIG. 17B  FIG. 17C  FIG. 17D
FIG. 17E  FIG. 17F  FIG. 17G  FIG. 17H

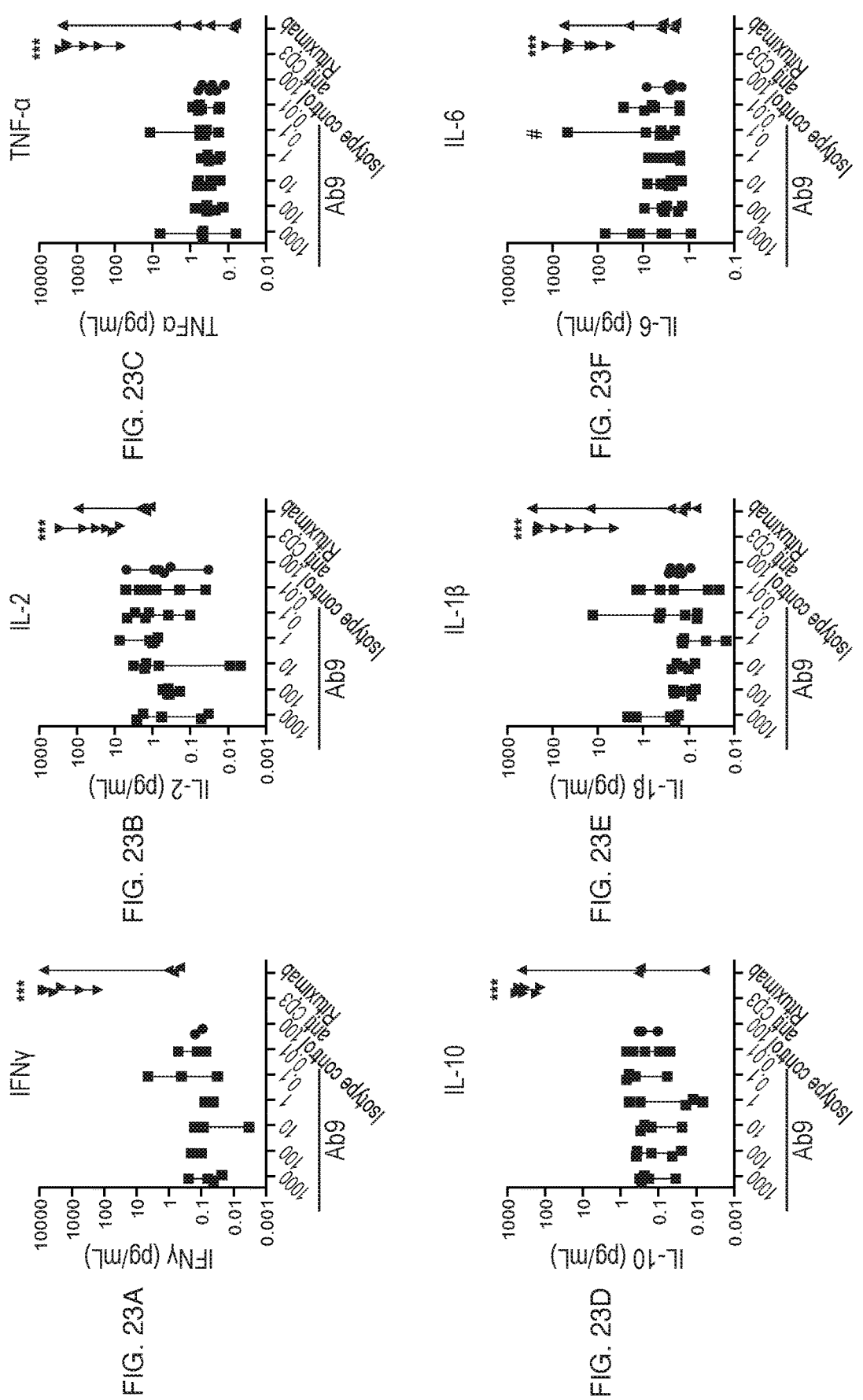

ANTI-CD161 ANTIBODIES AND USES THEREOF

CROSS-REFERENCE TO RELATED APPLICATION

This application is a continuation of International Application No.: PCT/US2022/075370 filed Aug. 23, 2022, which claims the benefit of and priority to U.S. Provisional Patent Application No. 63/236,122, filed Aug. 23, 2021, the entire disclosure of each of which is hereby incorporated herein by reference in their entirety for all purposes.

SEQUENCE LISTING

The instant application contains a Sequence Listing which has been submitted electronically in XML format. The Sequence Listing XML is hereby incorporated by reference in its entirety. The XML file, created on Aug. 11, 2022, is named IMT-001WO_SL.xml and is 206,992 bytes in size.

FIELD OF THE INVENTION

The invention relates generally to anti-CD161 antibodies, pharmaceutical compositions comprising these antibodies, and methods of using these antibodies for treating disorders associated with or mediated by CD161, for example, certain cancers. In addition, the invention also relates to expression vectors and host cells for making these antibodies.

BACKGROUND

Modulation of immune cell checkpoint receptors via antibody-directed therapeutic approaches has been gaining interest over the last decade. Many of these receptors are involved in T cell checkpoint modulation. However, B cell, natural killer (NK) cell, and myeloid cell checkpoint modulation, in particular, is highly desirable and is attracting attention. NK cells are part of the innate immunity which recognize and induce cytotoxicity against a wide range of target cells, such as tumor cells or virus infected cells. Activated NK cells typically kill target cells by means similar to cytotoxic T cells, i.e., via cytolytic granules that contain perforin and granzymes as well as via death receptor pathways. Activated NK cells also secrete inflammatory cytokines such as IFN-γ and chemokines that promote the recruitment of other leukocytes to the target tissue.

The NK cell receptors (NKR) are divided into two main structural classes: the immunoglobulin and C-type lectin-like (CLRs) superfamilies. NKR-Protein1 (NKR-P1) (e.g., CD161) are a family of CLR transmembrane molecules that are important immuno-regulatory genes and are expressed on various cell types, including spleen dendritic cells, subsets of T cells, and granulocytes. The Lectin-Like Transcript 1 (LLT1), C-Type Lectin Domain Family 2 Member D (CLEC2D) or osteoclast inhibitory lectin (OCIL) molecule is the cognate ligand for the CD161 receptor and this interaction inhibits the NK cell and T cell function. There are six splice variants of CLEC2D, isoform 1 being the canonical sequence which is expressed on NK cells, T cells, monocytes/macrophages, activated B cells and dendritic cells, and functions as a human NK cell activating receptor. The polypeptide chain of CLEC2D contains multiple domains including the N-terminal cytoplasmic domain, the trans-membrane domain, the stalk regions, and a C-terminal CLR ectodomain with two predicted N-glycosylation sites.

The interaction between CLEC2D and CD161 can result in certain disorders, including certain cancers, that evade the immune system of a subject. Such immune evasion or escape has been reported in human glioblastoma and other diseases. Moreover, CLEC2D expression on germinal center B cells is thought to regulate cross-talk between NK cells and antigen presenting cells (APC). Therefore, blocking CLEC2D-CD161 interaction provides a new therapeutic option for treating various cancers.

Although the downstream intracellular signaling of CLEC2D-CD161 interactions is poorly defined, the interaction between CLEC2D and CD161 has been shown to inhibit both NK and T cell function. Despite the progress that has been made in treating certain cancers, there still remains a need for new and innovative therapies for treating certain cancers, especially cancers that evade the immune system.

SUMMARY OF THE INVENTION

The invention is based, in part, upon the discovery of high affinity anti-CD161 antibodies that disrupt the CLEC2D-CD161 interaction that can be used, among other things, to prevent certain cancers from evading the immune system of a subject.

Accordingly, in one aspect, the present disclosure provides an isolated anti-CD161 antibody comprising a light chain variable region; and a heavy chain variable region comprising CDR-H1, CDR-H2, and CDR-H3 sequences, wherein: (a) the CDR-H1 sequence is $FX_1FX_2X_3X_4AMS$ (SEQ ID NO: 1); (b) the CDR-H2 sequence is $AISX_5X_6GGX_7TX_8YADSVKG$ (SEQ ID NO: 2); and (c) the CDR-H3 sequence is $AKPLDSSX_9WADFX_{10}X_{11}$ (SEQ ID NO: 3); wherein: $X_1$ is T or A; $X_2$ is G, S, or E; $X_3$ is Q, T, P, or R; $X_4$ is Y or F; $X_5$ is A or G; $X_6$ is A, V, or S; $X_7$ is T or S; $X_8$ is K, A, or Y; $X_9$ is Q, F, or L; $X_{10}$ is D or Q; and $X_{11}$ is L or A. In certain embodiments, the light chain variable region comprises CDR-L1, CDR-L2 and CDR-L3 sequences, wherein (d) the CDR-L1 sequence is $RASQX_{12}IX_{13}SWLA$ (SEQ ID NO: 4); (e) the CDR-L2 sequence is $X_{14}ASX_{15}LQX_{16}$ (SEQ ID NO: 5); and (f) the CDR-L3 sequence is $QQX_{17}X_{18}X_{19}LPIT$ (SEQ ID NO: 6); wherein: $X_{12}$ is G, D, or T; $X_{13}$ is D, S, or Y; $X_{14}$ is A, Y, or F; $X_{15}$ is S, A, G, or F; $X_{16}$ is D or S; $X_{17}$ is A, H, or Q; $X_{18}$ is S, D, W, or L; and $X_{19}$ is V, D, Y, or K.

In some embodiments, (a) the CDR-H1 sequence is SEQ ID NO: 8; (b) the CDR-H2 sequence is SEQ ID NO: 9; and (c) the CDR-H3 sequence is SEQ ID NO: 10. In some embodiments, alternatively or in addition, (d) the CDR-L1 sequence is SEQ ID NO: 12; (e) the CDR-L2 sequence is SEQ ID NO: 13; and (f) the CDR-L3 sequence is SEQ ID NO: 14.

In some embodiments, (a) the CDR-H1 sequence is SEQ ID NO: 16; (b) the CDR-H2 sequence is SEQ ID NO: 17; and (c) the CDR-H3 sequence is SEQ ID NO: 18. In some embodiments, alternatively or in addition, (d) the CDR-L1 sequence is SEQ ID NO: 20; (e) the CDR-L2 sequence is SEQ ID NO: 21; and (f) the CDR-L3 sequence is SEQ ID NO: 22.

In some embodiments, (a) the CDR-H1 sequence is SEQ ID NO: 24; (b) the CDR-H2 sequence is SEQ ID NO: 25; and (c) the CDR-H3 sequence is SEQ ID NO: 26. In some embodiments, alternatively or in addition, (d) the CDR-L1 sequence is SEQ ID NO: 28; (e) the CDR-L2 sequence is SEQ ID NO: 29; and (f) the CDR-L3 sequence is SEQ ID NO: 30.

In some embodiments, (a) the CDR-H1 sequence is SEQ ID NO: 32; (b) the CDR-H2 sequence is SEQ ID NO: 33; and (c) the CDR-H3 sequence is SEQ ID NO: 34. In some embodiments, alternatively or in addition, (d) the CDR-L1 sequence is SEQ ID NO: 36; (e) the CDR-L2 sequence is SEQ ID NO: 37; and (f) the CDR-L3 sequence is SEQ ID NO: 38.

In some embodiments, (a) the CDR-H1 sequence is SEQ ID NO: 40; (b) the CDR-H2 sequence is SEQ ID NO: 41; and (c) the CDR-H3 sequence is SEQ ID NO: 42. In some embodiments, alternatively or in addition, (d) the CDR-L1 sequence is SEQ ID NO: 44; (e) the CDR-L2 sequence is SEQ ID NO: 45; and (f) the CDR-L3 sequence is SEQ ID NO: 46.

In some embodiments, (a) the CDR-H1 sequence is SEQ ID NO: 48; (b) the CDR-H2 sequence is SEQ ID NO: 49; and (c) the CDR-H3 sequence is SEQ ID NO: 50. In some embodiments, alternatively or in addition, (d) the CDR-L1 sequence is SEQ ID NO: 52; (e) the CDR-L2 sequence is SEQ ID NO: 53; and (f) the CDR-L3 sequence is SEQ ID NO: 54.

In some embodiments, (a) the CDR-H1 sequence is SEQ ID NO: 56; (b) the CDR-H2 sequence is SEQ ID NO: 57; and (c) the CDR-H3 sequence is SEQ ID NO: 58. In some embodiments, alternatively or in addition, (d) the CDR-L1 sequence is SEQ ID NO: 60; (e) the CDR-L2 sequence is SEQ ID NO: 61; and (f) the CDR-L3 sequence is SEQ ID NO: 62.

In some embodiments, (a) the CDR-H1 sequence is SEQ ID NO: 64; (b) the CDR-H2 sequence is SEQ ID NO: 65; and (c) the CDR-H3 sequence is SEQ ID NO: 66. In some embodiments, alternatively or in addition, (d) the CDR-L1 sequence is SEQ ID NO: 68; (e) the CDR-L2 sequence is SEQ ID NO: 69; and (f) the CDR-L3 sequence is SEQ ID NO: 70.

In some embodiments, (a) the CDR-H1 sequence is SEQ ID NO: 72; (b) the CDR-H2 sequence is SEQ ID NO: 73; and (c) the CDR-H3 sequence is SEQ ID NO: 74. In some embodiments, alternatively or in addition, (d) the CDR-L1 sequence is SEQ ID NO: 76; (e) the CDR-L2 sequence is SEQ ID NO: 77; and (f) the CDR-L3 sequence is SEQ ID NO: 78.

In some embodiments, (a) the CDR-H1 sequence is SEQ ID NO: 80; (b) the CDR-H2 sequence is SEQ ID NO: 81; and (c) the CDR-H3 sequence is SEQ ID NO: 82. In some embodiments, alternatively or in addition, (d) the CDR-L1 sequence is SEQ ID NO: 84; (e) the CDR-L2 sequence is SEQ ID NO: 85; and (f) the CDR-L3 sequence is SEQ ID NO: 86.

In some embodiments, (a) the CDR-H1 sequence is SEQ ID NO: 88; (b) the CDR-H2 sequence is SEQ ID NO: 89; and (c) the CDR-H3 sequence is SEQ ID NO: 90. In some embodiments, alternatively or in addition, (d) the CDR-L1 sequence is SEQ ID NO: 92; (e) the CDR-L2 sequence is SEQ ID NO: 93; and (f) the CDR-L3 sequence is SEQ ID NO: 94.

In some embodiments, the present disclosure provides an isolated anti-CD161 antibody, wherein the heavy chain variable region comprises the amino acid sequence: EVQLLESGGGLVQPGGSLRLSCAASGFX$_1$FX$_2$X$_3$X$_4$AMSWVRQAPGKGLEWVSAISX$_5$X$_6$GGX$_7$TX$_8$YADSVKGRFTISRDNSKNTLYLQMNSLR AEDTAVYYCAKPLDSSX$_9$WADFX$_{10}$X$_{11}$WGRGTLVTVSS (SEQ ID NO: 188), wherein: X$_1$ is T or A; X$_2$ is G, S, or E; X$_3$ is Q, T, P, or R; X$_4$ is Y or F; X$_5$ is A or G; X$_6$ is A, V, or S; X$_7$ is T or S; X$_8$ is K, A, or Y; X$_9$ is Q, F, or L; X$_{10}$ is D or Q; and X$_{11}$ is L or A.

In some embodiments, the heavy chain variable region comprises an amino acid sequence at least 90% identical (e.g., at least 95% identical) to a sequence selected from the group consisting of: SEQ ID NO: 7, SEQ ID NO: 15, SEQ ID NO: 23, SEQ ID NO: 31, SEQ ID NO: 39, SEQ ID NO: 47, SEQ ID NO: 55, SEQ ID NO: 63, SEQ ID NO: 71, SEQ ID NO: 79, and SEQ ID NO: 87. In some embodiments, the heavy chain variable region comprises an amino acid sequence selected from the group consisting of: SEQ ID NO: 7, SEQ ID NO: 15, SEQ ID NO: 23, SEQ ID NO: 31, SEQ ID NO: 39, SEQ ID NO: 47, SEQ ID NO: 55, SEQ ID NO: 63, SEQ ID NO: 71, SEQ ID NO: 79, and SEQ ID NO: 87.

In some embodiments, the present disclosure provides an isolated anti-CD161 antibody, wherein the light chain variable region comprises the amino acid sequence: DIQX$_a$TQSPSSVSASVGDRVTITCRASQX$_{12}$IX$_{13}$SWL AWYQQKPGKAPKX$_b$LIYX$_{14}$ASX$_{15}$L QX$_{16}$GVPSRFSGSGSGTDFTLTIX$_c$SLQPEDFATYY CQQX$_{17}$X$_{18}$X$_{19}$LPITFGGGTKVEIK (SEQ ID NO: 189), wherein: X$_{12}$ is G, D, or T; X$_{13}$ is D, S, or Y; X$_{14}$ is A, Y, or F; X$_{15}$ is S, A, G, or F; X$_{16}$ is D or S; X$_{17}$ is A, H, or Q; X$_{18}$ is S, D, W, or L; X$_{19}$ is V, D, Y, or K; X$_a$ is M or L; X$_b$ is L or F; and X$_c$ is S or N.

In some embodiments, the light chain variable region comprises an amino acid sequence at least 90% identical (e.g., at least 95% identical) to a sequence selected from the group consisting of: SEQ ID NO: 11, SEQ ID NO: 19, SEQ ID NO: 27, SEQ ID NO: 35, SEQ ID NO: 43, SEQ ID NO: 51, SEQ ID NO: 59, SEQ ID NO: 67, SEQ ID NO: 75, SEQ ID NO: 83, and SEQ ID NO: 91. In some embodiments, the light chain variable region comprises an amino acid sequence selected from the group consisting of: SEQ ID NO: 11, SEQ ID NO: 19, SEQ ID NO: 27, SEQ ID NO: 35, SEQ ID NO: 43, SEQ ID NO: 51, SEQ ID NO: 59, SEQ ID NO: 67, SEQ ID NO: 75, SEQ ID NO: 83, and SEQ ID NO: 91.

In some embodiments, the heavy chain variable region comprises an amino acid sequence at least 90% identical (e.g., at least 95% identical) to the sequence of SEQ ID NO: 7 and the light chain variable region comprises an amino acid sequence at least 90% identical (e.g., at least 95% identical) to the sequence of SEQ ID NO: 11. In some embodiments, the heavy chain variable region comprises the sequence of SEQ ID NO: 7 and the light chain variable region comprises the sequence of SEQ ID NO: 11.

In some embodiments, the heavy chain variable region comprises an amino acid sequence at least 90% identical (e.g., at least 95% identical) to the sequence of SEQ ID NO: 15 and the light chain variable region comprises an amino acid sequence at least 90% identical (e.g., at least 95% identical) to the sequence of SEQ ID NO: 19. In some embodiments, the heavy chain variable region comprises the sequence of SEQ ID NO: 15 and the light chain variable region comprises the sequence of SEQ ID NO: 19.

In some embodiments, the heavy chain variable region comprises an amino acid sequence at least 90% identical (e.g., at least 95% identical) to the sequence of SEQ ID NO: 23 and the light chain variable region comprises an amino acid sequence at least 90% identical (e.g., at least 95% identical) to the sequence of SEQ ID NO: 27. In some embodiments, the heavy chain variable region comprises the sequence of SEQ ID NO: 23 and the light chain variable region comprises the sequence of SEQ ID NO: 27.

In some embodiments, the heavy chain variable region comprises an amino acid sequence at least 90% identical (e.g., at least 95% identical) to the sequence of SEQ ID NO: 31 and the light chain variable region comprises an amino acid sequence at least 90% identical (e.g., at least 95% identical) to the sequence of SEQ ID NO: 35. In some embodiments, the heavy chain variable region comprises the sequence of SEQ ID NO: 31 and the light chain variable region comprises the sequence of SEQ ID NO: 35.

In some embodiments, the heavy chain variable region comprises an amino acid sequence at least 90% identical (e.g., at least 95% identical) to the sequence of SEQ ID NO: 39 and the light chain variable region comprises an amino acid sequence at least 90% identical (e.g., at least 95% identical) to the sequence of SEQ ID NO: 43. In some embodiments, the heavy chain variable region comprises the sequence of SEQ ID NO: 39 and the light chain variable region comprises the sequence of SEQ ID NO: 43.

In some embodiments, the heavy chain variable region comprises an amino acid sequence at least 90% identical (e.g., at least 95% identical) to the sequence of SEQ ID NO: 47 and the light chain variable region comprises an amino acid sequence at least 90% identical (e.g., at least 95% identical) to the sequence of SEQ ID NO: 51. In some embodiments, the heavy chain variable region comprises the sequence of SEQ ID NO: 47 and the light chain variable region comprises the sequence of SEQ ID NO: 51.

In some embodiments, the heavy chain variable region comprises an amino acid sequence at least 90% identical (e.g., at least 95% identical) to the sequence of SEQ ID NO: 55 and the light chain variable region comprises an amino acid sequence at least 90% identical (e.g., at least 95% identical) to the sequence of SEQ ID NO: 59. In some embodiments, the heavy chain variable region comprises the sequence of SEQ ID NO: 55 and the light chain variable region comprises the sequence of SEQ ID NO: 59.

In some embodiments, the heavy chain variable region comprises an amino acid sequence at least 90% identical (e.g., at least 95% identical) to the sequence of SEQ ID NO: 63 and the light chain variable region comprises an amino acid sequence at least 90% identical (e.g., at least 95% identical) to the sequence of SEQ ID NO: 67. In some embodiments, the heavy chain variable region comprises the sequence of SEQ ID NO: 63 and the light chain variable region comprises the sequence of SEQ ID NO: 67.

In some embodiments, the heavy chain variable region comprises an amino acid sequence at least 90% identical (e.g., at least 95% identical) to the sequence of SEQ ID NO: 71 and the light chain variable region comprises an amino acid sequence at least 90% identical (e.g., at least 95% identical) to the sequence of SEQ ID NO: 75. In some embodiments, the heavy chain variable region comprises the sequence of SEQ ID NO: 71 and the light chain variable region comprises the sequence of SEQ ID NO: 75.

In some embodiments, the heavy chain variable region comprises an amino acid sequence at least 90% identical (e.g., at least 95% identical) to the sequence of SEQ ID NO: 79 and the light chain variable region comprises an amino acid sequence at least 90% identical (e.g., at least 95% identical) to the sequence of SEQ ID NO: 83. In some embodiments, the heavy chain variable region comprises the sequence of SEQ ID NO: 79 and the light chain variable region comprises the sequence of SEQ ID NO: 83.

In some embodiments, the heavy chain variable region comprises an amino acid sequence at least 90% identical (e.g., at least 95% identical) to the sequence of SEQ ID NO: 87 and the light chain variable region comprises an amino acid sequence at least 90% identical (e.g., at least 95% identical) to the sequence of SEQ ID NO: 91. In some embodiments, the heavy chain variable region comprises the sequence of SEQ ID NO: 87 and the light chain variable region comprises the sequence of SEQ ID NO: 91.

In another aspect, the present disclosure provides an isolated anti-CD161 antibody thereof comprising a light chain variable region; and a heavy chain variable region comprising CDR-H1, CDR-H2, and CDR-H3 sequences, wherein: (a) the CDR-H1 sequence is FTFX$_1$X$_2$YYMS (SEQ ID NO: 95); (b) the CDR-H2 sequence is YISPSGX$_3$TIX$_4$YADSVKG (SEQ ID NO: 96); and (c) the CDR-H3 sequence is ARSLMX$_5$TGTHLYFDL (SEQ ID NO: 97); wherein: X$_1$ is G, A, P, or S; X$_2$ is N, Q, or D; X$_3$ is A or S; X$_4$ is Y or A; and X$_5$ is A or S. In certain embodiments, the light chain variable region comprises CDR-L1, CDR-L2 and CDR-L3 sequences, wherein (a) the CDR-L1 sequence is RASX$_6$X$_7$ISX$_8$WLA (SEQ ID NO: 98); (b) the CDR-L2 sequence is AAX$_9$X$_{10}$LQS (SEQ ID NO: 99); and (c) the CDR-L3 sequence is QQXIITSX$_{12}$X$_{13}$PYT (SEQ ID NO: 100); wherein: X$_6$ is Q or S; X$_7$ is D or G; X$_8$ is D or S; X$_9$ is E or S; X$_{10}$ is S, A, G, V, or E; X$_{11}$ is A, S, or V; X$_{12}$ is F, T, V, Q, or A; and X$_{13}$ is L or P.

In some embodiments, the (a) the CDR-H1 sequence is SEQ ID NO: 102; (b) the CDR-H2 sequence is SEQ ID NO: 103; and (c) the CDR-H3 sequence is SEQ ID NO: 104. In some embodiments, alternatively or in addition, (d) the CDR-L1 sequence is SEQ ID NO: 106; (e) the CDR-L2 sequence is SEQ ID NO: 107; and (f) the CDR-L3 sequence is SEQ ID NO: 108.

In some embodiments, (a) the CDR-H1 sequence is SEQ ID NO: 110; (b) the CDR-H2 sequence is SEQ ID NO: 111; and (c) the CDR-H3 sequence is SEQ ID NO: I12. In some embodiments, alternatively or in addition, (d) the CDR-L1 sequence is SEQ ID NO: 114; (e) the CDR-L2 sequence is SEQ ID NO: 115; and (f) the CDR-L3 sequence is SEQ ID NO: 116.

In some embodiments, (a) the CDR-H1 sequence is SEQ ID NO: 118; (b) the CDR-H2 sequence is SEQ ID NO: 119; and (c) the CDR-H3 sequence is SEQ ID NO: 120. In some embodiments, alternatively or in addition, (d) the CDR-L1 sequence is SEQ ID NO: 122; (e) the CDR-L2 sequence is SEQ ID NO: 123; and (f) the CDR-L3 sequence is SEQ ID NO: 124.

In some embodiments, (a) the CDR-H1 sequence is SEQ ID NO: 126; (b) the CDR-H2 sequence is SEQ ID NO: 127; and (c) the CDR-H3 sequence is SEQ ID NO: 128. In some embodiments, alternatively or in addition, (d) the CDR-L1 sequence is SEQ ID NO: 130; (e) the CDR-L2 sequence is SEQ ID NO: 131; and (f) the CDR-L3 sequence is SEQ ID NO: 132.

In some embodiments, (a) the CDR-H1 sequence is SEQ ID NO: 134; (b) the CDR-H2 sequence is SEQ ID NO: 135; and (c) the CDR-H3 sequence is SEQ ID NO: 136. In some embodiments, alternatively or in addition, (d) the CDR-L1 sequence is SEQ ID NO: 138; (e) the CDR-L2 sequence is SEQ ID NO: 139; and (f) the CDR-L3 sequence is SEQ ID NO: 140.

In some embodiments, (a) the CDR-H1 sequence is SEQ ID NO: 142; (b) the CDR-H2 sequence is SEQ ID NO: 143; and (c) the CDR-H3 sequence is SEQ ID NO: 144. In some embodiments, alternatively or in addition, (d) the CDR-L1 sequence is SEQ ID NO: 146; (e) the CDR-L2 sequence is SEQ ID NO: 147; and (f) the CDR-L3 sequence is SEQ ID NO: 148.

In some embodiments, (a) the CDR-H1 sequence is SEQ ID NO: 150; (b) the CDR-H2 sequence is SEQ ID NO: 151; and (c) the CDR-H3 sequence is SEQ ID NO: 152. In some embodiments, alternatively or in addition, (d) the CDR-L1 sequence is SEQ ID NO: 154; (e) the CDR-L2 sequence is SEQ ID NO: 155; and (f) the CDR-L3 sequence is SEQ ID NO: 156.

In some embodiments, (a) the CDR-H1 sequence is SEQ ID NO: 158; (b) the CDR-H2 sequence is SEQ ID NO: 159; and (c) the CDR-H3 sequence is SEQ ID NO: 160. In some embodiments, alternatively or in addition, (d) the CDR-L1 sequence is SEQ ID NO: 162; (e) the CDR-L2 sequence is SEQ ID NO: 163; and (f) the CDR-L3 sequence is SEQ ID NO: 164.

In some embodiments, (a) the CDR-H1 sequence is SEQ ID NO: 166; (b) the CDR-H2 sequence is SEQ ID NO: 167; and (c) the CDR-H3 sequence is SEQ ID NO: 168. In some embodiments, alternatively or in addition, (d) the CDR-L1 sequence is SEQ ID NO: 170; (e) the CDR-L2 sequence is SEQ ID NO: 171; and (f) the CDR-L3 sequence is SEQ ID NO: 172.

In some embodiments, the heavy chain variable region comprises the amino acid sequence: QVQLVESGGGLVX$_a$PGGSLRLSCAASGFTFX$_1$X$_2$YYMSWIRQAPGKGLEWVSYISPSGX$_3$TIX$_4$YADSVKGRFTISRDNX$_b$KNX$_c$LYLQMNSLRAEDTAVYYCARSLMX$_5$TGTHLYFDLW GRGTLVTVSS (SEQ ID NO: 190), wherein: $X_1$ is G, A, P, or S; $X_2$ is N, Q, or D; $X_3$ is A or S; $X_4$ is Y or A; $X_5$ is A or S; $X_a$ is K or Q; $X_b$ is A or S; and $X_c$ is S or T.

In some embodiments, the heavy chain variable region comprises an amino acid sequence at least 90% identical (e.g., at least 95% identical) to a selected from the group consisting of: SEQ ID NO: 101, SEQ ID NO: 109, SEQ ID NO: 117, SEQ ID NO: 125, SEQ ID NO: 133, SEQ ID NO: 141, SEQ ID NO: 149, SEQ ID NO: 157, and SEQ ID NO: 165. In some embodiments, the heavy chain variable region comprises an amino acid sequence selected from the group consisting of: SEQ ID NO: 101, SEQ ID NO: 109, SEQ ID NO: 117, SEQ ID NO: 125, SEQ ID NO: 133, SEQ ID NO: 141, SEQ ID NO: 149, SEQ ID NO: 157, and SEQ ID NO: 165.

In some embodiments, the light chain variable region comprises the amino acid sequence: DIQLTQSPSSVSASVGDRVTITC RASX$_6$X$_7$ISX$_8$WLAWYQQKPGKAPKLLIYAAX$_9$X$_{10}$LQS GVPSRFSGSGSGTDFTLTISSLQPEDFATYYC QQX$_{11}$TSX$_{12}$X$_{13}$PYTFGGGTKVEIK (SEQ ID NO: 191), wherein: $X_6$ is Q or S; $X_7$ is D or G; $X_8$ is D or S; $X_9$ is E or S; $X_{10}$ is S, A, G, V, or E; $X_{11}$ is A, S, or V; $X_{12}$ is F, T, V, Q, or A; and $X_{13}$ is L or P.

In some embodiments, the light chain variable region comprises an amino acid sequence at least 90% identical (e.g., at least 95% identical) to a sequence selected from the group consisting of: SEQ ID NO: 105, SEQ ID NO: 113, SEQ ID NO: 121, SEQ ID NO: 129, SEQ ID NO: 137, SEQ ID NO: 145, SEQ ID NO: 153, SEQ ID NO: 161, and SEQ ID NO: 169. In some embodiments, the light chain variable region comprises an amino acid sequence selected from the group consisting of: SEQ ID NO: 105, SEQ ID NO: 113, SEQ ID NO: 121, SEQ ID NO: 129, SEQ ID NO: 137, SEQ ID NO: 145, SEQ ID NO: 153, SEQ ID NO: 161, and SEQ ID NO: 169.

In some embodiments, the heavy chain variable region comprises an amino acid sequence at least 90% identical (e.g., at least 95% identical) to the sequence of SEQ ID NO: 101 and the light chain variable region comprises an amino acid sequence at least 90% (e.g., at least 95% identical) identical to the sequence of SEQ ID NO: 105. In some embodiments, the heavy chain variable region comprises the sequence of SEQ ID NO: 101 and the light chain variable region comprises the sequence of SEQ ID NO: 105.

In some embodiments, the heavy chain variable region comprises an amino acid sequence at least 90% identical (e.g., at least 95% identical) to the sequence of SEQ ID NO: 109 and the light chain variable region comprises an amino acid sequence at least 90% identical (e.g., at least 95% identical) to the sequence of SEQ ID NO: 113. In some embodiments, the heavy chain variable region comprises the sequence of SEQ ID NO: 109 and the light chain variable region comprises the sequence of SEQ ID NO: 113.

In some embodiments, the heavy chain variable region comprises an amino acid sequence at least 90% identical (e.g., at least 95% identical) to the sequence of SEQ ID NO: 117 and the light chain variable region comprises an amino acid sequence at least 90% identical (e.g., at least 95% identical) to the sequence of SEQ ID NO: 121. In some embodiments, the heavy chain variable region comprises the sequence of SEQ ID NO: 117 and the light chain variable region comprises the sequence of SEQ ID NO: 121.

In some embodiments, the heavy chain variable region comprises an amino acid sequence at least 90% identical (e.g., at least 95% identical) to the sequence of SEQ ID NO: 125 and the light chain variable region comprises an amino acid sequence at least 90% identical (e.g., at least 95% identical) to the sequence of SEQ ID NO: 129. In some embodiments, the heavy chain variable region comprises the sequence of SEQ ID NO: 125 and the light chain variable region comprises the sequence of SEQ ID NO: 129.

In some embodiments, the heavy chain variable region comprises an amino acid sequence at least 90% identical (e.g., at least 95% identical) to the sequence of SEQ ID NO: 133 and the light chain variable region comprises an amino acid sequence at least 90% identical (e.g., at least 95% identical) to the sequence of SEQ ID NO: 137. In some embodiments, the heavy chain variable region comprises the sequence of SEQ ID NO: 133 and the light chain variable region comprises the sequence of SEQ ID NO: 137.

In some embodiments, the heavy chain variable region comprises an amino acid sequence at least 90% identical (e.g., at least 95% identical) to the sequence of SEQ ID NO: 141 and the light chain variable region comprises an amino acid sequence at least 90% identical (e.g., at least 95% identical) to the sequence of SEQ ID NO: 145. In some embodiments, the heavy chain variable region comprises the sequence of SEQ ID NO: 141 and the light chain variable region comprises the sequence of SEQ ID NO: 145.

In some embodiments, the heavy chain variable region comprises an amino acid sequence at least 90% identical (e.g., at least 95% identical) to the sequence of SEQ ID NO: 149 and the light chain variable region comprises an amino acid sequence at least 90% identical (e.g., at least 95% identical) to the sequence of SEQ ID NO: 153. In some embodiments, the heavy chain variable region comprises the sequence of SEQ ID NO: 149 and the light chain variable region comprises the sequence of SEQ ID NO: 153.

In some embodiments, the heavy chain variable region comprises an amino acid sequence at least 90% identical (e.g., at least 95% identical) to the sequence of SEQ ID NO: 157 and the light chain variable region comprises an amino acid sequence at least 90% identical (e.g., at least 95% identical) to the sequence of SEQ ID NO: 161. In some embodiments, the heavy chain variable region comprises the sequence of SEQ ID NO: 157 and the light chain variable region comprises the sequence of SEQ ID NO: 161.

In some embodiments, the heavy chain variable region comprises an amino acid sequence at least 90% identical (e.g., at least 95% identical) to the sequence of SEQ ID NO: 165 and the light chain variable region comprises an amino acid sequence at least 90% identical (e.g., at least 95% identical) to the sequence of SEQ ID NO: 169. In some embodiments, the heavy chain variable region comprises the sequence of SEQ ID NO: 165 and the light chain variable region comprises the sequence of SEQ ID NO: 169.

In some embodiments, the antibody is a monoclonal antibody. In some embodiments, the antibody is multispecific. In some embodiments, the antibody is an Fab, Fab', F(Ab')$_2$, Fv, scFv, (scFv)$_2$, single chain antibody molecule, dual variable domain antibody, single variable domain antibody, linear antibody, or V domain antibody. In some embodiments, the antibody comprises a scaffold. In some embodiments, the scaffold is Fc. In some embodiments, scaffold is human Fc. In some embodiments, the antibody comprises a heavy chain constant region of a class selected from the group consisting of: IgG, IgA, IgD, IgE, and IgM. In some embodiments, the antibody comprises a heavy chain constant region of the class IgG and a subclass selected from the group consisting of: IgG$_1$, IgG$_2$, IgG$_3$, and IgG4.

In certain embodiments, the monoclonal antibody is an aglycosylated human IgG$_1$ antibody. In certain embodiments, the monoclonal antibody comprises an IgG1 Fc region with modification at amino acid position N297 (e.g., N297A) according to EU numbering.

In another aspect, the present disclosure provides an isolated antibody that competes for binding to CD161 with the anti-CD161 antibody disclosed herein.

In some embodiments, the present disclosure provides an isolated antibody that specifically binds to the CD161 epitope bound by the anti-CD161 antibody disclosed herein. In some embodiments, the antibody competes for binding to CD161 with CLEC2D.

In some embodiments, the antibody reduces CD161 inhibitory signaling due to binding of CLEC2D to CD161. In some embodiments, the CD161 is expressed on the surface of a cell. In some embodiments, the cell is a T cell or an NK cell. In some embodiments, the cell is a human cell or a cynomolgus cell. In some embodiments, the antibody reduces suppression of T cell or NK cell activity by CLEC2D binding to CD161.

In some embodiments, the antibody of the present disclosure increases T cell or NK cell activity in the presence of CLEC2D as compared to such T cell or NK cell activity in the absence of the antibody. In some embodiments, the T cells or NK cells are disposed within a microenvironment comprising cells expressing CLEC2D. In some embodiments, the antibody increases T cell or NK cell activity in a tumor microenvironment containing tumor cells that express CLEC2D. In some embodiments, the increase in T cell activity is determined by an increase in NFAT signaling. In some embodiments, the antibody has an EC$_{50}$ value for T cell activation of between 1.5 nM and 4.1 nM. For example, the antibody has an EC$_{50}$ value for T cell activation of about 1.5 nM, about 1.7 nM, about 2.0 nM, about 2.3 nM, about 2.5 nM, about 2.8 nM, about 3.1 nM, about 3.3 nM, about 3.5 nM, about 3.8 nM, about 4.1 nM. In some embodiments, the antibody reverses CLEC2D-mediated inhibition and restores T cell activity. In some embodiments, the antibody enhances polyfunctionality of a primary antigen-specific human T cell. In some embodiments, the antibody of the present disclosure (i) enhances or restores direct T cell mediated cytotoxicity that was affected by CD161-CLEC2D interaction, (ii) increases secretion of TNFα, (iii) increases secretion of IL-2, (iv) increases secretion of IFNγ, or (v) exhibits any combination of features (i), (ii), (iii) or (iv).

In some embodiments, the increase in NK cell activity is determined by an increase in CD107a expression. In some embodiments, the antibody has an EC$_{50}$ value for NK cell activation of between 0.04 nM and 0.38 nM. For example, the antibody has an EC$_{50}$ value for NK cell activation of about 0.04 nM, about 0.06 nM, about 0.08 nM, about 0.1 nM, about 0.12 nM, about 0.14 nM, about 0.16 nM, about 0.18 nM, about 0.20 nM, about 0.22 nM, about 0.24 nM, about 0.28 nM, about 0.30 nM, about 0.32 nM, about 0.34 nM, about 0.36 nM, about 0.38 nM. In some embodiments, the increase in NK cell activity is determined by an increase in IFNγ expression. In some embodiments, the antibody has an EC$_{50}$ value for NK cell activation of between 0.1 nM and 0.5 nM. For example, the antibody has an EC$_{50}$ value for NK cell activation of about 0.1 nM, about 0.15 nM, about 0.2 nM, about 0.25 nM, about 0.3 nM, about 0.35 nM, about 0.4 nM, about 0.45 nM, about 0.5 nM.

In some embodiments, the antibody binds to human CD161 with a K$_d$ of less than or equal to 10 nM, less than or equal to 0.5 nM, less than or equal to 1 nM, less than or equal to 0.5 nM or less than or equal to 0.1 nM as measured by an Octet QK384 assay. In some embodiments, the antibody binds to human CD161 with a K$_d$ in the range of $1\times10^8$ to $1\times10^{-10}$ M as measured by an Octet QK384 assay. In some embodiments, the antibody has an EC$_{50}$ for HEK293 cells expressing CD161 of less than 5 nM, less than 1 nM, or less than 0.5 nM. In some embodiments, the antibody has an EC$_{50}$ for HEK293 cells expressing CD161 in the range of 0.1-0.5 nM. In some embodiments, the antibody reduces CLEC2D binding to CD161 expressed on the surface of a cell with an IC$_{50}$ in the range of 0.1 to 10 nM. In some embodiments, the antibody reduces CLEC2D binding to CD161 expressed on the surface of a cell with an IC$_{50}$ of less than 10 nM, less than 5 nM, less than 2 nM, less than 1 nM, or less than 0.5 nM. In some embodiments, the antibody has a K$_d$ of greater than 1,000 nM for hKLRF1, hKLRF2, hCLEC12B, hCLEC2D, or any combination thereof. In some embodiments, the antibody binds to less than 2%, less than 1.5%, less than 1.2%, less than 1.1%, or less than 1% of a population of CD161 homologs as compared to the antibody bound to CD161 under saturating antibody conditions. In some embodiments, the population of CD161 homologs comprise CLEC2D, KLRF1, KLRF2, CLEC12B, or any combination thereof.

In some embodiments, the antibody enhances NK cell killing of a CLEC2D expressing cell. For example, under certain circumstances, the antibody enhances NK cell killing of CLEC2D expressing cell by blocking the interaction of CD161 with CLEC2D.

In some embodiments, the antibody enhances reactivation of antigen-specific effector memory CD4 T cells. In some embodiments, the antibody enhances reactivation of antigen-specific effector memory CD4 T cells by blocking CD161 interaction with CLEC2D. In some embodiments, the antibody enhances the cytokine production of a MART-1-specific T cell. In some embodiments, the antibody enhances the cytotoxicity function of a MART-1-specific T cell. In some embodiments, the antibody does not cause cytokine release syndrome.

In certain embodiments, an antibody provided herein exhibits at least one or more of the following features (a)-(t), including: (a) binds human CD161; (b) binds human CD161 at a human CD161 binding site; (c) binds to the CD161 epitope bound by an anti-CD161 antibody or antigen-binding fragment thereof; (d) binds human CD161 at or near a CLEC2D binding site; (e) competes for binding to CD161 with CLEC2D; (f) reduces CD161 inhibitory signaling due to binding of CLEC2D to CD161; (g) reduces suppression of T cell activity by CLEC2D binding to CD161; (h) reduces suppression of NK cell activity by CLEC2D binding to CD161; (i) increases T cell activity in the presence of CLEC2D as compared to such T cell activity in the absence of the antibody or antigen-binding fragment thereof; (j) increases NK cell activity in the presence of CLEC2D as compared to such NK cell activity in the absence of the antibody or antigen-binding fragment thereof; (k) increases T cell activity disposed within a microenvironment comprising cells expressing CLEC2D; (l) increases NK cell activity disposed within a microenvironment comprising cells expressing CLEC2D; (m) increases T cell activity in a tumor microenvironment comprising tumor cells that express CLEC2D; (n) increases NK cell activity in a tumor microenvironment comprising tumor cells that express CLEC2D; (o) inhibits human T cell exhaustion; (p) induces or increases activation of a CD161-expressing human T cell in response to an antigen-expressing target cell; (q) induces or increases cytokine production by a CD161-expressing human T cell in response to an antigen-expressing target cell; (r) induces or increases granzyme B expression by a CD161-expressing human T cell in response to an antigen-expressing target cell; (s) reduces exhaustion of CD161-expressing human T cells in response to antigen-expressing target cells; and (t) any combination of (a)-(s).

In some embodiments, the antibody binds to human CD161 and cynomolgus CD161, wherein the binding affinity of the antibody for the human CD161 and the cynomolgus CD161 varies by no more than 5×, 10×, 20×, 50×, or 100×. In some embodiments, the antibody binds to human CD161 and cynomolgus CD161, wherein the binding avidity of the antibody for the human CD161 and the cynomolgus CD161 varies by no more than 5×, 10×, 20×, 50×, or 100×.

In another aspect, the present disclosure also provides a pharmaceutical composition comprising the antibody disclosed herein, and a pharmaceutically acceptable carrier.

In another aspect, the present disclosure also provides an isolated polynucleotide or plurality of polynucleotides encoding the antibody disclosed herein, a $V_H$ thereof, a $V_L$ thereof, a light chain thereof, a heavy chain thereof, or an antigen-binding portion thereof.

In another aspect, the present disclosure also provides a vector or plurality of vectors comprising the polynucleotide or plurality of polynucleotides disclosed herein.

In another aspect, the present disclosure also provides a host cell comprising the polynucleotide, plurality of polynucleotides, or the plurality of vectors disclosed herein.

In another aspect, the present disclosure also provides a method of producing an antibody comprising expressing the antibody with the host cell and isolating the expressed antibody.

In another aspect, the present disclosure also provides a kit comprising the antibody disclosed herein, or the pharmaceutical composition disclosed herein and instructions for use.

In another aspect, the present disclosure also provides a method of treating cancer in a subject in need thereof, the method comprising administering to the subject an effective amount of an immunotherapy (e.g., an anti-CD161 antibody) disclosed herein or an effective amount of the pharmaceutical composition disclosed herein. In some embodiments, the present disclosure provides a method of treating cancer in a subject in need thereof, the method comprising administering to the subject an effective amount of the anti-CD161 antibody disclosed herein or an effective amount of the pharmaceutical composition disclosed herein. In some embodiments, the cancer is characterized by expression of CLEC2D by cancer cells or other cells in the tumor microenvironment. In some embodiments, the cancer is characterized by an increased expression of CLEC2D by cancer cells or other cells in the tumor microenvironment. In some embodiments, the cancer is selected from the group consisting of: melanoma, lung, glioma, colorectal, and liver.

In another aspect, the present disclosure also provides a method for reducing or inhibiting tumor growth in a subject in need thereof, the method comprising administering to the subject an effective amount of the anti-CD161 antibody disclosed herein or an effective amount of the pharmaceutical composition disclosed herein.

In another aspect, the present disclosure also provides a method for inhibiting or blocking the interaction between human CD161 and CLEC2D in a subject in need thereof, the method comprising administering to the subject an effective amount of the anti-CD161 antibody disclosed herein or an effective amount of the pharmaceutical composition disclosed herein.

In another aspect, the present disclosure also provides a method for inducing or enhancing immune cell activation in a subject in need thereof, the method comprising administering to the subject, an effective amount of the anti-CD161 antibody disclosed herein or an effective amount of the pharmaceutical composition disclosed herein. In some embodiments, the immune cell activation occurs in a tumor microenvironment. In some embodiments, the immune cell is a T cell or a NK cell.

In some embodiments, the present disclosure provides a method for inducing or enhancing a cytotoxic T cell effector response in a subject in need thereof, the method comprising administering to the subject, an effective amount of the anti-CD161 antibody disclosed herein or an effective amount of the pharmaceutical composition disclosed herein. Depending upon the circumstances, the T cell effector response (i) is in a tumor microenvironment, (ii) is cytokine production (such as IL-2, TNFα, IFNγ, or a combination thereof), (iii) is secretion of granzyme B, or (iv) a combination of two or more of (i), (ii) and (iii).

These and other aspects and features of the invention are described in the following detailed description and claims.

DESCRIPTION OF THE DRAWINGS

The invention can be more completely understood with reference to the following drawings.

FIG. 3 shows alignment of human CD161 (KLRB1_human) (SEQ ID NO: 179) with its homologs (killer cell lectin-like receptor subfamily F member 1_human (KLRF1_human) (SEQ ID NO: 183), killer cell lectin-like receptor subfamily F member 2_human (KLRF2_human) (SEQ ID NO: 184), and C-type lectin domain family 12 member B_human (CL12B_human) (SEQ ID NO: 185).

FIG. 4 shows alignment of human CD161 (KLRB1_human) (SEQ ID NO: 179) with C-type lectin domain family 2 member D (CLC2D_human) (SEQ ID NO: 186).

FIGS. 12A-12B shows alignments of antibodies of the first family that were used to generate the consensus sequence of $V_H$ and $V_L$, respectively. FIG. 12A discloses SEQ ID Nos. 188, 7, 15, 23, 31, 39, 47, 55, 63, 71, 79, and 87, respectively, in order of appearance, which correspond to the consensus sequence (Cons) to Ab11, respectively. FIG. 12B discloses SEQ ID Nos. 189, 11, 19, 27, 35, 43, 51, 59, 67, 75, 83, and 91, respectively, in order of appearance, which correspond to the consensus sequence (Cons) to Ab11, respectively.

FIGS. 13A-13B shows alignments of antibodies of the second family that were used to generate the consensus sequence of $V_H$ and $V_L$, respectively. FIG. 13A discloses SEQ ID Nos. 190, 101, 109, 117, 125, 133, 141, 149, 157, and 165, respectively, in order of appearance, which correspond to the consensus sequence (Cons), and Ab12 to Ab20, respectively. FIG. 13B discloses SEQ ID Nos. 191, 105, 113, 121, 129, 137, 145, 153, 161, and 169, respectively, in order of appearance, which correspond to the consensus sequence (Cons), and Ab12 to Ab20, respectively.

FIGS. 17A-17B are graphs illustrating anti-CD161 antibody-mediated activation of human NK cells isolated from donor RTD165 as measured by CD107a expression in a dose-dependent manner in target K562 cells expressing CLEC2D (FIG. 17A) or target K562 cells expressing GFP (FIG. 17B). FIGS. 17C-17D are graphs illustrating anti-CD161 antibody-mediated activation of human NK cells isolated from donor RTD165 as measured by secretion of IFN-γ in a dose-dependent manner in target K562 cells expressing CLEC2D (FIG. 17C) or target K562 cells expressing GFP (FIG. 17D).

FIGS. 17E-17F are graphs illustrating anti-CD161 antibody-mediated activation of human NK cells isolated from donor MCB117 as measured by CD107a expression in a dose-dependent manner in target K562 cells expressing CLEC2D (FIG. 17E) or target K562 cells expressing GFP (FIG. 17F). FIGS. 17G-17H are graphs illustrating anti-CD161 antibody-mediated activation of human NK cells isolated from donor MCB117 as measured by secretion of IFN-γ in a dose-dependent manner in target K562 cells expressing CLEC2D (FIG. 17G) or target K562 cells expressing GFP (FIG. 17H).

FIGS. 23A-23F are graphs illustrating induction of cytokines from unstimulated healthy human PBMCs following incubation with soluble Ab9. Treatment of 6 donor human PBMCs with soluble Ab9, isotype control, anti-CD3 muromonab (anti-CD3), and rituximab treatment (*** p<0.0001). The Y axis is shown in log scale to depict the low concentrations of cytokines elicited by the addition of Ab9 and high concentrations released by muromonab treatment. The different points in the plot represent individual PBMC donors. "#" in the IL-6 plot (FIG. 23F) represents a high value that was observed for a single donor at a low concentration of Ab9 suggesting it is an outlier.

DETAILED DESCRIPTION

Figure 1A:
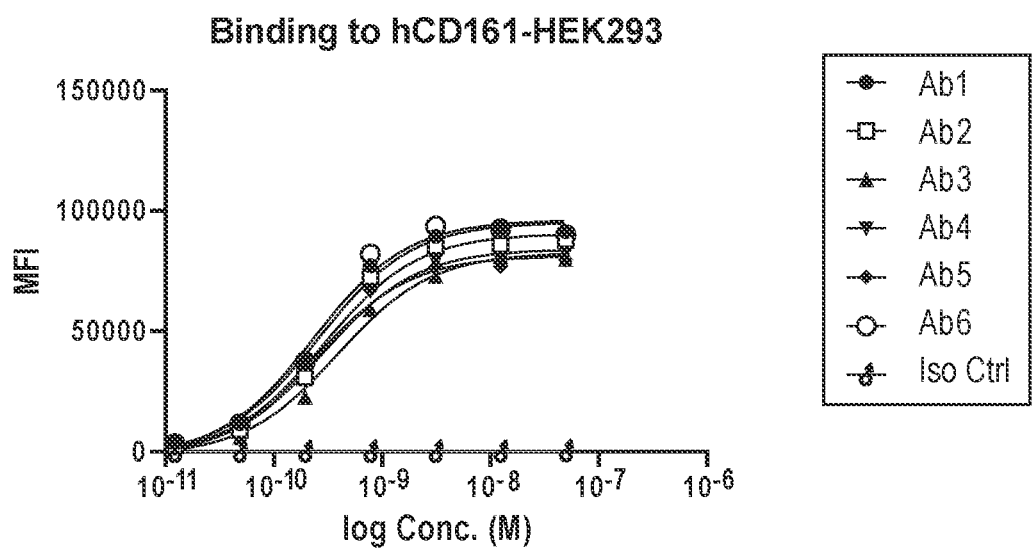
FIGS. 1A-1D are graphs showing binding of exemplary human anti-CD161 antibodies to HEK 293 cells exogenously expressing human CD161. Iso Ctrl denotes an isotype control antibody.
Figure 1B:
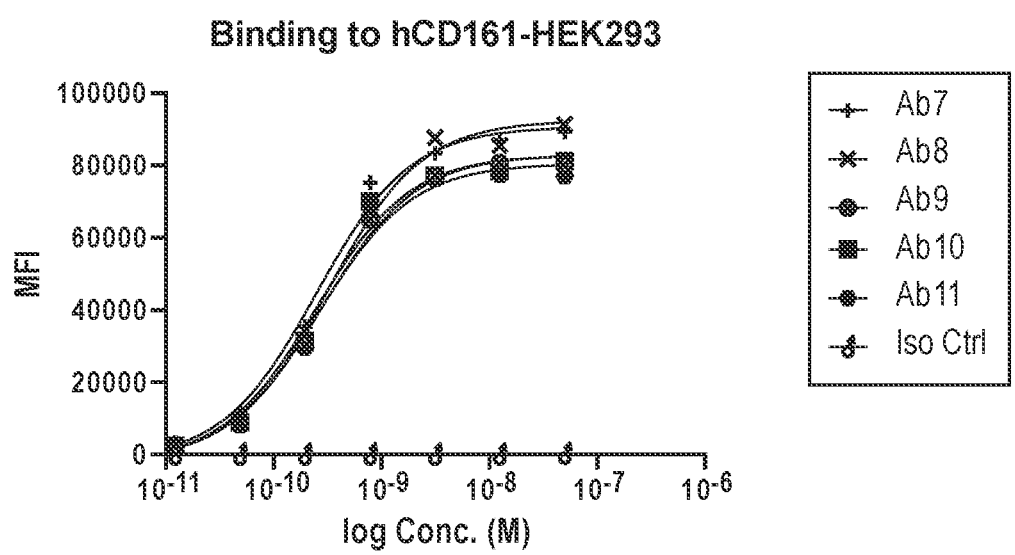
Figure 1C:
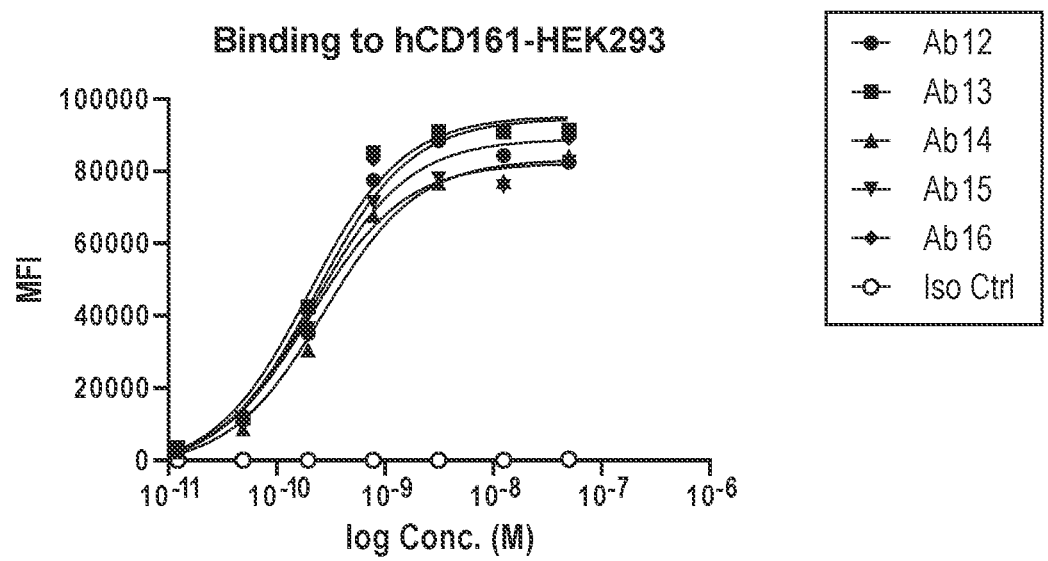
Figure 1D:
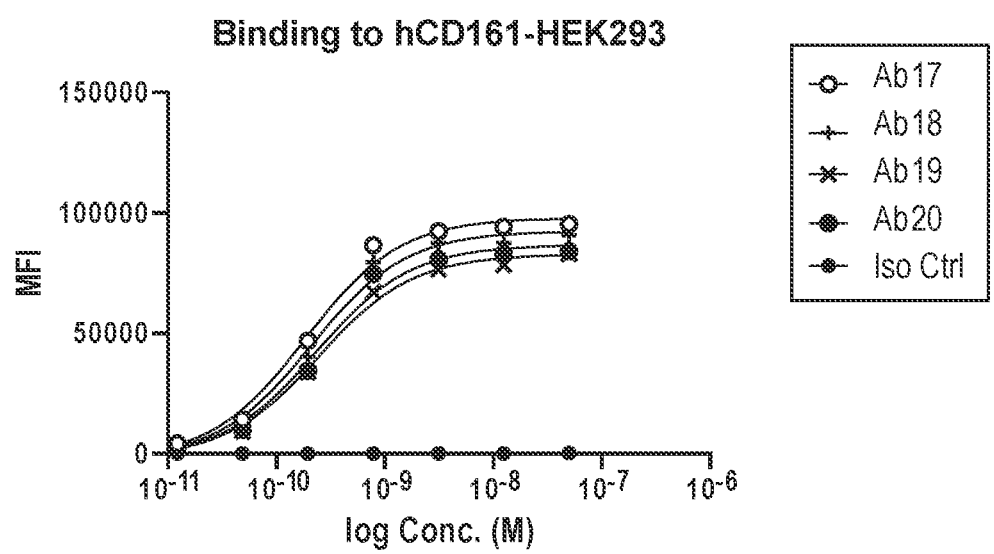
Figure 2A:
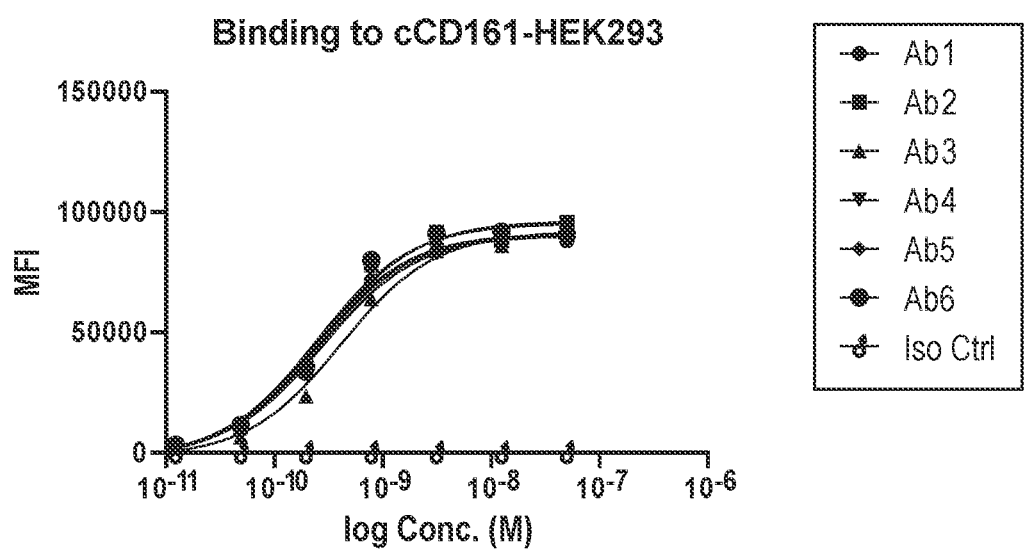
FIGS. 2A-2D are graphs showing binding of exemplary human anti-CD161 antibodies to HEK 293 cells exogenously expressing cynomolgus CD161. Iso Ctrl denotes an isotype control antibody.
Figure 2B:
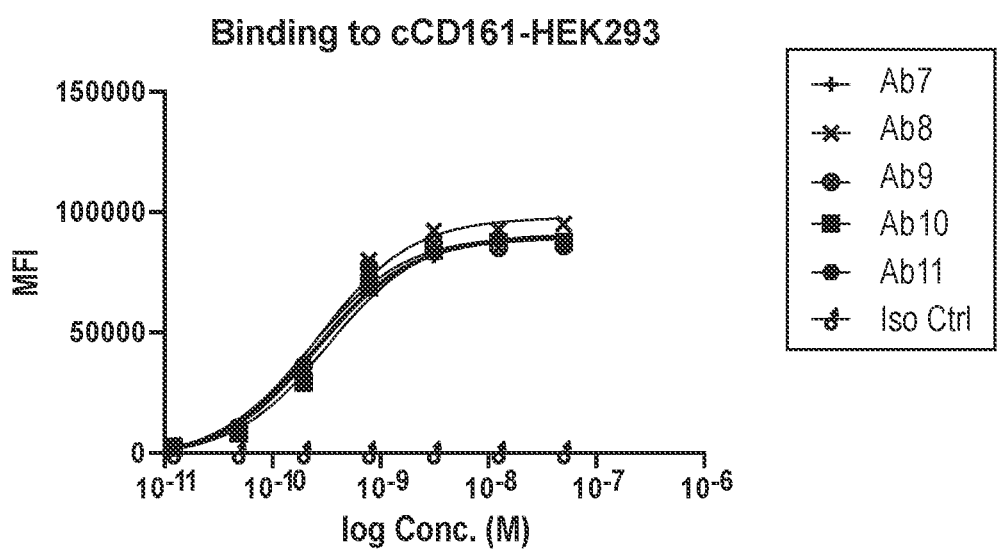
Figure 2C:
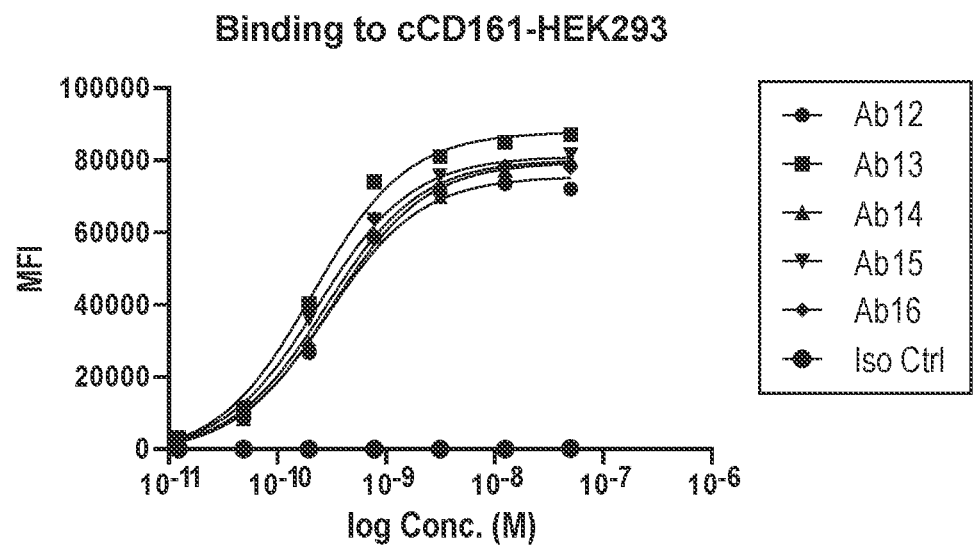
Figure 2D:
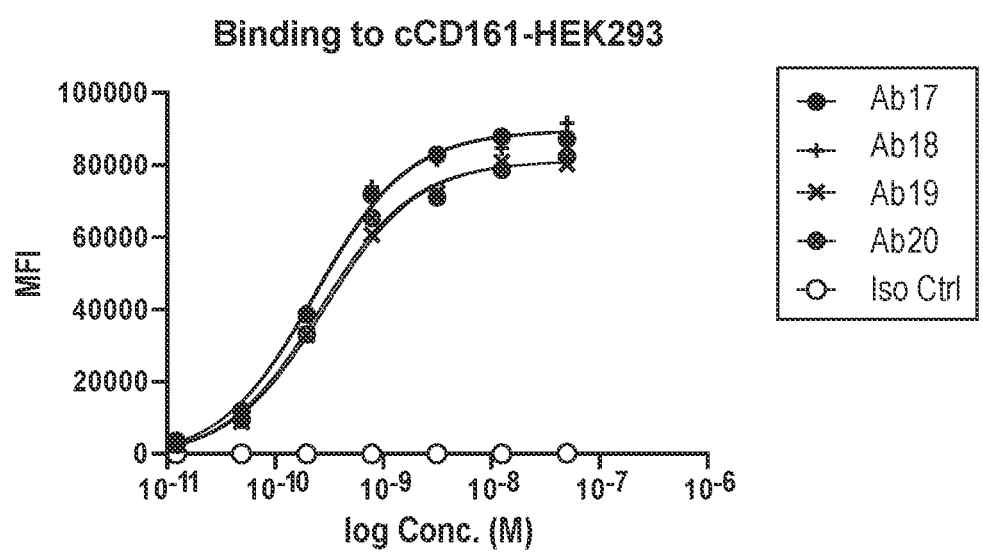

The invention is based, in part, upon the discovery of high affinity anti-CD161 antibodies that disrupt the CLEC2D-CD161 axis that can be used, among other things, to prevent certain cancers from evading the immune system of a subject. The present application further relates to pharmaceutical compositions and therapeutic methods using such antibodies and/or pharmaceutical compositions for the treatment of indications, such as cancer. Various features and aspects of the invention, including the antibodies described in the present application, are discussed in detail below.
Definitions To facilitate an understanding of the present application, a number of terms and phrases are defined below.

The terms "a" and "an" as used herein mean "one or more" and include the plural unless the context is inappropriate.

As used herein, the term "immunoglobulin" refers to a class of structurally related antibody proteins typically comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul (2013) FUNDAMENTAL IMMUNOLOGY 7TH ED., Ch. 5 Lippincott Williams & Wilkins, Philadelphia, PA. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

As used herein, unless otherwise indicated, the term "antibody" is understood to mean an intact antibody (e.g., an intact monoclonal antibody), or a fragment thereof, such as a Fc fragment of an antibody (e.g., an Fc fragment of a monoclonal antibody), or an antigen-binding fragment of an antibody (e.g., an antigen-binding fragment of a monoclonal antibody), including an intact antibody, antigen-binding fragment, or Fc fragment that has been modified, engineered, or chemically conjugated. Examples of antigen-binding fragments include Fab, Fab', (Fab')$_2$, Fv, single chain antibodies (e.g., scFv), minibodies, and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

As used herein, the term "anti-CD161 antibody" refers to an antibody that specifically binds to CD161 (e.g., human CD161). In certain embodiments, the anti-CD161 antibody can reduce or prevent the interaction of CD161 and CLEC2D.

The term "antigen-binding fragment" means the portion of an antibody that is capable of specifically binding to an antigen or epitope. Exemplary antigen-binding fragments include Fab, Fab', F(ab')$_2$, fragments or in a recombinant polypeptide such as an single chain antibody binding site (e.g., scFv) in which a heavy chain variable domain ($V_H$) is connected by a linker (e.g., a polypeptide linker) to the light chain variable domain ($V_L$) in a single polypeptide, a minibody, or a nanobody ($V_{HH}$). Antigen-binding fragments can be found in various contexts including antibodies and chimeric antigen receptors (CARs), for example CARs derived from antibodies or antibody fragments such as scFvs.

The terms "intact antibody," "full length antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini (2010) J. ALLERGY CLIN. IMMUNOL., 125: S41-52, incorporated by reference in its entirety. The Fc region may be a naturally occurring Fc region, or an Fc region modified as described in the art or elsewhere in this disclosure.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al. (1991) SEQUENCES OF PROTEINS OF IMMUNOLOGICAL INTEREST 5TH ED., Public Health Service, National Institutes of Health, Bethesda, MD, incorporated by reference in its entirety.

A "Complementarity Determining Region (CDR)" refers to one of three hypervariable regions (e.g., CDR-H1, CDR-H2 or CDR-H3) within the non-framework region of the immunoglobulin (Ig or antibody) $V_H$ β-sheet framework, or one of three hypervariable regions (e.g., CDR-L1, CDR-L2 or CDR-L3) within the non-framework region of the antibody $V_L$ β-sheet framework. CDRs are variable region sequences interspersed within the framework region sequences. CDRs are well recognized in the art and have been defined by, for example, Kabat as the regions of most hypervariability within the antibody variable (V) domains. See Kabat et al. (1977) J. BIOL. CHEM., 252: 6609-6616 and Kabat (1978) ADV. PROTEIN CHEM., 32: 1-75, each of which is incorporated by reference in its entirety. CDRs have also been defined structurally by Chothia as those residues that are not part of the conserved β-sheet framework, and thus are able to adapt different conformations. See Chothia and Lesk (1987) J. MOL. BIOL., 196: 901-917, incorporated by reference in its entirety. Both the Kabat and Chothia nomenclatures are well known in the art. AbM, Contact and IMGT also defined CDRs. CDR positions within a canonical antibody variable domain have been determined by comparison of numerous structures. See Morea et al. (2000) METHODS, 20: 267-279 and Al-Lazikani et al. (1997) J. MOL. BIOL., 273: 927-48, each of which is incorporated by reference in its entirety.

A number of hypervariable region delineations are in use and are included herein. The Kabat CDRs are based on sequence variability and are the most commonly used. See Kabat et al. (1992) SEQUENCES OF PROTEINS OF IMMUNOLOGICAL INTEREST, DIANE Publishing: 2719, incorporated by reference in its entirety. Chothia refers instead to the location of the structural loops (Chothia and Lesk, supra). The AbM hypervariable regions represent a compromise between the Kabat CDRs and Chothia structural loops, and are used by Oxford Molecular's AbM antibody modeling software. The Contact hypervariable regions are based on an analysis of the available complex crystal structures.

More recently, a universal numbering system ImMunoGeneTics (IMGT) Information System™ has been developed and widely adopted. See Lefranc et al. (2003) DEV. COMP. IMMUNOL., 27: 55-77, incorporated by reference in its entirety. IMGT is an integrated information system specializing in immunoglobulins (IG), T cell receptors (TR) and major histocompatibility complex (MHC) of human and other vertebrates. The IMGT CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. Correspondence between the Kabat, Chothia and IMGT numbering is also well known in the art (Lefranc et al., supra).

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: $IgG_1$, $IgG_2$, $IgG_3$, $IgG_4$, $IgA_1$, and $IgA_2$.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen-binding site. The constant domain contains the $C_{H1}$, $C_{H2}$ and $C_{H3}$ domains of the heavy chain and the $C_L$ domain of the light chain.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"$F(ab')_2$" fragments contain two Fab' fragments joined, near the hinge region, by disulfide bonds. $F(ab')_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. Any suitable linker may be used. In some embodiments, the linker is a $(GGGGS)_n$ (SEQ ID NO: 187), where, in certain embodiments, n=1, 2, 3, 4, 5, or 6.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$—$V_H$). Any suitable Fc domain known in the art or described herein may be used.

The term "single domain antibody" refers to a molecule in which one variable domain of an antibody specifically binds to an antigen without the presence of the other variable domain. Single domain antibodies, and fragments thereof, are described in Arabi Ghahroudi et al. (1998) FEBS LETTERS, 414: 521-526 and Muyldermans et al. (2001) TRENDS IN BIOCHEM. SCI., 26: 230-245, each of which is incorporated by reference in its entirety. Single domain antibodies are also known as sdAbs or nanobodies.

A "multispecific antibody" is an antibody that comprises two or more different antigen-binding domains that collectively specifically bind two or more different epitopes. The two or more different epitopes may be epitopes on the same antigen (e.g., a single CD161 molecule expressed by a cell) or on different antigens (e.g., a CD161 molecule and a non-CD161 molecule). In some aspects, a multi-specific antibody binds two different epitopes (i.e., a "bispecific antibody"). In some aspects, a multi-specific antibody binds three different epitopes (i.e., a "trispecific antibody"). In some aspects, a multi-specific antibody binds four different epitopes (i.e., a "quadspecific antibody"). In some aspects, a multi-specific antibody binds five different epitopes (i.e., a "quintspecific antibody"). In some aspects, a multi-specific antibody binds 6, 7, 8, or more different epitopes. Each binding specificity may be present in any suitable valency. Examples of multispecific antibodies are provided elsewhere in this disclosure.

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al. (1986) NATURE, 321: 522-525; Riechmann et al. (1988) NATURE, 332: 323-329; and Presta (1992) CURR. OP. STRUCT. BIOL., 2: 593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies do not include humanized antibodies.

An "isolated antibody" or "isolated nucleic acid" is an antibody or nucleic acid that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. In some embodiments, an isolated antibody may include an antibody in situ within recombinant cells, since at least one component of the antibody's natural environment is not present. In some aspects, an isolated antibody or isolated nucleic acid is prepared by at least one purification step. In some embodiments, an isolated antibody or isolated nucleic acid is purified to at least 80%, 85%, 90%, 95%, or 99% by weight. In some embodiments, an isolated antibody or isolated nucleic acid is purified to at least 80%, 85%, 90%, 95%, or 99% by volume. In some embodiments, an isolated antibody or isolated nucleic acid is provided as a solution comprising at least 85%, 90%, 95%, 98%, 99% to 100% antibody or nucleic acid by weight. In some embodiments, an isolated antibody or isolated nucleic acid is provided as a solution comprising at least 85%, 90%, 95%, 98%, 99% to 100% antibody or nucleic acid by volume.

"Affinity" refers to the strength of the sum total of non-covalent interactions between a binding site (e.g., a single binding site) of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®, using, for example, the Octet QK384 system).

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. In some aspects, the affinity of a CD161 antibody for a non-target molecule is less than about 40% of the affinity for CD161. In some aspects, the affinity of a CD161 antibody for a non-target molecule is less than about 30% of the affinity for CD161. In some aspects, the affinity of a CD161 antibody for a non-target molecule is less than about 20% of the affinity for CD161. In some aspects, the affinity of a CD161 antibody for a non-target molecule is less than about 10% of the affinity for CD161. In some aspects, the affinity of a CD161 antibody for a non-target molecule is less than about 1% of the affinity for CD161. In some aspects, the affinity of a CD161 antibody for a non-target molecule is less than about 0.1% of the affinity for CD161.

The term "$k_d$" ($sec^{-1}$), as used herein, refers to the dissociation rate constant of a particular antibody-antigen interaction. This value is also referred to as the $k_{off}$ value.

The term "$k_a$" ($M^{-1} \times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" ($M^{-1}$), as used herein, refers to the association equilibrium constant of a particular antibody-antigen interaction. $K_A=k_a/k_d$.

An "affinity matured" antibody is an antibody with one or more alterations (e.g., in one or more CDRs or FRs) relative to a parent antibody (i.e., an antibody from which the altered antibody is derived or designed) that result in an improvement in the affinity of the antibody for its antigen, compared to the parent antibody which does not possess the alteration(s). In some embodiments, an affinity matured antibody has nanomolar or picomolar affinity for the target antigen. Affinity matured antibodies may be produced using a variety of methods known in the art. For example, Marks et al. (1992) BIO/TECHNOLOGY, 10: 779-783, incorporated by reference in its entirety) describes affinity maturation by $V_H$ and $V_L$ domain shuffling. Random mutagenesis of CDR and/or framework residues is described by, for example, Barbas et al. (1994) PROC. NAT. ACAD. SCI. USA, 91: 3809-3813; Schier et al. (1995) GENE, 169: 147-155; Yelton et al. (1995) J. IMMUNOL., 155: 1994-2004; Jackson et al. (1995) J. IMMUNOL., 154:3310-33199; and Hawkins et al. (1992) J. MOL. BIOL., 226: 889-896; each of which is incorporated by reference in its entirety.

"Fc effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP).

When used herein in the context of two or more antibodies, the term "competes with" or "cross-competes with" indicates that the two or more antibodies compete for binding to an antigen (e.g., CD161). In one exemplary assay, CD161 is coated on a surface and contacted with a first CD161 antibody, after which a second CD161 antibody is added. In another exemplary assay, first a CD161 antibody is coated on a surface and contacted with CD161, and then a second CD161 antibody is added. If the presence of the first CD161 antibody reduces binding of the second CD161 antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the antibodies for CD161 and the valency of the antibodies. The assays described in this definition are illustrative, and a skilled artisan can utilize any suitable assay to determine if antibodies compete with each other. Suitable assays are described, for example, in Cox et al., "Immunoassay Methods," in ASSAY GUIDANCE MANUAL [INTERNET], Updated Dec. 24, 2014 (www.ncbi.nlm.nih.gov/books/NBK92434/; accessed Sep. 29, 2015); Silman et al. (2001) CYTOMETRY, 44: 30-37; and Finco et al. (2011) J. PHARM. BIOMED. ANAL., 54: 351-358; each of which is incorporated by reference in its entirety.

As used herein, an antibody that binds specifically to a human antigen is considered to specifically bind the same antigen of mouse origin when a $K_D$ value can be measured on a ForteBio Octet with the mouse antigen. In general, an antibody can be considered cross-reactive to a non-human species when the $K_D$ (as measured by ForteBio Octet) of that species is not more than 10-fold weaker (i.e., $K_D$ value 10-fold higher) than that of the human species. An antibody that binds specifically to a human antigen is considered to be "cross-reactive" with the same antigen of mouse origin when the $K_D$ value for the mouse antigen is no greater than 20 times the corresponding $K_D$ value for the respective human antigen.

As used herein, an antibody that binds specifically to a human antigen is considered to be "cross-reactive" with the same antigen of cynomolgus monkey origin when the $K_D$ value for the cynomolgus monkey antigen is no greater than 20 times the corresponding $K_D$ value for the respective human antigen.

The term "epitope" means a portion of an antigen that is specifically bound by an antibody. Epitopes frequently include surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to CD161 variants with different point-mutations, or to chimeric CD161 variants.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared. A "conservative substitution" or a "conservative amino acid substitution," refers to the substitution of an amino acid with a chemically or functionally similar amino acid. Conservative substitution tables providing similar amino acids are well known in the art. By way of example, the groups of amino acids provided in TABLES 1-3 are, in some embodiments, considered conservative substitutions for one another.

Selected groups of amino acids that are considered conservative substitutions for one another, in certain embodiments, are shown in TABLE 1.

TABLE 1

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

Additional selected groups of amino acids that are considered conservative substitutions for one another, in certain embodiments, are shown in TABLE 2.

TABLE 2

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

Further selected groups of amino acids that are considered conservative substitutions for one another, in certain embodiments, are shown in TABLE 3.

TABLE 3

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton (1993) PROTEINS: STRUCTURES AND MOLECULAR PROPERTIES 2ND ED. W. H. Freeman & Co., New York, NY. An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, ameliorating one or more symptoms, diminishment of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an antibody or pharmaceutical composition provided herein that, when administered to a subject, is sufficient to effect a beneficial or desired result, such as the antibody or pharmaceutical composition, when administered to a subject, is effective to treat a disease or disorder or is effective in ameliorating one or more symptoms of a disease or disorder. An effective amount can be administered in one or more administrations, applications or dosages and is not intended to be limited to a particular formulation or administration route.

As used herein, the term "subject" means a mammalian subject. Exemplary subjects include humans, monkeys, dogs, cats, mice, rats, cows, horses, camels, goats, rabbits, pigs and sheep. In certain embodiments, the subject is a human subject. In some embodiments the subject has a disease or condition that can be treated with an antibody provided herein. For example, the disease or condition is a cancer.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

The term "about" indicates and encompasses an indicated value and a range above and below that value. In certain embodiments, the term "about" indicates the designated value±10%, ±5%, or ±1%. In certain embodiments, where applicable, the term "about" indicates the designated value(s)±one standard deviation of that value(s).

At various places in the present specification, components, or features thereof are disclosed in groups or in ranges. It is specifically intended that the description include each and every individual sub-combination of the members of such groups and ranges. By way of other examples, an integer in the range of 1 to 20 is specifically intended to individually disclose 1, 2, 3, 4, 5, 6, 7, 8, 9, 10, 11, 12, 13, 14, 15, 16, 17, 18, 19, and 20.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

I. Anti-CD161 Antibodies

Human CD161 (also called NK receptor-P1A (NKR-P1A), killer cell lectin-like receptor subfamily B member 1 (KLRB1), or C-type lectin domain family 5 member B (CLEC5B)) is expressed on Th17 cells, natural killer (NK) cells, and NKT cells. CD161 belongs to the killer cell lectin-like receptor (KLR) family, and its members contain one C-type lectin-like domain in the extracellular region responsible for the ligand recognition. Although mice have several CD161 molecules, which are both activating and inhibitory receptors and known as the NKR-P1 family, humans have only one CD161 molecule, which is an inhibitory receptor. The CD161 receptor binds to a ligand known as C-type Lectin Domain Family 2 Member D (CLEC2D) (see Aldemir et al. (2005) J. IMMUNOL., 175(12): 7791-5, Rosen et al. (2005) J. IMMUNOL., 175(12): 7796-9). CLEC2D is also known as human lectin-like transcript-1 molecule (LLT1). The CD161 family molecules are type II transmembrane glycoproteins, which form disulfide-linked homodimers. Inhibiting interaction between CD161 and CLEC2D promotes activation of T cells in response to tumor cells. All orthologs and isoforms of CLEC2D and CD161 are considered to be within the scope of the present disclosure.

An amino acid sequence of human CD161 is represented by SEQ ID NO: 179. Amino acid residues 1-45, 46-66, and 67-225 of SEQ ID NO: 179 comprises a cytoplasmic domain, a transmembrane domain, and an extracellular domain, respectively. An amino acid sequence of cynomolgus CD161, mouse CD161, and rat CD161 is represented by SEQ ID NO: 180, 181, and 182, respectively.

An amino acid sequence of human CLEC2 is represented by SEQ ID NO: 186. Amino acid residues 1-38, 39-59, and 60-191 of SEQ ID NO: 186 comprise a cytoplasmic domain, a transmembrane domain, and an extracellular domain, respectively.

1. Sequences of Anti-CD161 Antibodies

In certain embodiments, the present disclosure provides an antigen-binding fragment that binds CD161 (e.g., human CD161) derived from the antibodies listed in TABLE 4.

Sequences of exemplary antibodies that bind CD161 are shown in TABLE 4.

TABLE 4

| Antibody | $V_H$ and H-CDRs | $V_L$ and L-CDRs |
|---|---|---|
| Ab1 | EVQLLESGGGLVQPGGSLRLSCAAS GFAFSTYAMSWVRQAPGKGLEWVS AISAAGGTTYYADSVKGRFTISRDN | DIQMTQSPSSVSASVGDRVTIT CRASQGIDSWLAWYQQKPGK APKLLIYAASSLQSGVPSRFSG |

TABLE 4-continued

| Antibody | V_H and H-CDRs | V_L and L-CDRs |
|---|---|---|
|  | SKNTLYLQMNSLRAEDTAVYYCAK PLDSSLWADFDLWGRGTLVTVSS (SEQ ID NO: 7) CDR-H1: FAFSTYAMS (SEQ ID NO: 8) CDR-H2: AISAAGGTTYYADSVKG (SEQ ID NO: 9) CDR-H3: AKPLDSSLWADFDL (SEQ ID NO: 10) | SGSGTDFTLTISSLQPEDFATY YCQQASVLPITFGGGTKVEIK (SEQ ID NO: 11) CDR-L1: RASQGIDSWLA (SEQ ID NO: 12) CDR-L2: AASSLQS (SEQ ID NO: 13) CDR-L3: QQASVLPIT (SEQ ID NO: 14) |
| Ab2 | EVQLLESGGGLVQPGGSLRLSCAAS GFAFSTYAMSWVRQAPGKGLEWVS AISGVGGTTYYADSVKGRFTISRDN SKNTLYLQMNSLRAEDTAVYYCAK PLDSSLWADFDLWGRGTLVTVSS (SEQ ID NO: 15) CDR-H1: FAFSTYAMS (SEQ ID NO: 16) CDR-H2: AISGVGGTTYYADSVKG (SEQ ID NO: 17) CDR-H3: AKPLDSSLWADFDL (SEQ ID NO: 18) | DIQLTQSPSSVSASVGDRVTIT CRASQGISSWLAWYQQKPGK APKLLIYYASSLQDGVPSRFSG SGSGTDFTLTISSLQPEDFATY YCQQASVLPITFGGGTKVEIK (SEQ ID NO: 19) CDR-L1: RASQGISSWLA (SEQ ID NO: 20) CDR-L2: YASSLQD (SEQ ID NO: 21) CDR-L3: QQASVLPIT (SEQ ID NO: 22) |
| Ab3 | EVQLLESGGGLVQPGGSLRLSCAAS GFTFERYAMSWVRQAPGKGLEWVS AISAAGGTTYYADSVKGRFTISRDN SKNTLYLQMNSLRAEDTAVYYCAK PLDSSQWADFDLWGRGTLVTVSS (SEQ ID NO: 23) CDR-H1: FTFERYAMS (SEQ ID NO: 24) CDR-H2: AISAAGGTTYYADSVKG (SEQ ID NO: 25) CDR-H3: AKPLDSSQWADFDL (SEQ ID NO: 26) | DIQLTQSPSSVSASVGDRVTIT CRASQDISSWLAWYQQKPGK APKFLIYAASALQSGVPSRFSG SGSGTDFTLTISSLQPEDFATY YCQQALVLPITFGGGTKVEIK (SEQ ID NO: 27) CDR-L1: RASQDISSWLA (SEQ ID NO: 28) CDR-L2: AASALQS (SEQ ID NO: 29) CDR-L3: QQALVLPIT (SEQ ID NO: 30) |
| Ab4 | EVQLLESGGGLVQPGGSLRLSCAAS GFTFERYAMSWVRQAPGKGLEWVS AISAVGGTTKYADSVKGRFTISRDN SKNTLYLQMNSLRAEDTAVYYCAK PLDSSLWADFDAWGRGTLVTVSS (SEQ ID NO: 31) CDR-H1: FTFERYAMS (SEQ ID NO: 32) CDR-H2: AISAVGGTTKYADSVKG (SEQ ID NO: 33) CDR-H3: AKPLDSSLWADFDA (SEQ ID NO: 34) | DIQLTQSPSSVSASVGDRVTIT CRASQGISSWLAWYQQKPGK APKLLIYAASGLQSGVPSRFSG SGSGTDFTLTISSLQPEDFATY YCQQASYLPITFGGGTKVEIK (SEQ ID NO: 35) CDR-L1: RASQGISSWLA (SEQ ID NO: 36) CDR-L2: AASGLQS (SEQ ID NO: 37) CDR-L3: QQASYLPIT (SEQ ID NO: 38) |
| Ab5 | EVQLLESGGGLVQPGGSLRLSCAAS GFTFGQYAMSWVRQAPGKGLEWV SAISAVGGTTAYADSVKGRFTISRD NSKNTLYLQMNSLRAEDTAVYYCA KPLDSSLWADFQLWGRGTLVTVSS (SEQ ID NO: 39) CDR-H1: FTFGQYAMS (SEQ ID NO: 40) CDR-H2: AISAVGGTTAYADSVKG (SEQ ID NO: 41) CDR-H3: AKPLDSSLWADFQL (SEQ ID NO: 42) | DIQLTQSPSSVSASVGDRVTIT CRASQDISSWLAWYQQKPGK APKLLIYFASSLQSGVPSRFSGS GSGTDFTLTISSLQPEDFATYY CQQASKLPITFGGGTKVEIK (SEQ ID NO: 43) CDR-L1: RASQDISSWLA (SEQ ID NO: 44) CDR-L2: FASSLQS (SEQ ID NO: 45) CDR-L3: QQASKLPIT (SEQ ID NO: 46) |
| Ab6 | EVQLLESGGGLVQPGGSLRLSCAAS GFTFGQYAMSWVRQAPGKGLEWV SAISAAGGTTYYADSVKGRFTISRD NSKNTLYLQMNSLRAEDTAVYYCA KPLDSSQWADFDLWGRGTLVTVSS (SEQ ID NO: 47) CDR-H1: FTFGQYAMS (SEQ ID NO: 48) CDR-H2: AISAAGGTTYYADSVKG (SEQ ID NO: 49) CDR-H3: AKPLDSSQWADFDL (SEQ ID NO: 50) | DIQLTQSPSSVSASVGDRVTIT CRASQGISSWLAWYQQKPGK APKLLIYAASSLQSGVPSRFSG SGSGTDFTLTINSLQPEDFATY YCQQAWVLPITFGGGTKVEIK (SEQ ID NO: 51) CDR-L1: RASQGISSWLA (SEQ ID NO: 52) CDR-L2: AASSLQS (SEQ ID NO: 53) CDR-L3: QQAWVLPIT (SEQ ID NO: 54) |
| Ab7 | EVQLLESGGGLVQPGGSLRLSCAAS GFTFGQYAMSWVRQAPGKGLEWV SAISAAGGTTYYADSVKGRFTISRD | DIQLTQSPSSVSASVGDRVTIT CRASQGISSWLAWYQQKPGK APKLLIYAASFLQSGVPSRFSG |

TABLE 4-continued

| Antibody | V_H and H-CDRs | V_L and L-CDRs |
|---|---|---|
| | NSKNTLYLQMNSLRAEDTAVYYCA KPLDSSQWADFDLWGRGTLVTVSS (SEQ ID NO: 55) CDR-H1: FTFGQYAMS (SEQ ID NO: 56) CDR-H2: AISAAGGTTYYADSVKG (SEQ ID NO: 57) CDR-H3: AKPLDSSQWADFDL (SEQ ID NO: 58) | SGSGTDFTLTISSLQPEDFATY YCQQASVLPITFGGGTKVEIK (SEQ ID NO: 59) CDR-L1: RASQGISSWLA (SEQ ID NO: 60) CDR-L2: AASFLQS (SEQ ID NO: 61) CDR-L3: QQASVLPIT (SEQ ID NO: 62) |
| Ab8 | EVQLLESGGGLVQPGGSLRLSCAAS GFTFGTFAMSWVRQAPGKGLEWVS AISGVGGTTYYADSVKGRFTISRDN SKNTLYLQMNSLRAEDTAVYYCAK PLDSSFWADFDLWGRGTLVTVSS (SEQ ID NO: 63) CDR-H1: FTFGTFAMS (SEQ ID NO: 64) CDR-H2: AISGVGGTTYYADSVKG (SEQ ID NO: 65) CDR-H3: AKPLDSSFWADFDL (SEQ ID NO: 66) | DIQLTQSPSSVSASVGDRVTIT CRASQTISSWLAWYQQKPGK APKLLIYAASSLQSGVPSRFSG SGSGTDFTLTISSLQPEDFATY YCQQQSVLPITFGGGTKVEIK (SEQ ID NO: 67) CDR-L1: RASQTISSWLA (SEQ ID NO: 68) CDR-L2: AASSLQS (SEQ ID NO: 69) CDR-L3: QQQSVLPIT (SEQ ID NO: 70) |
| Ab9 | EVQLLESGGGLVQPGGSLRLSCAAS GFTFSPYAMSWVRQAPGKGLEWVS AISASGGTTYYADSVKGRFTISRDNS KNTLYLQMNSLRAEDTAVYYCAKP LDSSFWADFDLWGRGTLVTVSS (SEQ ID NO: 71) CDR-H1: FTFSPYAMS (SEQ ID NO: 72) CDR-H2: AISASGGTTYYADSVKG (SEQ ID NO: 73) CDR-H3: AKPLDSSFWADFDL (SEQ ID NO: 74) | DIQLTQSPSSVSASVGDRVTIT CRASQGISSWLAWYQQKPGK APKLLIYAASSLQSGVPSRFSG SGSGTDFTLTISSLQPEDFATY YCQQHSVLPITFGGGTKVEIK (SEQ ID NO: 75) CDR-L1: RASQGISSWLA (SEQ ID NO: 76) CDR-L2: AASSLQS (SEQ ID NO: 77) CDR-L3: QQHSVLPIT (SEQ ID NO: 78) |
| Ab10 | EVQLLESGGGLVQPGGSLRLSCAAS GFTFSQYAMSWVRQAPGKGLEWVS AISAVGGSTYYADSVKGRFTISRDN SKNTLYLQMNSLRAEDTAVYYCAK PLDSSQWADFDLWGRGTLVTVSS (SEQ ID NO: 79) CDR-H1: FTFSQYAMS (SEQ ID NO: 80) CDR-H2: AISAVGGSTYYADSVKG (SEQ ID NO: 81) CDR-H3: AKPLDSSQWADFDL (SEQ ID NO: 82) | DIQLTQSPSSVSASVGDRVTIT CRASQDISSWLAWYQQKPGK APKLLIYAASALQSGVPSRFSG SGSGTDFTLTISSLQPEDFATY YCQQADVLPITFGGGTKVEIK (SEQ ID NO: 83) CDR-L1: RASQDISSWLA (SEQ ID NO: 84) CDR-L2: AASALQS (SEQ ID NO: 85) CDR-L3: QQADVLPIT (SEQ ID NO: 86) |
| Ab11 | EVQLLESGGGLVQPGGSLRLSCAAS GFTFSQYAMSWVRQAPGKGLEWVS AISAAGGTTYYADSVKGRFTISRDN SKNTLYLQMNSLRAEDTAVYYCAK PLDSSQWADFDLWGRGTLVTVSS (SEQ ID NO: 87) CDR-H1: FTFSQYAMS (SEQ ID NO: 88) CDR-H2: AISAAGGTTYYADSVKG (SEQ ID NO: 89) CDR-H3: AKPLDSSQWADFDL (SEQ ID NO: 90) | DIQLTQSPSSVSASVGDRVTIT CRASQGIYSWLAWYQQKPGK APKLLIYAASSLQSGVPSRFSG SGSGTDFTLTISSLQPEDFATY YCQQASDLPITFGGGTKVEIK (SEQ ID NO: 91) CDR-L1: RASQGIYSWLA (SEQ ID NO: 92) CDR-L2: AASSLQS (SEQ ID NO: 93) CDR-L3: QQASDLPIT (SEQ ID NO: 94) |
| Ab12 | QVQLVESGGGLVKPGGSLRLSCAAS GFTFAQYYMSWIRQAPGKGLEWVS YISPSGSTIA Y ADSVKGRFTISRDNA KNSLYLQMNSLRAEDTAVYYCARS LMATGTHLYFDLWGRGTLVTVSS (SEQ ID NO: 101) CDR-H1: FTFAQYYMS (SEQ ID NO: 102) CDR-H2: YISPSGSTIAYADSVKG (SEQ ID NO: 103) CDR-H3: ARSLMATGTHLYFDL (SEQ ID NO: 104) | DIQLTQSPSSVSASVGDRVTIT CRASQDISSWLAWYQQKPGK APKLLIYAASSLQSGVPSRFSG SGSGTDFTLTISSLQPEDFATY YCQQVTSFPPYTFGGGTKVEIK (SEQ ID NO: 105) CDR-L1: RASQDISSWLA (SEQ ID NO: 106) CDR-L2: AASSLQS (SEQ ID NO: 107) CDR-L3: QQVTSFPPYT (SEQ ID NO: 108) |
| Ab13 | QVQLVESGGGLVKPGGSLRLSCAAS GFTFANYYMSWIRQAPGKGLEWVS YISPSGATIAYADSVKGRFTISRDNA | DIQLTQSPSSVSASVGDRVTIT CRASSGISSWLAWYQQKPGKA PKLLIYAASELQSGVPSRFSGS |

TABLE 4-continued

| Antibody | V_H and H-CDRs | V_L and L-CDRs |
|---|---|---|
| | KNSLYLQMNSLRAEDTAVYYCARS LMATGTHLYFDLWGRGTLVTVSS (SEQ ID NO: 109) CDR-H1: FTFANYYMS (SEQ ID NO: 110) CDR-H2: YISPSGATIAYADSVKG (SEQ ID NO: 111) CDR-H3: ARSLMATGTHLYFDL (SEQ ID NO: 112) | GSGTDFTLTISSLQPEDFATYY CQQATSFPPYTFGGGTKVEIK (SEQ ID NO: 113) CDR-L1: RASSGISSWLA (SEQ ID NO: 114) CDR-L2: AASELQS (SEQ ID NO: 115) CDR-L3: QQATSFPPYT (SEQ ID NO: 116) |
| Ab14 | QVQLVESGGGLVKPGGSLRLSCAAS GFTFGQYYMSWIRQAPGKGLEWVS YISPSGATIAYADSVKGRFTISRDNA KNSLYLQMNSLRAEDTAVYYCARS LMSTGTHLYFDLWGRGTLVTVSS (SEQ ID NO: 117) CDR-H1: FTFGQYYMS (SEQ ID NO: 118) CDR-H2: YISPSGATIAYADSVKG (SEQ ID NO: 119) CDR-H3: ARSLMSTGTHLYFDL (SEQ ID NO: 120) | DIQLTQSPSSVSASVGDRVTIT CRASQGISDWLAWYQQKPGK APKLLIYAASSLQSGVPSRFSG SGSGTDFTLTISSLQPEDFATY YCQQVTSFPPYTFGGGTKVEIK (SEQ ID NO: 121) CDR-L1: RASQGISDWLA (SEQ ID NO: 122) CDR-L2: AASSLQS (SEQ ID NO: 123) CDR-L3: QQVTSFPPYT (SEQ ID NO: 124) |
| Ab15 | QVQLVESGGGLVKPGGSLRLSCAAS GFTFPQYYMSWIRQAPGKGLEWVS YISPSGATIYYADSVKGRFTISRDNA KNSLYLQMNSLRAEDTAVYYCARS LMSTGTHLYFDLWGRGTLVTVSS (SEQ ID NO: 125) CDR-H1: FTFPQYYMS (SEQ ID NO: 126) CDR-H2: YISPSGATIYYADSVKG (SEQ ID NO: 127) CDR-H3: ARSLMSTGTHLYFDL (SEQ ID NO: 128) | DIQLTQSPSSVSASVGDRVTIT CRASQGISSWLAWYQQKPGK APKLLIYAASSLQSGVPSRFSG SGSGTDFTLTISSLQPEDFATY YCQQVTSTPPYTFGGGTKVEI K (SEQ ID NO: 129) CDR-L1: RASQGISSWLA (SEQ ID NO: 130) CDR-L2: AASSLQS (SEQ ID NO: 131) CDR-L3: QQVTSTPPYT (SEQ ID NO: 132) |
| Ab16 | QVQLVESGGGLVKPGGSLRLSCAAS GFTFSDYYMSWIRQAPGKGLEWVS YISPSGATIAYADSVKGRFTISRDNS KNTLYLQMNSLRAEDTAVYYCARS LMATGTHLYFDLWGRGTLVTVSS (SEQ ID NO: 133) CDR-H1: FTFSDYYMS (SEQ ID NO: 134) CDR-H2: YISPSGATIAYADSVKG (SEQ ID NO: 135) CDR-H3: ARSLMATGTHLYFDL (SEQ ID NO: 136) | DIQLTQSPSSVSASVGDRVTIT CRASQGISSWLAWYQQKPGK APKLLIYAASGLQSGVPSRFSG SGSGTDFTLTISSLQPEDFATY YCQQSTSFPPYTFGGGTKVEIK (SEQ ID NO: 137) CDR-L1: RASQGISSWLA (SEQ ID NO: 138) CDR-L2: AASGLQS (SEQ ID NO: 139) CDR-L3: QQSTSFPPYT (SEQ ID NO: 140) |
| Ab17 | QVQLVESGGGLVKPGGSLRLSCAAS GFTFSDYYMSWIRQAPGKGLEWVS YISPSGATIYYADSVKGRFTISRDNA KNSLYLQMNSLRAEDTAVYYCARS LMSTGTHLYFDLWGRGTLVTVSS (SEQ ID NO: 141) CDR-H1: FTFSDYYMS (SEQ ID NO: 142) CDR-H2: YISPSGATIYYADSVKG (SEQ ID NO: 143) CDR-H3: ARSLMSTGTHLYFDL (SEQ ID NO: 144) | DIQLTQSPSSVSASVGDRVTIT CRASQGISSWLAWYQQKPGK APKLLIYAASSLQSGVPSRFSG SGSGTDFTLTISSLQPEDFATY YCQQVTSVPPYTFGGGTKVEI K (SEQ ID NO: 145) CDR-L1: RASQGISSWLA (SEQ ID NO: 146) CDR-L2: AASSLQS (SEQ ID NO: 147) CDR-L3: QQVTSVPPYT (SEQ ID NO: 148) |
| Ab18 | QVQLVESGGGLVKPGGSLRLSCAAS GFTFSQYYMSWIRQAPGKGLEWVS YISPSGATIAYADSVKGRFTISRDNA KNSLYLQMNSLRAEDTAVYYCARS LMATGTHLYFDLWGRGTLVTVSS (SEQ ID NO: 149) CDR-H1: FTFSQYYMS (SEQ ID NO: 150) CDR-H2: YISPSGATIAYADSVKG (SEQ ID NO: 151) CDR-H3: ARSLMATGTHLYFDL (SEQ ID NO: 152) | DIQLTQSPSSVSASVGDRVTIT CRASQGISSWLAWYQQKPGK APKLLIYAAESLQSGVPSRFSG SGSGTDFTLTISSLQPEDFATY YCQQVTSQPPYTFGGGTKVEI K (SEQ ID NO: 153) CDR-L1: RASQGISSWLA (SEQ ID NO: 154) CDR-L2: AAESLQS (SEQ ID NO: 155) CDR-L3: QQVTSQPPYT (SEQ ID NO: 156) |
| Ab19 | QVQLVESGGGLVKPGGSLRLSCAAS GFTFSQYYMSWIRQAPGKGLEWVS YISPSGATIYYADSVKGRFTISRDNA | DIQLTQSPSSVSASVGDRVTIT CRASQGISSWLAWYQQKPGK APKLLIYAASALQSGVPSRFSG |

TABLE 4-continued

| Antibody | V_H and H-CDRs | V_L and L-CDRs |
|---|---|---|
| | KNSLYLQMNSLRAEDTAVYYCARS<br>LMATGTHLYFDLWGRGTLVTVSS<br>(SEQ ID NO: 157)<br>CDR-H1: FTFSQYYMS (SEQ ID NO: 158)<br>CDR-H2: YISPSGATIYYADSVKG (SEQ ID NO: 159)<br>CDR-H3: ARSLMATGTHLYFDL (SEQ ID NO: 160) | SGSGTDFTLTISSLQPEDFATY<br>YCQQVTSAPPYTFGGGTKVEI<br>K (SEQ ID NO: 161)<br>CDR-L1: RASQGISSWLA (SEQ ID NO: 162)<br>CDR-L2: AASALQS (SEQ ID NO: 163)<br>CDR-L3: QQVTSAPPYT (SEQ ID NO: 164) |
| Ab20 | QVQLVESGGGLVQPGGSLRLSCAAS<br>GFTFSQYYMSWIRQAPGKGLEWVS<br>YISPSGATIAYADSVKGRFTISRDNA<br>KNSLYLQMNSLRAEDTAVYYCARS<br>LMSTGTHLYFDLWGRGTLVTVSS<br>(SEQ ID NO: 165)<br>CDR-H1: FTFSQYYMS (SEQ ID NO: 166)<br>CDR-H2: YISPSGATIAYADSVKG (SEQ ID NO: 167)<br>CDR-H3: ARSLMSTGTHLYFDL (SEQ ID NO: 168) | DIQLTQSPSSVSASVGDRVTIT<br>CRASQGISSWLAWYQQKPGK<br>APKLLIYAASVLQSGVPSRFSG<br>SGSGTDFTLTISSLQPEDFATY<br>YCQQVTSFLPYTFGGGTKVEI<br>K (SEQ ID NO: 169)<br>CDR-L1: RASQGISSWLA (SEQ ID NO: 170)<br>CDR-L2: AASVLQS (SEQ ID NO: 171)<br>CDR-L3: QQVTSFLPYT (SEQ ID NO: 172) |

1.1 $V_H$ Domains

In some embodiments, an antibody provided herein comprises a $V_H$ sequence selected from SEQ ID NOs: 7, 15, 23, 31, 39, 47, 55, 63, 71, 79, 87, 101, 109, 117, 125, 133, 141, 149, 157, and 165.

In some embodiments, an antibody provided herein comprises a $V_H$ sequence of SEQ ID NO: 7. In some embodiments, an antibody provided herein comprises a $V_H$ sequence of SEQ ID NO: 15. In some embodiments, an antibody provided herein comprises a $V_H$ sequence of SEQ ID NO: 23. In some embodiments, an antibody provided herein comprises a $V_H$ sequence of SEQ ID NO: 31. In some embodiments, an antibody provided herein comprises a $V_H$ sequence of SEQ ID NO: 39. In some embodiments, an antibody provided herein comprises a $V_H$ sequence of SEQ ID NO: 47. In some embodiments, an antibody provided herein comprises a $V_H$ sequence of SEQ ID NO: 55. In some embodiments, an antibody provided herein comprises a $V_H$ sequence of SEQ ID NO: 63. In some embodiments, an antibody provided herein comprises a $V_H$ sequence of SEQ ID NO: 71. In some embodiments, an antibody provided herein comprises a $V_H$ sequence of SEQ ID NO: 79. In some embodiments, an antibody provided herein comprises a $V_H$ sequence of SEQ ID NO: 87. In some embodiments, an antibody provided herein comprises a $V_H$ sequence of SEQ ID NO: 101. In some embodiments, an antibody provided herein comprises a $V_H$ sequence of SEQ ID NO: 109. In some embodiments, an antibody provided herein comprises a $V_H$ sequence of SEQ ID NO: 117. In some embodiments, an antibody provided herein comprises a $V_H$ sequence of SEQ ID NO: 125. In some embodiments, an antibody provided herein comprises a $V_H$ sequence of SEQ ID NO: 133. In some embodiments, an antibody provided herein comprises a $V_H$ sequence of SEQ ID NO: 141. In some embodiments, an antibody provided herein comprises a $V_H$ sequence of SEQ ID NO: 149. In some embodiments, an antibody provided herein comprises a $V_H$ sequence of SEQ ID NO: 157. In some embodiments, an antibody provided herein comprises a $V_H$ sequence of SEQ ID NO: 165.

In some embodiments, an antibody provided herein comprises a $V_H$ sequence having at least about 50%, about 60%, about 70%, about 75%, about 80%, about 85%, about 90%, about 95%, about 96%, about 97%, about 98%, or about 99% identity to an illustrative $V_H$ sequence provided in SEQ ID NOs: 7, 15, 23, 31, 39, 47, 55, 63, 71, 79, 87, 101, 109, 117, 125, 133, 141, 149, 157, and 165. In some embodiments, an antibody provided herein comprises a $V_H$ sequence provided in SEQ ID NOs: 7, 15, 23, 31, 39, 47, 55, 63, 71, 79, 87, 101, 109, 117, 125, 133, 141, 149, 157, and 165, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

1.2 $V_L$ Domains

In some embodiments, an antibody provided herein comprises a $V_L$ sequence selected from SEQ ID NOs: 11, 19, 27, 35, 43, 51, 59, 67, 75, 83, 91, 105, 113, 121, 129, 137, 145, 153, 161, and 169.

In some embodiments, an antibody provided herein comprises a $V_L$ sequence of SEQ ID NO: 11. In some embodiments, an antibody provided herein comprises a $V_L$ sequence of SEQ ID NO: 19. In some embodiments, an antibody provided herein comprises a $V_L$ sequence of SEQ ID NO: 27. In some embodiments, an antibody provided herein comprises a $V_L$ sequence of SEQ ID NO: 35. In some embodiments, an antibody provided herein comprises a $V_L$ sequence of SEQ ID NO: 43. In some embodiments, an antibody provided herein comprises a $V_L$ sequence of SEQ ID NO: 51. In some embodiments, an antibody provided herein comprises a $V_L$ sequence of SEQ ID NO: 59. In some embodiments, an antibody provided herein comprises a $V_L$ sequence of SEQ ID NO: 67. In some embodiments, an antibody provided herein comprises a $V_L$ sequence of SEQ ID NO: 75. In some embodiments, an antibody provided herein comprises a $V_L$ sequence of SEQ ID NO: 83. In some embodiments, an antibody provided herein comprises a $V_L$ sequence of SEQ ID NO: 91. In some embodiments, an antibody provided herein comprises a $V_L$ sequence of SEQ ID NO: 105. In some embodiments, an antibody provided herein comprises a $V_L$ sequence of SEQ ID NO: 113. In some embodiments, an antibody provided herein comprises a $V_L$ sequence of SEQ ID NO: 121. In some embodiments, an antibody provided herein comprises a $V_L$ sequence of SEQ ID NO: 129. In some embodiments, an antibody provided herein comprises a $V_L$ sequence of SEQ ID NO: 137. In some embodiments, an antibody provided herein comprises a $V_L$ sequence of SEQ ID NO: 145. In some embodiments, an antibody provided herein comprises a $V_L$ sequence of SEQ ID NO: 153. In some embodiments, an antibody provided herein comprises a $V_L$ sequence of SEQ ID NO: 161. In some embodiments, an antibody provided herein comprises a $V_L$ sequence of SEQ ID NO: 169.

In some embodiments, an antibody provided herein comprises a $V_L$ sequence having at least about 50%, about 60%, about 70%, about 75%, about 80%, about 85%, about 90%, about 95%, about 96%, about 97%, about 98%, or about 99% identity to an illustrative $V_L$ sequence provided in SEQ ID NOs: 11, 19, 27, 35, 43, 51, 59, 67, 75, 83, 91, 105, 113, 121, 129, 137, 145, 153, 161, and 169. In some embodiments, an antibody provided herein comprises a $V_L$ sequence provided in SEQ ID NOs: 11, 19, 27, 35, 43, 51, 59, 67, 75, 83, 91, 105, 113, 121, 129, 137, 145, 153, 161, and 169, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

1.3 $V_H$-$V_L$ Combinations

In some embodiments, an antibody provided herein comprises a $V_H$ sequence selected from SEQ ID NOs: 7, 15, 23, 31, 39, 47, 55, 63, 71, 79, 87, 101, 109, 117, 125, 133, 141, 149, 157, and 165 and a $V_L$ sequence selected from SEQ ID NOs: 11, 19, 27, 35, 43, 51, 59, 67, 75, 83, 91, 105, 113, 121, 129, 137, 145, 153, 161, and 169.

In some embodiments, an antibody provided herein comprises a $V_H$ sequence of SEQ ID NO: 7 and a $V_L$ sequence of SEQ ID NO: 11. In some embodiments, an antibody provided herein comprises a $V_H$ sequence of SEQ ID NO: 15 and a $V_L$ sequence of SEQ ID NO: 19. In some embodiments, an antibody provided herein comprises a $V_H$ sequence of SEQ ID NO: 23 and a $V_L$ sequence of SEQ ID NO: 27. In some embodiments, an antibody provided herein comprises a $V_H$ sequence of SEQ ID NO: 31 and a $V_L$ sequence of SEQ ID NO: 35. In some embodiments, an antibody provided herein comprises a $V_H$ sequence of SEQ ID NO: 39 and a $V_L$ sequence of SEQ ID NO: 43. In some embodiments, an antibody provided herein comprises a $V_H$ sequence of SEQ ID NO: 47 and a $V_L$ sequence of SEQ ID NO: 51. In some embodiments, an antibody provided herein comprises a $V_H$ sequence of SEQ ID NO: 55 and a $V_L$ sequence of SEQ ID NO: 59. In some embodiments, an antibody provided herein comprises a $V_H$ sequence of SEQ ID NO: 63 and a $V_L$ sequence of SEQ ID NO: 67. In some embodiments, an antibody provided herein comprises a $V_H$ sequence of SEQ ID NO: 71 and a $V_L$ sequence of SEQ ID NO: 75. In some embodiments, an antibody provided herein comprises a $V_H$ sequence of SEQ ID NO: 79 and a $V_L$ sequence of SEQ ID NO: 83. In some embodiments, an antibody provided herein comprises a $V_H$ sequence of SEQ ID NO: 87 and a $V_L$ sequence of SEQ ID NO: 91. In some embodiments, an antibody provided herein comprises a $V_H$ sequence of SEQ ID NO: 101 and a $V_L$ sequence of SEQ ID NO: 105. In some embodiments, an antibody provided herein comprises a $V_H$ sequence of SEQ ID NO: 109 and a $V_L$ sequence of SEQ ID NO: 113. In some embodiments, an antibody provided herein comprises a $V_H$ sequence of SEQ ID NO: 117 and a $V_L$ sequence of SEQ ID NO: 121. In some embodiments, an antibody provided herein comprises a $V_H$ sequence of SEQ ID NO: 125 and a $V_L$ sequence of SEQ ID NO: 129. In some embodiments, an antibody provided herein comprises a $V_H$ sequence of SEQ ID NO: 133 and a $V_L$ sequence of SEQ ID NO: 137. In some embodiments, an antibody provided herein comprises a $V_H$ sequence of SEQ ID NO: 141 and a $V_L$ sequence of SEQ ID NO: 145. In some embodiments, an antibody provided herein comprises a $V_H$ sequence of SEQ ID NO: 149 and a $V_L$ sequence of SEQ ID NO: 153. In some embodiments, an antibody provided herein comprises a $V_H$ sequence of SEQ ID NO: 157 and a $V_L$ sequence of SEQ ID NO: 161. In some embodiments, an antibody provided herein comprises a $V_H$ sequence of SEQ ID NO: 165 and a $V_L$ sequence of SEQ ID NO: 169.

In some embodiments, an antibody provided herein comprises a $V_H$ sequence having at least about 50%, about 60%, about 70%, about 75%, about 80%, about 85%, about 90%, about 95%, about 96%, about 97%, about 98%, or about 99% identity to an illustrative $V_H$ sequence provided in SEQ ID NOs: 7, 15, 23, 31, 39, 47, 55, 63, 71, 79, 87, 101, 109, 117, 125, 133, 141, 149, 157, and 165, and a $V_L$ sequence having at least about 50%, about 60%, about 70%, about 75%, about 80%, about 85%, about 90%, about 95%, about 96%, about 97%, about 98%, or about 99% identity to an illustrative $V_L$ sequence provided in SEQ ID NOs: 11, 19, 27, 35, 43, 51, 59, 67, 75, 83, 91, 105, 113, 121, 129, 137, 145, 153, 161, and 169. In some embodiments, an antibody provided herein comprises a $V_H$ sequence provided in SEQ ID NOs: 7, 15, 23, 31, 39, 47, 55, 63, 71, 79, 87, 101, 109, 117, 125, 133, 141, 149, 157, and 165, with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a $V_L$ sequence provided in SEQ ID NOs: 11, 19, 27, 35, 43, 51, 59, 67, 75, 83, 91, 105, 113, 121, 129, 137, 145, 153, 161, and 169, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 7, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 11.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 15, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 19.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 23, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 27.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 31, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 35.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 39, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 43.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 47, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 51.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 55, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 59.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 63, and an immunoglobulin light chain variable region comprising an amino acid sequence that is at least 60%, 70%, 75%, 80%, 85%, 90%, 95%, 96%, 97%, 98%, or 99% identical to SEQ ID NO: 67.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 71, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 75.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 79, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 83.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 87, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 91.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 101, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 105.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 109, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 113.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 117, and an immunoglobulin light chain variable region comprising an amino acid sequence that is at least 60%, 70%, 75%, 80%, 85%, 90%, 95%, 96%, 97%, 98%, or 99% identical to SEQ ID NO: 121.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 125, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 129.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 133, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 137.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 141, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 145.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 149, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 153.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 157, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 161.

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 165, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 169.

In certain embodiments, it is contemplated that a heavy chain variable region sequence, for example, the $V_H$ sequence of SEQ ID NOs: 7, 15, 23, 31, 39, 47, 55, 63, 71, 79, 87, 101, 109, 117, 125, 133, 141, 149, 157, or 165, or the amino acid variants thereof, may be covalently linked to a variety of heavy chain constant region sequences known in the art. Similarly, it is contemplated that a light chain variable region sequence, for example, the $V_L$ of SEQ ID NOs: 11, 19, 27, 35, 43, 51, 59, 67, 75, 83, 91, 105, 113, 121, 129, 137, 145, 153, 161, or 169, or the amino acid variants thereof, may be covalently linked to a variety of light chain constant region sequences known in the art.

For example, the antibody molecule may have a heavy chain constant region chosen from, e.g., the heavy chain constant regions of $IgG_1$, $IgG_2$, $IgG_3$, $IgG_4$, IgM, $IgA_1$, $IgA_2$, IgD, and IgE; particularly, chosen from, e.g., the (e.g., human) heavy chain constant regions of $IgG_1$, $IgG_2$, $IgG_3$, and $IgG_4$. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment, the antibody has effector function and can fix complement. In other embodiments, the antibody does not recruit effector cells or fix complement. In another embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

1.4 CDRs

In some embodiments, an antibody provided herein comprises one to three CDRs of a $V_H$ domain selected from SEQ ID NOs: 7, 15, 23, 31, 39, 47, 55, 63, 71, 79, 87, 101, 109, 117, 125, 133, 141, 149, 157, and 165. In some embodiments, an antibody provided herein comprises two to three CDRs of a $V_H$ domain selected from SEQ ID NOs: 7, 15, 23, 31, 39, 47, 55, 63, 71, 79, 87, 101, 109, 117, 125, 133, 141, 149, 157, and 165. In some embodiments, an antibody provided herein comprises three CDRs of a $V_H$ domain selected from SEQ ID NOs: 7, 15, 23, 31, 39, 47, 55, 63, 71, 79, 87, 101, 109, 117, 125, 133, 141, 149, 157, and 165. In some aspects, the CDRs are annotated using Kabat numbering system. In some aspects, the CDRs are annotated using Chothia numbering system. In some aspects, the CDRs are annotated using AbM numbering system. In some aspects, the CDRs are annotated using Contact numbering system. In some aspects, the CDRs are annotated using IMGT numbering system. In some aspects, the CDRs are annotated using an exemplary numbering system, wherein amino acid residues at positions 27-35, 50-65, and 93-102 denote CDR-H1, CDR-H2, and CDR-H3, respectively.

In some embodiments, the CDRs are CDRs having at least about 50%, about 60%, about 70%, about 75%, about 80%, about 85%, about 90%, about 95%, about 96%, about 97%, about 98%, or about 99% identity with a CDR-H1, CDR-H2, or CDR-H3 of SEQ ID NOs: 7, 15, 23, 31, 39, 47, 55, 63, 71, 79, 87, 101, 109, 117, 125, 133, 141, 149, 157, and 165. In some embodiments, the CDR-H1 is a CDR-H1 of a $V_H$ domain selected from SEQ ID NOs: 7, 15, 23, 31, 39, 47, 55, 63, 71, 79, 87, 101, 109, 117, 125, 133, 141, 149, 157, and 165, with up to 1, 2, 3, 4, or 5 amino acid substitutions. In some embodiments, the CDR-H2 is a CDR-H2 of a $V_H$ domain selected from SEQ ID NOs: 7, 15, 23, 31, 39, 47, 55, 63, 71, 79, 87, 101, 109, 117, 125, 133, 141, 149, 157, and 165, with up to 1, 2, 3, 4, 5, 6, 7, or 8 amino acid substitutions. In some embodiments, the CDR-H3 is a CDR-H3 of a $V_H$ domain selected from SEQ ID NOs: 7, 15, 23, 31, 39, 47, 55, 63, 71, 79, 87, 101, 109, 117, 125, 133, 141, 149, 157, and 165, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a $V_L$ domain selected from SEQ ID NOs: 11, 19, 27, 35, 43, 51, 59, 67, 75, 83, 91, 105, 113, 121, 129, 137, 145, 153, 161, and 169. In some embodiments, an antibody provided herein comprises two to three CDRs of a $V_L$ domain selected from SEQ ID NOs: 11, 19, 27, 35, 43, 51, 59, 67, 75, 83, 91, 105, 113, 121, 129, 137, 145, 153, 161, and 169. In some embodiments, an antibody provided herein comprises three CDRs of a $V_L$ domain selected from SEQ ID NOs: 11, 19, 27, 35, 43, 51, 59, 67, 75, 83, 91, 105, 113, 121, 129, 137, 145, 153, 161, and 169. In some aspects, the CDRs are annotated using Kabat numbering system. In some aspects, the CDRs are annotated using Chothia numbering system. In some aspects, the CDRs are annotated using AbM numbering system. In some aspects, the CDRs are annotated using Contact numbering system. In some aspects, the CDRs are annotated using IMGT numbering system. In some aspects, the CDRs are annotated using an exemplary numbering system, wherein amino acid residues at positions 24-34, 50-56, and 89-97 denote CDR-L1, CDR-L2, and CDR-L3, respectively.

In some embodiments, the CDRs are CDRs having at least about 50%, about 60%, about 70%, about 75%, about 80%, about 85%, about 90%, about 95%, about 96%, about 97%, about 98%, or about 99% identity with a CDR-L1, CDR-L2, or CDR-L3 of SEQ ID NOs: 11, 19, 27, 35, 43, 51, 59, 67, 75, 83, 91, 105, 113, 121, 129, 137, 145, 153, 161, and 169. In some embodiments, the CDR-L1 is a CDR-L1 of a $V_L$ domain selected from SEQ ID NOs: 11, 19, 27, 35, 43, 51, 59, 67, 75, 83, 91, 105, 113, 121, 129, 137, 145, 153, 161, and 169, with up to 1, 2, 3, 4, or 5 amino acid substitutions. In some embodiments, the CDR-L2 is a CDR-L2 of a $V_L$ domain selected from SEQ ID NOs: 11, 19, 27, 35, 43, 51, 59, 67, 75, 83, 91, 105, 113, 121, 129, 137, 145, 153, 161, and 169, with up to 1, 2, 3, 4, 5, 6, 7, or 8 amino acid substitutions. In some embodiments, the CDR-L3 is a CDR-L3 of a $V_L$ domain selected from SEQ ID NOs: 11, 19, 27, 35, 43, 51, 59, 67, 75, 83, 91, 105, 113, 121, 129, 137, 145, 153, 161, and 169, and 760, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a $V_H$ domain selected from SEQ ID NOs: 7, 15, 23, 31, 39, 47, 55, 63, 71, 79, 87, 101, 109, 117, 125, 133, 141, 149, 157, and 165 and one to three CDRs of a $V_L$ domain selected from SEQ ID NOs: 11, 19, 27, 35, 43, 51, 59, 67, 75, 83, 91, 105, 113, 121, 129, 137, 145, 153, 161, and 169. In some embodiments, an antibody provided herein comprises two to three CDRs of a $V_H$ domain selected from SEQ ID NOs: 7, 15, 23, 31, 39, 47, 55, 63, 71, 79, 87, 101, 109, 117, 125, 133, 141, 149, 157, and 165 and two to three CDRs of a $V_L$ domain selected from SEQ ID NOs: 11, 19, 27, 35, 43, 51, 59, 67, 75, 83, 91, 105, 113, 121, 129, 137, 145, 153, 161, and 169. In some embodiments, an antibody provided herein comprises three CDRs of a $V_H$ domain selected from SEQ ID NOs: 7, 15, 23, 31, 39, 47, 55, 63, 71, 79, 87, 101, 109, 117, 125, 133, 141, 149, 157, and 165 and three CDRs of a $V_L$ domain selected from SEQ ID NOs: 11, 19, 27, 35, 43, 51, 59, 67, 75, 83, 91, 105, 113, 121, 129, 137, 145, 153, 161, and 169. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs. In some aspects, the CDRs are exemplary CDRs.

In some embodiments, the CDRs are CDRs having at least about 50%, about 60%, about 70%, about 75%, about 80%, about 85%, about 90%, about 95%, about 96%, about 97%, about 98%, or about 99% identity with a CDR-H1, CDR-H2, or CDR-H3 of SEQ ID NOs: 7, 15, 23, 31, 39, 47, 55, 63, 71, 79, 87, 101, 109, 117, 125, 133, 141, 149, 157, and 165 and at least about 50%, about 60%, about 70%, about 75%, about 80%, about 85%, about 90%, about 95%, about 96%, about 97%, about 98%, or about 99% identity with a CDR-L1, CDR-L2, or CDR-L3 of SEQ ID NOs: 11, 19, 27, 35, 43, 51, 59, 67, 75, 83, 91, 105, 113, 121, 129, 137, 145, 153, 161, and 169. In some embodiments, the CDR-H1 is a CDR-H1 of a $V_H$ domain selected from SEQ ID NOs: 7, 15, 23, 31, 39, 47, 55, 63, 71, 79, 87, 101, 109, 117, 125, 133, 141, 149, 157, and 165, with up to 1, 2, 3, 4, or 5 amino acid substitutions; the CDR-H2 is a CDR-H2 of a $V_H$ domain selected from SEQ ID NOs: 7, 15, 23, 31, 39, 47, 55, 63, 71, 79, 87, 101, 109, 117, 125, 133, 141, 149, 157, and 165, with up to 1, 2, 3, 4, 5, 6, 7, or 8 amino acid substitutions; the CDR-H3 is a CDR-H3 of a $V_H$ domain selected from SEQ ID NOs: 7, 15, 23, 31, 39, 47, 55, 63, 71, 79, 87, 101, 109, 117, 125, 133, 141, 149, 157, and 165, with up to 1, 2, 3, 4, 5, 6, 7, or 8 amino acid substitutions; the CDR-L1 is a CDR-L1 of a $V_L$ domain selected from SEQ ID NOs: 11, 19, 27, 35, 43, 51, 59, 67, 75, 83, 91, 105, 113, 121, 129, 137, 145, 153, 161, and 169, with up to 1, 2, 3, 4, 5, or 6 amino acid substitutions; the CDR-L2 is a CDR-L2 of a $V_L$ domain selected from SEQ ID NOs: 11, 19, 27, 35, 43, 51, 59, 67, 75, 83, 91, 105, 113, 121, 129, 137, 145, 153, 161, and 169, with up to 1, 2, 3, or 4 amino acid substitutions; and the CDR-L3 is a CDR-L3 of a $V_L$ domain selected from SEQ ID NOs: 11, 19, 27, 35, 43, 51, 59, 67, 75, 83, 91, 105, 113, 121, 129, 137, 145, 153, 161, and 169, with up to 1, 2, 3, 4, or 5 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 10, 18, 26, 34, 42, 50, 58, 66, 74, 82, 90, 104, 112, 120, 128, 136, 144, 152, 160, and 168, as determined by the exemplary numbering system wherein amino acid residues at position 93-102 denote CDR-H3. In some aspects, the CDR-H3 has at least about 50%, about 60%, about 70%, about 75%, about 80%, about 85%, about 90%, about 95%, about 96%, about 97%, about 98%, or about 99% identity with a CDR-H3 of SEQ ID NOs: 10, 18, 26, 34, 42, 50, 58, 66, 74, 82, 90, 104, 112, 120, 128, 136, 144, 152, 160, and 168. In some embodiments, the CDR-H3 is a CDR-H3 selected from SEQ ID NOs: 10, 18, 26, 34, 42, 50, 58, 66, 74, 82, 90, 104, 112, 120, 128, 136, 144, 152, 160, and 168, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H2 selected from SEQ ID NOs: 9, 17, 25, 33, 41, 49, 57, 65, 73, 81, 89, 103, 111, 119, 127, 135, 143, 151, 159, and 167, as determined by the exemplary numbering system wherein amino acid residues at position 50-65 denote CDR-H2. In some aspects, the CDR-H2 has at least about 50%, about 60%, about 70%, about 75%, about 80%, about 85%, about 90%, about 95%, about 96%, about 97%, about 98%, or about 99% identity with a CDR-H2 of SEQ ID NOs: 9, 17, 25, 33, 41, 49, 57, 65, 73, 81, 89, 103, 111, 119, 127, 135, 143, 151, 159, and 167. In some embodiments, the CDR-H2 is a CDR-H2 selected from SEQ ID NOs: 9, 17, 25, 33, 41, 49, 57, 65, 73, 81, 89, 103, 111, 119, 127, 135, 143, 151, 159, and 167, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 selected from SEQ ID NOs: 8, 16, 24, 32, 40, 48, 56, 64, 72, 80, 88, 102, 110, 118, 126, 134, 142, 150, 158, and 166, as determined by the exemplary numbering system wherein amino acid residues at position 27-35 denote CDR-H1. In some aspects, the CDR-H1 has at least about 50%, about 60%, about 70%, about 75%, about 80%, about 85%, about 90%, about 95%, about 96%, about 97%, about 98%, or about 99% identity with a CDR-H1 of SEQ ID NOs: 8, 16, 24, 32, 40, 48, 56, 64, 72, 80, 88, 102, 110, 118, 126, 134, 142, 150, 158, and 166. In some embodiments, the CDR-H1 is a CDR-H1 selected from SEQ ID NOs: 8, 16, 24, 32, 40, 48, 56, 64, 72, 80, 88, 102, 110, 118, 126, 134, 142, 150, 158, and 166, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 10, 18, 26, 34, 42, 50, 58, 66, 74, 82, 90, 104, 112, 120, 128, 136, 144, 152, 160, and 168 and a CDR-H2 selected from SEQ ID NOs: 9, 17, 25, 33, 41, 49, 57, 65, 73, 81, 89, 103, 111, 119, 127, 135, 143, 151, 159, and 167. In some embodiments, an antibody provided herein comprises a CDR-H3 selected from SEQ ID NOs: 10, 18, 26, 34, 42, 50, 58, 66, 74, 82, 90, 104, 112, 120, 128, 136, 144, 152, 160, and 168, a CDR-H2 selected from SEQ ID NOs: 9, 17, 25, 33, 41, 49, 57, 65, 73, 81, 89, 103, 111, 119, 127, 135, 143, 151, 159, and 167, and a CDR-H1 selected from SEQ ID NOs: 8, 16, 24, 32, 40, 48, 56, 64, 72, 80, 88, 102, 110, 118, 126, 134, 142, 150, 158, and 166. In some embodiments, the CDR-H3 has at least about 50%, about 60%, about 70%, about 75%, about 80%, about 85%, about 90%, about 95%, about 96%, about 97%, about 98%, or about 99% identity with a CDR-H3 of SEQ ID NOs: 10, 18, 26, 34, 42, 50, 58, 66, 74, 82, 90, 104, 112, 120, 128, 136, 144, 152, 160, and 168, the CDR-H2 has at least about 50%, about 60%, about 70%, about 75%, about 80%, about 85%, about 90%, about 95%, about 96%, about 97%, about 98%, or about 99% identity with a CDR-H2 of SEQ ID NOs: 9, 17, 25, 33, 41, 49, 57, 65, 73, 81, 89, 103, 111, 119, 127, 135, 143, 151, 159, and 167, and the CDR-H1 has at least about 50%, about 60%, about 70%, about 75%, about 80%, about 85%, about 90%, about 95%, about 96%, about 97%, about 98%, or about 99% identity with a CDR-H1 of SEQ ID NOs: 8, 16, 24, 32, 40, 48, 56, 64, 72, 80, 88, 102, 110, 118, 126, 134, 142, 150, 158, and 166. In some embodiments, the CDR-H3 is a CDR-H3 selected from SEQ ID NOs: 10, 18, 26, 34, 42, 50, 58, 66, 74, 82, 90, 104, 112, 120, 128, 136, 144, 152, 160, and 168, with up to 1, 2, 3, 4, 5, 6, 7, or 8 amino acid substitutions; the CDR-H2 is a CDR-H2 selected from SEQ ID NOs: 9, 17, 25, 33, 41, 49, 57, 65, 73, 81, 89, 103, 111, 119, 127, 135, 143, 151, 159, and 167, with up to 1, 2, 3, 4, 5, 6, 7, or 8 amino acid substitutions; and the CDR-H1 is a CDR-H1 selected from SEQ ID NOs: 8, 16, 24, 32, 40, 48, 56, 64, 72, 80, 88, 102, 110, 118, 126, 134, 142, 150, 158, and 166, with up to 1, 2, 3, 4, or 5 amino acid substitutions. In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 selected from SEQ ID NOs: 14, 22, 30, 38, 46, 54, 62, 70, 78, 86, 94, 108, 116, 124, 132, 140, 148, 156, 164, and 172, as determined by the exemplary numbering system wherein amino acid residues at position 89-97 denote CDR-L3. In some aspects, the CDR-L3 has at least about 50%, about 60%, about 70%, about 75%, about 80%, about 85%, about 90%, about 95%, about 96%, about 97%, about 98%, or about 99% identity with a CDR-L3 of SEQ ID NOs: 14, 22, 30, 38, 46, 54, 62, 70, 78, 86, 94, 108, 116, 124, 132, 140, 148, 156, 164, and 172. In some embodiments, the CDR-L3 is a CDR-L3 selected from SEQ ID NOs: 14, 22, 30, 38, 46, 54, 62, 70, 78, 86, 94, 108, 116, 124, 132, 140, 148, 156, 164, and 172, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L2 selected from SEQ ID NOs: 13, 21, 29, 37, 45, 53, 61, 69, 77, 85, 93, 107, 115, 123, 131, 139, 147, 155, 163, and 171, as determined by the exemplary numbering system wherein amino acid residues at position 50-56 denote CDR-L2. In some aspects, the CDR-L2 has at least about 50%, about 60%, about 70%, about 75%, about 80%, about 85%, about 90%, about 95%, about 96%, about 97%, about 98%, or about 99% identity with a CDR-L2 of SEQ ID NOs: 13, 21, 29, 37, 45, 53, 61, 69, 77, 85, 93, 107, 115, 123, 131, 139, 147, 155, 163, and 171. In some embodiments, the CDR-L2 is a CDR-L2 selected from SEQ ID NOs: 13, 21, 29, 37, 45, 53, 61, 69, 77, 85, 93, 107, 115, 123, 131, 139, 147, 155, 163, and 171, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L1 selected from SEQ ID NOs: 12, 20, 28, 36, 44, 52, 60, 68, 76, 84, 92, 106, 114, 122, 130, 138, 146, 154, 162, and 170, as determined by the exemplary numbering system wherein amino acid residues at position 24-34 denote CDR-L1. In some aspects, the CDR-L1 has at least about 50%, about 60%, about 70%, about 75%, about 80%, about 85%, about 90%, about 95%, about 96%, about 97%, about 98%, or about 99% identity with a CDR-L1 of SEQ ID NOs: 12, 20, 28, 36, 44, 52, 60, 68, 76, 84, 92, 106, 114, 122, 130, 138, 146, 154, 162, and 170. In some embodiments, the CDR-L1 is a CDR-L1 selected from SEQ ID NOs: 12, 20, 28, 36, 44, 52, 60, 68, 76, 84, 92, 106, 114, 122, 130, 138, 146, 154, 162, and 170, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 selected from SEQ ID NOs: 14, 22, 30, 38, 46, 54, 62, 70, 78, 86, 94, 108, 116, 124, 132, 140, 148, 156, 164, and 172 and a CDR-L2 selected from SEQ ID NOs: 13, 21, 29, 37, 45, 53, 61, 69, 77, 85, 93, 107, 115, 123, 131, 139, 147, 155, 163, and 171. In some embodiments, an antibody provided herein comprises a CDR-L3 selected from SEQ ID NOs: 14, 22, 30, 38, 46, 54, 62, 70, 78, 86, 94, 108, 116, 124, 132, 140, 148, 156, 164, and 172, a CDR-L2 selected from SEQ ID NOs: 13, 21, 29, 37, 45, 53, 61, 69, 77, 85, 93, 107, 115, 123, 131, 139, 147, 155, 163, and 171, and a CDR-L1 selected from SEQ ID NOs: 12, 20, 28, 36, 44, 52, 60, 68, 76, 84, 92, 106, 114, 122, 130, 138, 146, 154, 162, and 170. In some embodiments, the CDR-L3 has at least about 50%, about 60%, about 70%, about 75%, about 80%, about 85%, about 90%, about 95%, about 96%, about 97%, about 98%, or about 99% identity with a CDR-L3 of SEQ ID NOs: 14, 22, 30, 38, 46, 54, 62, 70, 78, 86, 94, 108, 116, 124, 132, 140, 148, 156, 164, and 172, the CDR-L2 has at least about 50%, about 60%, about 70%, about 75%, about 80%, about 85%, about 90%, about 95%, about 96%, about 97%, about 98%, or about 99% identity with a CDR-L2 of SEQ ID NOs: 13, 21, 29, 37, 45, 53, 61, 69, 77, 85, 93, 107, 115, 123, 131, 139, 147, 155, 163, and 171, and the CDR-L1 has at least about 50%, about 60%, about 70%, about 75%, about 80%, about 85%, about 90%, about 95%, about 96%, about 97%, about 98%, or about 99% identity with a CDR-L1 of SEQ ID NOs: 12, 20, 28, 36, 44, 52, 60, 68, 76, 84, 92, 106, 114, 122, 130, 138, 146, 154, 162, and 170. In some embodiments, the CDR-L3 is a CDR-L3 selected from SEQ ID NOs: 14, 22, 30, 38, 46, 54, 62, 70, 78, 86, 94, 108, 116, 124, 132, 140, 148, 156, 164, and 172, with up to 1, 2, 3, 4, or 5 amino acid substitutions; the CDR-L2 is a CDR-L2 selected from SEQ ID NOs: 13, 21, 29, 37, 45, 53, 61, 69, 77, 85, 93, 107, 115, 123, 131, 139, 147, 155, 163, and 171, with up to 1, 2, 3, or 4 amino acid substitutions; and the CDR-L1 is a CDR-L1 selected from SEQ ID NOs: 12, 20, 28, 36, 44, 52, 60, 68, 76, 84, 92, 106, 114, 122, 130, 138, 146, 154, 162, and 170, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 10, 18, 26, 34, 42, 50, 58, 66, 74, 82, 90, 104, 112, 120, 128, 136, 144, 152, 160, and 168, a CDR-H2 selected from SEQ ID NOs: 9, 17, 25, 33, 41, 49, 57, 65, 73, 81, 89, 103, 111, 119, 127, 135, 143, 151, 159, and 167, a CDR-H1 selected from SEQ ID NOs: 8, 16, 24, 32, 40, 48, 56, 64, 72, 80, 88, 102, 110, 118, 126, 134, 142, 150, 158, and 166, a CDR-L3 selected from SEQ ID NOs: 14, 22, 30, 38, 46, 54, 62, 70, 78, 86, 94, 108, 116, 124, 132, 140, 148, 156, 164, and 172, a CDR-L2 selected from SEQ ID NOs: 13, 21, 29, 37, 45, 53, 61, 69, 77, 85, 93, 107, 115, 123, 131, 139, 147, 155, 163, and 171, and a CDR-L1 selected from SEQ ID NOs: 12, 20, 28, 36, 44, 52, 60, 68, 76, 84, 92, 106, 114, 122, 130, 138, 146, 154, 162, and 170. In some embodiments, the CDR-H3 has at least about 50%, about 60%, about 70%, about 75%, about 80%, about 85%, about 90%, about 95%, about 96%, about 97%, about 98%, or about 99% identity with a CDR-H3 of SEQ ID NOs: 10, 18, 26, 34, 42, 50, 58, 66, 74, 82, 90, 104, 112, 120, 128, 136, 144, 152, 160, and 168, the CDR-H2 has at least about 50%, about 60%, about 70%, about 75%, about 80%, about 85%, about 90%, about 95%, about 96%, about 97%, about 98%, or about 99% identity with a CDR-H2 of SEQ ID NOs: 9, 17, 25, 33, 41, 49, 57, 65, 73, 81, 89, 103, 111, 119, 127, 135, 143, 151, 159, and 167, the CDR-H1 has at least about 50%, about 60%, about 70%, about 75%, about 80%, about 85%, about 90%, about 95%, about 96%, about 97%, about 98%, or about 99% identity with a CDR-H1 of SEQ ID NOs: 8, 16, 24, 32, 40, 48, 56, 64, 72, 80, 88, 102, 110, 118, 126, 134, 142, 150, 158, and 166, the CDR-L3 has at least about 50%, about 60%, about 70%, about 75%, about 80%, about 85%, about 90%, about 95%, about 96%, about 97%, about 98%, or about 99% identity with a CDR-L3 of SEQ ID NOs: 14, 22, 30, 38, 46, 54, 62, 70, 78, 86, 94, 108, 116, 124, 132, 140, 148, 156, 164, and 172, the CDR-L2 has at least about 50%, about 60%, about 70%, about 75%, about 80%, about 85%, about 90%, about 95%, about 96%, about 97%, about 98%, or about 99% identity with a CDR-L2 of SEQ ID NOs: 13, 21, 29, 37, 45, 53, 61, 69, 77, 85, 93, 107, 115, 123, 131, 139, 147, 155, 163, and 171, and the CDR-L1 has at least about 50%, about 60%, about 70%, about 75%, about 80%, about 85%, about 90%, about 95%, about 96%, about 97%, about 98%, or about 99% identity with a CDR-L1 of SEQ ID NOs: 12, 20, 28, 36, 44, 52, 60, 68, 76, 84, 92, 106, 114, 122, 130, 138, 146, 154, 162, and 170. In some embodiments, the CDR-H3 is a CDR-H3 selected from SEQ ID NOs: 10, 18, 26, 34, 42, 50, 58, 66, 74, 82, 90, 104, 112, 120, 128, 136, 144, 152, 160, and 168, with up to 1, 2, 3, 4, 5, 6, 7, or 8 amino acid substitutions; the CDR-H2 is a CDR-H2 selected from SEQ ID NOs: 9, 17, 25, 33, 41, 49, 57, 65, 73, 81, 89, 103, 111, 119, 127, 135, 143, 151, 159, and 167, with up to 1, 2, 3, 4, 5, 6, 7, or 8 amino acid substitutions; the CDR-H1 is a CDR-H1 selected from SEQ ID NOs: 8, 16, 24, 32, 40, 48, 56, 64, 72, 80, 88, 102, 110, 118, 126, 134, 142, 150, 158, and 166, with up to 1, 2, 3, 4, or 5 amino acid substitutions; the CDR-L3 is a CDR-L3 selected from SEQ ID NOs: 14, 22, 30, 38, 46, 54, 62, 70, 78, 86, 94, 108, 116, 124, 132, 140, 148, 156, 164, and 172, with up to 1, 2, 3, 4, or 5 amino acid substitutions; the CDR-L2 is a CDR-L2 selected from SEQ ID NOs: 13, 21, 29, 37, 45, 53, 61, 69, 77, 85, 93, 107, 115, 123, 131, 139, 147, 155, 163, and 171, with up to 1, 2, 3, or 4 amino acid substitutions; and the CDR-L1 is a CDR-L1 selected from SEQ ID NOs: 12, 20, 28, 36, 44, 52, 60, 68, 76, 84, 92, 106, 114, 122, 130, 138, 146, 154, 162, and 170, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO: 8, a CDR-H2 of SEQ ID NO: 9, a CDR-H3 of SEQ ID NO: 10, a CDR-L1 of SEQ ID NO: 12, a CDR-L2 of SEQ ID NO: 13, and a CDR-L3 of SEQ ID NO: 14, as determined by the exemplary numbering system.

In some embodiments, an antibody provided herein comprises a CDR-H1 of SEQ ID NO: 16, a CDR-H2 of SEQ ID NO: 17, a CDR-H3 of SEQ ID NO: 18, a CDR-L1 of SEQ ID NO: 20, a CDR-L2 of SEQ ID NO: 21, and a CDR-L3 of SEQ ID NO: 22, as determined by the exemplary numbering system.

In some embodiments, an antibody provided herein comprises a CDR-H1 of SEQ ID NO: 24, a CDR-H2 of SEQ ID NO: 25, a CDR-H3 of SEQ ID NO: 26, a CDR-L1 of SEQ ID NO: 28, a CDR-L2 of SEQ ID NO: 29, and a CDR-L3 of SEQ ID NO: 30, as determined by the exemplary numbering system.

In some embodiments, an antibody provided herein comprises a CDR-H1 of SEQ ID NO: 32, a CDR-H2 of SEQ ID NO: 33, a CDR-H3 of SEQ ID NO: 34, a CDR-L1 of SEQ ID NO: 36, a CDR-L2 of SEQ ID NO: 37, and a CDR-L3 of SEQ ID NO: 38, as determined by the exemplary numbering system.

In some embodiments, an antibody provided herein comprises a CDR-H1 of SEQ ID NO: 40, a CDR-H2 of SEQ ID NO: 41, a CDR-H3 of SEQ ID NO: 42, a CDR-L1 of SEQ ID NO: 44, a CDR-L2 of SEQ ID NO: 45, and a CDR-L3 of SEQ ID NO: 46, as determined by the exemplary numbering system.

In some embodiments, an antibody provided herein comprises a CDR-H1 of SEQ ID NO: 48, a CDR-H2 of SEQ ID NO: 49, a CDR-H3 of SEQ ID NO: 50, a CDR-L1 of SEQ ID NO: 52, a CDR-L2 of SEQ ID NO: 53, and a CDR-L3 of SEQ ID NO: 54, as determined by the exemplary numbering system.

In some embodiments, an antibody provided herein comprises a CDR-H1 of SEQ ID NO: 56, a CDR-H2 of SEQ ID NO: 57, a CDR-H3 of SEQ ID NO: 58, a CDR-L1 of SEQ ID NO: 60, a CDR-L2 of SEQ ID NO: 61, and a CDR-L3 of SEQ ID NO: 62, as determined by the exemplary numbering system.

In some embodiments, an antibody provided herein comprises a CDR-H1 of SEQ ID NO: 64, a CDR-H2 of SEQ ID NO: 65, a CDR-H3 of SEQ ID NO: 66, a CDR-L1 of SEQ ID NO: 68, a CDR-L2 of SEQ ID NO: 69, and a CDR-L3 of SEQ ID NO: 70, as determined by the exemplary numbering system.

In some embodiments, an antibody provided herein comprises a CDR-H1 of SEQ ID NO: 72, a CDR-H2 of SEQ ID NO: 73, a CDR-H3 of SEQ ID NO: 74, a CDR-L1 of SEQ ID NO: 76, a CDR-L2 of SEQ ID NO: 77, and a CDR-L3 of SEQ ID NO: 78, as determined by the exemplary numbering system.

In some embodiments, an antibody provided herein comprises a CDR-H1 of SEQ ID NO: 80, a CDR-H2 of SEQ ID NO: 81, a CDR-H3 of SEQ ID NO: 82, a CDR-L1 of SEQ ID NO: 84, a CDR-L2 of SEQ ID NO: 85, and a CDR-L3 of SEQ ID NO: 86, as determined by the exemplary numbering system.

In some embodiments, an antibody provided herein comprises a CDR-H1 of SEQ ID NO: 88, a CDR-H2 of SEQ ID NO: 89, a CDR-H3 of SEQ ID NO: 90, a CDR-L1 of SEQ ID NO: 92, a CDR-L2 of SEQ ID NO: 93, and a CDR-L3 of SEQ ID NO: 94, as determined by the exemplary numbering system.

In some embodiments, an antibody provided herein comprises a CDR-H1 of SEQ ID NO: 102, a CDR-H2 of SEQ ID NO: 103, a CDR-H3 of SEQ ID NO: 104, a CDR-L1 of SEQ ID NO: 106, a CDR-L2 of SEQ ID NO: 107, and a CDR-L3 of SEQ ID NO: 108, as determined by the exemplary numbering system.

In some embodiments, an antibody provided herein comprises a CDR-H1 of SEQ ID NO: 110, a CDR-H2 of SEQ ID NO: 111, a CDR-H3 of SEQ ID NO: 112, a CDR-L1 of SEQ ID NO: 114, a CDR-L2 of SEQ ID NO: 115, and a CDR-L3 of SEQ ID NO: 116, as determined by the exemplary numbering system.

In some embodiments, an antibody provided herein comprises a CDR-H1 of SEQ ID NO: 118, a CDR-H2 of SEQ ID NO: 119, a CDR-H3 of SEQ ID NO: 120, a CDR-L1 of SEQ ID NO: 122, a CDR-L2 of SEQ ID NO: 123, and a CDR-L3 of SEQ ID NO: 124, as determined by the exemplary numbering system.

In some embodiments, an antibody provided herein comprises a CDR-H1 of SEQ ID NO: 126, a CDR-H2 of SEQ ID NO: 127, a CDR-H3 of SEQ ID NO: 128, a CDR-L1 of SEQ ID NO: 130, a CDR-L2 of SEQ ID NO: 131, and a CDR-L3 of SEQ ID NO: 132, as determined by the exemplary numbering system.

In some embodiments, an antibody provided herein comprises a CDR-H1 of SEQ ID NO: 134, a CDR-H2 of SEQ ID NO: 135, a CDR-H3 of SEQ ID NO: 136, a CDR-L1 of SEQ ID NO: 138, a CDR-L2 of SEQ ID NO: 139, and a CDR-L3 of SEQ ID NO: 140, as determined by the exemplary numbering system.

In some embodiments, an antibody provided herein comprises a CDR-H1 of SEQ ID NO: 142, a CDR-H2 of SEQ ID NO: 143, a CDR-H3 of SEQ ID NO: 144, a CDR-L1 of SEQ ID NO: 146, a CDR-L2 of SEQ ID NO: 147, and a CDR-L3 of SEQ ID NO: 148, as determined by the exemplary numbering system.

In some embodiments, an antibody provided herein comprises a CDR-H1 of SEQ ID NO: 150, a CDR-H2 of SEQ ID NO: 151, a CDR-H3 of SEQ ID NO: 152, a CDR-L1 of SEQ ID NO: 154, a CDR-L2 of SEQ ID NO: 155, and a CDR-L3 of SEQ ID NO: 156, as determined by the exemplary numbering system.

In some embodiments, an antibody provided herein comprises a CDR-H1 of SEQ ID NO: 158, a CDR-H2 of SEQ ID NO: 159, a CDR-H3 of SEQ ID NO: 160, a CDR-L1 of SEQ ID NO: 162, a CDR-L2 of SEQ ID NO: 163, and a CDR-L3 of SEQ ID NO: 164, as determined by the exemplary numbering system.

In some embodiments, an antibody provided herein comprises a CDR-H1 of SEQ ID NO: 166, a CDR-H2 of SEQ ID NO: 167, a CDR-H3 of SEQ ID NO: 168, a CDR-L1 of SEQ ID NO: 170, a CDR-L2 of SEQ ID NO: 171, and a CDR-L3 of SEQ ID NO: 172, as determined by the exemplary numbering system.

1.5 Consensus Sequences

Consensus sequences were developed representing the $V_H$ and $V_L$ sequences of the representative antibodies of each family, as well as their corresponding CDR sequences. Positions where the amino acid varies within a position of each CDR are represented by $X_1, X_2, X_3 \ldots$ Positions where the amino acid varies within a framework region of the $V_H$ and $V_L$ sequences are represented by $X_a, X_b, X_c \ldots$ Possible amino acids representing the consensus sequence at each X position are identified herein.

In some embodiments, provided herein is a first family of antibodies (see, FIGS. 12A-12B), wherein an antibody of such family comprises the following six CDR sequences: (a) a CDR-H1 having the sequence $FX_1FX_2X_3X_4AMS$ (SEQ ID NO: 1), wherein $X_1$ is T or A, $X_2$ is G, S, or E, $X_3$ is Q, T, P, or R, and $X_4$ is Y or F; (b) a CDR-H2 having the sequence $AISX_5X_6GGX_7TX_8YADSVKG$ (SEQ ID NO: 2), wherein $X_5$ is A or G, $X_6$ is A, V, or S, $X_7$ is T or S, and $X_8$ is K, A, or Y; (c) a CDR-H3 having the sequence $AKPLDSSX_9WADFX_{10}X_{11}$ (SEQ ID NO: 3), wherein $X_9$ is Q, F, or L, $X_{10}$ is D or Q, and $X_{11}$ is L or A; (d) a CDR-L1 having the sequence $RASQX_{12}IX_{13}SWLA$ (SEQ ID NO: 4), wherein $X_{12}$ is G, D, or T and $X_{13}$ is D, S, or Y; (e) a CDR-L2 having the sequence $X_{14}ASX_{15}LQX_{16}$ (SEQ ID NO: 5), wherein $X_{14}$ is A, Y, or F, $X_{15}$ is S, A, G, or F, and $X_{16}$ is D or S; and (f) a CDR-L3 having the sequence $QQX_{17}X_{15}X_{19}LPIT$ (SEQ ID NO: 6), wherein $X_{17}$ is A, H, or Q; $X_{18}$ is S, D, W, or L; and $X_{19}$ is V, D, Y, or K.

In some embodiments, an antibody of such family comprises a $V_H$ sequence of SEQ ID NO: 188 and a $V_L$ sequence of SEQ ID NO: 189. In some embodiments, provided herein is an antibody within such first family. FIGS. 12A-12B shows alignment of antibodies of first family that were used to generate the consensus sequence of each $V_H$ and $V_L$, respectively.

In some embodiments, provided herein is a second family of antibodies (see, FIGS. 13A-13B), wherein an antibody of such family comprises the following six CDR sequences: (a) a CDR-H1 having the sequence $FTFX_1X_2YYMS$ (SEQ ID NO: 95), wherein $X_1$ is G, A, P, or S and $X_2$ is N, Q, or D; (b) a CDR-H2 having the sequence $YISPSGX_3TIX_4YADSVKG$ (SEQ ID NO: 96), wherein $X_3$ is A or S and $X_4$ is Y or A; (c) a CDR-H3 having the sequence $ARSLMX_5TGTHLYFDL$ (SEQ ID NO: 97), wherein $X_5$ is A or S; (d) a CDR-L1 having the sequence $RASX_6X_7ISX_8WLA$ (SEQ ID NO: 98), wherein $X_6$ is Q or S, $X_7$ is D or G, and $X_8$ is D or S; (e) a CDR-L2 having the sequence $AAX_9X_{10}LQS$ (SEQ ID NO: 99), wherein $X_9$ is E or S and $X_{10}$ is S, A, G, V, or E; and (f) a CDR-L3 having the sequence $QQX_{11}TSX_{12}X_{13}PYT$ (SEQ ID NO: 100), wherein $X_{11}$ is A, S, or V, $X_{12}$ is F, T, V, Q, or A, and $X_{13}$ is L or P.

In some embodiments, an antibody of such family comprises a $V_H$ sequence of SEQ ID NO: 190 and a $V_L$ sequence of SEQ ID NO: 191. In some embodiments, provided herein is an antibody within such second family. FIGS. 13A-13B shows alignment of antibodies of second family that were used to generate the consensus sequence of each $V_H$ and $V_L$, respectively.

2. Functional Properties of Anti-CD161 Antibodies

In some embodiments, the CD161 antibodies bind (e.g., specifically bind) CD161. In some embodiments, the human CD161 is represented by SEQ ID NO: 179. In some embodiments, the CD161 antibodies bind to human CD161 and induce or promote activation of human NK cells. In some embodiments, the CD161 antibodies bind to human CD161 and induce or promote activation of human T cells.

In some embodiments, the CD161 antibodies bind to human CD161 with a $K_D$ lower than or equal to (i.e., binding stronger than or equal to) 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM, as measured using standard binding assays, for example, surface plasmon resonance, bio-layer interferometry, or an Octet QK384 assay. For example, in certain embodiments, the antibody binds human CD161 with a $K_D$ in the range of about 10 pM-about 1 nM, about 10 pM-about 0.9 nM, about 10 pM-about 0.8 nM, about 10 pM-about 0.7 nM, about 10 pM-about 0.6 nM, about 10 pM-about 0.5 nM, about 10 pM-about 0.4 nM, about 10 pM-about 0.3 nM, about 10 pM-about 0.2 nM, about 10 pM-about 0.1 nM, about 10 pM-about 50 pM, about 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 1 nM-about 10 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, or about 9 nM-about 10 nM.

In certain embodiments, in addition to binding human CD161, a disclosed antibody also binds to Macaca fascicularis (cynomolgus) CD161. In some embodiments, the cynomolgus CD161 is represented by SEQ ID NO: 180. In some embodiments, the CD161 antibodies bind to cynomolgus CD161 and induce or promote activation of cynomolgus NK cells. In some embodiments, the CD161 antibodies bind to cynomolgus CD161 and induce or promote activation of cynomolgus T cells. For example, the antibody binds cynomolgus CD161 with a $K_D$ lower than or equal to (i.e., binding stronger than or equal to) 20 nM, 15 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 90 pM, 80 pM, 70 pM, 60 pM, 50 pM, 40 pM, 30 pM, 20 pM, or 10 pM, as measured using standard binding assays, for example, surface plasmon resonance, bio-layer interferometry, or an Octet QK384 assay. In certain embodiments, the antibody binds cynomolgus CD161 with a $K_D$ in the range of about 10 pM-about 1 nM, about 10 pM-about 0.9 nM, about 10 pM-about 0.8 nM, about 10 pM-about 0.7 nM, about 10 pM-about 0.6 nM, about 10 pM-about 0.5 nM, about 10 pM-about 0.4 nM, about 10 pM-about 0.3 nM, about 10 pM-about 0.2 nM, about 10 pM-about 0.1 nM, about 10 pM-about 50 pM, 0.1 nM-about 10 nM, about 0.1 nM-about 9 nM, about 0.1 nM-about 8 nM, about 0.1 nM-about 7 nM, about 0.1 nM-about 6 nM, about 0.1 nM-about 5 nM, about 0.1 nM-about 4 nM, about 0.1 nM-about 3 nM, about 0.1 nM-about 2 nM, about 0.1 nM-about 1 nM, about 0.1 nM-about 0.5 nM, about 0.5 nM-about 10 nM, about 1 nM-about 10 nM, about 2 nM-about 10 nM, about 3 nM-about 10 nM, about 4 nM-about 10 nM, about 5 nM-about 10 nM, about 6 nM-about 10 nM, about 7 nM-about 10 nM, about 8 nM-about 10 nM, or about 9 nM-about 10 nM, as measured using standard binding assays, for example, surface plasmon resonance, bio-layer interferometry, or an Octet QK384 assay.

In certain embodiments, the affinity of an antibody disclosed herein for human CD161 as indicated by $EC_{50}$ measured with HEK293 expressing CD161 cells is 20 nM, 15 nM, 10 nM, 9 nM, 8 nM, 7 nM, 6 nM, 5 nM, 4 nM, 3 nM, 2 nM, 1 nM, 0.75 nM, 0.5 nM, 0.1 nM, 0.075 nM, or 0.05 nM or lower. In certain embodiments, the affinity of an antibody disclosed herein for human CD161 as indicated by $EC_{50}$ measured with HEK293 expressing CD161 cells is from about 20 nM to about 0.05 nM, from about 20 nM to about 0.075 nM, from about 20 nM to about 0.1 nM, from about 20 nM to about 0.5 nM, from about 20 nM to about 1 nM, from about 10 nM to about 0.05 nM, from about 10 nM to about 0.075 nM, from about 10 nM to about 0.1 nM, from about 10 nM to about 0.5 nM, from about 10 nM to about 1 nM, from about 5 nM to about 0.05 nM, from about 5 nM to about 0.075 nM, from about 5 nM to about 0.1 nM, from about 5 nM to about 0.5 nM, from about 5 nM to about 1 nM, from about 3 nM to about 0.05 nM, from about 3 nM to about 0.075 nM, from about 3 nM to about 0.1 nM, from about 3 nM to about 0.5 nM, from about 3 nM to about 1 nM, from about 3 nM to about 2 nM, from about 2 nM to about 0.05 nM, from about 2 nM to about 0.075 nM, from about 2 nM to about 0.1 nM, from about 2 nM to about 0.5 nM, from about 2 nM to about 1 nM, from about 1 nM to about 0.05 nM, from about 1 nM to about 0.075 nM, from about 1 nM to about 0.1 nM, from about 1 nM to about 0.5 nM, from about 0.5 nM to about 0.05 nM, from about 0.5 nM to about 0.075 nM, from about 0.5 nM to about 0.1 nM, from about 0.1 nM to about 0.05 nM, from about 0.1 nM to about 0.075 nM, or from about 0.075 nM to about 0.05 nM. In certain embodiments, the affinity of an antibody disclosed herein for human CD161 as indicated by $EC_{50}$ measured with HEK293 expressing CD161 cells is about 0.5 nM to about 0.1 nM (e.g., about 0.45 nM, about 0.4 nM, about 0.35 nM, about 0.3 nM, about 0.25 nM, about 0.2 nM, about 0.15 nM, or about 0.05 nM).

In certain embodiments, the present disclosure provides antibodies that bind to the same epitope present in CD161 as that bound by a disclosed antibody. In certain embodiments, the present disclosure provides antibodies that compete for binding to CD161 with a disclosed antibody.

Competition assays for determining whether an antibody binds to the same epitope as, or competes for binding with a disclosed antibody are known in the art. Exemplary competition assays include immunoassays (e.g., ELISA assays, RIA assays), surface plasmon resonance, (e.g., BIAcore analysis), bio-layer interferometry, and flow cytometry. Typically, a competition assay involves the use of an antigen (e.g., a human CD161 protein or fragment thereof) bound to a solid surface or expressed on a cell surface, a test CD161-binding antibody and a reference antibody. The reference antibody is labeled and the test antibody is unlabeled. Competitive inhibition is measured by determining the amount of labeled reference antibody bound to the solid surface or cells in the presence of the test antibody. Usually the test antibody is present in excess (e.g., 1×, 5×, 10×, 20× or 100×). Antibodies identified by competition assay (i.e., competing antibodies) include antibodies binding to the same epitope, or similar (e.g., overlapping) epitopes, as the reference antibody, and antibodies binding to an adjacent epitope sufficiently proximal to the epitope bound by the reference antibody for steric hindrance to occur.

A competition assay can be conducted in both directions to ensure that the presence of the label does not interfere or otherwise inhibit binding. For example, in the first direction the reference antibody is labeled and the test antibody is unlabeled, and in the second direction, the test antibody is labeled and the reference antibody is unlabeled. A test antibody competes with the reference antibody for specific binding to the antigen if an excess of one antibody (e.g., 1×, 5×, 10×, 20× or 100×) inhibits binding of the other antibody, e.g., by at least 50%, 75%, 90%, 95% or 99% as measured in a competitive binding assay.

Two antibodies may be determined to bind to the same epitope if essentially all amino acid mutations in the antigen that reduce or eliminate binding of one antibody reduce or eliminate binding of the other. Two antibodies may be determined to bind to overlapping epitopes if only a subset of the amino acid mutations that reduce or eliminate binding of one antibody reduce or eliminate binding of the other.

Several reports have shown that activation of CD161 by CLEC2D on tumor cells and immune-suppressing cells weakens the T cell response against tumor cells. Accordingly, the present application relates to CD161 antibodies that bind to CD161 and have the ability to inhibit the interaction of CD161 with CLEC2D. In some embodiments, the CD161 antibodies of the present disclosure block, inhibit, or antagonize binding of CLEC2D. In some embodiments, the CD161 antibodies of the present disclosure compete for binding to CD161 with CLEC2D. In some embodiments, the CD161 antibodies of the present disclosure reduce CD161 inhibitory signaling due to binding of CLEC2D to CD161. In some embodiments, CD161 is expressed on the surface of a cell. In certain embodiments, the present disclosure provides antibodies that compete for binding to CD161 with CLEC2D.

In some embodiments, the CD161 antibodies binds to a region of CD161 that overlaps with a ligand-binding region of CD161. In some embodiments, the CD161 antibodies binds at or near the ligand-binding region of CD161. In some embodiments, the ligand-binding region of CD161 is a CLEC2D-binding region. In some embodiments, binding of CD161 antibody or antigen-binding fragment thereof to CD161 prevents binding of CLEC2D to CD161. In some embodiments, the blocking of CD161 is measured by determining the concentrations of cytokines produced by CD161-expressing immune cells. In some embodiments, the immune cell is a NK cell or a T cell. In some embodiments, the blocking of CD161 is measured by determining concentration of cytokines produced by CD161-expressing T cells in response to a target cell (e.g., tumor cell). In some embodiments, an increase in cytokine production by immune cells indicates blocking of CD161. In some embodiments, blocking of CD161 is measured by analyzing proliferation of CD161-expressing immune cells. In some embodiments, an increase in immune cell proliferation indicates blocking of CD161. In some embodiments, blocking of CD161 is measured by measuring the level of cell signaling either by quantification of phosphorylation or expression of a gene reporter induced by relevant transcription factor. In some embodiments, increased cell signaling indicates blocking of CD161.

In certain embodiments, the CD161 antibodies of the present disclosure reduces CLEC2D binding to CD161 expressed on the surface of a cell with an $IC_{50}$ of 20 nM, 15 nM, 10 nM, 9 nM, 8 nM, 7 nM, 6 nM, 5 nM, 4 nM, 3 nM, 2 nM, 1 nM, 0.75 nM, 0.5 nM, 0.1 nM, 0.075 nM, or 0.05 nM or lower. In certain embodiments, the antibody reduces CLEC2D binding with an $IC_{50}$ from about 20 nM to about 0.05 nM, from about 20 nM to about 0.075 nM, from about 20 nM to about 0.1 nM, from about 20 nM to about 0.5 nM, from about 20 nM to about 1 nM, from about 10 nM to about 0.05 nM, from about 10 nM to about 0.075 nM, from about 10 nM to about 0.1 nM, from about 10 nM to about 0.5 nM, from about 10 nM to about 1 nM, from about 5 nM to about 0.05 nM, from about 5 nM to about 0.075 nM, from about 5 nM to about 0.1 nM, from about 5 nM to about 0.5 nM, from about 5 nM to about 1 nM, from about 3 nM to about 0.05 nM, from about 3 nM to about 0.075 nM, from about 3 nM to about 0.1 nM, from about 3 nM to about 0.5 nM, from about 3 nM to about 1 nM, from about 3 nM to about 2 nM, from about 2 nM to about 0.05 nM, from about 2 nM to about 0.075 nM, from about 2 nM to about 0.1 nM, from about 2 nM to about 0.5 nM, from about 2 nM to about 1 nM, from about 1 nM to about 0.05 nM, from about 1 nM to about 0.075 nM, from about 1 nM to about 0.1 nM, from about 1 nM to about 0.5 nM, from about 0.5 nM to about 0.05 nM, from about 0.5 nM to about 0.075 nM, from about 0.5 nM to about 0.1 nM, from about 0.1 nM to about 0.05 nM, from about 0.1 nM to about 0.075 nM, or from about 0.075 nM to about 0.05 nM. In certain embodiments, the antibody reduces CLEC2D binding with an $IC_{50}$ of about 0.1 nM to about 10 nM (e.g., about 0.15 nM, about 0.2 nM, about 0.25 nM, about 0.3 nM, about 0.35 nM, about 0.4 nM, about 0.45 nM, about 0.5 nM, about 0.55 nM, about 0.6 nM, about 0.65 nM, about 0.7 nM, about 0.75 nM, about 0.8 nM, about 0.85 nM, about 0.9 nM, about 0.95 nM, about 1 nM, about 1.5 nM, about 2 nM, about 2.5 nM, about 3 nM, about 3.5 nM, about 4 nM, about 4.5 nM, about 5 nM, about 5.5 nM, about 6 nM, about 6.5 nM, about 7 nM, about 7.5 nM, about 8 nM, about 8.5 nM, about 9 nM, and about 9.5 nM).

In certain embodiments, the CD161 antibodies bind to hKLRF1, hKLRF2, hCLEC12B, hCLEC2D, or any combination thereof with a $K_D$ of 500 nM, 600 nM, 700 nM, 800 nM, 900 nM, 1,000 nM, 1,500 nM, 2,000 nM, 3,000 nM, 4,000 nM, 5,000 nM, 10,000 nM, or 20,000 nM or greater. In some embodiments, the CD161 antibodies do not bind to human KLRF1. In some embodiments, the CD161 antibodies do not bind to human KLRF2. In some embodiments, the CD161 antibodies do not bind to human CLEC12B. In some embodiments, the CD161 antibodies do not bind to human CLEC2D.

In certain embodiments, the CD161 antibodies bind to human CD161 and cynomolgus CD161. In certain embodiments, the binding affinity, $K_D$ (as measured by a monovalent affinity assay) for human CD161 is within about 1.5-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, or about 100-fold, the affinity for cynomolgus CD161.

In some embodiments, the CD161 antibodies of the present disclosure reduce suppression of T cell or NK cell activity by CLEC2D binding to CD161. In some embodiments, the suppression of T cell or NK cell activity by CLEC2D binding to CD161 is at least reduced by about 1.5-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, or about 100-fold compared to a control antibody (e.g., an antibody that does not bind CD161).

In some embodiments, the CD161 antibodies increase T cell or NK cell activity in the presence of CLEC2D as compared to such T cell or NK cell activity in the absence of the antibody or antigen binding fragment. In certain embodiments, the T cell or NK cell activity is increased by about 1.5-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, or about 100-fold compared to a control antibody (e.g., an antibody that does not bind CD161).

In some embodiments, the T cells or NK cells are disposed within a microenvironment comprising cells expressing CLEC2D. In some embodiments, the CD161 antibodies increase T cell or NK cell activity in a tumor microenvironment containing tumor cells that express CLEC2D. In some embodiments, the increase in T cell activity is determined by an increase in NFAT signaling. In some embodiments, the increase in NK cell activity is determined by an increase in CD107a expression. In certain embodiments, the T cell or NK cell activity in a tumor microenvironment is increased by about 1.5-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, or about 100-fold compared to a control antibody (e.g., an antibody that does not bind CD161).

In some embodiments, an antibody or antigen-binding fragment thereof provided herein reduces CD161 inhibitory signaling, as measured by one or more assays or biological effects described herein. In some embodiments, the CD161 antibodies of the present disclosure reduces CD161 inhibitory signaling due to binding of CLEC2D to CD161. In certain embodiments, CD161 inhibitory signaling is reduced by about 1.5-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, or about 100-fold compared to a control antibody (e.g., an antibody that does not bind CD161).

In some embodiments, the CD161 antibodies of the present disclosure promote activation and cytokine production of CD8+ T cells within the tumor microenvironment. In certain embodiments, an antibody or antigen-binding fragment thereof activates and increases cytokine production of CD8+ T cells within the tumor microenvironment by about 1.5-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, or about 100-fold compared to a control antibody (e.g., an antibody that does not bind CD161).

In certain embodiments, an antibody provided herein comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 7, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 11, and (ii) competes for binding to human CD161 with and/or binds to same epitope on human CD161 as an antibody comprising an immunoglobulin heavy chain variable region comprising the amino acid sequence of SEQ ID NO: 7, and an immunoglobulin light chain variable region comprising the amino acid sequence of SEQ ID NO: 11.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 15, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 19, and (ii) competes for binding to human CD161 with and/or binds to same epitope on human CD161 as an antibody comprising an immunoglobulin heavy chain variable region comprising the amino acid sequence of SEQ ID NO: 15, and an immunoglobulin light chain variable region comprising the amino acid sequence of SEQ ID NO: 19.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 23, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 27, and (ii) competes for binding to human CD161 with and/or binds to same epitope on human CD161 as an antibody comprising an immunoglobulin heavy chain variable region comprising the amino acid sequence of SEQ ID NO: 23, and an immunoglobulin light chain variable region comprising the amino acid sequence of SEQ ID NO: 27.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 31, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 35, and (ii) competes for binding to human CD161 with and/or binds to same epitope on human CD161 as an antibody comprising an immunoglobulin heavy chain variable region comprising the amino acid sequence of SEQ ID NO: 31, and an immunoglobulin light chain variable region comprising the amino acid sequence of SEQ ID NO: 35.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 39, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 43, and (ii) competes for binding to human CD161 with and/or binds to same epitope on human CD161 as an antibody comprising an immunoglobulin heavy chain variable region comprising the amino acid sequence of SEQ ID NO: 39, and an immunoglobulin light chain variable region comprising the amino acid sequence of SEQ ID NO: 43.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 47, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 51, and (ii) competes for binding to human CD161 with and/or binds to same epitope on human CD161 as an antibody comprising an immunoglobulin heavy chain variable region comprising the amino acid sequence of SEQ ID NO: 47, and an immunoglobulin light chain variable region comprising the amino acid sequence of SEQ ID NO: 51.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 55, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 59, and (ii) competes for binding to human CD161 with and/or binds to same epitope on human CD161 as an antibody comprising an immunoglobulin heavy chain variable region comprising the amino acid sequence of SEQ ID NO: 55, and an immunoglobulin light chain variable region comprising the amino acid sequence of SEQ ID NO: 59.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 63, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 67, and (ii) competes for binding to human CD161 with and/or binds to same epitope on human CD161 as an antibody comprising an immunoglobulin heavy chain variable region comprising the amino acid sequence of SEQ ID NO: 63, and an immunoglobulin light chain variable region comprising the amino acid sequence of SEQ ID NO: 67.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 71, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 75, and (ii) competes for binding to human CD161 with and/or binds to same epitope on human CD161 as an antibody comprising an immunoglobulin heavy chain variable region comprising the amino acid sequence of SEQ ID NO: 71, and an immunoglobulin light chain variable region comprising the amino acid sequence of SEQ ID NO: 75.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 79, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 83, and (ii) competes for binding to human CD161 with and/or binds to same epitope on human CD161 as an antibody comprising an immunoglobulin heavy chain variable region comprising the amino acid sequence of SEQ ID NO: 79, and an immunoglobulin light chain variable region comprising the amino acid sequence of SEQ ID NO: 83.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 87, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 91, and (ii) competes for binding to human CD161 with and/or binds to same epitope on human CD161 as an antibody comprising an immunoglobulin heavy chain variable region comprising the amino acid sequence of SEQ ID NO: 87, and an immunoglobulin light chain variable region comprising the amino acid sequence of SEQ ID NO: 91.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 101, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 105, and (ii) competes for binding to human CD161 with and/or binds to same epitope on human CD161 as an antibody comprising an immunoglobulin heavy chain variable region comprising the amino acid sequence of SEQ ID NO: 101, and an immunoglobulin light chain variable region comprising the amino acid sequence of SEQ ID NO: 105.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 109, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 113, and (ii) competes for binding to human CD161 with and/or binds to same epitope on human CD161 as an antibody comprising an immunoglobulin heavy chain variable region comprising the amino acid sequence of SEQ ID NO: 109, and an immunoglobulin light chain variable region comprising the amino acid sequence of SEQ ID NO: 113.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 117, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 121, and (ii) competes for binding to human CD161 with and/or binds to same epitope on human CD161 as an antibody comprising an immunoglobulin heavy chain variable region comprising the amino acid sequence of SEQ ID NO: 117, and an immunoglobulin light chain variable region comprising the amino acid sequence of SEQ ID NO: 121.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 125, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 129, and (ii) competes for binding to human CD161 with and/or binds to same epitope on human CD161 as an antibody comprising an immunoglobulin heavy chain variable region comprising the amino acid sequence of SEQ ID NO: 125, and an immunoglobulin light chain variable region comprising the amino acid sequence of SEQ ID NO: 129.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 133, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 137, and (ii) competes for binding to human CD161 with and/or binds to same epitope on human CD161 as an antibody comprising an immunoglobulin heavy chain variable region comprising the amino acid sequence of SEQ ID NO: 133, and an immunoglobulin light chain variable region comprising the amino acid sequence of SEQ ID NO: 137.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 141, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 145, and (ii) competes for binding to human CD161 with and/or binds to same epitope on human CD161 as an antibody comprising an immunoglobulin heavy chain variable region comprising the amino acid sequence of SEQ ID NO: 141, and an immunoglobulin light chain variable region comprising the amino acid sequence of SEQ ID NO: 145.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 149, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 153, and (ii) competes for binding to human CD161 with and/or binds to same epitope on human CD161 as an antibody comprising an immunoglobulin heavy chain variable region comprising the amino acid sequence of SEQ ID NO: 149, and an immunoglobulin light chain variable region comprising the amino acid sequence of SEQ ID NO: 153.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 157, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 161, and (ii) competes for binding to human CD161 with and/or binds to same epitope on human CD161 as an antibody comprising an immunoglobulin heavy chain variable region comprising the amino acid sequence of SEQ ID NO: 157, and an immunoglobulin light chain variable region comprising the amino acid sequence of SEQ ID NO: 161.

In certain embodiments, an antibody provided herein (i) comprises an immunoglobulin heavy chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 165, and an immunoglobulin light chain variable region comprising an amino acid sequence that is at least 60%, at least 70%, at least 75%, at least 80%, at least 85%, at least 90%, at least 95%, at least 96%, at least 97%, at least 98%, or at least 99% identical to SEQ ID NO: 169, and (ii) competes for binding to human CD161 with and/or binds to same epitope on human CD161 as an antibody comprising an immunoglobulin heavy chain variable region comprising the amino acid sequence of SEQ ID NO: 165, and an immunoglobulin light chain variable region comprising the amino acid sequence of SEQ ID NO: 169.

The antibodies disclosed herein may be further optimized (e.g., affinity-matured) to improve biochemical characteristics including affinity and/or specificity, improve biophysical properties including aggregation, stability, precipitation and/or non-specific interactions, and/or to reduce immunogenicity. For example, diversity can be introduced into an immunoglobulin heavy chain and/or an immunoglobulin light chain by DNA shuffling, chain shuffling, CDR shuffling, random mutagenesis and/or site-specific mutagenesis.

In certain embodiments, isolated human antibodies contain one or more somatic mutations. In these cases, antibodies can be modified to a human germline sequence to optimize the antibody (i.e., a process referred to as germlining).

Generally, an optimized antibody has at least the same, or substantially the same, affinity for the antigen as the non-optimized (or parental) antibody from which it was derived. Preferably, an optimized antibody has a higher affinity for the antigen when compared to the parental antibody.

An antibody disclosed herein can be conjugated to an effector agent such as a small molecule toxin or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

In certain embodiments, an antibody or an antigen-binding fragment thereof provided herein has one or more of the characteristics listed in the following (a)-(t): (a) binds human CD161; (b) binds human CD161 at a human CD161 binding site; (c) binds to the CD161 epitope bound by an anti-CD161 antibody or antigen-binding fragment thereof; (d) binds human CD161 at or near a CLEC2D binding site; (e) competes for binding to CD161 with CLEC2D; (f) reduces CD161 inhibitory signaling due to binding of CLEC2D to CD161; (g) reduces suppression of T cell activity by CLEC2D binding to CD161; (h) reduces suppression of NK cell activity by CLEC2D binding to CD161; (i) increases T cell activity in the presence of CLEC2D as compared to such T cell activity in the absence of the antibody or antigen-binding fragment thereof; (j) increases NK cell activity in the presence of CLEC2D as compared to such NK cell activity in the absence of the antibody or antigen-binding fragment thereof; (k) increases T cell activity disposed within a microenvironment comprising cells expressing CLEC2D; (l) increases NK cell activity disposed within a microenvironment comprising cells expressing CLEC2D; (m) increases T cell activity in a tumor microenvironment comprising tumor cells that express CLEC2D; (n) increases NK cell activity in a tumor microenvironment comprising tumor cells that express CLEC2D; (o) inhibits human T cell exhaustion; (p) induces or increases activation of a CD161-expressing human T cell in response to an antigen-expressing target cell; (q) induces or increases cytokine production by a CD161-expressing human T cell in response to an antigen-expressing target cell; (r) induces or increases granzyme B expression by a CD161-expressing human T cell in response to an antigen-expressing target cell; (s) reduces exhaustion of CD161-expressing human T cells in response to antigen-expressing target cells; and (t) any combination of (a)-(s).

3. Monospecific and Multispecific Anti-CD161 Antibodies

In certain embodiments, the antibodies provided herein are monospecific antibodies. However, in certain embodiments, the antibodies provided herein are multispecific antibodies. For example, a multispecific antibody can bind more than one antigen, e.g., two antigens, three antigens, for antigens or five antigens. In some embodiments, a multispecific antibody can bind more than one epitope on a CD161 antigen, e.g., two epitopes on a CD161 antigen or three epitopes on a CD161 antigen.

Many multispecific antibody constructs are known in the art, and the antibodies provided herein may be provided in the form of any suitable multispecific suitable construct. In some embodiments, the multispecific antibody comprises an immunoglobulin comprising at least two different heavy chain variable regions each paired with a common light chain variable region (i.e., a "common light chain antibody"). The common light chain variable region forms a distinct antigen-binding domain with each of the two different heavy chain variable regions (see Merchant et al. (1998) NATURE BIOTECHNOL., 16: 677-681, incorporated by reference in its entirety).

In some embodiments, the multispecific antibody comprises an immunoglobulin comprising an antibody attached to one or more of the N- or C-termini of the heavy or light chains of such immunoglobulin (see Coloma and Morrison (1997) NATURE BIOTECHNOL., 15: 159-163, incorporated by reference in its entirety). In some aspects, such antibody comprises a tetravalent bispecific antibody. In some embodiments, the multispecific antibody comprises a hybrid immunoglobulin comprising at least two different heavy chain variable regions and at least two different light chain variable regions (see Milstein and Cuello (1983) NATURE, 305: 537-540; and Staerz and Bevan (1986) PROC. NATL. ACAD. SCI. USA, 83: 1453-1457; each of which is incorporated by reference in its entirety).

In some embodiments, the multispecific antibody comprises immunoglobulin chains with alterations to reduce the formation of side products that do not have multi-specificity. In some aspects, the antibodies comprise one or more "knobs-into-holes" modifications as described in U.S. Pat. No. 5,731,168, incorporated by reference in its entirety. In some embodiments, the multispecific antibody comprises immunoglobulin chains with one or more electrostatic modifications to promote the assembly of Fc hetero-multimers (see WO2009/089004, incorporated by reference in its entirety). In some embodiments, the multispecific antibody comprises a bispecific single chain molecule (see Traunecker et al. (1991) EMBO J., 10: 3655-3659; and Gruber et al. (1994) J. IMMUNOL., 152: 5368-5374; each of which is incorporated by reference in its entirety).

In some embodiments, the multispecific antibody comprises a heavy chain variable domain and a light chain variable domain connected by a polypeptide linker, where the length of the linker is selected to promote assembly of multispecific antibodies with the desired multispecificity. For example, monospecific scFvs generally form when a heavy chain variable domain and light chain variable domain are connected by a polypeptide linker of more than 12 amino acid residues (see U.S. Pat. Nos. 4,946,778 and 5,132,405, each of which is incorporated by reference in its entirety). In some embodiments, reduction of the polypeptide linker length to less than 12 amino acid residues prevents pairing of heavy and light chain variable domains on the same polypeptide chain, thereby allowing pairing of heavy and light chain variable domains from one chain with the complementary domains on another chain. The resulting antibodies therefore have multi-specificity, with the specificity of each binding site contributed by more than one polypeptide chain. Polypeptide chains comprising heavy and light chain variable domains that are joined by linkers between 3 and 12 amino acid residues form predominantly dimers (termed diabodies). With linkers between 0 and 2 amino acid residues, trimers (termed triabodies) and tetramers (termed tetrabodies) may be favored. However, the exact type of oligomerization appears to depend on the amino acid residue composition and the order of the variable domain in each polypeptide chain (e.g., $V_H$-linker-$V_L$ vs. $V_L$-linker-$V_H$), in addition to the linker length. A skilled person can select the appropriate linker length based on the desired level of multispecificity.

In some embodiments, the multispecific antibody comprises a diabody (see Hollinger et al. (1993) PROC. NATL. ACAD. SCI. USA, 90: 6444-6448, incorporated by reference in its entirety) or a triabody (see Todorovska et al. (2001) J. IMMUNOL. METHODS, 248: 47-66, incorporated by reference in its entirety) or a tetrabody (see id., incorporated by reference in its entirety).

In some embodiments, the multispecific antibody comprises a trispecific F(ab')₃ derivative (see Tutt et al. (1991) J. IMMUNOL., 147: 60-69, incorporated by reference in its entirety).

In some embodiments, the multispecific antibody comprises a cross-linked antibody (see U.S. Pat. No. 4,676,980; Brennan et al. (1985) SCIENCE, 229: 81-83; Staerz et al. (1985) NATURE, 314: 628-631; and EP 0453082; each of which is incorporated by reference in its entirety). In some embodiments, the multispecific antibody comprises antigen-binding domains assembled by leucine zippers (see Kostelny et al. (1992) J. IMMUNOL., 148: 1547-1553, incorporated by reference in its entirety).

In some embodiments, the multispecific antibody comprises a DuoBody®, for example, as in Labrijn et al. (2013) PROC. NATL. ACAD. SCI. USA, 110: 5145-5150; Gramer et al. (2013) MABS, 5: 962-972; and Labrijn et al. (2014) NATURE PROTOCOLS, 9: 2450-2463; each of which is incorporated by reference in its entirety.

4. Glycosylation Variants

In certain embodiments, an antibody provided herein may be altered to increase, decrease or eliminate the extent to which it is glycosylated. Glycosylation of polypeptides is typically either "N-linked" or "O-linked." "N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. "O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to or from an antibody provided herein may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

In some embodiments, an antibody provided herein comprises a glycosylation motif that is different from a naturally occurring antibody. Any suitable naturally occurring glycosylation motif can be modified in the antibodies provided herein. The structural and glycosylation properties of immunoglobulins, for example, are known in the art and summarized, for example, in Schroeder and Cavacini (2010) J. ALLERGY CLIN. IMMUNOL., 125: S41-52, incorporated by reference in its entirety.

In some embodiments, an antibody provided herein comprises an $IgG_1$ Fc region with modification to the oligosaccharide attached to asparagine 297 (Asn 297). Naturally occurring $IgG_1$ antibodies produced by mammalian cells typically comprise a branched, biantennary oligosaccharide that is generally attached by an N-linkage to Asn 297 of the $CH_2$ domain of the Fc region (see Wright et al. (1997) TIBTECH, 15: 26-32, incorporated by reference in its entirety). The oligosaccharide attached to Asn 297 may include various carbohydrates such as mannose, N-acetyl glucosamine (GlcNAc), galactose, and sialic acid, as well as a fucose attached to a GlcNAc in the "stem" of the biantennary oligosaccharide structure.

In some embodiments, the oligosaccharide attached to Asn 297 is modified to create antibodies having altered ADCC. In some embodiments, the oligosaccharide is altered to improve ADCC. In some embodiments, the oligosaccharide is altered to reduce ADCC.

In some aspects, an antibody provided herein comprises an $IgG_1$ domain with reduced fucose content at position Asn 297 compared to a naturally occurring $IgG_1$ domain. Such Fc domains are known to have improved ADCC (see Shields et al. (2002) J. BIOL. CHEM., 277: 26733-26740, incorporated by reference in its entirety). In some aspects, such antibodies do not comprise any fucose at position Asn 297. The amount of fucose may be determined using any suitable method, for example as described in WO2008/077546, incorporated by reference in its entirety.

In some embodiments, an antibody provided herein comprises a bisected oligosaccharide, such as a biantennary oligosaccharide attached to the Fc region of the antibody that is bisected by GlcNAc. Such antibody variants may have reduced fucosylation and/or improved ADCC function. Examples of such antibody variants are described, for example, in WO 2003/011878; and U.S. Pat. No. 6,602,684; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO1997/30087; WO1998/58964; and WO1999/22764; each of which is incorporated by reference in its entirety.

Examples of cell lines capable of producing defucosylated antibodies include Lec13 CHO cells, which are deficient in protein fucosylation (see Ripka et al. (1986) ARCH. BIOCHEM. BIOPHYS., 249: 533-545; U.S. Patent Publication No. 2003/0157108; WO2004/056312; each of which is incorporated by reference in its entirety), and knockout cell lines, such as alpha-1,6-fucosyltransferase gene or FUT8 knockout CHO cells (see Yamane-Ohnuki et al. (2004) BIOTECH. BIOENG., 87: 614-622; Kanda et al. (2006) BIOTECHNOL. BIOENG., 94: 680-688; and WO2003/085107; each of which is incorporated by reference in its entirety).

In some embodiments, an antibody provided herein is an aglycosylated antibody. An aglycosylated antibody can be produced using any method known in the art or described herein. In some aspects, an aglycosylated antibody is produced by modifying the antibody to remove all glycosylation sites. In some aspects, the glycosylation sites are removed only from the Fc region of the antibody. In some aspects, an aglycosylated antibody is produced by expressing the antibody in an organism that is not capable of glycosylation, such as E. coli, or by expressing the antibody in a cell-free reaction mixture.

In some embodiments, an antibody provided herein has a constant region with reduced effector function compared to a native $IgG_1$ antibody. In some embodiments, the affinity of a constant region of an Fc region of an antibody provided herein for Fc receptor is less than the affinity of a native $IgG_1$ constant region for such Fc receptor.

5. Fc Region

The anti-CD161 antibody of the present disclosure is an IgG type antibody. For example, each of the anti-CD161 antibodies disclosed in TABLE 4 is fused to an Immunoglobulin Fc domain (e.g., an Immunoglobulin Fc domain derived from a human $IgG_1$, a human $IgG_2$, a human $IgG_3$, a human $IgG_4$, a human $IgA_1$, a human $IgA_2$, a human IgD, a human IgE, or a human IgM Fc domain). In an exemplary embodiment, each of the anti-CD161 antibodies disclosed in TABLE 4 is fused to an Immunoglobulin Fc domain derived from a human $IgG_1$.

In certain embodiments, an antibody provided herein comprises an Fc region with one or more amino acid substitutions, insertions, or deletions in comparison to a naturally occurring Fc region. In some aspects, such substitutions, insertions, or deletions yield antibodies with altered stability, glycosylation, or other characteristics. In some aspects, such substitutions, insertions, or deletions yield aglycosylated antibodies.

In certain embodiments, the immunoglobulin Fc domain is derived from a human IgG$_1$, IgG$_2$, IgG$_3$, IgG$_4$, IgA$_1$, IgA$_2$, IgD, IgE, and IgM Fc domain. A single amino acid substitution (S228P according to Kabat numbering; designated IgG$_4$Pro) may be introduced to abolish the heterogeneity observed in recombinant IgG$_4$ antibody (see Angal, S. et al. (1993) MOL. IMMUNOL., 30:105-108).

In some aspects, the Fc region of an antibody provided herein is modified to yield an antibody with altered affinity for an Fc receptor, or an antibody that is more immunologically inert. In some embodiments, the antibody variants provided herein possess some, but not all, effector functions. Such antibodies may be useful, for example, when the half-life of the antibody is important in vivo, but when certain effector functions (e.g., complement activation and ADCC) are unnecessary or deleterious.

In some embodiments, the Fc region of an antibody provided herein is a human IgG$_4$ Fc region comprising one or more of the hinge stabilizing mutations S228P and L235E (see Aalberse et al. (2002) IMMUNOLOGY, 105: 9-19, incorporated by reference in its entirety). In some embodiments, the IgG$_4$ Fc region comprises one or more of the following mutations: E233P, F234V, and L235A (see Armour et al. (2003) MOL. IMMUNOL., 40: 585-593, incorporated by reference in its entirety). In some embodiments, the IgG$_4$ Fc region comprises a deletion at position G236.

In some embodiments, the Fc region of an antibody provided herein is a human IgG$_1$ Fc region comprising one or more mutations to reduce Fc receptor binding. In some embodiments, the Fc domain comprises one or more mutation such as those described in U.S. Pat. No. 8,394,925, which is hereby incorporated by reference in its entirety. In some embodiments, the Fc region is a variant Fc region comprising amino acid substitutions at positions 428 and 434, wherein the amino acid substitutions are a leucine that is not the wild-type amino acid at position 428 and a serine that is not the wild-type amino acid at position 434, wherein the polypeptide is an antibody and wherein numbering is according to the EU Index in Kabat et al. In some embodiments, the Fc region comprises a S228P, L235E, M428L, or N434S substitution. In some embodiments, the Fc region comprises a M428L substitution. In some embodiments, the Fc region comprises a N434S substitution. In some embodiments, the Fc region comprises a M428L and a N434S substitution. In some embodiments, the Fc region comprises a M252Y, S254T, and/or T256E substitution. In some aspects, the antibody comprises a PVA236 mutation. PVA236 means that the amino acid sequence ELLG (SEQ ID NO: 195), from amino acid position 233 to 236 of IgG$_1$ or EFLG (SEQ ID NO: 196) of IgG$_4$, is replaced by PVA (see U.S. Pat. No. 9,150,641, incorporated by reference in its entirety).

In some embodiments, the Fc region of an antibody provided herein is a human IgG$_2$ Fc region comprising one or more of mutations A330S and P331S.

In some embodiments, the Fc region of an antibody provided herein has an amino acid substitution at one or more positions selected from 238, 265, 269, 270, 297, 327 and 329 (see U.S. Pat. No. 6,737,056, incorporated by reference in its entirety). Such Fc mutants include Fc mutants with substitutions at two or more of amino acid positions 265, 269, 270, 297 and 327, including the so-called "DANA" Fc mutant with substitution of residues 265 and 297 with alanine (see U.S. Pat. No. 7,332,581, incorporated by reference in its entirety). In some embodiments, the antibody comprises an alanine at amino acid position 265. In some embodiments, the antibody comprises an alanine at amino acid position 297. In certain embodiments, the human IgG$_1$ constant region is modified at amino acid Asn297 to prevent to glycosylation of the antibody, for example Asn297Ala (N297A). In certain embodiments, the mutation is effective in eliminating the binding of the anti-CD161 antibody disclosed herein to the Fc receptor (e.g. RI, RIIA, RIIB/C, RIIA, and RIIIB). In certain embodiments, the mutation is effective in significantly reducing the binding of the anti-CD161 antibody disclosed herein to the Fc receptor (e.g. RI, RIIA, RIIB/C, RIIA, and RIIIB). In an exemplary embodiment, each of the anti-CD161 antibodies disclosed in TABLE 4 is fused to human IgG$_1$ constant region modified at amino acid Asn297.

In certain embodiments, an antibody provided herein comprises an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330, as described in Lazar et al. (2006) PROC. NATL. ACAD. SCI. USA, 103: 4005-4010, incorporated by reference in its entirety.

In some embodiments, an antibody provided herein comprises one or more alterations to increase half-life. In some embodiments, the Fc domain comprises a mutation such as those described in U.S. Pat. No. 7,670,600, which is hereby incorporated by reference in its entirety. In some embodiments, the constant region comprises a mutation at position at amino acid residue 428 relative to a wild-type human IgG constant domain, numbered according to the EU numbering index of Kabat. Without being bound to any particular theory, an antibody comprising a mutation that corresponds to residue 428 can have an increased half-life compared to the half-life of an IgG having the wild-type human IgG constant domain. In some embodiments, the mutation is a substitution of the native residue with a threonine, leucine, phenylalanine or serine. In some embodiments, the antibody further comprises one or more amino acid substitutions relative to the corresponding wild-type human IgG constant domain at one or more of amino acid residues 251-256, 285-290, 308-314, 385-389, and 429-436, numbered according to the Kabat EU numbering index. The specific mutations or substitutions at these positions are described in U.S. Pat. No. 7,670,600, which is hereby incorporated by reference in its entirety.

6. Antibodies with Reduced Immunogenicity

When the antibodies are to be administered to a human, the antibodies preferably are human antibodies or are engineered to reduce or eliminate antigenicity in humans. Preferably, each humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, PROC. NAT. ACAD. SCI. 81:6851-6855, Neuberger et al., 1984, NATURE 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human framework regions (FRs). In some embodiments, the CDRs of the light and heavy chain variable regions of an antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al. (1986) NATURE 321: 522-525; Riechmann et al. (1988) NATURE 332: 323-327; Verhoeyen et al. (1988) SCIENCE 239: 1534-1536; and Winter (1998) FEBS LETT 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. IMMUNOL. 169:1119-1125.

Other methods to reduce immunogenicity include "reshaping," "hyperchimerization," and "veneering/resurfacing." See, e.g., Vaswami et al., 1998, ANNALS OF ALLERGY, ASTHMA, & IMMUNOL. 81:105; Roguska et al., 1996, PROT. ENGINEER 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, NY), which involves a vaccinia virus-based vector to express antibodies in mammalian cells. High levels of combinatorial diversity of IgG heavy and light chains can be produced. See, e.g., U.S. Pat. No. 6,706,477 (Zauderer); U.S. Pat. No. 6,800,442 (Zauderer); and 6,872,518 (Zauderer). Another approach for converting a mouse antibody into a form suitable for use in humans is technology practiced commercially by KaloBios Pharmaceuticals, Inc. (Palo Alto, CA). This technology involves the use of a proprietary human "acceptor" library to produce an "epitope focused" library for antibody selection. Another approach for modifying a mouse antibody into a form suitable for medical use in humans is HUMAN ENGINEERING™ technology, which is practiced commercially by XOMA (US) LLC. See, e.g., International (PCT) Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka), each of which is incorporated by reference in its entirety.

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., NATURE 368:856-859, 1994; Fishwild et al., NATURE BIOTECHNOLOGY 14:845-851, 1996; and Mendez et al., NATURE GENETICS 15:146-156, 1997. Fully human monoclonal antibodies can also be prepared and optimized from phage display libraries by techniques referenced in, e.g., Knappik et al., J. MOL. BIOL. 296:57-86, 2000; and Krebs et al., J. IMMUNOL. METH. 254:67-84 2001).

7. Anti-CD161 Antibody-Drug Conjugates

The present disclosure further provides antibody conjugates containing one or more of the antibodies disclosed herein. As used herein, unless otherwise indicated, the term "antibody conjugate" is understood to refer to an antibody, or a functional fragment thereof, that comprises antigen-binding activity (e.g., anti-CD161 antigen-binding activity) and/or Fc receptor-binding activity, conjugated (e.g., covalently coupled) to an additional functional moiety.

In certain embodiments, the antibody conjugates are antibody-drug conjugates (ADCs) that comprise an antibody that binds specifically to CD161 and a cytotoxic agent. The cytotoxic agent can be linked directly or indirectly to the anti-CD161 antibody. In some embodiments, the ADCs further comprise a linker that covalently links the cytotoxic agent to the anti-CD161 antibody.

Exemplary cytotoxic agents useful in created ADCs include, for example, certain anti-tumor or anti-cancer agents known in the art. In some embodiments, the cytotoxic agents cause destruction of cancer cells. In some embodiments, the cytotoxic agents inhibit the growth or proliferation of cancer cells. Exemplary cytotoxic agents include anti-angiogenic agents, pro-apoptotic agents, anti-mitotic agents, anti-kinase agents, alkylating agents, hormones, hormone agonists, hormone antagonists, chemokines, drugs, prodrugs, toxins, enzymes, antimetabolites, antibiotics, alkaloids, and radioactive isotopes.

In certain embodiments, the cytotoxic agent is coupled to the anti-CD161 antibody via a linker. In some embodiments, an linker used to create the ADC comprises two reactive termini: an antibody conjugation reactive termini and an cytotoxic agent conjugation reactive termini. The antibody conjugation reactive terminus of the linker can be conjugated to the antibody through a cysteine thiol or lysine amine group on the antibody, for example, via a thiol-reactive group such as a double bond, a leaving group such as a chloro, bromo or iodo, an R-sulfanyl group or sulfonyl group, or an amine-reactive group such as a carboxyl group. The cytotoxic agent conjugation reactive terminus of the linker can be conjugated to the cytotoxic agent, for example, through formation of an amide bond with a basic amine or carboxyl group on the cytotoxin, typically a carboxyl or basic amine group.

Depending upon the intended purpose of the ADC, the linker can be a non-cleavable linker or a cleavable linker.

8. Methods of Making CD161 Antibodies 8.1 CD161 Antigen Preparation

The CD161 antigen used for isolation of the antibodies provided herein may be intact CD161 or a fragment of CD161. The CD161 antigen may be, for example, in the form of an isolated protein or a protein expressed on the surface of a cell. In some embodiments, the CD161 antigen is a non-naturally occurring variant of CD161, such as a CD161 protein having an amino acid sequence or post-translational modification that does not occur in nature.

In some embodiments, the CD161 antigen is truncated by removal of, for example, intracellular or membrane-spanning sequences, or signal sequences. In some embodiments, the CD161 antigen is fused at its C-terminus to a human IgG₁ Fc domain or a polyhistidine tag.

8.2 Methods of Making Monoclonal Antibodies

Monoclonal antibodies may be obtained, for example, using the hybridoma method first described by Kohler et al. (1975) NATURE, 256: 495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage-display libraries (see e.g., U.S. Pat. No. 8,258,082, which is incorporated by reference in its entirety) or, alternatively, using yeast-based libraries (see e.g., U.S. Pat. Nos. 8,691,730 and 9,354,228, which is incorporated by reference in its entirety).

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell (see Goding J. W. (1986) MONOCLONAL ANTIBODIES: PRINCIPLES AND PRACTICE 3' ED., Academic Press, San Diego, CA, incorporated by reference in its entirety).

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, CA), and SP-2 or X63-Ag8-653 cells (available from the American Type Culture Collection, Rockville, MD). Human myeloma and mouse-human heteromyeloma cell lines also have been described for the production of human monoclonal antibodies (see e.g., Kozbor (1984) J. IMMUNOL., 133: 3001, incorporated by reference in its entirety).

After the identification of hybridoma cells that produce antibodies of the desired specificity, affinity, and/or biological activity, selected clones may be subcloned by limiting dilution procedures and grown by standard methods (see Goding, supra). Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

8.3 Methods of Making Antibodies with Reduced Immunogenicity

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein (1991) NATURE, 349: 293-299; Rader et al. (1998) PROC. NAT. ACAD. SCI. USA, 95: 8910-8915; Steinberger et al. (2000) J. BIOL. CHEM., 275: 36073-36078; Queen et al. (1989) PROC. NATL. ACAD. SCI. USA, 86: 10029-10033; and U.S. Pat. Nos. 5,585,089, 5,693,761, 5,693,762, and 6,180,370; each of which is incorporated by reference in its entirety.

Human antibodies can be generated by a variety of techniques known in the art, for example by using transgenic animals (e.g., humanized mice). See, e.g., Jakobovits et al. (1993) PROC. NATL. ACAD. SCI. USA, 90: 2551; Jakobovits et al. (1993) NATURE, 362: 255-258; Bruggermann et al. (1993) YEAR IN IMMUNO., 7: 33; and U.S. Pat. Nos. 5,591,669, 5,589,369 and 5,545,807; each of which is incorporated by reference in its entirety. Human antibodies can also be derived from phage-display libraries (see e.g., Hoogenboom et al. (1991) J. MOL. BIOL., 227: 381-388; Marks et al. (1991) J. MOL. BIOL., 222: 581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. Nos. 8,691,730 and 9,354,228, incorporated by reference in its entirety).

Illustrative methods of making chimeric antibodies are described, for example, in U.S. Pat. No. 4,816,567; and Morrison et al. (1984) PROC. NATL. ACAD. SCI. USA, 81: 6851-6855; each of which is incorporated by reference in its entirety. In some embodiments, a chimeric antibody is made by using recombinant techniques to combine a non-human variable region (e.g., a variable region derived from a mouse, rat, hamster, rabbit, or non-human primate, such as a monkey) with a human constant region.

8.4 Methods of Making Antibody Fragments

The antibody fragments provided herein may be made by any suitable method, including the illustrative methods described herein or those known in the art. Suitable methods include recombinant techniques and proteolytic digestion of whole antibodies. Illustrative methods of making antibody fragments are described, for example, in Hudson et al. (2003) NAT. MED., 9: 129-134, incorporated by reference in its entirety. Methods of making scFv antibodies are described, for example, in Phückthun (1994) THE PHARMACOLOGY OF MONOCLONAL ANTIBODIES, VOL. 113, Rosenburg and Moore eds., Springer-Verlag, New York, pp. 269-315; WO93/16185; and U.S. Pat. Nos. 5,571,894 and 5,587,458; each of which is incorporated by reference in its entirety.

8.5 Methods of Making Multispecific Antibodies

The multispecific antibodies provided herein may be made by any suitable method, including the illustrative methods described herein or those known in the art. Methods of making common light chain antibodies are described in Merchant et al. (1998) NATURE BIOTECHNOL., 16: 677-681, incorporated by reference in its entirety. Methods of making tetravalent bispecific antibodies are described in Coloma and Morrison (1997) NATURE BIOTECHNOL., 15: 159-163, incorporated by reference in its entirety. Methods of making hybrid immunoglobulins are described in Milstein and Cuello (1983) NATURE, 305: 537-540; and Staerz and Bevan (1986) PROC. NATL. ACAD. SCI. USA, 83: 1453-1457; each of which is incorporated by reference in its entirety. Methods of making immunoglobulins with knobs-into-holes modification are described in U.S. Pat. No. 5,731,168, incorporated by reference in its entirety. Methods of making immunoglobulins with electrostatic modifications are provided in WO 2009/089004, incorporated by reference in its entirety. Methods of making bispecific single chain antibodies are described in Traunecker et al. (1991) EMBO J., 10: 3655-3659; and Gruber et al. (1994) J. IMMUNOL., 152: 5368-5374; each of which is incorporated by reference in its entirety. Methods of making single-chain antibodies, whose linker length may be varied, are described in U.S. Pat. Nos. 4,946,778 and 5,132,405, each of which is incorporated by reference in its entirety. Methods of making diabodies are described in Hollinger et al. (1993) PROC. NATL. ACAD. SCI. USA, 90: 6444-6448, incorporated by reference in its entirety. Methods of making triabodies and tetrabodies are described in Todorovska et al. (2001) J. IMMUNOL. METHODS, 248: 47-66, incorporated by reference in its entirety. Methods of making trispecific F(ab')$_3$ derivatives are described in Tutt et al. (1991) J. IMMUNOL., 147: 60-69, incorporated by reference in its entirety. Methods of making cross-linked antibodies are described in U.S. Pat. No. 4,676,980; Brennan et al. (1985) SCIENCE, 229: 81-83; Staerz et al. (1985) NATURE, 314: 628-631; and EP 0453082; each of which is incorporated by reference in its entirety.

8.6 Methods of Making Variants

In some embodiments, an antibody provided herein is an affinity matured variant of a parent antibody, which may be generated, for example, using phage display-based affinity maturation techniques. Briefly, one or more CDR residues may be mutated and the variant antibodies, or portions thereof, displayed on phage and screened for affinity. Such alterations may be made in CDR "hotspots," or residues encoded by codons that undergo mutation at high frequency during the somatic maturation process (see Chowdhury (2008) METHODS MOL. BIOL., 207: 179-196, incorporated by reference in its entirety), and/or residues that contact the antigen.

Any suitable method can be used to introduce variability into a polynucleotide sequence(s) encoding an antibody, including error-prone PCR, chain shuffling, and oligonucleotide-directed mutagenesis such as trinucleotide-directed mutagenesis (TRIM). In some aspects, several CDR residues (e.g., 4-6 residues at a time) are randomized. CDR residues involved in antigen binding may be specifically identified, for example, using alanine scanning mutagenesis or modeling. CDR-H3 and CDR-L3 in particular are often targeted for mutation.

The introduction of diversity into the variable regions and/or CDRs can be used to produce a secondary library. The secondary library is then screened to identify antibody variants with improved affinity. Affinity maturation by constructing and reselecting from secondary libraries has been described, for example, in Hoogenboom et al. (2001) METHODS MOL. BIOL., 178: 1-37, incorporated by reference in its entirety.

8.7 Vectors, Host Cells, and Recombinant Methods

Also provided are isolated nucleic acids encoding CD161 antibodies, vectors comprising the nucleic acids, and host cells comprising the vectors and nucleic acids, as well as recombinant techniques for the production of the antibodies.

For recombinant production of an antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells include any suitable prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X$_{1776}$, and *E. coli* W3110 are also suitable.

In addition to prokaryotes, eukaryotic microbes such as filamentous fungi or yeast are also suitable cloning or expression hosts for CD161 antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus* K. wickeramii, *K. waltii, K. drosophilarum, K. thermotolerans*, and *K. marxianus*), *Yarrowia, Pichia pastoris, Candida* (*C. albicans*), *Trichoderma* reesia, *Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells, baby hamster kidney (BHK) cells, Chinese hamster ovary (CHO), mouse sertoli cells, African green monkey kidney cells (VERO-76), and the like.

The host cells used to produce the CD161 antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al. (1979) METH. ENZ., 58: 44; Barnes et al. (1980) ANAL. BIOCHEM., 102: 255; and U.S. Pat. Nos. 4,767,704, 4,657,866, 4,927,762, 4,560,655, and 5,122,469; or WO1990/03430 and WO1987/00195, each of which is incorporated by reference in its entirety, may be used.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (1992) BIO/TECHNOLOGY, 10: 163-167, incorporated by reference in its entirety) describes a procedure for isolating antibodies which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al. (2012) MABS, 4: 217-225, incorporated by reference in its entirety. In some aspects, the cell-free system utilizes a cell-free extract from a eukaryotic cell or from a prokaryotic cell. In some aspects, the prokaryotic cell is E. coli. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that comprise human γ1, γ2, or γ4 heavy chains (Lindmark et al. (1983) J. IMMUNOL. METH., 62: 1-13, incorporated by reference in its entirety). Protein G is useful for all mouse isotypes and for human γ3 (Guss et al. (1986) EMBO J., 5: 1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

9. Functional Assays

A variety of assays known in the art may be used to identify and characterize anti-CD161 antibodies and anti-CD161 ADCs provided herein.

9.1 Binding, Competition, and Epitope Mapping Assays 9.1.1 Antigen-Binding Assays In some embodiments, the antigen-binding activity is determined using an antigen-binding assay. In some embodiments, the antigen-binding assay determines a binding affinity ($K_D$) of the antibodies disclosed herein. In some embodiments, the antigen-binding assay determines kinetic rate constants (e.g., $k_{on}$, $k_{off}$) for the binding interaction of an anti-CD161 antibody for a CD161 polypeptide. In some embodiments, kinetic characteristics of the binding interaction of a CD161 antibody to a target molecule are determined using an Octet QK384 assay.

Although examples of antigen-binding activity assays are provided herein, specific antigen-binding activity of the CD161 antibodies provided herein may also be evaluated by any suitable method, including using surface plasmon resonance (SPR), biolayer interferometry (BLI), enzyme-linked immunosorbent assay (ELISA), kinetic exclusion assay (KinExA), gel-shift assays, pull-down assays, quantitative immunoblot, equilibrium dialysis, analytical ultracentrifugation, fluorescence anisotropy, solution equilibrium titration, kinetic exclusion assay, and isothermal titration calorimetry. These methods are well-known in the art.

In some embodiments, the antigen-binding assay comprises measuring binding affinity of a labeled anti-CD161 antibody for a CD161 polypeptide expressed on a cell surface. In some embodiments, the anti-CD161 antibody is labeled with a fluorescent molecule (e.g., a fluorescent dye). In some embodiments, binding is detected using a method of fluorescence detection (e.g., flow cytometry). In some embodiments, binding of an anti-CD161 antibody disclosed herein to a cell expressing the antigen is compared relative to a reference cell lacking expression of the antigen.

In some embodiments, the antigen binding assay is surface plasmon resonance. "Surface plasmon resonance" includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, NJ). For further descriptions, see Jönsson, U., et al. (1993) ANN. BIOL. CLIN., 51: 19-26; Jönsson, U., et al. (1991) BIOTECHNIQUES, 11: 620-627; Johnsson, B., et al. (1995) J. MOL. RECOGNIT., 8: 125-131; and Johnnson, B., et al. (1991) ANAL. BIOCHEM., 198: 268-277.

In some embodiments, the antigen binding assay is biolayer interferometry (BLI). The phrase "biolayer interferometry" or "BLI" includes an optical phenomenon that allows for the measurement of sub-nanometer changes in the thickness of its optical layer detection surface. In some embodiments, biomolecules binds at a sensor surface and change the optical layer thickness. The magnitude of the optical layer thickness change is proportional to the mass or molecular weight of the binding molecule. In some embodiments, CD161 is immobilized to the sensor surface to measure binding by an antibody, wherein binding creates a changes in the molecular weight to produce a corresponding change in the optical layer thickness. In some embodiments wherein CD161 is immobilized to the sensor surface, samples of the anti-CD161 antibody are prepared by serial dilution and injected, and $K_D$ values are calculated from modeling of the curve of binding relative to antibody concentration. In some embodiments, BLI is performed with an Octet QK384 system (ForteBio), i.e., the antigen-binding assay is an Octet QK384 assay.

9.1.2 Ligand-Binding Assays

In some embodiments, an anti-CD161 antibody described herein binds human CD161 and blocks or inhibits binding by CLEC2D as determined by a ligand binding assay. A ligand binding assay is an assay that provides a measure of the interactions and/or degree of affinity that occur between a receptor and ligand. For example, in some embodiments, a ligand binding assay is used to determine the extent of binding of a ligand molecule (e.g., CLEC2D) to a receptor (e.g., CD161). In some embodiments, a ligand binding assay comprises detecting the formation of a complex between a ligand and a receptor. In some embodiments, to determine the extent of ligand binding to a receptor, a ligand binding assay comprises determining the dissociation of a ligand: receptor complex. In some embodiments, the formation and/or dissociation of a ligand: receptor complex is determined by detection of a fluorescently-labeled ligand in complex with a receptor. In some embodiments, the formation and/or dissociation of a ligand: receptor complex is determined by detection and/or quantification of an amount of fluorescently-labeled receptor in complex with a ligand. In some embodiments, the formation and/or dissociation of a ligand: receptor complex is determined by detection and/or quantification of an amount of a fluorescently-labeled antibody that specifically binds to the ligand: receptor complex. Methods of detecting and quantifying fluorescence are known in the art and include, but are not limited to, fluorescence polarization (FP), fluorescence anisotropy (FA), flow cytometry and microscopy. In some embodiments, the formation and/or dissociation of a ligand: receptor complex is determined by detection and/or quantification of an amount of a radioactively-labeled ligand in complex with a receptor. In some embodiments, the formation and/or dissociation of a ligand: receptor complex is determined by detection and/or quantification of an amount of radioactively-labeled receptor in complex with a ligand. In some embodiments, the formation and/or dissociation of a ligand: receptor complex is determined by detection and/or quantification of an amount of a radioactively-labeled antibody that specifically binds to the ligand: receptor complex.

In some embodiments, an antibody of the present disclosure (e.g., an anti-CD161 antibody) binds to a receptor (e.g., CD161) and disrupts, inhibits, or blocks the formation of ligand: receptor complex (e.g., a CD161:CLEC2D complex).

9.1.3 Competition Assays

Assays for measuring competition between two antibodies, or an antibody and another molecule (e.g., one or more ligands of CD161) are well-known in the art, for example, in Harlow and Lane (1988) ANTIBODIES: A LABORATORY MANUAL CH. 14, Cold Spring Harbor Laboratory, Cold Spring Harbor, N.Y, incorporated by reference in its entirety.

9.1.4 Epitope Mapping Assays

CD161 antibodies described herein are characterized by epitope binding on CD161. In some embodiments, the binding epitope of each CD161 antibody on CD161 ligand is determined by surface plasmon resonance, e.g., using a Biacore 8K instrument. Assays for mapping the epitopes to which the antibodies provided herein bind are described, for example, in Morris (1996) "Epitope Mapping Protocols," in METHODS IN MOLECULAR BIOLOGY, vol. 66, Humana Press, Totowa, N.J., incorporated by reference in its entirety. In some embodiments, the epitope is determined by peptide competition. In some embodiments, the epitope is determined by mass spectrometry. In some embodiments, the epitope is determined by crystallography (e.g., x-ray crystallography). A crystal structure of a bonded antibody-antigen pair enables very accurate determination of key interactions between individual amino acids from both side chains and main chain atoms in both the epitope of the antigen and the paratope of the antibody. Amino acids that are within 4 angstroms (Å) of each other are generally considered to be contacting residues. The methodology typically involves purification of antibody and antigen, formation and purification of the complex, followed by successive rounds of crystallization screens and optimization to obtain diffraction-quality crystals. Structural solution is obtained following x-ray crystallography frequently at a synchrotron source. Accordingly, the anti-CD161 antibodies or antigen-binding portions thereof provided by the disclosure may be assessed through x-ray crystallographic analysis of a crystal structure comprising an antibody bound to human CD161, or a fragment or portion thereof. In some aspects, the epitopes that are bound by the antibodies provided by the disclosure are identified by determining the residues on the human CD161 antigen that reside or are located within 4 angstroms (Å) of an antibody paratope residue. Other structural methods for epitope mapping include, but are not limited to, hydrogen-deuterium exchange coupled to mass spectrometry, crosslinking-coupled mass spectrometry, and nuclear magnetic resonance (NMR) (see, e.g., Morris (1996), supra; Abbott et al. (2014) IMMUNOLOGY, 142(4): 526-535).

Functional methods for epitope mapping are well known in the art and typically involve an assessment or quantification of antibody binding to whole proteins, protein fragments or peptides. Functional methods for epitope mapping can be used, for example, to identify linear or conformational epitopes and/or can be used to infer when two or more distinct antibodies bind to the same or similar epitopes. Functional methods for epitope mapping include, for example, immunoblotting assays, immunoprecipitation assays, and fluorescence-based labeling assays, wherein overlapping or contiguous peptides from CD161 are tested for reactivity with an anti-CD161 antibody (e.g., HP-3G10). Other functional methods for epitope mapping include array-based oligopeptide scanning (alternatively known as "overlapping peptide scanning" or "pepscan analysis"), site-directed mutagenesis (e.g., alanine-scanning mutagenesis), and high-throughput mutagenesis mapping (e.g., shotgun mutagenesis mapping).

In some embodiments, the epitope bound by an anti-CD161 antibody described herein is determined using site-directed mutagenesis or alanine scanning mutagenesis. The site-directed mutagenesis method involves targeted site-directed mutagenesis where critical amino acids are identified by systematically introducing substitutions along the protein sequence and then determining the effects of each substitution on antibody binding. This may be done by "alanine scanning mutagenesis" (Cunningham and Wells (1989) SCIENCE, 244: 1081-085), or some other form of point mutagenesis of amino acid residues in CD161. As described herein, alanine scanning is a technique that involves the substitution of an alanine residue for a wild-type residue in a polypeptide, followed by an assessment of the stability or function(s) (e.g., binding affinity) of the alanine-substituted derivative or mutant polypeptide and comparison to the wild-type polypeptide. Without being bound by theory, two or more antibodies (e.g., a test antibody and a reference antibody) have the same epitope if essentially all amino acid mutations in the antigen that reduce or eliminate binding of the first antibody reduce or eliminate binding of the second or more antibodies. In some embodiments, the epitope bound by an anti-CD161 antibody described herein is determined using shotgun mutagenesis. Shotgun mutagenesis mapping utilizes a comprehensive plasmid-mutation library for the target gene, with each clone in the library bearing a unique amino acid mutation and the entire library covering every amino acid in the target protein. The clones that constitute the mutation library are individually arranged in microplates, expressed within living mammalian cells, and tested for immunoreactivity with antibodies of interest. Amino acids critical for antibody epitopes are identified by a loss of reactivity and are then mapped onto a protein structure to visualize epitopes. Expression of the target protein antigen within mammalian cells often provides the native structure of the target protein antigen, which allows both linear and conformational epitope structures to be mapped on complex proteins. (Paes et al. (2009) J. AM. CHEM. SOC., 131(20): 6952-6954; Banik and Doranz (2010) GENETIC ENGINEERING AND BIOTECHNOLOGY NEWS, 3(2): 25-28).

In some embodiments, the epitope bound by an anti-CD161 antibody described herein is determined using peptide scanning methods. In peptide scanning, libraries of short peptide sequences from overlapping segments of the target protein (e.g., CD161) are tested for their ability to bind antibodies of interest. The peptides are synthesized and screened for binding, e.g. using ELISA or BIACORE, or on a chip, by any of the multiple methods for solid-phase screening (Reineke et al. (2001) CURR. OPIN. BIOTECHNOL., 12: 59-64, ) as in the "pepscan" methodology (WO1984/03564; WO1993/09872, each of which is incorporated by reference in its entirety). Conformation epitopes may be identified via chemical linkage of peptides onto scaffolds (CLIPS). The loose ends of the peptides are affixed onto synthetic scaffolds, so that the scaffolded peptide may be able to adopt the same spatial structure as the corresponding sequence in the intact protein. CLIPS technology is used to fix linear peptides into cyclic structures ('single-loop' format), and to bring together different parts of a protein binding site ('double-loop', 'triple-loop', etc. format), so as to create conformational epitopes that may be assayed for antibody binding. (U.S. Pat. No. 7,972,993). The epitopes bound by antibodies provided by the disclosure may also be mapped using computational methods. In these methods, for example, libraries of peptide fragments are displayed on the surface of the phage or cell. Epitopes are then mapped by screening antibodies against these fragments using selective binding assays. A number of computational tools have been developed which allow the prediction of conformational epitopes based upon linear affinity-selected peptides obtained using phage display (Mayrose et al. (2007) BIOINFORMATICS, 23: 3244-3246). Methods are also available for the detection of conformational epitopes by phage display. Microbial display systems may also be used to express properly folded antigenic fragments on the cell surface for identification of conformational epitopes (Cochran et al. (2004) J. IMMUNOL. METH., 287: 147-158; Rockberg et al. (2008) NATURE METHODS, 5: 1039-1045). Methods involving proteolysis and mass spectroscopy may also be used to determine antibody epitopes (Baerga-Ortiz et al. (2002) PROTEIN SCI., 11(6): 1300-1308). In limited proteolysis, the antigen is cleaved by different proteases, in the presence and in the absence of the antibody, and the fragments are identified by mass spectrometry. The epitope is the region of the antigen that becomes protected from proteolysis upon binding of the antibody (Suckau et al. (1990) PROC. NATL. ACAD. SCI. USA, 87: 9848-9852). Additional proteolysis based methods include, for example, selective chemical modification (Fiedler et al. (1998) BIOCONJUGATE CHEMISTRY, 9(2): 236-234), epitope excision (Van de Water et al. (1997) CLIN. IMMUNOL. IMMUNOPATHOL., 85(3): 229-235), and the recently developed method of hydrogen-deuterium (H/D) exchange (Flanagan, N. (2010) GENETIC ENGINEERING AND BIOTECHNOLOGY NEWS 3(2): 25-28).

9.1.5 Assays for Effector Functions

In some embodiments, an anti-CD161 antibody as described herein binds to CD161 and induces or promotes activation of immune cell effector function, wherein the immune cell is any CD161-expressing immune cell, or wherein the immune cell is a CD161-expressing T cell, a CD161-expressing NK cell, or a combination thereof. In some embodiments, an anti-CD161 antibody as described herein binds to CD161 and induces or promotes activation, proliferation, cytokine production, cytolytic function or any combination thereof of a CD161-expressing T cell or a CD161-expressing NK cell. In some embodiments, an anti-CD161 antibody as described herein activates a mucosal-associated invariant T cell (MAIT cell). In some embodiments, the anti-CD161 antibody of the present disclosure activates a MAIT cell by CD161 blockade. In some embodiments, an anti-CD161 antibody as described herein binds to CD161 and induces or promotes T cell activation, a cytotoxic T lymphocyte (CTL) response, T cell proliferation, cytokine production, or a combination thereof.

In some embodiments, an anti-CD161 antibody as described herein binds to and competes with or blocks CD161 binding to CLEC2D. In some embodiments, blocking of CD161 is measured by determining ligand (e.g., CLEC2D) binding. In some embodiments, an anti-CD161 antibody as described herein binds to CD161 on a CD161-expressing T cell or a CD161-expressing NK cell and induces or promotes activation of the T cell or NK cell immune cell effector function in the presence of CLEC2D.

In some embodiments, activation of a CD161-expressing NK cell is determined by adding an anti-CD161 antibody to a culture of CD161-expressing NK cells in the presence of CLEC2D. In some embodiments, the CLEC2D ligand is expressed in human cancer cells co-cultured with the NK cells. Activation of human NK cells can be measured by CD107a expression of NK cells after exposure to an anti-CD161 antibody, e.g., in a dose-dependent manner. Activation of human NK cells can be measured by IFNγ secretion after exposure to an anti-CD161 antibody, e.g., in a dose-dependent manner. In some embodiments, the CD161 antibody effectiveness to block inhibitory signaling in human NK cells in the presence of CLEC2D is provided as an $EC_{50}$ (nM) value, for example, as determined in Example 7. In some embodiments, the $EC_{50}$ value for CD161 antibody activation or blocking of human NK cells in the presence of CLEC2D is between 0.04 nM and 0.38 nM.

In some embodiments, activation of a CD161-expressing T cell is determined by adding an anti-CD161 antibody to a culture of CD161-expressing T cells in the presence of CLEC2D. In some embodiments, the CLEC2D ligand is expressed in human cancer cells co-cultured with the T cells. In some embodiments, T cell activation is measured using an NFAT-Luciferase reporter gene system (InvivoGen) in engineered T cells. In some embodiments, the anti-CD161 effectiveness to block inhibitory signaling in T cells in the presence of CLEC2D is provided as described, for example, in Examples 8 and 9. In some embodiments, the $EC_{50}$ value for CD161 antibody activation or blocking of human T cells in the presence of CLEC2D is between 1.5 nM and 4.1 nM.

In some embodiments, the antibody of the present disclosure reverses CLEC2D-mediated inhibition and restores primary NK cell and T cell functions, as well as enhanced T cell recall response to antigen and direct T cell mediated cytotoxicity in a TCR-dependent manner. In some embodiments, the antibody disclosed herein reverses inhibition of NK cell killing by blocking the interaction of CD161 on NK cells with CLEC2D on target cells as described, for example, in Example 13. In certain embodiments, the antibody restores cytotoxic degranulation by NK cells, as well as expression of IFNγ. In certain embodiments, restoration of NK cell activation can be measured by CD107a expression of NK cells after exposure to an anti-CD161 antibody, e.g., in a dose-dependent manner. Activation of human NK cells can be measured by IFNγ secretion after exposure to an anti-CD161 antibody, e.g., in a dose-dependent manner.

In some embodiments, the antibody disclosed herein enhances NK cell killing of CLEC2D expressing target cells. In certain embodiments, the antibody disclosed herein enhances NK cell killing of CLEC2D expressing target cells by blocking the interaction of CD161 on NK cells with CLEC2D on target cells as described, for example in Example 14.

In some embodiments, the antibody disclosed herein enhances re-activation of antigen specific effector memory CD4 T cells by blocking CD161 (expressed on T cells) interaction with CLEC2D (expressed on monocyte-derived DCs) as described, for example in Example 15. In some embodiments, the antibody results in enhanced cytokine production and increased proliferation (e.g., as measured by Ki-67 expression) by antigen-specific effector memory T (EM cells). In some embodiments, the antibody disclosed herein enhances the cytokine production of MART-1-specific T cells as described, for example in Example 16. In some embodiments, the antibody disclosed herein enhances the production of interferon gamma (IFNγ), interleukin-2 (IL-2) and tumor necrosis factor alpha (TNFα) from CD8+ T cells, e.g., in a concentration-dependent manner. In some embodiments, the antibody of the present disclosure enhances cytotoxicity function of MART-1 specific T cells as described, for example in Example 17. In some embodiments, the antibody of the present disclosure increases the frequency of Granzyme B producing T cells, e.g., in a concentration-dependent manner.

In some embodiments, antibody of the present disclosure did not induce cytokine release in unstimulated human PBMCs from healthy donors (e.g., cytokine release syndrome).

Effector function assays using a variety of in vitro and in vivo assays known in the art, including those described in Ravetch and Kinet (1991) ANNU. REV. IMMUNOL., 9: 457-492; U.S. Pat. Nos. 5,500,362, 5,821,337; Hellstrom et al. (1986) PROC. NAT'L ACAD. SCI. USA, 83: 7059-7063; Hellstrom et al. (1985) PROC. NAT'L ACAD. SCI. USA, 82:1499-1502; Bruggemann et al. (1987) J. EXP. MED., 166: 1351-1361; Clynes et al. (1998) PROC. NAT'L ACAD. SCI. USA, 95: 652-656; WO2006/029879; WO2005/100402; Gazzano-Santoro et al. (1996) J. IMMUNOL. METHODS, 202: 163-171; Cragg et al. (2003) BLOOD, 101: 1045-1052; Cragg et al. (2004) BLOOD, 103: 2738-2743; and Petkova et al. (2006) INT'L. IMMUNOL., 18: 1759-1769; each of which is incorporated by reference in its entirety.

10. Pharmaceutical Compositions

For therapeutic use, an antibody or antigen binding fragment thereof or antibody conjugate preferably is combined with a pharmaceutically acceptable carrier. The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to buffers, carriers, and excipients suitable for use in contact with the tissues of human beings and animals without excessive toxicity, irritation, allergic response, or other problem or complication, commensurate with a reasonable benefit/risk ratio. Pharmaceutically acceptable carriers include any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin (1975) REMINGTON'S PHARMACEUTICAL SCIENCES, 15TH ED., Mack Publ. Co., Easton, PA. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

In certain embodiments, a pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants (see, e.g, REMINGTON'S PHARMACEUTICAL SCIENCES, 18th ed. (Mack Publishing Company, 1990) and Adeboye Adejare, REMINGTON: THE SCIENCE AND PRACTICE OF PHARMACY (23d ed. 2020)).

In certain embodiments, a pharmaceutical composition may contain nanoparticles, e.g., polymeric nanoparticles, liposomes, or micelles (see Anselmo et al. (2016) BIOENG. TRANSL. MED., 1: 10-29).

In certain embodiments, a pharmaceutical composition may contain a sustained- or controlled-delivery formulation. Techniques for formulating sustained- or controlled-delivery means, such as liposome carriers, bio-erodible microparticles or porous beads and depot injections, are also known to those skilled in the art. Sustained-release preparations may include, e.g., porous polymeric microparticles or semipermeable polymer matrices in the form of shaped articles, e.g., films, or microcapsules. Sustained release matrices may include polyesters, hydrogels, polylactides, copolymers of L-glutamic acid and gamma ethyl-L-glutamate, poly (2-hydroxyethyl-methacrylate), ethylene vinyl acetate, or poly-D (−)-3-hydroxybutyric acid. Sustained release compositions may also include liposomes that can be prepared by any of several methods known in the art.

Pharmaceutical compositions containing an antibody or antigen binding fragment thereof, or an antibody conjugate disclosed herein can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. In certain embodiments, an antibody, or antigen binding fragment thereof, or an antibody conjugate disclosed herein is administered by IV infusion. In certain embodiments, an antibody or antigen binding fragment thereof, or an antibody conjugate disclosed herein is administered by intratumoral injection. Useful formulations can be prepared by methods known in the pharmaceutical art (see, e.g., REMINGTON'S PHARMACEUTICAL SCIENCES, 18th ed. (Mack Publishing Company, 1990) and Adeboye Adejare, REMINGTON: THE SCIENCE AND PRACTICE OF PHARMACY (23d ed. 2020)). Formulation components suitable for parenteral administration include a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor EL™ (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (e.g., glycerol, propylene glycol, and liquid polyethylene glycol), and suitable mixtures thereof.

In certain embodiments, a pharmaceutical composition may contain a stabilizing agent. In certain embodiments, the stabilizing agent is a cation, such as a divalent cation. In certain embodiments, the cation is calcium or magnesium. The cation can be in the form of a salt, such as calcium chloride ($CaCl_2$) or magnesium chloride ($MgCl_2$).

In certain embodiments, the stabilizing agent is present in an amount from about 0.05 mM to about 5 mM. For example, the stabilizing agent may be present in an amount of from about 0.05 mM to about 4 mM, from about 0.05 mM to about 3 mM, from about 0.05 mM to about 2 mM, from about 0.05 mM to about 1 mM, from about 0.05 mM to about 0.5 mM, from about 0.5 mM to about 4 mM, from about 0.5 mM to about 3 mM, from about 0.5 mM to about 2 mM, from about 0.5 mM to about 1 mM, from about 1 mM to about 4 mM, from about 1 mM to about 3 mM, of from about 1 mM to about 2 mM.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The compositions described herein may be administered locally or systemically. Administration will generally be parenteral administration. In a preferred embodiment, the pharmaceutical composition is administered subcutaneously and in an even more preferred embodiment intravenously. Preparations for parenteral administration include sterile aqueous or non-aqueous solutions, suspensions, and emulsions.

Generally, a therapeutically effective amount of active component, for example, an antibody, is in the range of about 0.1 mg/kg to about 100 mg/kg, e.g., about 1 mg/kg to about 100 mg/kg, about 1 mg/kg to about 10 mg/kg. The amount administered will depend on variables such as the weight of the patient, the type and extent of disease or indication to be treated, the overall health of the patient, the in vivo potency of the antibody, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from about 0.1 mg/kg to about 20 mg/kg. Dosing frequency can vary depending on factors such as route of administration, dosage amount, serum half-life of the antibody, and the disease being treated. Exemplary dosing frequencies are once per day, once per week, once every two weeks, once every three weeks. A preferred route of administration is parenteral, e.g., intravenous infusion. In certain embodiments, an antibody is lyophilized, and then reconstituted in buffered saline, at the time of administration. In certain embodiments, a starting dose of 6 mg (0.1 mg/kg based on a 60 kg patient weight) of the anti-CD161 antibody is administered (e.g., via IV) once every three weeks.

11. Dosage and Unit Dosage Forms

In human therapeutics, the doctor will determine the posology which he or she considers most appropriate according to a preventive or curative treatment and according to the age, weight, condition and other factors specific to the subject to be treated. In certain embodiments, a composition provided herein is a pharmaceutical composition or a single unit dosage form. Pharmaceutical compositions and single unit dosage forms provided herein comprise a therapeutically effective amount of one or more therapeutic antibodies.

The amount of the antibody which will be effective in the prevention or treatment of a disorder or one or more symptoms thereof can vary with the nature and severity of the disease or condition, and the route by which the antibody is administered. The frequency and dosage can also vary according to factors specific for each subject depending on the specific therapy (e.g., a therapeutic or prophylactic) administered, the severity of the disorder, disease, or condition, the route of administration, as well as age, body, weight, response, and the past medical history of the subject. Effective doses may be extrapolated from dose-response curves derived from in vitro or animal model test systems.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies or ADCs provided herein are also encompassed by the dosage amounts and dose frequency schedules provided herein. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

As discussed in more detail elsewhere in this disclosure an antibody provided herein may optionally be administered with one or more additional agents useful to prevent or treat a disease or disorder. The effective amount of such additional agents may depend on the amount of agent present in the formulation, the type of disorder or treatment, and the other factors known in the art or described herein.

12. Therapeutic Applications

It is contemplated that an antibody disclosed herein can be administered to a mammal, generally a human, in a pharmaceutically acceptable dosage form via one or more of the administrations approaches described herein.

Any antibody described herein may be used to treat any disease or condition associated with CD161. It is contemplated that the agents described herein can be used in the treatment of cancer which may be achieved by administering to the subject an effective amount of an immunotherapy (e.g., an anti-CD161 antibody) disclosed herein. It is also contemplated that the agents described herein can be used to treat an autoimmune disorder, which may be achieved by administering to the subject an effective amount of an anti-CD161 antibody disclosed herein.

The present disclosure provides a method of treating cancer in a subject in need thereof, the method comprising administering to the subject an effective amount of an immunotherapy (e.g., an anti-CD161 antibody) disclosed herein or an effective amount of the pharmaceutical composition disclosed herein. In some embodiments, the present disclosure provides a method of treating cancer in a subject in need thereof, the method comprising administering to the subject an effective amount of the anti-CD161 antibody disclosed herein or an effective amount of the pharmaceutical composition disclosed herein. In some embodiments, the cancer is characterized by expression of CLEC2D by cancer cells or other cells in the tumor microenvironment. In some embodiments, the cancer is characterized by an increased expression of CLEC2D by cancer cells or other cells in the tumor microenvironment.

Any suitable cancer may be treated with the agents disclosed herein. Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodysplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung cancer (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma and metastatic Merkel cell carcinoma (MCC)).

In certain embodiments, the cancer is lymphoma. In certain embodiments, the cancer is head and neck squamous cell carcinoma (HNSCC). In certain embodiments, the cancer is non-small cell lung cancer (NSCLC). In certain embodiments, the cancer is hepatocellular carcinoma (HCC). In certain embodiments, the cancer is triple-negative breast cancer (TNBC). In certain embodiments, the cancer is melanoma. In certain embodiments, the cancer is glioblastoma. In certain embodiments, the cancer is colorectal cancer. In certain embodiments, the cancer is liver cancer. In some embodiments, the cancer is cervical cancer. In certain embodiments, the cancer is prostate cancer. In certain embodiments, the cancer is renal cancer. In certain embodiments, the cancer is lung adenocarcinoma. In certain embodiments, the cancer is glioma. In certain some embodiments, the cancer is lung cancer. In certain embodiments, the cancer is bladder cancer. In certain embodiments, the cancer is colon adenocarcinoma. In certain embodiments, the cancer is kidney cancer.

In certain embodiments, the cancers that can benefit from CD161 blockade immunotherapy are cancers with high density of $CLEC2D^+$ and $CD161^+$ cells, as identified using immunofluorescence data. In certain embodiments, the cancer is a cancer with high density of $CLEC2D^+$ and $CD161^+$ cells. In certain embodiments, the cancer is diffuse large B cell lymphoma (DLBCL), follicular lymphoma, Hodgkin's lymphoma, and T cell lymphomas including peripheral T cell lymphoma—not otherwise specified (PTCL-NOS), NK/T cell lymphoma, anaplastic large cell lymphoma (ALCL). In certain embodiments, the cancer is a non-small cell lung cancer (NSCLC) e.g., NSCLC-squamous cell carcinoma or NSCLC-adenocarcinoma, head and neck squamous cell carcinoma (HNSCC), triple negative breast cancer (TNBC), or cutaneous squamous cell carcinoma.

Under certain circumstances, the cancer is selected from the group consisting of: melanoma, lung, glioma, colorectal, and liver.

In addition, the present disclosure provides a method for reducing or inhibiting tumor growth in a subject in need thereof, the method comprising administering to the subject an effective amount of the anti-CD161 antibody disclosed herein or an effective amount of the pharmaceutical composition disclosed herein.

The present disclosure also provides a method for inhibiting or blocking the interaction between human CD161 and CLEC2D in a subject in need thereof, the method comprising administering to the subject an effective amount of the anti-CD161 antibody disclosed herein or an effective amount of the pharmaceutical composition disclosed herein.

The present disclosure also provides a method for inducing or enhancing immune cell activation in a subject in need thereof, the method comprising administering to the subject, an effective amount of the anti-CD161 antibody disclosed herein or an effective amount of the pharmaceutical composition disclosed herein. In some embodiments, the immune cell activation occurs in a tumor microenvironment. In some embodiments, the immune cell is a T cell or a NK cell.

In some embodiments, the present disclosure provides a method for inducing or enhancing a cytotoxic T cell effector response in a subject in need thereof, the method comprising administering to the subject, an effective amount of the anti-CD161 antibody disclosed herein or an effective amount of the pharmaceutical composition disclosed herein. Depending upon the circumstances, the T cell effector response (i) is in a tumor microenvironment, (ii) is cytokine production (such as IL-2, TNFα, IFNγ, or a combination thereof), (iii) is secretion of granzyme B, or (iv) a combination of two or more of (i), (ii) and (iii).

In some embodiments, the present disclosure provides a method for reducing CD161 inhibitory signaling caused due to binding of CLEC2D to CD161. In some embodiments, the present disclosure provides a method for reducing suppression of T cell activity caused due to CLEC2D binding to CD161. In some embodiments, the present disclosure provides a method for reducing suppression of NK cell activity caused due to CLEC2D binding to CD161. In some embodiments, the present disclosure provides a method for increasing T cell activity in the presence of CLEC2D as compared to such T cell activity in the absence of the antibody or antigen-binding fragment thereof disclosed herein. In some embodiments, the present disclosure provides a method for increasing NK cell activity in the presence of CLEC2D as compared to such NK cell activity in the absence of the antibody or antigen-binding fragment thereof disclosed herein. In some embodiments, the present disclosure provides a method for increasing T cell activity disposed within a microenvironment comprising cells expressing CLEC2D. In some embodiments, the present disclosure provides a method for increasing NK cell activity disposed within a microenvironment comprising cells expressing CLEC2D. In some embodiments, the present disclosure provides a method for increasing T cell activity in a tumor microenvironment comprising tumor cells that express CLEC2D. In some embodiments, the present disclosure provides a method for increasing NK cell activity in a tumor microenvironment comprising tumor cells that express CLEC2D. In some embodiments, the present disclosure provides a method for inhibiting human T cell exhaustion. In some embodiments, the present disclosure provides a method for inducing or increasing activation of a CD161-expressing human T cell in response to an antigen-expressing target cell. In some embodiments, the present disclosure provides a method for inducing or increasing cytokine production by a CD161-expressing human T cell in response to an antigen-expressing target cell. In some embodiments, the present disclosure provides a method for inducing or increasing granzyme B expression by a CD161-expressing human T cell in response to an antigen-expressing target cell. In some embodiments, the present disclosure provides a method for reducing exhaustion of CD161-expressing human T cells in response to antigen-expressing target cells.

In certain embodiments, provided herein is a method of delaying the onset of a cancer in a subject in need thereof by administering to a subject an effective amount of an immunotherapy (e.g., an immunotherapeutic agent) disclosed herein (e.g., an anti-CD161 antibody or an antigen binding fragment thereof or an antibody conjugate). In certain embodiments, provided herein is a method of preventing the onset of a cancer in a subject in need thereof by administering to the subject an effective amount of an agent disclosed herein. In some embodiments, provided herein is a method of reducing the size of a tumor in a subject in need thereof by administering to the subject an effective amount of an agent disclosed herein. In certain embodiments, provided herein is a method of reducing the number of metastases in a subject in need thereof by administering to the subject an effective amount of an of an agent disclosed herein. In certain embodiments, provided herein is a method for extending the period of overall survival, median survival time, or progression-free survival in a subject in need thereof by administering to the subject of an agent disclosed herein. In certain embodiments, provided herein is a method for treating a subject who has become resistant to a standard of care therapeutic by administering to subject an effective amount of an of an agent disclosed herein.

13. Combination Therapies

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, a method or composition described herein, is administered in combination with one or more additional therapies, e.g., surgery, radiation therapy, or administration of another therapeutic preparation. In certain embodiments, the additional therapy may include chemotherapy, e.g., a cytotoxic agent. In certain embodiments the additional therapy may include a targeted therapy, e.g. a tyrosine kinase inhibitor, a proteasome inhibitor, or a protease inhibitor. In certain embodiments, the additional therapy may include an anti-inflammatory, anti-angiogenic, anti-fibrotic, or anti-proliferative compound, e.g., a steroid, a biologic immunomodulator, a monoclonal antibody, an antibody fragment, an aptamer, an siRNA, an antisense molecule, a fusion protein, a cytokine, a cytokine receptor, a bronchodilator, a statin, an anti-inflammatory agent (e.g. methotrexate), or an NSAID. In certain embodiments, the additional therapy may include a combination of therapeutics of different classes.

In certain embodiments, a method or composition described herein is administered in combination with a second checkpoint inhibitor. The checkpoint inhibitor may, for example, be selected from a PD-1 antagonist, a second PD-L1 antagonist, CTLA-4 antagonist, adenosine A2A receptor antagonist, B7-H3 antagonist, B7-H4 antagonist, BTLA antagonist, KIR antagonist, LAG3 antagonist, TIM-3 antagonist, VISTA antagonist or TIGIT antagonist.

In certain embodiments, the checkpoint inhibitor is a PD-1 or a second PD-L1 inhibitor. PD-1 is a receptor present on the surface of T cells that serves as an immune system checkpoint that inhibits or otherwise modulates T cell activity at the appropriate time to prevent an overactive immune response. Cancer cells, however, can take advantage of this checkpoint by expressing ligands, for example, PD-L1, that interact with PD-1 on the surface of T cells to shut down or modulate T cell activity. Exemplary PD-1/PD-L1 based immune checkpoint inhibitors include antibody based therapeutics. Exemplary treatment methods that employ PD-1/PD-L1 based immune checkpoint inhibition are described in U.S. Pat. Nos. 8,728,474 and 9,073,994, and EP Patent No. 1537878B1, and, for example, include the use of anti-PD-1 antibodies. Exemplary anti-PD-1 antibodies are described, for example, in U.S. Pat. Nos. 8,952,136, 8,779,105, 8,008,449, 8,741,295, 9,205,148, 9,181,342, 9,102,728, 9,102,727, 8,952,136, 8,927,697, 8,900,587, 8,735,553, and 7,488,802. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies are described, for example, in U.S. Pat. Nos. 9,273,135, 7,943,743, 9,175,082, 8,741,295, 8,552,154, and 8,217,149. Exemplary anti-PD-L1 antibodies include, atezolizumab (Tecentriq®, Genentech), durvalumab (AstraZeneca), MEDI4736, avelumab, and BMS 936559 (Bristol Myers Squibb Co.).

In certain embodiments, a method or composition described herein is administered in combination with a CTLA-4 inhibitor. In the CTLA-4 pathway, the interaction of CTLA-4 on a T cell with its ligands (e.g., CD80, also known as B7-1, and CD86) on the surface of an antigen presenting cells (rather than cancer cells) leads to T cell inhibition. Exemplary CTLA-4 based immune checkpoint inhibition methods are described in U.S. Pat. Nos. 5,811,097, 5,855,887, 6,051,227. Exemplary anti-CTLA-4 antibodies are described in U.S. Pat. Nos. 6,984,720, 6,682,736, 7,311,910; 7,307,064, 7,109,003, 7,132,281, 6,207,156, 7,807,797, 7,824,679, 8,143,379, 8,263,073, 8,318,916, 8,017,114, 8,784,815, and 8,883,984, International (PCT) Publication Nos. WO1998/42752, WO2000/37504, and WO2001/14424, and European Patent No. EP 1212422 B1, each of which is incorporated by reference in its entirety. Exemplary CTLA-4 antibodies include ipilimumab or tremelimumab.

In certain embodiments, a method or composition described herein is administered in combination with a CTLA-4 inhibitor, e.g., a CTLA-4 inhibitor disclosed herein.

In certain embodiments, a method or composition described herein is administered in combination with an IDO inhibitor. Exemplary IDO inhibitors include 1-methyl-D-tryptophan (known as indoximod), epacadostat (INCB24360), navoximod (GDC-0919), and BMS-986205.

Exemplary cytotoxic agents that can be administered in combination with a method or composition described herein include, for example, antimicrotubule agents, topoisomerase inhibitors, antimetabolites, protein synthesis and degradation inhibitors, mitotic inhibitors, alkylating agents, platinating agents, inhibitors of nucleic acid synthesis, histone deacetylase inhibitors (HDAC inhibitors, e.g., vorinostat (SAHA, MK0683), entinostat (MS-275), panobinostat (LBH589), trichostatin A (TSA), mocetinostat (MGCD0103), belinostat (PXD101), romidepsin (FK228, depsipeptide)), DNA methyltransferase inhibitors, nitrogen mustards, nitrosoureas, ethylenimines, alkyl sulfonates, triazenes, folate analogs, nucleoside analogs, ribonucleotide reductase inhibitors, *vinca* alkaloids, taxanes, epothilones, intercalating agents, agents capable of interfering with a signal transduction pathway, agents that promote apoptosis and radiation, or antibody molecule conjugates that bind surface proteins to deliver a toxic agent. In one embodiment, the cytotoxic agent that can be administered with a method or composition described herein is a platinum-based agent (such as cisplatin), cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes (e.g., paclitaxel or docetaxel), cytochalasin B, gramicidin D, ethidium bromide, emetine, mitomycin, etoposide, tenoposide, vincristine, vinblastine, vinorelbine, colchicin, anthracyclines (e.g., doxorubicin or epirubicin) daunorubicin, dihydroxy anthracin dione, mitoxantrone, mithramycin, actinomycin D, adriamycin, 1-dehydrotestosterone, glucocorticoids, procaine, tetracaine, lidocaine, propranolol, puromycin, ricin, or maytansinoids.

The invention also provides a method of increasing the expression of HLA-DR, CD86, CD83, IFNγ, IL-1b, IL-6, TNFα, IL-17A, IL-2, or IL-6 in a cell, tissue, or subject. The method comprises contacting the cell, tissue, or subject with an effective amount of an antibody, fusion protein, and/or antibody conjugate, e.g., an antibody, fusion protein, or antibody conjugate disclosed herein. In certain embodiments, the cell is selected from a dendritic cell and a peripheral blood mononuclear cell (PBMC).

In certain embodiments, expression of HLA-DR, CD86, CD83, IFNγ, IL-1b, IL-6, TNFα, IL-17A, IL-2, or IL-6 in the cell, tissue, or subject is increased by at least about 10%, at least about 20%, at least about 50%, at least about 75%, at least about 100%, at least about 150%, at least about 200%, at least about 250%, at least about 300%, at least about 400%, at least about 500%, at least about 600%, at least about 700%, at least about 800%, at least about 900%, or at least about 1,000%, relative to a similar or otherwise identical cell or tissue that has not been contacted with the antibody, fusion protein, or antibody conjugate. Gene expression may be measured by any suitable method known in the art, for example, by ELISA, or by Luminex multiplex assays.

The invention also provides a method of promoting infiltration of immune cells into a tumor in a subject in need thereof. The method comprises administering to the subject an effective amount of an antibody disclosed herein. In certain embodiments, the immune cells are T cells, e.g., CD4$^+$ and/or CD8$^+$ T cells, e.g., CD69$^+$CD8$^+$ and/or GzmB$^+$CD8$^+$ T cells. In certain embodiments, the immune cells are natural killer (NK) cells. In certain embodiments, the infiltration of immune cells into the tumor in the subject is increased by at least about 10%, at least about 20%, at least about 50%, at least about 75%, at least about 100%, at least about 150%, at least about 200%, at least about 250%, at least about 300%, at least about 400%, at least about 500%, at least about 600%, at least about 700%, at least about 800%, at least about 900%, or at least about 1,000%, relative to a similar or otherwise identical tumor and/or subject that has not received the agent. Infiltration of immune cells into a tumor may be measured by any suitable method known in the art, for example, antibody staining.

The invention also provides a method of increasing expression of Cd3, Cd4, Cd8, Cd274, Ctla4, Icos, Pdcd1, Lag3, Il6, Il1b, Il2, Ifng, Ifna1, Mx1, Gzmb, Cxcl9, Cxcl12, and/or Ccl5 in a cell, tissue, or subject. The method comprises contacting the cell, tissue, or subject with an effective amount of an antibody disclosed herein, so as to increase the expression of Cd3, Cd4, Cd8, Cd274, Ctla4, Icos, Pdcd1, Lag3, Il6, Il1b, Il2, Ifng, Ifna1, Mx1, Gzmb, Cxcl9, Cxcl12, and/or Ccl5 relative to the cell, tissue or subject prior to contact with such an agent. In certain embodiments, expression of Cd3, Cd4, Cd8, Cd274, Ctla4, Icos, Pdcd1, Lag3, Il6, Il1b, Il2, Ifng, Ifna1, Mx1, Gzmb, Cxcl9, Cxcl12, and/or Ccl5 in the cell, tissue, or subject is increased by at least about 10%, at least about 20%, at least about 50%, at least about 75%, at least about 100%, at least about 150%, at least about 200%, at least about 250%, at least about 300%, at least about 400%, at least about 500%, at least about 600%, at least about 700%, at least about 800%, at least about 900%, or at least about 1,000%, relative to a similar or otherwise identical cell, tissue, or subject that has not been contacted with such an agent. Gene expression may be measured by any suitable method known in the art, for example, by ELISA, Luminex multiplex assays, or Nanostring technology.

In certain embodiments, the cell effected by the treatment is tumor cell, dendritic cell (DC) or monocyte. In certain embodiments, the cell is a monocyte, and the method results in increased expression of an MHC-II molecule (e.g., HLA-DR) on the monocyte. In certain embodiments, expression of an MHC-II molecule in the cell or tissue is increased by at least about 10%, at least about 20%, at least about 50%, at least about 75%, at least about 100%, at least about 150%, at least about 200%, at least about 250%, at least about 300%, at least about 400%, at least about 500%, at least about 600%, at least about 700%, at least about 800%, at least about 900%, or at least about 1,000%, relative to a similar or otherwise identical cell or tissue that has not been contacted with such an agent. Gene expression may be measured by any suitable method known in the art, for example, by ELISA, by Luminex multiplex assays, or by flow cytometry.

14. Diagnostic Methods

Also provided are methods for detecting the presence of CD161 on cells from a subject. Such methods may be used, for example, to predict and evaluate responsiveness to treatment with an antibody disclosed herein.

In some embodiments, the method can be used to detect CD161 in a subject having or suspected of having a disease or condition. In some embodiments, the methods comprise (a) receiving a sample from the subject; and (b) detecting the presence or the level of CD161 in the sample by contacting the sample with an antibody disclosed herein. In certain embodiments, the disease or condition is a cancer. The antibody provided herein can be labeled with a detectable label, for example, a fluorescent label, radiolabel, or enzyme label.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention

EXAMPLES

The invention now being generally described, will be more readily understood by reference to the following examples, which are included merely for purposes of illustration of certain aspects and embodiments of the present invention, and is not intended to limit the invention.

Example 1—Generation of CD161 Antibodies

This example describes the generation of CD161 antibodies by Adimab™ yeast-based antibody presentation using the biotinylated recombinant CD161 proteins as screening antigens, as described below.

1. Recombinant Protein Production

Several recombinant proteins were produced to support antibody discovery and subsequent screening and characterization, comprising different forms of the extracellular domains (ECDs) of human and cynomolgus CD161 target and CLEC2D ligand. All proteins were produced by transient transfection of HEK293 cells (ThermoFisher Scientific). Proteins were produced with either a C-terminal or an N-terminal human IgG$_1$ Fc fusion domain to create a bivalent antigen. These proteins include:

(1) hCD161 ECD (Q67-S225)-hFc or hKLRB1 ECD (Q67-S225)-hFc—a human CD161 ECD (amino acid residues Q67-S225, Uniprot #Q12918) with a C-terminal human IgG$_1$ Fc domain; represented by SEQ ID NO: 173;

(2) cCD161 ECD (Q67-L227)-hFc or cKLRB1 ECD (Q67-L227)-hFc—a cynomolgus CD161 ECD (amino acid residues Q67-L227, Uniprot #AOA2K5WYI1) with a C-terminal human IgG$_1$ Fc domain; represented by SEQ ID NO: 176);

(3) hFc-hCD161 ECD (Q67-S225) or hFc-hKLRB1 ECD (Q67-S225)—a human CD161 ECD (amino acid residues Q67-S225, Uniprot #Q12918) with an N-terminal human IgG$_1$ Fc domain; represented by SEQ ID NO: 194;

(4) hCLEC2D ECD (L71-V191)-hFc or hLLT1 ECD (L71-V191)-hFc—a human CLEC2D ECD (amino acid residues L71-V191, Uniprot #Q9UHP7) with a C-terminal human IgG$_1$ Fc domain; represented by SEQ ID NO: 193); and (5) hFc-hCLEC2D ECD (L71-H176C-V191) or hFc-hLLT1 ECD(L71-H176C-V191)—a human CLEC2D ECD comprising an H176C mutation (amino acid residues L71-H176C-V191, Uniprot #Q9UHP7) with an N-terminal human IgG$_1$ Fc domain; represented by SEQ ID NO: 175. The mutation H176C introduced an additional disulfide bridge to increase the stability and homogeneity of the expressed protein.

Additionally, the following monovalent ECD proteins were produced:

(1) hCD161 ECD (Q67-S225)-6xHis—a human CD161 ECD (amino acid residues Q67-S225, Uniprot #Q12918) with a C-terminal 6xHis tag (SEQ ID NO: 197); represented by SEQ ID NO: 174;

(2) hFc-cyCD161 ECD (K68-C74A-S225) monomer—a cyno CD161 ECD comprising a C74A mutation (amino acid residues K68-C74A-S225) with an N-terminal Fc heterodimer fusion partner. This construct was created by co-transfecting HEK293 cells with two chains, one which consisted an N-terminal FLAG tag followed by the human IgG$_1$ Fc (represented by SEQ ID NO: 178) and the other chain contained N-terminal human IgG$_1$ Fc followed by cyno CD161 ECD (represented by SEQ ID NO: 177); and (3) cCD161-IHM or cKLRB1-IHM—This is an antigen format in which monomeric cyno KLRB1 Fc fusion protein was expressed as a murine IgG$_1$ fusion by pairing FLAG-murine IgG$_1$ Fc with cyno KLRB1 IgG$_1$ Fc.

Following transfection and harvest using standard methods, proteins containing Fc domains were purified by Protein A chromatography and proteins containing His tags were purified by Ni-NTA affinity chromatography. Polishing and removal of aggregates was done as needed using size-exclusion chromatography. For the cyno CD161 Fc monomer protein (cCD161-IHM or cKLRB1-IHM), an additional FLAG tag purification was used after Protein A purification in order to remove Fc homodimers lacking the CD161 domain; the desired heterodimers were then isolated using size-exclusion chromatography (see Brown M E et al. (2020) PLOS ONE 15(3): e0229206). The foregoing protein sequences are listed in TABLE 5, which summarizes recombinant proteins used for antibody discovery and screening.

TABLE 5

| | |
|---|---|
| hCD161 ECD (Q67-S225)-hFc | QKSSIEKCSVDIQQSRNKTTERPGLLNCPIYWQQLREKCLLFSHTVNPW NNSLADCSTKESSLLLIRDKDELIHTQNLIRDKAILFWIGLNFSLSEKNW KWINGSFLNSNDLEIRGDAKENSCISISQTSVYSEYCSTEIRWICQKELTP VRNKVYPDSGSGSDKTHTCPPCPAPELLGGPSVFLFPPKPKDTLMISRTP EVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDG SFFLYSKLTVDKSRWQQGNVFSCSVMHEALHNHYTQKSLSLSPGK (SEQ ID NO: 173) |
| hCD161 ECD (Q67-S225)-6xHis | QKSSIEKCSVDIQQSRNKTTERPGLLNCPIYWQQLREKCLLFSHTVNPW NNSLADCSTKESSLLLIRDKDELIHTQNLIRDKAILFWIGLNFSLSEKNW KWINGSFLNSNDLEIRGDAKENSCISISQTSVYSEYCSTEIRWICQKELTP VRNKVYPDSHHHHHH (SEQ ID NO: 174) |
| hFc-hCLEC2D ECD (L71-H176C-V191) | EPKSCDKTHTCPPCPAPELLGGPSVFLFPPKPKDTLMISRTPEVTCVVVD VSHEDPEVKFNWYVDGVEVHNAKTKPREEQYNSTYRVVSVLTVLHQD WLNGKEYKCKVSNKALPAPIEKTISKAKGQPREPQVYTLPPSRDELTKN QVSLTCLVKGFYPSDIAVEWESNGQPENNYKTTPPVLDSDGSFFLYSKL TVDKSRWQQGNVFSCSVMHEALHNHYTQKSLSLSPGKGGGGSLQAAC PESWIGFQRKCFYFSDDTKNWTSSQRFCDSQDADLAQVESFQELNFLLR YKGPSDHWIGLSREQGQPWKWINGTEWTRQFPILGAGECAYLNDKGAS SARCYTERKWICSKSDIHV (SEQ ID NO: 175) |
| cyCD161 ECD (Q67-L227)-hFc | QKPSIGKCSVDIQQNRTKTTERPDLLNCPIYWQQVQEKCLLFSHTVNPW NNSLADCSTKESSLLLIQDKDELTRTQNLIHDKAISFWIGLNFSLSEKN WKWINGSFLSSNDLKITGDAKENSCVYISQTSVYSEYCSTEMKWICQKE LTLVRNKVSPDSWLGSGSDKTHTCPPCPAPELLGGPSVFLFPPKPKDTL MISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVY TLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSP GK (SEQ ID NO: 176) |
| hFc-cyCD161 ECD (K68-C74A-S225) monomer | Chain 1:<br>EPKSCDKTHTCPPCPAPELLGGPSVFLFPPKPKDTLMISRTPEVTCVVV VDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELT KNQVSLTCLVKGFYPSDIAVEWESNGQPENNYKTTPPVLDSDGSFFLY SKLTVDKSRWQQGNVFSCSVMHEALHNHYTQKSLSLSPGKGGGGSKPS IGKCSVDIQQNRTKTTERPDLLNCPIYWQQVQEKCLLFSHTVNPWNNS LADCSTKESSLLLIQDKDELTRTQNLIHDKAISFWIGLNFSLSEKNWK WINGSFLSSNDLKITGDAKENSCVYISQTSVYSEYCSTEMKWICQKEL TLVRNKVSPDS (SEQ ID NO: 177)<br><br>Chain 2:<br>DYKDDDDKEPKSCDKTHTCPPCPAPELLGGPSVFLFPPKPKDTLMISRTP EVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDG SFFLYSKLTVDKSRWQQGNVFSCSVMHEALHNHYTQKSLSLSPGK (SEQ ID NO: 178) |
| hCLEC2D ECD (L71-V191)-hFc | LQAACPESWIGFQRKCFYFSDDTKNWTSSQRFCDSQDADLAQVESFQE LNFLLRYKGPSDHWIGLSREQGQPWKWINGTEWTRQFPILGAGECAYL NDKGASSARHYTERKWICSKSDIHVGSGDKTHTCPPCPAPELLGGPSV FLFPPKPKDTLMISRTPEVTCVVVDVSHEDPEVKFNWYVDGVEVHNAK TKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHN HYTQKSLSLSPGK (SEQ ID NO: 193) |

TABLE 5-continued

```
hFc-        EPKSCDKTHTCPPCPAPELLGGPSVFLFPPKPKDTLMISRTPEVTCVVV
hCD161      DVSHEDPEVKFNWYVDGVEVHNAKTKPREEQYNSTYRVVSVLTVLHQD
ECD (Q67-   WLNGKEYKCKVSNKALPAPIEKTISKAKGQPREPQVYTLPPSRDELTKN
S225)       QVSLTCLVKGFYPSDIAVEWESNGQPENNYKTTPPVLDSDGSFFLYSKL
            TVDKSRWQQGNVFSCSVMHEALHNHYTQKSLSLSPGKGGGGSQKSSIE
            KCSVDIQQSRNKTTERPGLLNCPIYWQQLREKCLLFSHTVNPWNNSLAD
            CSTKESSLLLIRDKDELIHTQNLIRDKAILFWIGLNFSLSEKNWKWING
            SFLNSNDLEIRGDAKENSCISISQTSVYSEYCSTEIRWICQKELTPVRN
            KVYPDS (SEQ ID NO: 194)
```

2. Antigen and Cell Line Preparation

Antigens (hKLRB 1 LCD (Q67-S225)-hFc; cKLRB 1 LCD (Q67-L227)-hFc; hFc-hKLRB1 LCD (Q67-S225); hLLT1 LCD (L71-V191)-hFc; cKLRB1-IHM; and hFc-hLLT1 ECD(L71-H176C-V191) were biotinylated using the EZ-Link Sulfo-NHS-Biotinylation Kit (Thermo Scientific, Cat #21425).

The antigens were concentrated to ~1 mg/mnL and buffer exchanged into PBS before addition of 1:7.5 molar ratio biotinylation reagent. The mixture was held at 4° C. overnight prior to another buffer exchange to remove free biotin in the solution. Biotinylation was confirmed through streptavidin sensor binding of the labeled proteins via ForteBio.

3. Library Interrogation and Selection Methodology for Isolation of Anti-CD161 Antibodies Naïve Library Selections Eight naïve human synthetic yeast libraries each of ~10$^9$ diversity were propagated as previously described (see, e.g., Xu et al. (2013) PROTEIN ENG. DES. SEL., 26(10): 663-70; WO2009/036379; WO2010/105256; and WO2012/009568), each of which is incorporated by reference in its entirety.

For the first two rounds of selection, a magnetic bead sorting technique utilizing the Miltenyi MACS system was performed, as previously described (see, e.g., Siegel et al., J. IMMUNOL. METHODS 286(1-2), 141-153 (2004)). Briefly, yeast cells (~10$^{10}$ cells/library) were incubated with biotinylated dimeric human CD161-Fc for 30 min at 24° C. in wash buffer (phosphate-buffered saline (PBS)/0.1% bovine serum albumin (BSA)). After washing once with 40 mL ice-cold wash buffer, the cell pellet was resuspended in 20 mL wash buffer, and Streptavidin MicroBeads (500 µL) were added to the yeast and incubated for 15 min at 4° C. Next the yeast were pelleted, resuspended in 5 mL wash buffer, and loaded onto a Miltenyi LS column. After the 5 mL were loaded, the column was washed 3 times with 3 mL wash buffer. The column was then removed from the magnetic field, and the yeast were eluted with 5 mL of growth media and then grown overnight.

The following rounds of selection were performed using flow cytometry (FACS). Yeast were pelleted, washed three times with wash buffer, and incubated at 24° C. with decreasing concentrations of biotinylated dimeric human CD161 (10 nM), monomeric human CD161 (500 nM to 4 nM) under equilibrium conditions, biotinylated dimeric cyno CD161 (5 nM), monomeric cyno CD161 (500 nM to 4 nM—in order to obtain species cross-reactivity), biotinylated dimeric human CLEC2D$_{H176C}$ (10 nM—to counter-select against this highly structurally similar CD161 ligand to obtain CD161-specificity), or with a polyspecificity reagent (PSR) to remove non-specific antibodies from the selection. For the PSR depletion, the libraries were incubated with a 1:10 dilution of biotinylated PSR reagent as previously described (see, e.g., Xu et al. (2013) PROTEIN ENG. DES. SEL., 26(10): 663-70.) Yeast were then washed twice with wash buffer and stained with goat F(ab')$_2$ anti-human kappa-FITC (LC-FITC) diluted 1:100 (Southern Biotech, Cat #2062-02) and either Streptavidin-AF633 (SA-633) diluted 1:500 (Life Technologies, Cat #S21375) or Extravidin-phycoerthyrin (EA-PE) diluted 1:50 (Sigma-Aldrich, Cat #E4011), secondary reagents for 15 min at 4° C. After washing twice with ice-cold wash buffer, the cell pellets were resuspended in 0.3 mL wash buffer and transferred to strainer-capped sort tubes. Sorting was performed using a FACS ARIA sorter (BD Biosciences) and sort gates were determined to select for antibodies with desired characteristics. Selection rounds were repeated until populations with all desired characteristics were obtained. After the final round of sorting, yeast were plated and individual colonies were picked for characterization.

Light Chain Batch Shuffle Diversification

Heavy chains from naïve output were used to prepare light chain diversification libraries used for additional selection rounds. Selections were performed on these libraries as described above, i.e., with one round of MACS and four rounds of FACS. In the different FACS selection rounds, the libraries were evaluated for, e.g., PSR binding, species cross-reactivity, and affinity pressure by antigen titration, and epitopic coverage using high affinity antibodies with diverse bins identified during the naïve selection. Sorting was performed to obtain populations with the desired characteristics. Individual colonies from each terminal FACS selection round were picked for sequencing and characterization.

Affinity Maturation

Optimization of parent clones was carried out utilizing three maturation strategies: light chain diversification; diversification of CDRH1 and CDRH2; and diversification of CDRH3, CDRL1, CDRL2, and CDRL3.

Light Chain Diversification: The heavy chain from clones selected from the naïve selection procedure were transformed into a light chain library with a diversity of 1×10$^6$. Selections were performed as described above with one round of MACS sorting and four rounds of FACS sorting using biotinylated dimeric or monomeric cyno CD161 antigen for respective rounds.

CDRH1 and CDRH2 Selection: The CDRH3s from clones selected from the light chain diversification procedure were recombined into a premade library with CDRH1 and CDRH2 variants of a diversity of 1×10$^8$ and selections were performed using monomeric human and cyno CD161 antigens. Affinity pressures were applied by using decreasing concentrations of biotinylated monomeric CD161 antigen (50 nM to 1 nM) under equilibrium conditions at room temperature and by preincubating the biotinylated antigen with parental Fab for 30 minutes and then applying that precomplexed mixture to the yeast library for lengths of time which would either allow the selection mixture to reach an equilibrium or favor increased associate rates. The higher affinity antibodies were then able to be sorted.

CDRH3, CDRL1, CDRL2, and CDRL3 selection: Oligonucleotides were purchased from IDT which encoded the CDRH3 and the CDRL3 as well as a flanking region on either side of the CDR3. Each oligonucleotide variegated one amino acid in the CDR3 via NNK diversity. The CDRH3 oligonucleotides were recombined with heavy chain FR1-FR3 variable regions containing selected variants from the CDRH1 and CDRH2 selections, and the CDRL3 was recombined into a premade library with CDRL1 and CDRL2 variants, for a combined library diversity of ~10'. Selections were performed similar to previous cycles using FACS sorting for four rounds. For each FACS round, the libraries were interrogated for PSR binding and affinity pressure, and sorting was performed in order to obtain populations with the desired characteristics. Affinity pressures for these selections were performed as described above in the CDRH1 and CDRH2 selection.

IgG and Fab Production and Purification

In order to produce sufficient amounts of selected antibodies (antibody variable domain sequences shown in TABLE 6) for further characterization, the yeast clones were grown to saturation and then induced for 48 hours at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect (GE Healthcare LifeSciences).

TABLE 6

| Antibody | Sequence |
|---|---|
| Ab1_VH | EVQLLESGGGLVQPGGSLRLSCAASGFAFSTYAMSWVRQAPGKGLEW VSAISAAGGTTYYADSVKGRFTISRDNSKNTLYLQMNSLRAEDTAVYY CAKPLDSSLWADFDLWGRGTLVTVSS (SEQ ID NO: 7) |
| Ab2_VH | EVQLLESGGGLVQPGGSLRLSCAASGFAFSTYAMSWVRQAPGKGLEW VSAISGVGGTTYYADSVKGRFTISRDNSKNTLYLQMNSLRAEDTAVYY CAKPLDSSLWADFDLWGRGTLVTVSS (SEQ ID NO: 15) |
| Ab3_VH | EVQLLESGGGLVQPGGSLRLSCAASGFTFERYAMSWVRQAPGKGLEW VSAISAAGGTTYYADSVKGRFTISRDNSKNTLYLQMNSLRAEDTAVYY CAKPLDSSQWADFDLWGRGTLVTVSS (SEQ ID NO: 23) |
| Ab4_VH | EVQLLESGGGLVQPGGSLRLSCAASGFTFERYAMSWVRQAPGKGLEW VSAISAVGGTTKYADSVKGRFTISRDNSKNTLYLQMNSLRAEDTAVYY CAKPLDSSLWADFDAWGRGTLVTVSS (SEQ ID NO: 31) |
| Ab5_VH | EVQLLESGGGLVQPGGSLRLSCAASGFTFGQYAMSWVRQAPGKGLE WVSAISAVGGTTAYADSVKGRFTISRDNSKNTLYLQMNSLRAEDTAV YYCAKPLDSSLWADFQLWGRGTLVTVSS (SEQ ID NO: 39) |
| Ab6_VH | EVQLLESGGGLVQPGGSLRLSCAASGFTFGQYAMSWVRQAPGKGLE WVSAISAAGGTTYYADSVKGRFTISRDNSKNTLYLQMNSLRAEDTAV YYCAKPLDSSQWADFDLWGRGTLVTVSS (SEQ ID NO: 47) |
| Ab7_VH | EVQLLESGGGLVQPGGSLRLSCAASGFTFGQYAMSWVRQAPGKGLE WVSAISAAGGTTYYADSVKGRFTISRDNSKNTLYLQMNSLRAEDTAV YYCAKPLDSSQWADFDLWGRGTLVTVSS (SEQ ID NO: 55) |
| Ab8_VH | EVQLLESGGGLVQPGGSLRLSCAASGFTFGTFAMSWVRQAPGKGLEW VSAISGVGGTTYYADSVKGRFTISRDNSKNTLYLQMNSLRAEDTAVYY CAKPLDSSFWADFDLWGRGTLVTVSS (SEQ ID NO: 63) |
| Ab9_VH | EVQLLESGGGLVQPGGSLRLSCAASGFTFSPYAMSWVRQAPGKGLEW VSAISASGGTTYYADSVKGRFTISRDNSKNTLYLQMNSLRAEDTAVYY CAKPLDSSFWADFDLWGRGTLVTVSS (SEQ ID NO: 71) |
| Ab10_VH | EVQLLESGGGLVQPGGSLRLSCAASGFTFSQYAMSWVRQAPGKGLEW VSAISAVGGSTYYADSVKGRFTISRDNSKNTLYLQMNSLRAEDTAVYY CAKPLDSSQWADFDLWGRGTLVTVSS (SEQ ID NO: 79) |
| Ab11_VH | EVQLLESGGGLVQPGGSLRLSCAASGFTFSQYAMSWVRQAPGKGLEW VSAISAAGGTTYYADSVKGRFTISRDNSKNTLYLQMNSLRAEDTAVYY CAKPLDSSQWADFDLWGRGTLVTVSS (SEQ ID NO: 87) |
| Ab12_VH | QVQLVESGGGLVKPGGSLRLSCAASGFTFAQYYMSWIRQAPGKGLEW VSYISPSGSTIAYADSVKGRFTISRDNAKNSLYLQMNSLRAEDTAVYY CARSLMATGTHLYFDLWGRGTLVTVSS (SEQ ID NO: 101) |
| Ab13_VH | QVQLVESGGGLVKPGGSLRLSCAASGFTFANYYMSWIRQAPGKGLEW VSYISPSGATIAYADSVKGRFTISRDNAKNSLYLQMNSLRAEDTAVYY CARSLMATGTHLYFDLWGRGTLVTVSS (SEQ ID NO: 109) |
| Ab14_VH | QVQLVESGGGLVKPGGSLRLSCAASGFTFGQYYMSWIRQAPGKGLEW VSYISPSGATIAYADSVKGRFTISRDNAKNSLYLQMNSLRAEDTAVYY CARSLMSTGTHLYFDLWGRGTLVTVSS (SEQ ID NO: 117) |

TABLE 6-continued

| Antibody | Sequence |
|---|---|
| Ab15_VH | QVQLVESGGGLVKPGGSLRLSCAASGFTFPQYYMSWIRQAPGKGLEW VSYISPSGATIYYADSVKGRFTISRDNAKNSLYLQMNSLRAEDTAVYY CARSLMSTGTHLYFDLWGRGTLVTVSS (SEQ ID NO: 125) |
| Ab16_VH | QVQLVESGGGLVKPGGSLRLSCAASGFTFSDYYMSWIRQAPGKGLEW VSYISPSGATIAYADSVKGRFTISRDNSKNTLYLQMNSLRAEDTAVYY CARSLMATGTHLYFDLWGRGTLVTVSS (SEQ ID NO: 133) |
| Ab17_VH | QVQLVESGGGLVKPGGSLRLSCAASGFTFSDYYMSWIRQAPGKGLEW VSYISPSGATIYYADSVKGRFTISRDNAKNSLYLQMNSLRAEDTAVYY CARSLMSTGTHLYFDLWGRGTLVTVSS (SEQ ID NO: 141) |
| Ab18_VH | QVQLVESGGGLVKPGGSLRLSCAASGFTFSQYYMSWIRQAPGKGLEW VSYISPSGATIAYADSVKGRFTISRDNAKNSLYLQMNSLRAEDTAVYY CARSLMATGTHLYFDLWGRGTLVTVSS (SEQ ID NO: 149) |
| Ab19_VH | QVQLVESGGGLVKPGGSLRLSCAASGFTFSQYYMSWIRQAPGKGLEW VSYISPSGATIYYADSVKGRFTISRDNAKNSLYLQMNSLRAEDTAVYY CARSLMATGTHLYFDLWGRGTLVTVSS (SEQ ID NO: 157) |
| Ab20_VH | QVQLVESGGGLVQPGGSLRLSCAASGFTFSQYYMSWIRQAPGKGLEW VSYISPSGATIAYADSVKGRFTISRDNAKNSLYLQMNSLRAEDTAVYY CARSLMSTGTHLYFDLWGRGTLVTVSS (SEQ ID NO: 165) |
| Ab1_VL | DIQMTQSPSSVSASVGDRVTITCRASQGIDSWLA WYQQKPGKAPKLLI YAASSLQSGVPSRFSGSGSGTDFTLTISSLQPEDFATYYCQQASVLPITF GGGTKVEIK (SEQ ID NO: 11) |
| Ab2_VL | DIQLTQSPSSVSASVGDRVTITCRASQGISSWLAWYQQKPGKAPKLLIY YASSLQDGVPSRFSGSGSGTDFTLTISSLQPEDFATYYCQQASVLPITFG GGTKVEIK (SEQ ID NO: 19) |
| Ab3_VL | DIQLTQSPSSVSASVGDRVTITCRASQDISSWLAWYQQKPGKAPKFLIY AASALQSGVPSRFSGSGSGTDFTLTISSLQPEDFATYYCQQALVLPITFG GGTKVEIK (SEQ ID NO: 27) |
| Ab4_VL | DIQLTQSPSSVSASVGDRVTITCRASQGISSWLAWYQQKPGKAPKLLIY AASGLQSGVPSRFSGSGSGTDFTLTISSLQPEDFATYYCQQASYLPITFG GGTKVEIK (SEQ ID NO: 35) |
| Ab5_VL | DIQLTQSPSSVSASVGDRVTITCRASQDISSWLAWYQQKPGKAPKLLIY FASSLQSGVPSRFSGSGSGTDFTLTISSLQPEDFATYYCQQASKLPITFG GGTKVEIK (SEQ ID NO: 43) |
| Ab6_VL | DIQLTQSPSSVSASVGDRVTITCRASQGISSWLAWYQQKPGKAPKLLIY AASSLQSGVPSRFSGSGSGTDFTLTINSLQPEDFATYYCQQAWVLPITF GGGTKVEIK (SEQ ID NO: 51) |
| Ab7_VL | DIQLTQSPSSVSASVGDRVTITCRASQGISSWLAWYQQKPGKAPKLLIY AASFLQSGVPSRFSGSGSGTDFTLTISSLQPEDFATYYCQQASVLPITFG GGTKVEIK (SEQ ID NO: 59) |
| Ab8_VL | DIQLTQSPSSVSASVGDRVTITCRASQTISSWLAWYQQKPGKAPKLLIY AASSLQSGVPSRFSGSGSGTDFTLTISSLQPEDFATYYCQQQSVLPITFG GGTKVEIK (SEQ ID NO: 67) |
| Ab9_VL | DIQLTQSPSSVSASVGDRVTITCRASQGISSWLAWYQQKPGKAPKLLIY AASSLQSGVPSRFSGSGSGTDFTLTISSLQPEDFATYYCQQHSVLPITFG GGTKVEIK (SEQ ID NO: 75) |
| Ab10_VL | DIQLTQSPSSVSASVGDRVTITCRASQDISSWLAWYQQKPGKAPKLLIY AASALQSGVPSRFSGSGSGTDFTLTISSLQPEDFATYYCQQADVLPITFG GGTKVEIK (SEQ ID NO: 83) |
| Ab11_VL | DIQLTQSPSSVSASVGDRVTITCRASQGIYSWLAWYQQKPGKAPKLLIY AASSLQSGVPSRFSGSGSGTDFTLTISSLQPEDFATYYCQQASDLPITFG GGTKVEIK (SEQ ID NO: 91) |
| Ab12_VL | DIQLTQSPSSVSASVGDRVTITCRASQDISSWLAWYQQKPGKAPKLLIY AASSLQSGVPSRFSGSGSGTDFTLTISSLQPEDFATYYCQQVTSFPPYTF GGGTKVEIK (SEQ ID NO: 105) |
| Ab13_VL | DIQLTQSPSSVSASVGDRVTITCRASSGISSWLAWYQQKPGKAPKLLIY AASELQSGVPSRFSGSGSGTDFTLTISSLQPEDFATYYCQQATSFPPYTF GGGTKVEIK (SEQ ID NO: 113) |

TABLE 6-continued

| Antibody | Sequence |
|---|---|
| Ab14_VL | DIQLTQSPSSVSASVGDRVTITCRASQGISDWLAWYQQKPGKAPKLLIY<br>AASSLQSGVPSRFSGSGSGTDFTLTISSLQPEDFATYYCQQVTSFPPYTF<br>GGGTKVEIK (SEQ ID NO: 121) |
| Ab15_VL | DIQLTQSPSSVSASVGDRVTITCRASQGISSWLAWYQQKPGKAPKLLIY<br>AASSLQSGVPSRFSGSGSGTDFTLTISSLQPEDFATYYCQQVTSTPPYTF<br>GGGTKVEIK (SEQ ID NO: 129) |
| Ab16_VL | DIQLTQSPSSVSASVGDRVTITCRASQGISSWLAWYQQKPGKAPKLLIY<br>AASGLQSGVPSRFSGSGSGTDFTLTISSLQPEDFATYYCQQSTSFPPYTF<br>GGGTKVEIK (SEQ ID NO: 137) |
| Ab17_VL | DIQLTQSPSSVSASVGDRVTITCRASQGISSWLAWYQQKPGKAPKLLIY<br>AASSLQSGVPSRFSGSGSGTDFTLTISSLQPEDFATYYCQQVTSVPPYTF<br>GGGTKVEIK (SEQ ID NO: 145) |
| Ab18_VL | DIQLTQSPSSVSASVGDRVTITCRASQGISSWLAWYQQKPGKAPKLLIY<br>AAESLQSGVPSRFSGSGSGTDFTLTISSLQPEDFATYYCQQVTSQPPYTF<br>GGGTKVEIK (SEQ ID NO: 153) |
| Ab19_VL | DIQLTQSPSSVSASVGDRVTITCRASQGISSWLAWYQQKPGKAPKLLIY<br>AASALQSGVPSRFSGSGSGTDFTLTISSLQPEDFATYYCQQVTSAPPYTF<br>GGGTKVEIK (SEQ ID NO: 161) |
| Ab20_VL | DIQLTQSPSSVSASVGDRVTITCRASQGISSWLAWYQQKPGKAPKLLIY<br>AASVLQSGVPSRFSGSGSGTDFTLTISSLQPEDFATYYCQQVTSFLPYTF<br>GGGTKVEIK (SEQ ID NO: 169) |

Example 2—Binding Affinities of CD161 Antibodies

This example describes the kinetics and affinity of various CD161 antibodies created in Example 1.

ForteBio affinity measurements were performed on an Octet HTX generally as previously described (see, e.g., Estep et al. (2013) MAbs, 5(2): 270-8). Briefly, ForteBio affinity measurements were performed by loading IgGs on-line onto AHC sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3-10 min for off-rate measurement. Avidity (Avid) and monovalent affinity assessment, were performed using dimeric or monovalent antigens, respectively. During optimization, monovalent affinity was also assessed using Fabs. For this assessment the unbiotinylated Fc fusion antigen was loaded on-line onto the AHC sensors. Sensors were equilibrated off-line in assay buffer for 30 min and then monitored on-line for 60 seconds for baseline establishment. Sensors with loaded antigen were exposed to 100 nM Fab for 3 minutes, and afterwards they were transferred to assay buffer for 10 min for off-rate measurement. Kinetic data was analyzed and fitted using the 1:1 binding model and the $K_D$ was calculated by dividing the $k_{off}$ by the $k_{on}$.

The $K_D$ values of the CD161 antibodies measured by the Octet-based experiments (antibody binding kinetics of anti-CD161 antibodies) are shown in TABLE 7, and as indicated the antibody affinities are between $10^{-7}$ M and $10^{-10}$ M.

TABLE 7

| mAb | Human $K_D$, Avid (M) [hKLRB1-Fc in solution] | Cynomolgus $K_D$, Avid (M) [cKLRB1-Fc in solution] | Human $K_D$, Monovalent (M) [Antibody Fab in solution] | Cynomolgus $K_D$, Monovalent (M) [Antibody Fab in solution] | Human $K_D$, Monovalent (M) [hKLRB1-His in solution] |
|---|---|---|---|---|---|
| Ab1 | 9.55E−10 | 3.51E−10 | 9.11E−09 | n/a | 8.09E−09 |
| Ab2 | 6.09E−10 | 1.26E−10 | 1.37E−09 | 1.98E−09 | 1.99E−09 |
| Ab3 | 5.42E−10 | 1.93E−10 | 6.62E−10 | 1.02E−09 | 6.02E−10 |
| Ab4 | 7.50E−10 | 1.91E−10 | 3.82E−10 | 8.26E−10 | 4.48E−10 |
| Ab5 | 7.53E−10 | 2.32E−10 | 3.35E−10 | 6.59E−10 | 3.29E−10 |
| Ab6 | 6.32E−10 | 1.99E−10 | 5.85E−10 | 6.76E−10 | 7.76E−10 |
| Ab7 | 6.31E−10 | 1.31E−10 | 9.04E−10 | 1.62E−09 | 1.30E−09 |
| Ab8 | 6.86E−10 | 2.22E−10 | 3.52E−10 | 6.89E−10 | 4.96E−10 |
| Ab9 | 8.14E−10 | 1.68E−10 | 4.57E−10 | 9.81E−10 | 6.86E−10 |
| Ab10 | 7.01E−10 | 1.64E−10 | 2.39E−10 | 4.16E−10 | 1.96E−10 |
| Ab11 | 5.88E−10 | 1.93E−10 | 1.02E−09 | 1.48E−09 | 1.14E−09 |
| Ab12 | 5.94E−10 | 5.20E−10 | 2.27E−09 | 2.11E−07 | 2.49E−09 |
| Ab13 | 6.72E−10 | 3.24E−10 | 7.01E−10 | 5.29E−08 | 9.87E−10 |
| Ab14 | 6.10E−10 | 2.42E−10 | 6.98E−10 | n/a | 1.08E−09 |
| Ab15 | 5.33E−10 | 2.40E−10 | 6.08E−10 | 2.45E−08 | 6.57E−10 |
| Ab16 | 4.10E−10 | 3.05E−10 | 1.27E−09 | 1.39E−07 | 1.58E−09 |
| Ab17 | 6.20E−10 | 3.43E−10 | 8.56E−10 | 5.49E−08 | 1.20E−09 |
| Ab18 | 6.13E−10 | 3.12E−10 | 9.20E−10 | 6.87E−08 | 1.21E−09 |

TABLE 7-continued

| mAb | Human $K_D$, Avid (M) [hKLRB1-Fc in solution] | Cynomolgus $K_D$, Avid (M) [cKLRB1-Fc in solution] | Human $K_D$, Monovalent (M) [Antibody Fab in solution] | Cynomolgus $K_D$, Monovalent (M) [Antibody Fab in solution] | Human $K_D$, Monovalent (M) [hKLRB1-His in solution] |
|---|---|---|---|---|---|
| Ab19 | 6.31E-10 | 3.60E-10 | 2.38E-09 | 6.10E-08 | 1.93E-09 |
| Ab20 | 4.75E-10 | 2.84E-10 | 5.55E-10 | 7.99E-08 | 5.48E-10 |

Example 3—Anti-CD161 Antibodies Bind to CD161—On-Cell Target Binding

This example describes the capacity of anti-CD161 antibodies to bind to HEK293 cells exogenously expressing human and cynomolgus monkey CD161.

HEK293 cells were engineered to overexpress human (h) or cynomolgus monkey (c) CD161 (amino acid sequence in TABLE 8) by lipid-based transfection, random integration into the genome and antibiotic selection.

TABLE 8

| | |
|---|---|
| Human CD161, full length (Uniprot #Q12918) | MDQQAIYAELNLPTDSGPESSSPSSLPRDVCQGSPWHQFALKLSCAGII LLVLVVTGLSVSVTSLIQKSSIEKCSVDIQQSRNKTTERPGLLNCPIYWQ QLREKCLLFSHTVNPWNNSLADCSTKESSLLLIRDKDELIHTQNLIRDK AILFWIGLNFSLSEKNWKWINGSFLNSNDLEIRGDAKENSCISISQTSVY SEYCSTEIRWICQKELTPVRNKVYPDS (SEQ ID NO: 179) |
| Cynomolgus monkey CD161, full length (Uniprot # A0A2K5WYI1) | MDQQMMYAELTLPKDSGPESSSPSSLPRDVCQGSPWHQFALKLSCAGI ILLVLVVTGLSLSVASLLQKPSIGKCSVDIQQNRTKTTERPDLLNCPIY WQQVQEKCLLFSHTVNPWNNSLADCSTKESSLLLIQDKDELTRTQNLI HDKAISFWIGLNFSLSEKNWKWINGSFLSSNDLKITGDAKENSCVYISQ TSVYSEYCSTEMKWICQKELTLVRNKVSPDSWL (SEQ ID NO: 180) |
| Mouse CD161, full length (Uniprot # Q99JB4) | MDSTTLVYADLNLARIQEPKHDSPPSLSPDTCRCPRWHRLALKFGCAG LILLVLVVIGLCVLVLSVQKSSVQKICADVQENRTHTTGCSAKLECPQ DWLSHRDKCFHVSQVSNTWKECRIDCDKKGATLLLIQDQEELRFLLD SIKEKYNSFWIGLSYTLTDMNWKWINGTAFNSDVLKITGVTENGSCAA ISGEKVTSEGCSSDNRWICQKELNHETPCNDS (SEQ ID NO: 181) |
| Rat CD161, full length (Uniprot # Q5NKN4) | MDTAVVYADLHLARTGEPKHKSPPSLSPDTCQCPRWHRLALKLGCAC LILLVLSVIGLGVLVLTLLQKPLIQNSPADVQENRTKTTDSPTKLKCPK DWHSHQDKCFHVSQAPNTWNKSLADCGGKGATLLLIQDQEELRFLR NLTKGKDRSFWIGLNYTLPDKNWKWINSSTLNSDVLSIFGDTKQNSCA SISQDKVLSESCDSDNLWICQKELKCECMCNGS (SEQ ID NO: 182) |

For the antibody binding assay, hCD161-HEK293, cCD161-HEK293, and Null-HEK293 cells were washed in phosphate-buffered saline with 0.1% bovine serum albumin (PBSA) and seeded in a 96 well plate at a density of $1 \times 10^4$ cells per well. Washed cells were resuspended in antibody titrations diluted in PBSA and incubated at 4° C. for 4 hours. Cells were washed in PBSA, resuspended in Alexa Fluor® 647 anti-human IgG (Jackson ImmunoResearch, catalog #109-605-190) diluted 1:1000 in PBSA and incubated at 4° C. for 30 minutes. Cells were washed in PBS, resuspended in PBS with 2% formaldehyde, incubated at room temperature for 20 minutes and analyzed by flow cytometry with a BD Symphony flow cytometer.

Data were analyzed using FlowJo software. MFI at each concentration was calculated and exported into Graphpad Prism. $EC_{50}$ values were calculated with a 3 parameter non-linear regression fit.

FIGS. 1A-1D are graphs showing binding of human anti-CD161 antibodies to HEK 293 cells exogenously expressing human CD161. Iso Ctrl denotes isotype control antibody.

FIGS. 2A-2D are graphs showing binding of human anti-CD161 antibodies to HEK 293 cells exogenously expressing cynomolgus CD161. Iso Ctrl denotes isotype control antibody.

As shown in TABLE 9, FIGS. 1A-1D, and FIGS. 2A-2D, the human anti-CD161 antibodies bind to hCD161-HEK293 and cCD161-HEK293 in a dose dependent manner and have EC50 values measuring between approximately 0.1-0.5 nM. No binding was observed to untransfected (null) cells, indicating the binding was specific to CD161.

TABLE 9

| | hCD161 $EC_{50}$ (nM) | cCD161 $EC_{50}$ (nM) | Null $EC_{50}$ (nM) |
|---|---|---|---|
| Ab1 | 0.2566 | 0.2784 | — |
| Ab2 | 0.2853 | 0.2718 | — |
| Ab3 | 0.3908 | 0.4107 | — |
| Ab4 | 0.2872 | 0.2565 | — |
| Ab5 | 0.249 | 0.2376 | — |
| Ab6 | 0.2322 | 0.2461 | — |
| Ab7 | 0.2478 | 0.2494 | — |
| Ab8 | 0.3158 | 0.2625 | — |
| Ab9 | 0.2794 | 0.2227 | — |
| Ab10 | 0.2465 | 0.3222 | — |
| Ab11 | 0.2603 | 0.2648 | — |
| Ab12 | 0.2211 | 0.2879 | — |
| Ab13 | 0.1983 | 0.2096 | — |
| Ab14 | 0.2701 | 0.3117 | — |
| Ab15 | 0.2056 | 0.2376 | — |
| Ab16 | 0.2292 | 0.2789 | — |
| Ab17 | 0.186 | 0.2362 | — |

TABLE 9-continued

| | hCD161 EC$_{50}$ (nM) | cCD161 EC$_{50}$ (nM) | Null EC$_{50}$ (nM) |
|---|---|---|---|
| Ab18 | 0.211 | 0.2271 | — |
| Ab19 | 0.2465 | 0.2831 | — |
| Ab20 | 0.2331 | 0.2569 | — |
| Isotype ctrl. | — | — | — |

Example 4—On-Cell Homolog Binding (FACS KLRF1, KLRF2, CLEC12B, CLEC2D)

This example describes the binding of anti-CD161 antibodies to HEK 293 cells exogenously expressing CD161 homologs as a measure of antibody specificity for CD161. Homologous proteins of interest in this assay were based on sequence similarity; an alignment of proteins of interest is shown in FIG. 3. Specificity was also tested against CLEC2D; an alignment of CD161 and CLEC2D is shown in FIG. 4.

HEK293 cells were engineered to overexpress KLRF1, KLRF2, CLEC12B, or CLEC2D (CD161 homolog sequences in TABLE 10) by lipid-based transfection, transposon mediated integration and antibiotic selection. Stable integration of the construct was validated by qPCR.

TABLE 10

| Construct | Sequence |
|---|---|
| hKLRF1 (Uniprot #Q9NZS2) | MQDEERYMTLNVQSKKRSSAQTSQLTFKDYSVTLHWYKILLGISGTVN GILTLTLISLILLVSQGVLLKCQKGSCSNATQYEDTGDLKVNNGTRRNIS NKDLCASRSADQTVLCQSEWLKYQGKCYWFSNEMKSWSDSYVYCLER KSHLLIIHDQLEMAFIQKNLRQLNYVWIGLNFTSLKMTWTWVDGSPIDS KIFFIKGPAKENSCAAIKESKIFSETCSSVFKWICQY (SEQ ID NO: 183) |
| hKLRF2 (Uniprot #D3WOD1) | MENEDGYMTLSFKNRCKSKQKSKDFSLYPQYYCLLLIFGCIVILIFIMTGI DLKFWHKKMDFSQNVNVSSLSGHNYLCPNDWLLNEGKCYWFSTSFKT WKESQRDCTQLQAHLLVIQNLDELEFIQNSLKPGHFGWIGLYVTFQGNL WMWIDEHFLVPELFSVIGPTDDRSCAVITGNWVYSEDCSSTFKGICQRD AILTHNGTSGV (SEQ ID NO: 184) |
| hCLEC12B (Uniprot #Q2HXU8) | MSEEVTYATLTFQDSAGARNNRDGNNLRKRGHPAPSPIWRHAALGLVT LCLMLLIGLVTLGMMFLQISNDINSDSEKLSQLQKTIQQQQDNLSQQLG NSNNLSMEEEFLKSQISSVLKRQEQMAIKLCQELIIHTSDHRCNPCPKMW QWYQNSCYYFTTNEEKTWANSRKDCIDKNSTLVKIDSLEEKDFLMSQPL LMFSFFWLGLSWDSSGRSWFWEDGSVPSPSLFSTKELDQINGSKGCAYF QKGNIYISRCSAEIFWICEKTAAPVKTEDLD (SEQ ID NO: 185) |
| hCLEC2D (Uniprot #Q9UHP7) | MHDSNNVEKDITPSELPANPGCLHSKEHSIKATLIWRLFFLIMFLTIIVCG MVAALSAIRANCHQEPSVCLQAACPESWIGFQRKCFYFSDDTKNWTSSQ RFCDSQDADLAQVESFQELNFLLRYKGPSDHWIGLSREQGQPWKWING TEWTRQFPILGAGECAYLNDKGASSARHYTERKWICSKSDIHV (SEQ ID NO: 186) |

CD161 antibodies were screened for binding against each cell line mentioned above at a single saturating concentration, as detailed below.

For the antibody binding assay, all cell lines were washed in phosphate-buffered saline with 0.1% bovine serum albumin (PBSA) and seeded in a 96 well plate at a density of $4 \times 10^4$ cells per well. Washed cells were resuspended in 100 nM of antibody (a saturating concentration to measure maximum binding on cells) and incubated at room temperature for 30 minutes. Cells were washed in PBSA, resuspended in Alexa Fluor® 647 anti-human IgG (Jackson ImmunoResearch, catalog #109-605-190) diluted 1:1000 in PBSA and incubated at 4° C. for 30 minutes. Cells were analyzed by flow cytometry with a Thermno Fisher Attune flow cytometer.

Figure 5A:
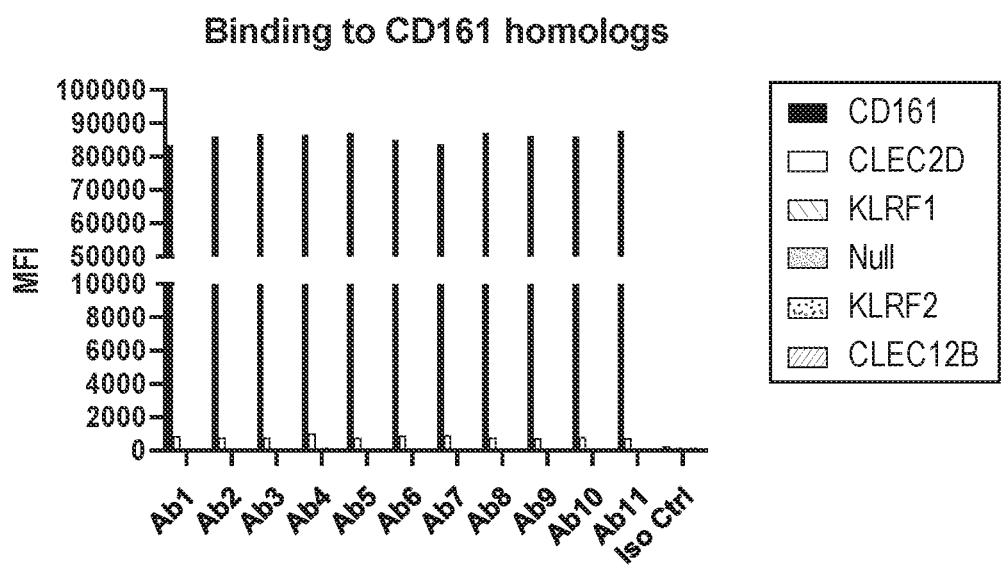
FIGS. 5A-5B are graphs showing binding of exemplary human anti-CD161 antibodies to HEK 293 cells exogenously expressing CD161 or CD161 homologs (CLEC2D, KLRF1, KLRF2, and CLEC12B). Iso Ctrl denotes isotype control antibody, and null represents control HEK 293 cells.
Figure 5B:
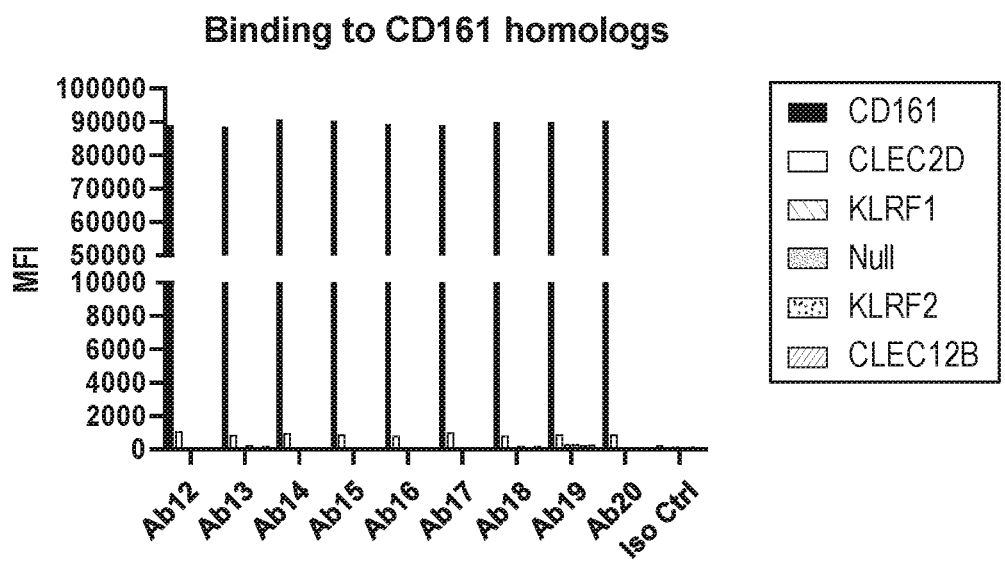
Figure 6A:
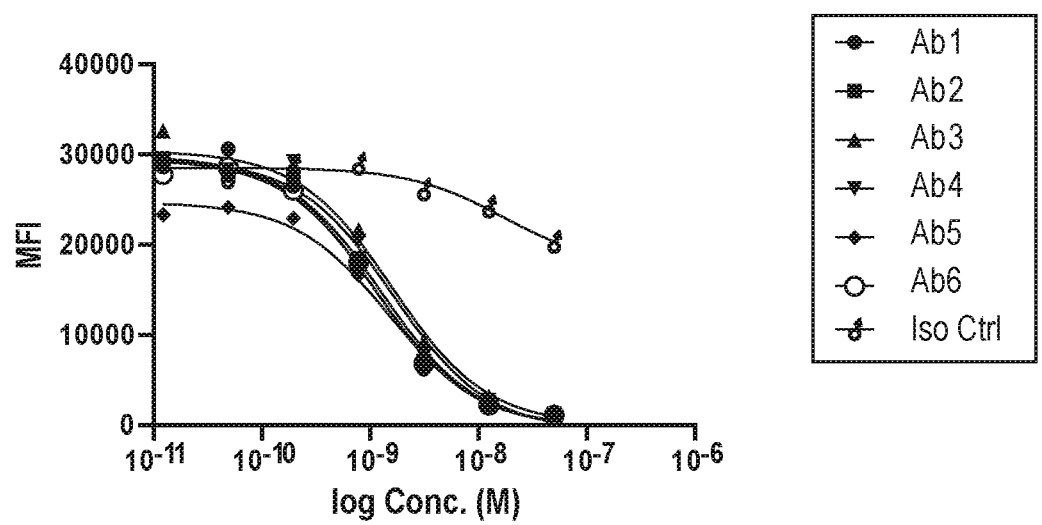
FIGS. 6A-6D are graphs illustrating human anti-CD161 antibody-mediated blocking of interaction between CD161 and CLEC2D, using HEK293 cells overexpressing the human CD161 protein and soluble, biotinylated Fc-human CLEC2D (H176C) protein. Iso Ctrl denotes isotype control antibody.
Figure 6B:
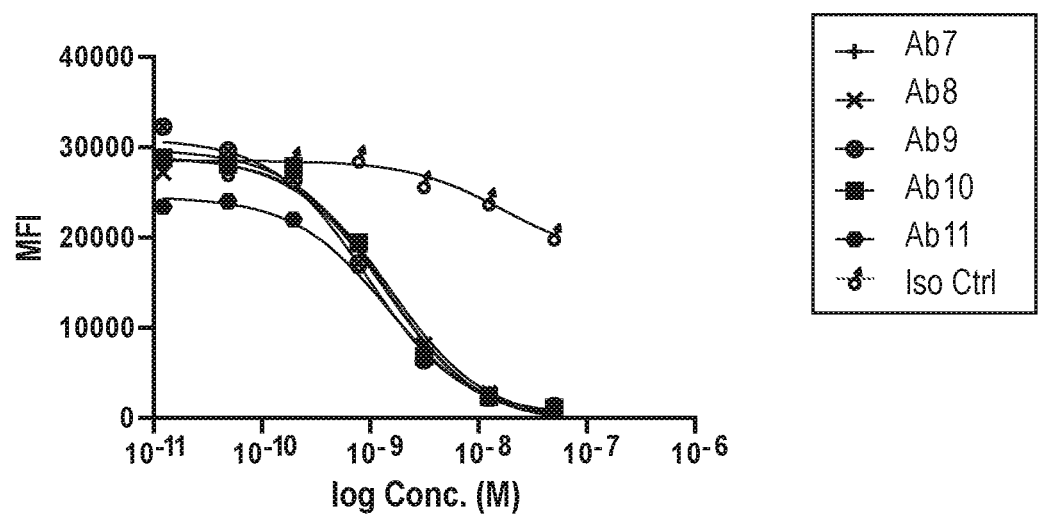
Figure 6C:
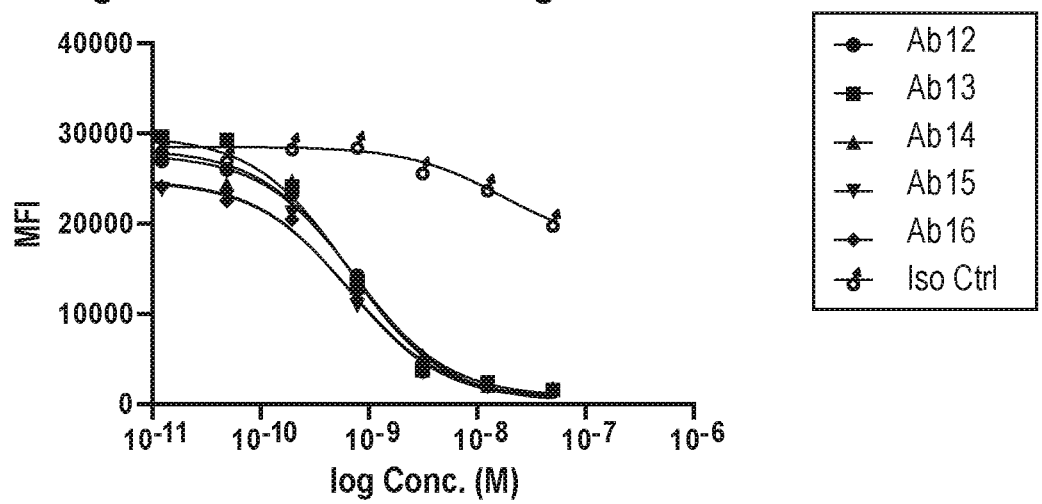
Figure 6D:
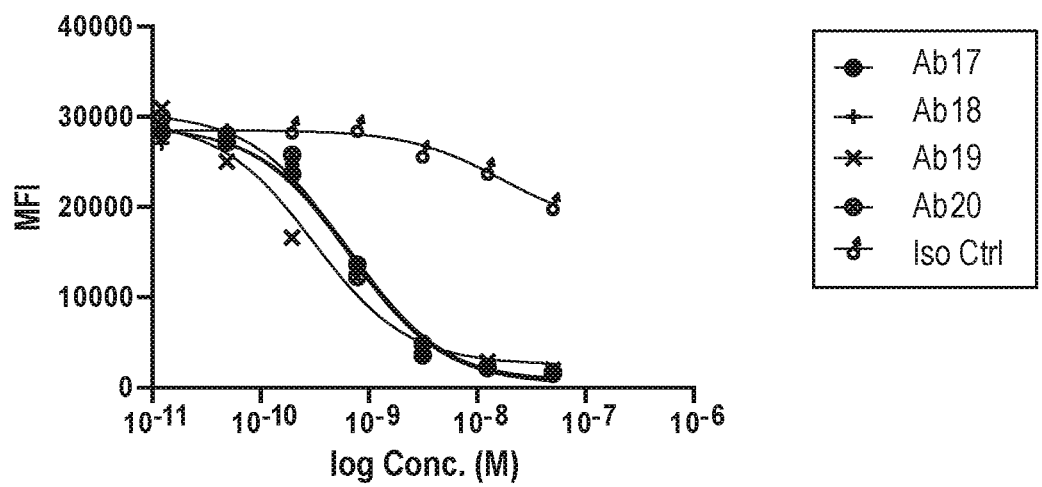
Figure 7A:
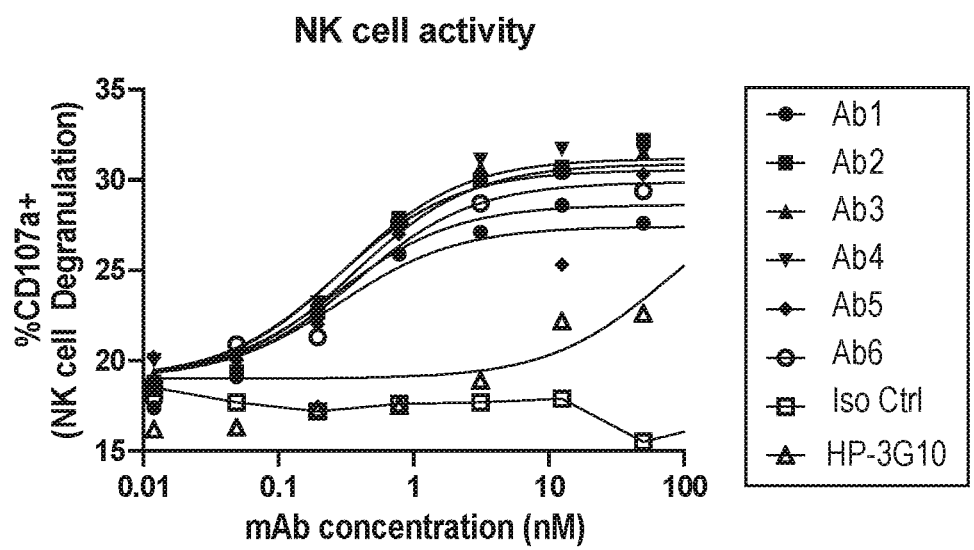
FIGS. 7A-7D are graphs illustrating anti-CD161 antibody-mediated activation of human NK cells as measured by CD107a expression in a dose-dependent manner. HP-3G10 denotes mouse anti-human CD161 antibody. Iso Ctrl denotes isotype control antibody.
Figure 7B:
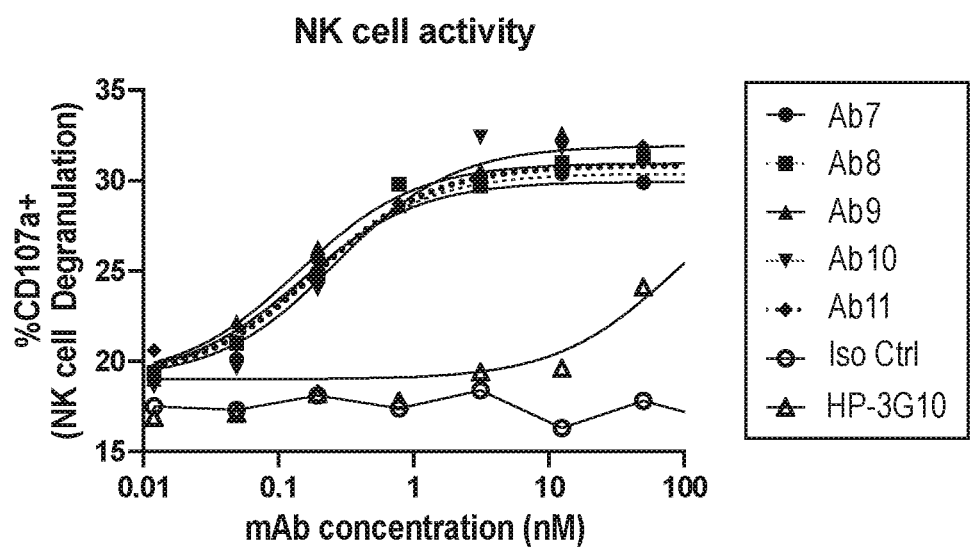
Figure 7C:
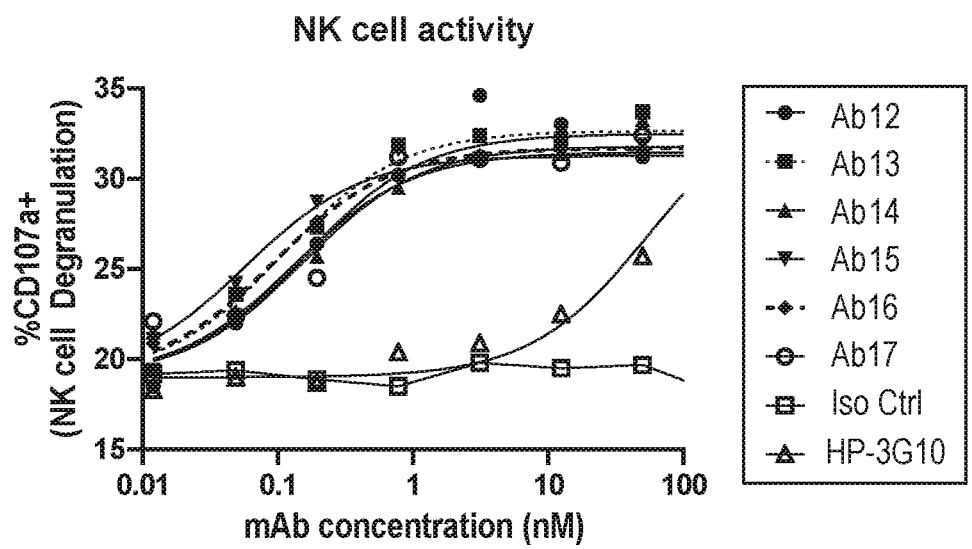
Figure 7D:
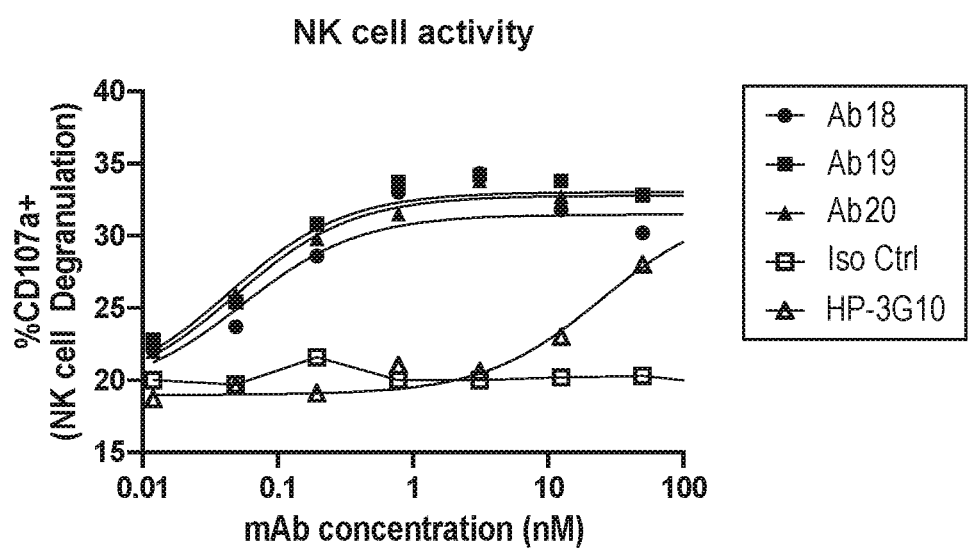
Figure 8A:
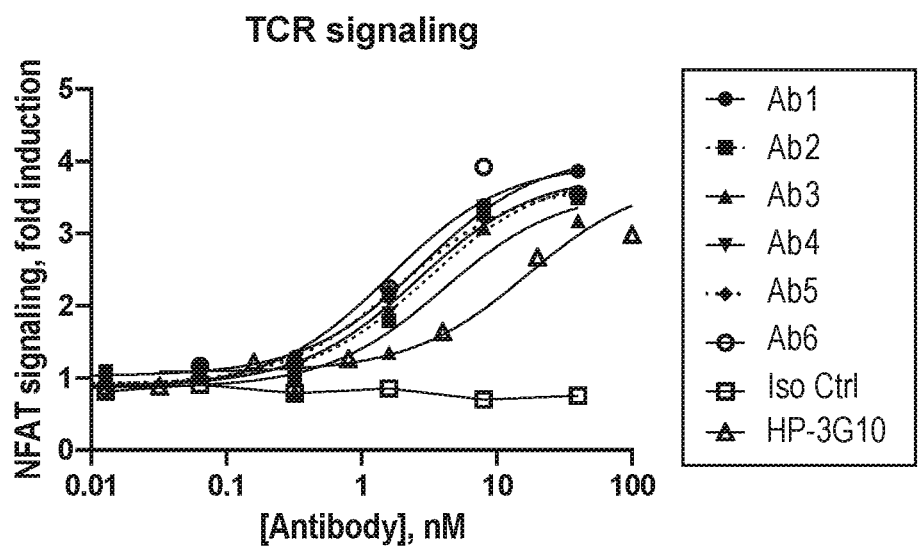
FIGS. 8A-8D are graphs illustrating anti-CD161 antibody-mediated activation of T cells in a co-culture assay with exogenous CLEC2D expression as measured by nuclear factor of activated T cells (NFAT) signaling. HP-3G10 denotes mouse anti-human CD161 antibody. Isotype control antibody (Iso Ctrl) was used as a control.
Figure 8B:
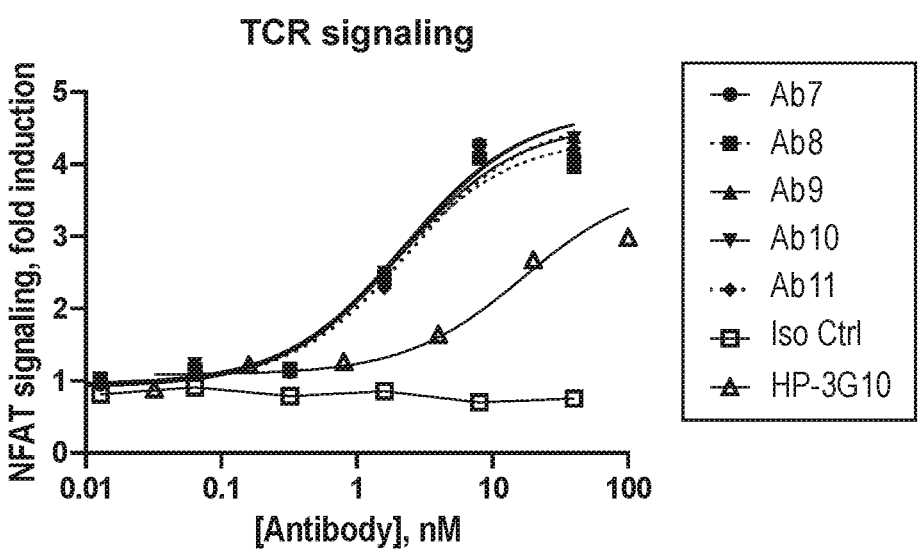
Figure 8C:
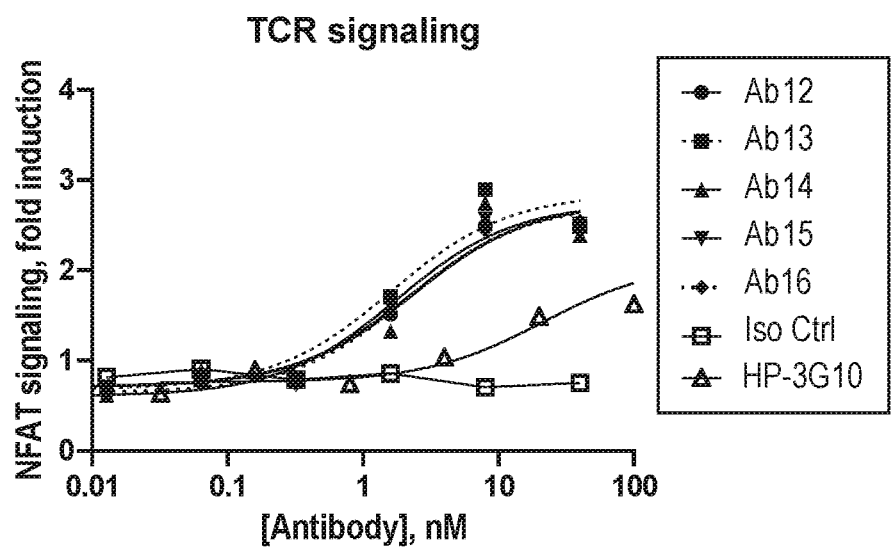
Figure 8D:
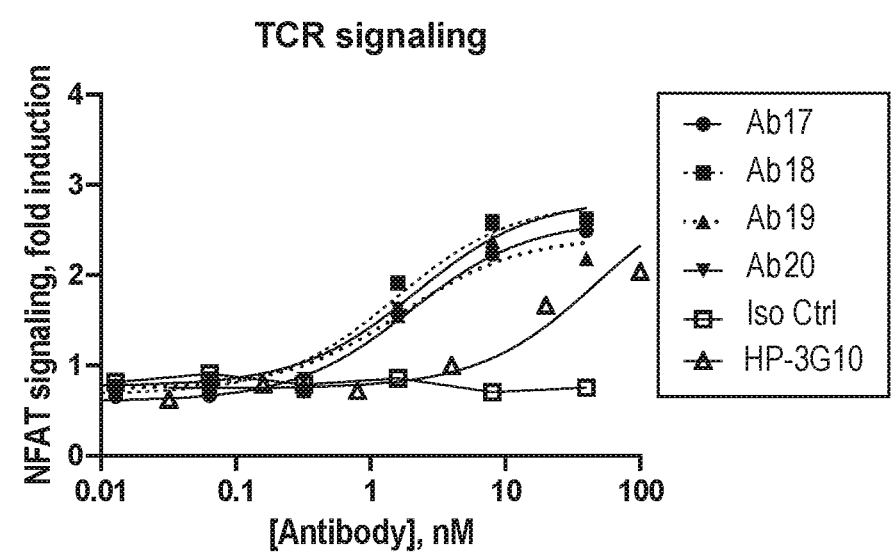

FIGS. 5A-5B are graphs showing binding of human anti-CD161 antibodies to HEK 293 cells exogenously expressing CD161 or CD161 homologs (CLEC2D), KLRF1, KLRF2, and CLEC12B). Iso Ctrl denotes isotype control antibody. Null represents control HEK 293 cells.

Data were analyzed using FlowJo software. MFI for each sample was calculated and exported into Graphpad Prism. As shown in FIGS. 5A-5B, and TABLE 11, no significant binding was observed to any HEK293 cell lines expressing a CD161 homolog.

Off-target binding assessment of anti-CD161 antibodies to cells expressing CD161 homologs, as percentage of CD161 binding at saturating antibody concentration (100 nM) is shown in TABLE 11.

TABLE 11

| ID | KLRB1 (%) | CLEC2D (%) | KLRF1 (%) | KLRF2 (%) | CLEC12B (%) | Null (%) |
|---|---|---|---|---|---|---|
| Ab1 | 100.000 | 0.975 | 0.073 | 0.036 | 0.040 | 0.066 |
| Ab2 | 100.000 | 0.863 | 0.032 | 0.049 | 0.057 | 0.071 |
| Ab3 | 100.000 | 0.832 | 0.011 | -0.007 | -0.042 | 0.035 |
| Ab4 | 100.000 | 1.106 | 0.095 | 0.056 | 0.074 | 0.179 |
| Ab5 | 100.000 | 0.872 | 0.059 | 0.035 | 0.056 | 0.118 |
| Ab6 | 100.000 | 1.012 | 0.036 | 0.029 | 0.011 | 0.047 |
| Ab7 | 100.000 | 1.087 | 0.018 | 0.040 | 0.011 | 0.018 |

TABLE 11-continued

| ID | KLRB1 (%) | CLEC2D (%) | KLRF1 (%) | KLRF2 (%) | CLEC12B (%) | Null (%) |
|---|---|---|---|---|---|---|
| Ab8 | 100.000 | 0.846 | 0.031 | 0.038 | 0.049 | 0.084 |
| Ab9 | 100.000 | 0.808 | 0.042 | 0.028 | 0.025 | 0.063 |
| Ab10 | 100.000 | 0.935 | 0.046 | 0.004 | -0.004 | 0.053 |
| Ab11 | 100.000 | 0.785 | 0.024 | 0.021 | -0.003 | 0.038 |
| Ab12 | 100.000 | 1.161 | 0.065 | 0.055 | 0.061 | 0.085 |
| Ab13 | 100.000 | 0.907 | 0.106 | 0.089 | 0.175 | 0.209 |
| Ab14 | 100.000 | 1.024 | 0.090 | 0.054 | 0.064 | 0.120 |
| Ab15 | 100.000 | 0.935 | 0.114 | 0.067 | 0.071 | 0.108 |
| Ab16 | 100.000 | 0.865 | 0.061 | 0.048 | 0.088 | 0.099 |
| Ab17 | 100.000 | 1.077 | 0.078 | 0.051 | 0.038 | 0.096 |

TABLE 11-continued

| ID | KLRB1 (%) | CLEC2D (%) | KLRF1 (%) | KLRF2 (%) | CLEC12B (%) | Null (%) |
|---|---|---|---|---|---|---|
| Ab18 | 100.000 | 0.865 | 0.121 | 0.101 | 0.169 | 0.196 |
| Ab19 | 100.000 | 0.970 | 0.305 | 0.220 | 0.260 | 0.285 |
| Ab20 | 100.000 | 0.968 | 0.132 | 0.054 | 0.061 | 0.127 |

Example 5—Anti-CD161 Antibodies Block Lectin-like Transcript 1 (CLEC2D)Binding—Ligand Blocking Assay This example describes CD161 antibody-mediated blocking of the interaction between CD161 and CLEC2D, using HEK293 cells overexpressing the human CD161 protein and soluble, biotinylated Fc-human CLEC2D (H176C) protein described in Example 1 and shown in TABLE 5.

For the antibody-mediated blocking of CD161/CLEC2D, HEK293-hCD161 cells were washed in phosphate-buffered saline with 0.1% bovine serum albumin (PBSA) and seeded in a 96 well plate at a density of $1 \times 10^4$ cells per well. Antibody titrations were diluted in PBSA, biotinylated Fc-H176C CLEC2D was added to each titration of antibody to a final concentration of 100 nM and the antibody/CLEC2D solution was incubated with HEK293-hCD161 cells at 4° C. for 4 hours. Cells were washed in PBSA, and then biotinylated Fc-H176C CLEC2D binding was detected by Streptavidin, Alexa Fluor™ 647 conjugate (Thermo Fisher, catalog #S21374) diluted 1:1000 in PBSA and incubated at 4° C. for 30 minutes. Cells were washed in PBS, resuspended in PBS with 2% formaldehyde, incubated at room temperature for 20 minutes and analyzed by flow cytometry with a Thermo Fisher Attune flow cytometer.

Data were analyzed using FlowJo software. MFI at each concentration was calculated and exported into Graphpad Prism. $EC_{50}$ values were calculated with a 3 parameter non-linear regression fit.

FIGS. 6A-6D are graphs illustrating human anti-CD161 antibody-mediated blocking of interaction between CD161 and CLEC2D, using HEK293 cells overexpressing the human CD161 protein and soluble, biotinylated Fc-human CLEC2D (H176C) protein. Iso Ctrl denotes isotype control antibody.

Antibody mediated blocking of human Fc-H176C CLEC2D binding to hCD161-HEK293 cells is shown in TABLE 12.

TABLE 12

| Antibody | IC50 (nM) |
|---|---|
| Ab1 | 1.13 |
| Ab2 | 1.27 |
| Ab3 | 1.61 |
| Ab4 | 1.62 |
| Ab5 | 1.49 |
| Ab6 | 1.17 |
| Ab7 | 1.38 |
| Ab8 | 1.52 |
| Ab9 | 0.94 |
| Ab10 | 1.35 |
| Ab11 | 1.47 |
| Ab12 | 0.77 |
| Ab13 | 0.64 |
| Ab14 | 0.71 |
| Ab15 | 0.66 |
| Ab16 | 0.66 |
| Ab17 | 0.67 |
| Ab18 | 0.71 |
| Ab19 | 0.31 |
| Ab20 | 0.61 |
| Iso Ctrl | — |

In the absence of antibody, the interaction between hCD161 on the HEK293 cells and biotinylated H176C Fc-CLEC2D was detected by the Streptavidin, Alexa Fluor™ 647 conjugate. As shown in TABLE 12 and in FIGS. 6A-6D, the presence of anti-CD161 antibody inhibited the interaction between soluble biotinylated Fc-H176C CLEC2D and hCD161-HEK cell in a dose dependent manner. All $IC_{50}$ values are between 0.3 and 1.7 nM.

Example 6—CD161-Antibodies Activate NK Cells in Co-Culture Assay with Exogenous CLEC2D Expression This example describes the ability of anti-CD161 antibodies to block inhibitory signaling on human NK cells mediated by target cells overexpressing ligand CLEC2D.

Briefly, NK cells (CD3⁻CD56⁺) were isolated using negative selection with magnetic beads from human PBMCs, and the purity of the isolated NK cells was typically >90%. Isolated NK cells were cultured in media containing 100 ng/mL IL-2 for activation. IL-2-activated NK cells were used 24 hours after activation.

K562 human cancer cells were engineered to overexpress human CLEC2D by transposon engineering. Cells were cultured in IMDM (Iscove's Modified Dulbecco's Medium) with selection antibiotics prior to assay setup.

K562 human cancer cells expressing human CLEC2D were harvested and resuspended in culture media at $2 \times 10^6$ cells/mL. Human anti-CD161 antibodies and mouse anti-human CD161 antibody (HP-3G10) were diluted in culture media. Activated NK cells were harvested, washed, and resuspended at $2 \times 10^6$ cells/mL in culture media. K562 cancer cells were then mixed with anti-CD161 antibodies and activated NK cells in the presence of IL-2. CD107a staining was analyzed in CD3⁻CD56⁺ cells to assess NK cell activation.

FIGS. 7A-7D are graphs illustrating anti-CD161 antibody-mediated activation of human NK cells as measured by CD107a expression in a dose-dependent manner. Iso Ctrl denotes isotype control antibody.

As shown in FIGS. 7A-7D, human anti-CD161 antibodies increased NK cell activation as measured by CD107a expression in a dose-dependent manner relative to NK cell activation achieved using mouse anti-human CD161 antibody, while isotype controls had no effect on NK cell function. Further, when K562 cells lacking CLEC2D were used as target cells in the assay, the typical amount of CD107a was approximately 30%, indicating that the antibodies here have completely alleviated the CLEC2D-mediated inhibition of NK cells. The $EC_{50}$ for this effect for each antibody is listed in TABLE 13 (Antibody mediated restoration of NK cell function).

TABLE 13

| Antibody | EC50 (nM) |
|---|---|
| Ab1 | 0.29 |
| Ab2 | 0.37 |
| Ab3 | 0.28 |

TABLE 13-continued

| Antibody | EC$_{50}$ (nM) |
|---|---|
| Ab4 | 0.31 |
| Ab5 | 0.27 |
| Ab6 | 0.38 |
| Ab7 | 0.15 |
| Ab8 | 0.17 |
| Ab9 | 0.14 |
| Ab10 | 0.27 |
| Ab11 | 0.19 |
| Ab12 | 0.16 |
| Ab13 | 0.11 |
| Ab14 | 0.13 |
| Ab15 | 0.06 |
| Ab16 | 0.09 |
| Ab17 | 0.16 |
| Ab18 | 0.05 |
| Ab19 | 0.04 |
| Ab20 | 0.05 |
| Iso Ctrl | >10 |

Example 7—Antibody Activation of T Cells in Co-Culture Assay with Exogenous CLEC2D Expression This example describes the ability of anti-CD161 antibodies to block inhibitory signaling on Jurkat T cells mediated by target cells overexpressing ligand.

Jurkat T cells with an NFAT-Luciferase reporter gene (InvivoGen) were engineered to overexpress both an NY-ESO-1-specific TCR and human CD161 by lentiviral transduction. Cells were cultured in IMDM media with selection antibiotics prior to assay setup.

K562 human cancer cells were engineered to overexpress MHC-I (HLA-A0201) by lentiviral transduction and human CLEC2D by transposon engineering. Cells were cultured in IMDM media with selection antibiotics prior to assay setup.

On Day 0, engineered K562 cells were seeded at density of 5×10$^5$ cells/mL in media containing 10 μg/mL NY-ESO-1 peptide antigen, SLLMWITQV (SEQ ID NO: 192) and incubated at 37° C., 5% CO$_2$ overnight.

On Day 1, Jurkat effector cells and peptide-loaded K562 target cells were plated at a ratio of 1:4 in 96-well plates. Anti-CD161 antibodies (human anti-CD161 antibodies and mouse anti-human CD161 antibody (HP-3G10)) were pre-diluted in assay media and added to the co-culture at a 1:1 volume ratio. Plates were incubated at 37° C., 5% CO$_2$ overnight.

On Day 2, 20 μL of assay supernatants were transferred to white-walled 96-well plates containing 50 μL of QUANTI-Luc luciferase detection reagent (Invivogen). End-point luminescence was read on EnVision plate reader. Fold induction was calculated by normalizing luminescence value of each well by the average luminescence value of control wells containing no antibody.

FIGS. 8A-8D are graphs illustrating nuclear factor of activated T cells (NFAT) signaling anti-CD161 antibody-mediated activation of T cells in a co-culture assay with exogenous CLEC2D expression as measured by NFAT signaling. Isotype control antibody was used as a control.

In the absence of antibody, the interaction between CD161 on the Jurkat cells and CLEC2D on the K562 cells inhibits NFAT signaling. In the presence of anti-CD161 antibody, the inhibitory signal is blocked and NFAT signaling through the TCR/MHC-I interaction is restored in a dose-dependent manner, as is shown in FIGS. 8A-8D. As shown in FIGS. 8A-8D, the human anti-CD161 antibodies disclosed herein are better at restoring NFAT signaling (denoted as TCR signaling) in comparison to HP-3G10. TABLE 14 lists calculated EC$_{50}$ values.

TABLE 14

| Antibody | EC$_{50}$ (nM) |
|---|---|
| Ab1 | 2.78 |
| Ab2 | 3.07 |
| Ab3 | 4.05 |
| Ab4 | 2.59 |
| Ab5 | 1.93 |
| Ab6 | 1.62 |
| Ab7 | 2.08 |
| Ab8 | 1.91 |
| Ab9 | 2.31 |
| Ab10 | 2.19 |
| Ab11 | 2.44 |
| Ab12 | 2.26 |
| Ab13 | 1.62 |
| Ab14 | 2.36 |
| Ab15 | 1.77 |
| Ab16 | 2.14 |
| Ab17 | 1.98 |
| Ab18 | 1.54 |
| Ab19 | 1.72 |
| Ab20 | 2.17 |
| Iso Ctrl | >10 |

Example 8—Antibody Activation of T Cells in Co-Culture Assay with Endogenous CLEC2D Expression This example describes the ability of anti-CD161 antibodies to block inhibitory signaling on Jurkat T cells mediated by target cells with endogenous ligand expression.

Jurkat T cells with an NFAT-Luciferase reporter gene (InvivoGen) were engineered to overexpress both an NY-ESO-1-specific TCR and human CD161 by lentiviral transduction. Cells were cultured in IMDM media with selection antibiotics prior to assay setup.

NALM6 human cancer cells, which endogenously express MHC-I (HLA-A0201) and CLEC2D, were cultured in RPMI media prior to assay setup.

On Day 0, the NALM6 cells were seeded at a density of 5×10$^5$ cells/mL in media containing 1 μg/mL NY-ESO-1 peptide antigen (SEQ ID NO: 192) and incubated overnight.

On Day 1, the Jurkat effector cells and the peptide-loaded NALM6 target cells were plated at a ratio of 1:4 in 96-well plates. Anti-CD161 antibodies were pre-diluted in assay media and added to the co-culture at a 1:1 volume ratio. Plates were incubated overnight at 37° C., 5% CO$_2$.

On Day 2, 20 μL of assay supernatants were transferred to white-walled 96-well plates containing 50 μL of QUANTI-Luc luciferase detection reagent (Invivogen). End-point luminescence was read on EnVision plate reader. Fold induction was calculated by normalizing the luminescence value of each well by the average luminescence value of control wells containing no antibody.

Figure 9:
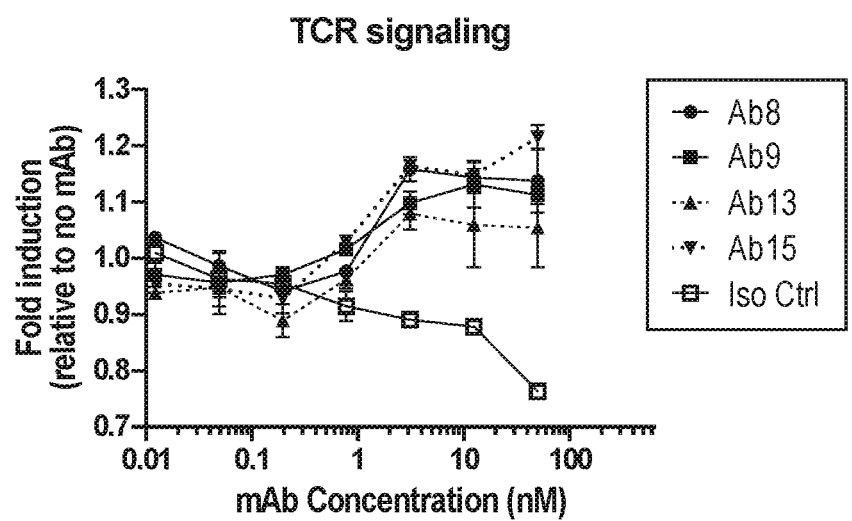
FIG. 9 is a graph showing restoration of NFAT signaling in a dose-dependent manner in the presence of human anti-CD161 antibodies, Ab8, Ab9, Ab13, and Ab15. Isotype control antibody (Iso Ctrl) was used as a control.

FIG. 9 is a graph showing restoration of NFAT signaling in a dose-dependent manner.

In the absence of antibody, the interaction between CD161 on the Jurkat cells and CLEC2D on the NALM6 cells inhibits NFAT signaling. In the presence of anti-CD161 antibody, the inhibitory signal is blocked and NFAT signaling through the TCR/MHC-I interaction is restored in a dose-dependent manner as is shown in FIG. 9.

Example 9—Developability of Anti-CD161 Antibodies

This example assesses manufacturing feasibility, formulatability for a specific administration route, and compatibility with in vivo environment, such as immunogenicity, off-target effect, and half-life of the anti-CD161 antibodies.
Polyspecificity ELISA This method was used to establish antibody binding to microtiter plate-immobilized polyspecificity targets (dsDNA, Insulin, baculovirus particles (BVP), HSP70). Antibody binding to these targets has correlated with rapid antibody clearance in vivo (Avery el al. (2018) MABS, 10(2): 244-255; Jain et al. (2017) PROC. NATL. ACAD. SCI. USA, 114(5): 944-949; Kelly et al. (2017) MABS, 9(7): 1036-1040). To account for potential plate-to-plate variability in assay signal, the assay was performed using three control antibodies on each ELISA plate. The controls were selected based on their low (AdalimumAb, Lapadula et al. (2014) INT. J. IMMUNOPATHOL. PHARMACOL., 27(1 Suppl): 33-38), moderate (Ustekinumab, Benson et al. (2011) MABS, 3(6): 535-545), or high (Briakinumab, Misselwitza et al. (2020) DIGESTION, 101(Suppl 1): 69-82) polyreactivity (Jain et al. (2017) PROC. NATL. ACAD. SCI. USA, 114(5): 944-949; Kelly et al. (2017) MABS, 9(7): 1036-1040).

37° C., the plate was washed three times and HRP-conjugated goat anti-human IgG antibody (Fc gamma fragment specific, Jackson Immunoresearch, cat #109-035-098) was added (25 µL per well) for 45 min at 37° C. Antibody that was bound to plate-immobilized target was determined using HRP substrate (3,3',5,5'-tetramethylbenzidine (TMB; SeraCare, cat #5120-0077) with absorbance at 450 nm. For each antibody, duplicate values were averaged, and average assay background subtracted.

TABLE 15 shows that all 20 anti-CD161 antibodies (11 antibodies generated from parental monoclonal antibody from first family (F1) and 9 antibodies generated from parental monoclonal antibody for second family (F2)) had low binding to the plate-immobilized polyspecificity targets. Test antibody binding was 0.92-fold to 2.8-fold that of the control low polyreactive antibody AdalimumAb, and 1.0-fold to 2.14-fold for insulin, 0.46-fold to 1.92-fold for BVP and 0.64-fold to 4.07-fold for HSP70. In contrast, the highly polyreactive control antibody, Briakinumab, bound much tighter to the plate-immobilized targets than AdalimumAb with binding ~5-fold greater against dsDNA, ~17-fold against insulin, ~8-fold with BVP, and ~10-fold more against HSP70. These results confirmed the anti-CD161 antibody's low propensity for polyreactivity.

TABLE 15

| Antibody | Parent mAb | dsDNA A450 nm | dsDNA Norm[1] | Insulin A450 nm | Insulin Norm | BVP A450 nm | BVP Norm | HSP70 A450 nm | HSP70 Norm | BSA A450 nm |
|---|---|---|---|---|---|---|---|---|---|---|
| Ab1 | F1 | 1.34 | 2.79 | 0.15 | 2.14 | 0.30 | 1.25 | 0.15 | 1.07 | 0.15 |
| Ab2 | F1 | 0.53 | 1.10 | 0.09 | 1.29 | 0.21 | 0.88 | 0.18 | 1.29 | 0.10 |
| Ab3 | F1 | 0.66 | 1.38 | 0.08 | 1.14 | 0.22 | 0.92 | 0.11 | 0.79 | 0.09 |
| Ab4 | F1 | 0.84 | 1.75 | 0.13 | 1.86 | 0.38 | 1.58 | 0.24 | 1.71 | 0.08 |
| Ab5 | F1 | 0.70 | 1.46 | 0.07 | 1.00 | 0.13 | 0.54 | 0.12 | 0.86 | 0.08 |
| Ab6 | F1 | 0.61 | 1.27 | 0.09 | 1.29 | 0.11 | 0.46 | 0.09 | 0.64 | 0.09 |
| Ab7 | F1 | 0.51 | 1.06 | 0.12 | 1.71 | 0.28 | 1.17 | 0.22 | 1.57 | 0.08 |
| Ab8 | F1 | 0.63 | 1.31 | 0.12 | 1.71 | 0.32 | 1.33 | 0.20 | 1.43 | 0.10 |
| Ab9 | F1 | 0.67 | 1.40 | 0.11 | 1.57 | 0.28 | 1.17 | 0.14 | 1.00 | 0.10 |
| Ab10 | F1 | 1.18 | 2.46 | 0.15 | 2.14 | 0.42 | 1.75 | 0.26 | 1.86 | 0.10 |
| Ab11 | F1 | 1.18 | 2.46 | 0.13 | 1.86 | 0.46 | 1.92 | 0.24 | 1.71 | 0.12 |
| Ab12 | F2 | 0.55 | 1.15 | 0.11 | 1.57 | 0.30 | 1.25 | 0.25 | 1.79 | 0.10 |
| Ab13 | F2 | 0.68 | 1.42 | 0.11 | 1.57 | 0.40 | 1.67 | 0.28 | 2.00 | 0.12 |
| Ab14 | F2 | 0.85 | 1.77 | 0.13 | 1.86 | 0.23 | 0.96 | 0.25 | 1.79 | 0.08 |
| Ab15 | F2 | 0.86 | 1.79 | 0.14 | 2.00 | 0.25 | 1.04 | 0.33 | 2.36 | 0.10 |
| Ab16 | F2 | 0.56 | 1.17 | 0.09 | 1.29 | 0.11 | 0.46 | 0.09 | 0.64 | 0.11 |
| Ab17 | F2 | 0.75 | 1.56 | 0.10 | 1.43 | 0.17 | 0.71 | 0.17 | 1.21 | 0.10 |
| Ab18 | F2 | 0.44 | 0.92 | 0.08 | 1.14 | 0.11 | 0.46 | 0.15 | 1.07 | 0.10 |
| Ab19 | F2 | 0.73 | 1.52 | 0.12 | 1.71 | 0.31 | 1.29 | 0.57 | 4.07 | 0.06 |
| Ab20 | F2 | 0.56 | 1.17 | 0.15 | 2.14 | 0.27 | 1.13 | 0.38 | 2.71 | 0.08 |
| AdalimumAb | n/a | 0.48 | 1.00 | 0.07 | 1.00 | 0.24 | 1.00 | 0.14 | 1.00 | 0.07 |
| Ustekinumab | n/a | 1.21 | 2.52 | 0.16 | 2.29 | 1.18 | 4.92 | 0.52 | 3.71 | 0.10 |
| Briakinumab | n/a | 2.19 | 4.56 | 1.22 | 17.43 | 2.03 | 8.46 | 1.46 | 10.43 | 0.19 |

[1]Each value represents the assay signal for test antibody divided by the assay signal for the low polyreactive control antibody, AdalimumAb.

A typical ELISA was performed by coating, overnight at 4° C., test wells of a high binding half-well plate (Corning, cat #3690) with 3 µg/mL/25 µl per well of a polyspecificity reagent (dsDNA (Millipore, cat #11691112001), human insulin (MP Biomedicals, cat #193900), BVP (LakePharma, cat #25690), human HSP70 (R&D Systems, cat #AP-100)) in PBS, pH 7.4. Background control wells on the plate were left uncoated. Plates were washed three times with wash buffer (PBS containing 0.05% tween 20, pH 7.4) and immediately blocked with blocking buffer (3% BSA in PBS, pH 7.4) for 1 hour at 37° C. Into test and control (just blocked) wells, 100 nM anti-CD161 or control antibodies were added (25 µL per well) in duplicate in assay buffer (blocking buffer containing 0.05% tween 20). After incubation for 45 min at HIC binding (HPLC)

IgG samples were assayed by hydrophobic interaction chromatography, as this methodology has been shown to be a useful correlate of poor biophysical behavior or non-specificity (Jain et al. (2017) PROC. NATL. ACAD. SCI. USA, 114(5): 944-949). Based on this previous work, two thresholds for retention time were defined as flags for concern were used to assess the behavior of the antibody candidates.

The methodology for this assay has been previously described (Estep, et al. (2015) MABS, 7(3): 553-561). Briefly, 5 µg purified IgG samples at 1 mg/mL were spiked in with a mobile phase A solution (1.8 M ammonium sulfate and 0.1 M sodium phosphate at pH 6.5) to achieve a final ammonium sulfate concentration of about 1 M before analysis. A Sepax Proteomix HIC butyl-NP5 column was used with a liner gradient of mobile phase A and mobile phase B solution (0.1 M sodium phosphate, pH 6.5) over 20 min at a flow rate of 1 mL/min with UV absorbance monitoring at 280 nm. Retention time was measured and compared to the developability flags: a retention time of under 10.5 min was considered to be of no concern; between 10.5-11.5 min was of low concern; and >11.5 min was of high concern. The retention times for the IgGs are listed in TABLE 16.

As shown in TABLE 16, retention time for all tested antibody candidates was under 10.5 mins.

TABLE 16

| Antibody | HIC retention time (min) |
| --- | --- |
| Ab1 | 9.1 |
| Ab2 | 9.6 |
| Ab3 | 9.1 |
| Ab4 | 9.2 |
| Ab5 | 10.0 |
| Ab6 | 9.1 |
| Ab7 | 9.4 |
| Ab8 | 9.4 |
| Ab9 | 9.5 |
| Ab10 | 9.0 |
| Ab11 | 9.1 |
| Ab12 | 9.2 |
| Ab13 | 9.1 |
| Ab14 | 9.1 |
| Ab15 | 9.1 |
| Ab16 | 9.2 |
| Ab17 | 9.1 |
| Ab18 | 9.2 |
| Ab19 | 9.3 |
| Ab20 | 9.2 |

Example 10—Profiling of Anti-CD161 Antibodies Binding to Human and Cynomolgus PBMCs This example characterizes the binding of anti-CD161 antibodies to primary immune cells from human or cynomolgus monkey in order to assess the affinity and specificity of the antibodies to cells with endogenous target expression. Binding to human and cynomolgus monkey NK cells in a PBMC population.

The ability of the anti-CD161 antibodies to bind to NK cells, which are known to express CD161, in a human and cynomolgus monkey PBMC population was measured.

Human PBMCs (Hemacare, catalog #20062234) were washed in PBSA and seeded in a 96 well plate at a density of $2\times10^5$ cells per well then incubated with Live/Dead Aqua stain (Thermo Fisher, catalog #L34957) diluted 1:1000 in PBS at room temperature for 20 minutes. Cells were washed in PBSA, then resuspended in Fc block diluted 1:200 in PBSA at 4° C. for 20 minutes. Cells were washed in PBSA, then resuspended in an antibody cocktail containing APC conjugated antibody titrations, anti-human CD3 Alexa Fluor® 700 (Biolegend, catalog #300424), anti-human CD56 BB700 (BD, catalog #566573), anti-human CD16 V450 (BD, catalog #644489) diluted in PBSA and incubated at 4° C. for 2 hours. Cells were washed in PBSA and analyzed by flow cytometry with a BD Symphony flow cytometer.

Cynomolgus PBMCs (Worldwide Primates, catalog #bc347H) were washed in PBSA and seeded in a 96 well plate at a density of $2\times10^5$ cells per well then incubated with Live/Dead Aqua stain (Thermo Fisher, catalog #L34957) diluted 1:1000 in PBS at room temperature for 20 minutes. Cells were washed in PBSA, then resuspended in Fc block diluted 1:200 in PBSA at 4° C. for 20 minutes. Cells were washed in PBSA, then resuspended in an antibody cocktail containing APC conjugated antibody titrations, anti-human CD3 APC-Cy™7 (Biolegend, catalog #557757), anti-human NKp80 PE (Biolegend, catalog #346706), anti-human CD16 V450 (BD, catalog #644489) diluted in PBSA and incubated at 4° C. for 2 hours. Cells were washed in PBSA and analyzed by flow cytometry with a BD Symphony flow cytometer.

Data were analyzed using FlowJo software. Human NK cells were identified by CD3 negative/CD16 positive/CD56 positive markers. Cynomolgus monkey NK cells were identified by CD3 negative/CD16 positive/NKp80 positive markers. CD161 percentage positive of NK cells at each concentration was calculated and exported into Graphpad Prism. $EC_{50}$ values were calculated with a 3 parameter non-linear regression fit.

Figure 10A:
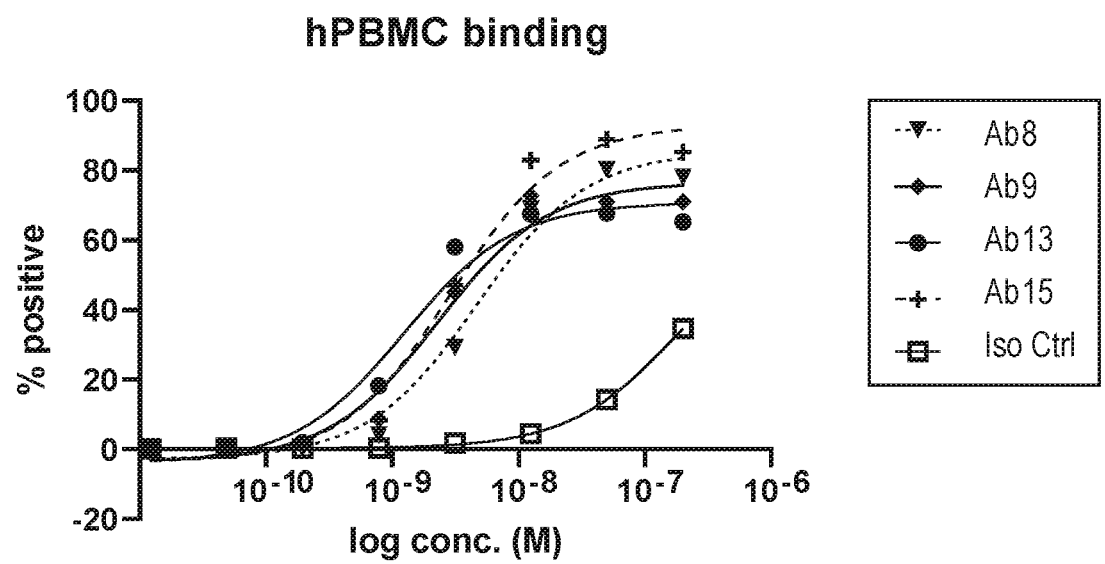
FIGS. 10A-10B are graphs showing binding of human anti-CD161 antibodies, Ab8, Ab9, Ab13, and Ab15 to human PBMCs (FIG. 10A) and cynomolgus PBMCs (FIG. 10B). Iso Ctrl denotes an isotype control antibody.
Figure 10B:
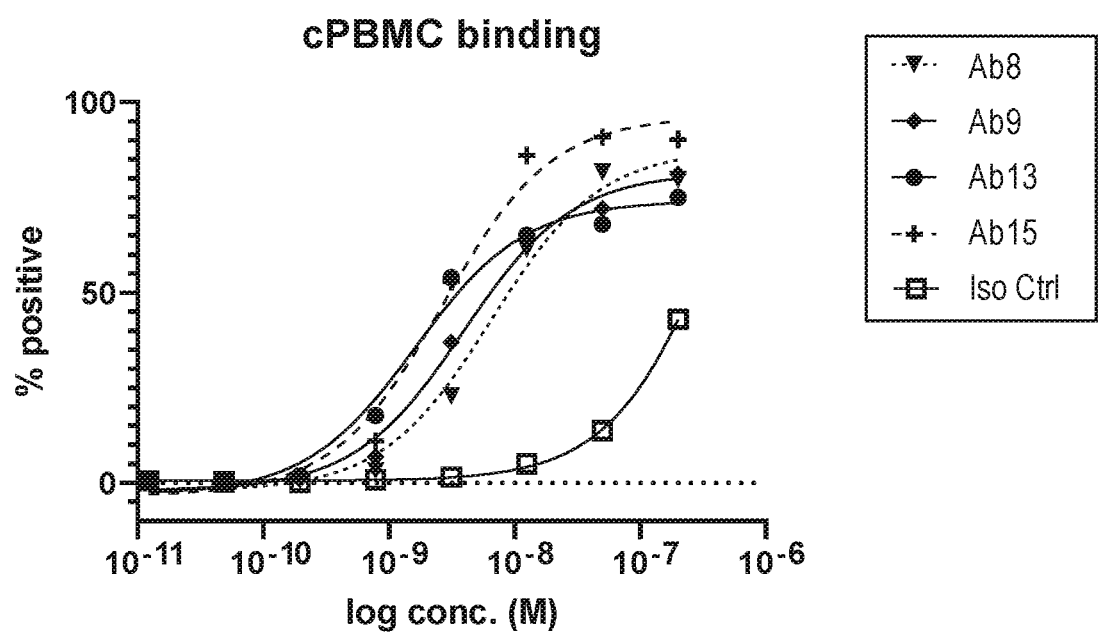

FIGS. 10A-10B are graphs showing binding of anti-CD161 antibodies to human PBMCs (FIG. 10A) and cynomolgus PBMCs (FIG. 10B).

Anti-CD161 binding to hPBMCs and cPBMCs is shown in TABLE 17.

TABLE 17

|  | hPBMC EC50 (nM) | cPBMC (EC50 (nM) |
| --- | --- | --- |
| Ab8 | 4.6 | 6.5 |
| Ab9 | 2.3 | 3.9 |
| Ab13 | 1.2 | 1.6 |
| Ab15 | 2.9 | 2.6 |
| Iso Ctrl | 184.3 | 487.7 |

As shown in TABLE 17 and FIGS. 10A-10B, the antibodies bound to human and cynomolgus monkey primary NK cells in a PBMC population in a dose dependent manner.

Example 11—Profiling of Anti-CD161 Antibodies Binding to Human PBMCs to Test Cell Type Specificity The ability of the anti-CD161 antibodies to specifically bind only to immune cell populations in human PBMCs known to express CD161 was evaluated. Within human PBMCs, it has been shown that mucosa-associated invariant T (MAIT) cells strongly express CD161 (Martin, et al., *PLoS Biol.*, 2009, 7(3): e1000054), while other immune cell types such as B cells, monocytes and dendritic cells lack expression of CD161.

Human PBMCs (Hemacare, catalog #20062234) were washed in 1×PBS and seeded in a 96 well plate at a density of 250,000 cells per well then incubated with Live/Dead Aqua stain (Thermo Fisher, catalog #L34957) diluted 1:1000 in PBS at room temperature for 20 minutes. Cells were washed in staining buffer (1×PBS with 3% Fetal Bovine serum and 0.2 mM EDTA), then resuspended in Fc block diluted 1:200 in staining buffer at 4° C. for 20 minutes. Cells were washed in staining buffer, then resuspended in an antibody cocktail containing APC conjugated anti CD161 antibody at 30 nM, anti-human CD3 Alexa Fluor® 700 (Biolegend, catalog #300424), anti-human CD56 BB700 (BD, catalog #566573), anti-human CD16 BV786 (Biolegend, catalog #302046), anti-human CD8 BV711 (Biolegend, catalog #301044), anti-human TCRva7.2 BV421 (Biolegend, Catalog #351794), anti-human CD11c FITC (Biolegend, catalog #371516), anti-human CD4 APC-Cy7 (Biolegend, Catalog #300518), anti-human CD14 PE-Cy7 (Biolegend, catalog #367112) and anti-human CD20 PE (Biolegend, catalog #302306) diluted in staining buffer and incubated at 4° C. for 30 min. Cells were washed in staining buffer and analyzed by flow cytometry with a BD Symphony flow cytometer.

Data were analyzed using FlowJo software. Human MAIT T cells were identified by CD3 positive/TCRva 7.2 positive markers. Human B cells were identified by CD3 negative/CD20 positive markers, human monocytes were identified by CD3 negative/CD14 positive markers and human dendritic cells were identified by CD3 negative/CD11c positive markers. CD161 MFI of different cells was calculated at 30 nM and exported into GraphPad Prism.

Figure 11:
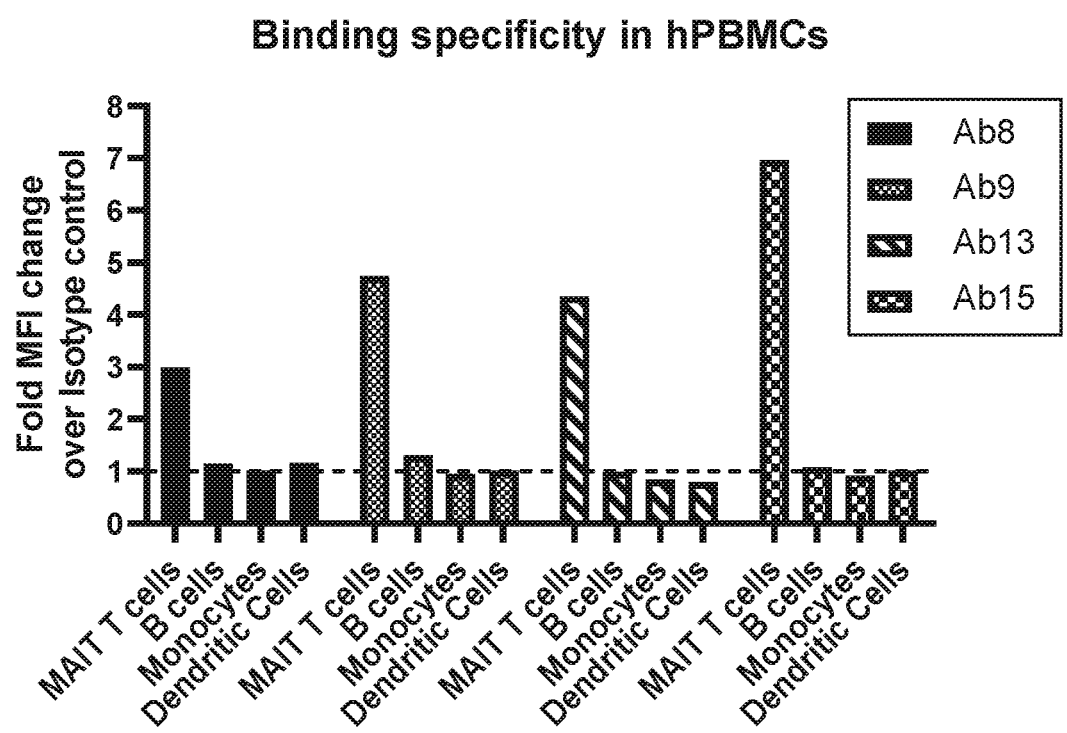
FIG. 11 is a bar graph showing binding of human anti-CD161 antibodies, Ab8, Ab9, Ab13, and Ab15 to immune cell populations in human PBMCs (MAIT T cells, B cells, monocytes, and dendritic cells).

FIG. 11 is a bar graph showing binding of anti-CD161 antibodies to immune cell populations in human PBMCs (MAIT T cells, B cells, monocytes, dendritic cells.

Fold MFI change of anti CD161 binding to respective cells over Isotype control is shown in TABLE 18.

TABLE 18

|  | MAIT T cells (CD3+ TCR Vb7.2+) | B cells (CD20+) | Monocytes (CD14+) | Dendritic Cells (CD11c+) |
|---|---|---|---|---|
| Ab8 | 2.99078341 | 1.147165 | 1.0114895 | 1.160389898 |
| Ab9 | 4.746543779 | 1.307884 | 0.9524005 | 1.012848914 |
| Ab13 | 4.350230415 | 0.987828 | 0.8354534 | 0.79973416 |
| Ab15 | 6.963133641 | 1.077455 | 0.9146492 | 1.007089056 |

As shown in TABLE 18 and FIG. 11, the anti CD161 antibodies bound to human primary MAIT T cells with a higher specificity (fold change over isotype control >1) than B cells, Monocytes and DCs (fold change over isotype control </=1) in human PBMCs.

Example 12—An N297A Amino Acid Substitution in the Fc Region of Ab9 Reduced Binding to FcγRII and Eliminated Binding to FcγRI and FcγRIII This example tested the binding affinity of Ab9, a monoclonal, aglycosylated human $IgG_1$ antibody directed against CD161, to FcγRs and FcRn, when compared to the wild type human $IgG_1$ antibody ("WT").

The Fc portion of IgG antibodies has various regions associated with specific immune functions when engaged with the Fc receptors found on immune cells. Three distinct Fc receptors for IgG (FcγR), FcγRI, FcγRII, and FcγRIII are known to be associated with human myeloid cells, including monocytes, lymphocytes, polymorphonuclear cells (PMNs). Engagement of the Fc portion of the IgG with one of these FcγR can lead to cytolysis of a cell that expresses the antigen specific to the Fab portion of the IgG.

Ab9, a human $IgG_1$, blocks the binding of CD161 to its ligand, CLEC2D. Ab9 was engineered with an alanine (A) to asparagine (N) substitution (N297A) in the Fc region, in order to abrogate binding to Fcγ receptors, and eliminate any undesirable cytolysis.

The experiments described in this example demonstrate that the engineered amino acid switch of alanine-to-asparagine is effective in either eliminating or significantly reducing the binding of Ab9 to the Fcγ receptors RI, RIIA, RIIB/C, RIIIA, and RIIIB. The mutation did not significantly alter binding to FcRn, which binds to $IgG_1$'s in a different location from the FcγRs. It is a recycling receptor responsible for the long half-life of IgGs and therefore will not impact the activity of Ab9.

Fcγ Receptor Binding by ELISA

The binding of antibody Ab9 to Briefly, streptavidin coated clear 96-well plate with blocking buffer was washed three times with wash buffer. 100 µL/well of biotinylated FcγR at 0.25 µg/mL in PBSA was added to the plate according to plate map. The plate was incubated for 1 hour at room temperature. During incubation, Ab9 and WT, were preincubated with a mouse antibody to Kappa light chain (Abcam anti-kappa) at a 2:1 ratio for 1 hour at room temperature. The plate was then washed three times with wash buffer. 100 µL/well of 3-fold, 7 point, titrated IgG complex or IgG alone in PBSA was added according to the plate map (top concentration of 25,000 ng/mL for IgG complex, top concentration of 500 ng/mL for IgG alone). The plate was incubated for 2 hours at room temperature and then washed three times with wash buffer. 100 uL/well of HRP conjugated Fab-anti-human Fab fragment specific, diluted 1:5000 in PBSA was added to the plate followed by incubation for 1 hour at room temperature. The plate was then washed three times with wash buffer followed by addition of HRP substrate (TMB (TMB or equivalent, i.e. Seracare Life Sciences Inc, Fishercat #50-674-93), 100 µL/well). Once color was developed, stop solution was added (100 µL/well), and the plate was read with absorbance at 450 nm. $EC_{50}$ values were calculated with a 3 parameter non-linear regression.

Figure 14A:
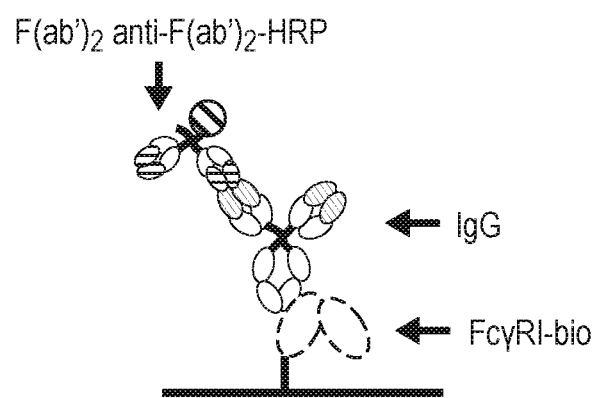
FIGS. 14A-14B illustrate ELISA assay format, which shows soluble receptor binding to FcγRI (FIG. 14A) and FcγRII and FcγRIII (FIG. 14B). Biotinylated FcγRI, FcγRII, and FcγRIII are denoted as "FcγRI-bio," "FcγRII-bio," "FcγRIII-bio," respectively. Mouse antibody that binds kappa light chain is denoted as "Mouse anti-kappa." HRP-conjugated Fab-anti-human Fab fragment is denoted as "F(ab')2 anti-F(ab')2-HRP)."
Figure 14B:
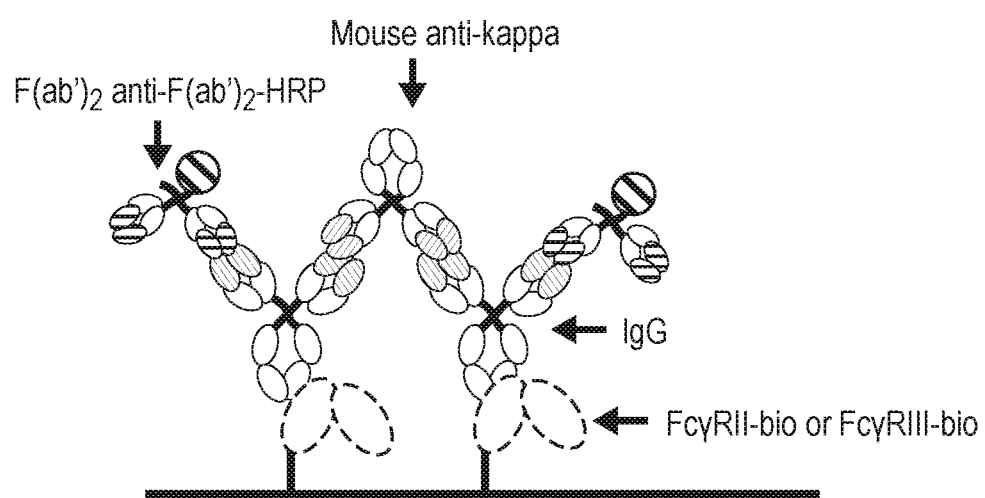
Figure 15A:
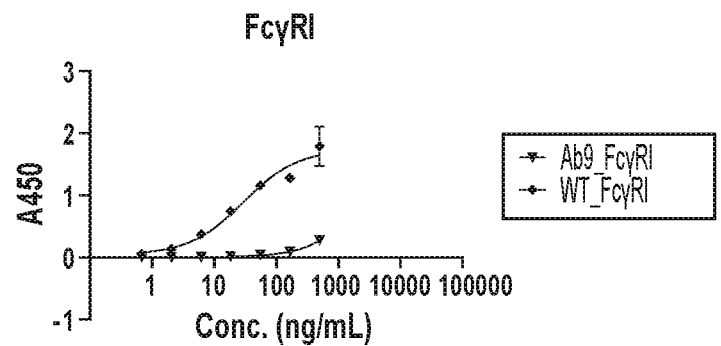
FIGS. 15A-15E are ELISA binding curves illustrating binding kinetics of Ab9 or wildtype human IgG1 antibody ("WT") to Fc receptors, FcγRI (FIG. 15A), FcγRIIA (FIG. 15B), FcγRIIB/C (FIG. 15C), FcγRIIIA (FIG. 15D), and FcγRIIIB (FIG. 15E). H167 and R167 denote two allelic variants of FcγRIIA that differ in their ability to ligate human IgG2. F176 and V176 denote two FcγRIIIA alleles which differ in their ability to bind human $IgG_1$ and IgG3; F176 is the low-binding allele, V176 is high binding allele.
Figure 15B:
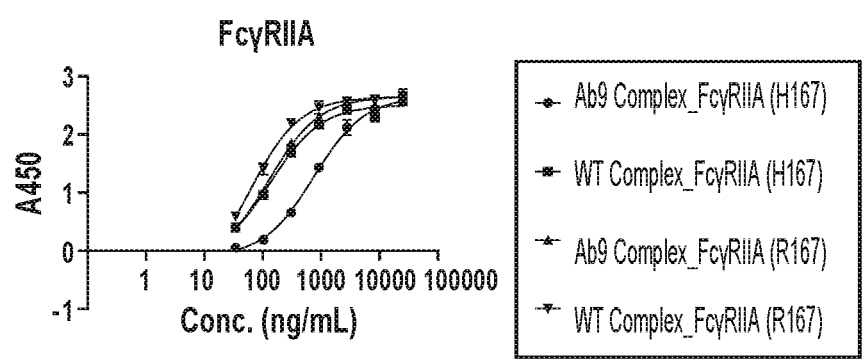
Figure 15C:
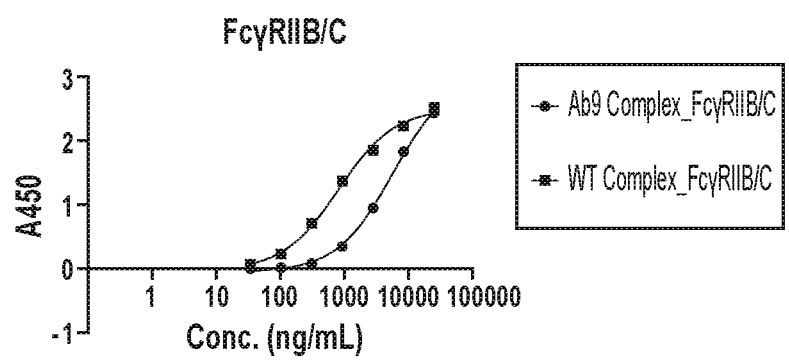
Figure 15D:
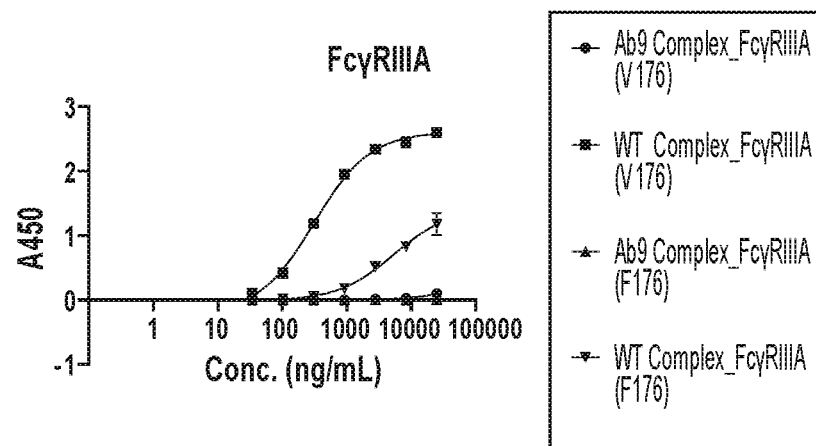
Figure 15E:
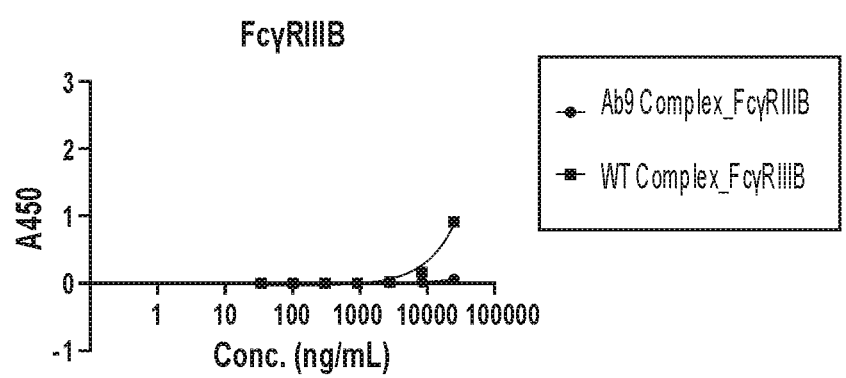

FIGS. 14A-14B illustrate ELISA assay format, which shows soluble receptor binding to FcγRI (FIG. 14A) and FcγRII and FcγRIII (FIG. 14B). Biotinylated FcγRI is shown as "FcγRI-bio." FIGS. 15A-15E are ELISA binding curves illustrating binding kinetics of Ab9 to Fcγ receptors, FcγRI (FIG. 15A), FcγRIIA (FIG. 15B), FcγRIIB/C (FIG. 15C), FcγRIIIA (FIG. 15D), and FcγRIIIB (FIG. 15E).

As shown in FIGS. 15A-15E, the alanine (A) to asparagine (N) substitution (N297A) in the Fc region of Ab9 reduced binding to FcγRII and eliminated binding to FcγRI and FcγRIII compared to wild-type human $IgG_1$. FcγRIIA (R167) and FcγRIIA (H167) represent two allelic variants of FcγRIIA that differ in their ability to ligate human $IgG_2$. Similarly, FcγRIIIa alleles, F176 and V176, which differ in one amino acid at position 176 in the extracellular domain and differ in their ability to bind human $IgG_1$ and $IgG_3$; F176 is the low-binding allele, V176 is high binding.

TABLE 21

| | $EC_{50}$ values as determined by ELISA. | | | | | | |
|---|---|---|---|---|---|---|---|
| | FcγRI | FcγRIIA (H167) | FcγRIIA (R167) | FcγRIIB/C | FcγRIIIA (F176) | FcγRIIIA (V176) | FcγRIIIB |
| Ab9 | n.b. | 752.1 | 127.2 | 5659 | n.b. | n.b. | n.b. |
| WT | 29.6 | 137.1 | 58.6 | 808 | 5368 | 311.7 | n.b. |
| Relative Affinity | 0 | 0.18 | 0.46 | 0.14 | 0 | 0 | 0 |

Abbreviations used in the table: n.b.—no binding.

Fcγ Receptor Binding by Octet

Figure 16A:
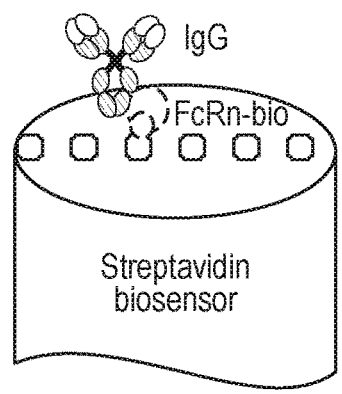
FIG. 16A illustrate the FcRn binding method by Octet.

The binding kinetics of Ab9 to Fc receptors was also assessed via biolayer interferometry on an Octet system (FortdBio). FIG. 16A illustrate the FcRn binding method by Octet. 3 μg/mL of Acro FcRn-Bio in pH 5.0 octet buffer was loaded onto streptavidin biosensors for 90 seconds. Association (100 nM, 3-fold, 7-point titration, pH 5.0 buffer) for 180 seconds and dissociation in pH 5.0 buffer for 600 seconds were measured. Results were analyzed using ForteBio Data Analysis 12.0.2.11 software. A reference sample well containing immobilized load sample and no analyte during association was subtracted from each sample. The top three concentrations were excluded due to non-specific effects and poor model fit. Kinetic constants were calculated using a global 1:1 kinetic binding model.

Figure 16B:
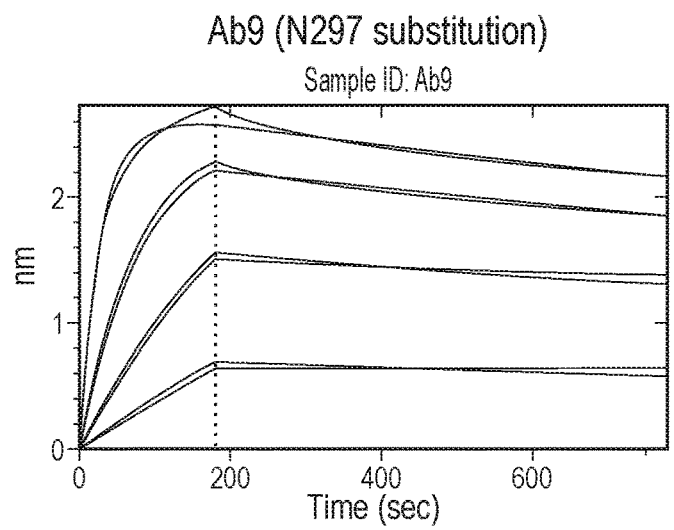
FIGS. 16B-16C are exemplary binding curves for Ab9 (FIG. 16B) and wildtype human $IgG_1$ antibody ("WT") (FIG. 16C), determined by Octet.
Figure 16C:
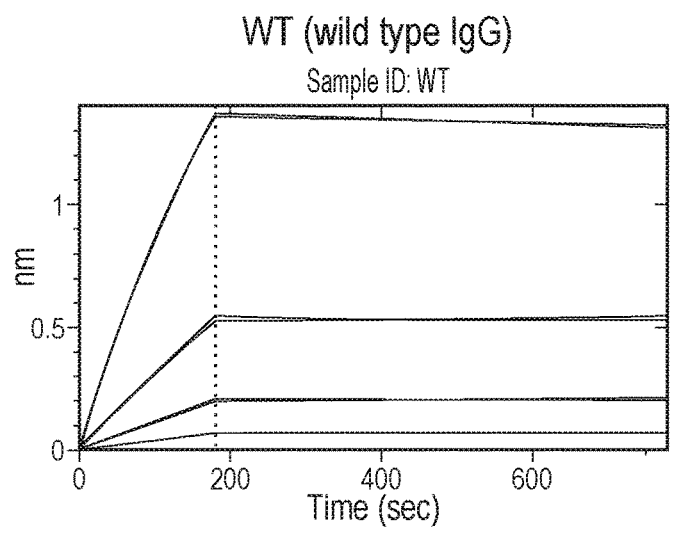

Similar to the ELISA assay, tight binding to FcRn was observed for both Ab9 and WT. A good 1:1 model fit was also observed across 4 concentrations tested. As shown in FIGS. 16B-16C, the increased sensitivity of the Octet format demonstrated clearly that the N297A mutation does not significantly alter the binding of Ab9 to FcRn. Calculated $K_D$ value for Ab9 and WT was 0.086 nM and 0.13 nM, respectively.

Example 13—Anti-CD161 Antibody, Ab9, Reverses CLEC2D-Mediated Inhibition and Restores NK Cell Degranulation and IFN-γ Production This examples assesses the ability of anti-CD161 antibody, Ab9, to reverse inhibition of NK cell killing by blocking the interaction of CD161 on NK cells with CLEC2D on target cells. Briefly, this example was conducted to determine whether the activity of NK cells differed for target cells with cell surface expression of CLEC2D versus those that did not have CLEC2D on their surface, in the presence and absence of the anti-CD161 antibody, Ab9. CD107a was utilized as a marker of degranulation of NK cells, and secretion of IFN-γ was examined as an additional measure of NK cell activation.

K562 Degranulation Assay

NK cells were isolated from human PBMCs (RTD165 and PBMC-030 (MCB-117)) and stimulated with IL-2 overnight using NK isolation kit. An eight-color flow cytometry antibody panel was designed to study the isolated CD56$^+$ NK cells (effectors) for phenotype and function within the assay. The IL-2 stimulated NK cells (effector cells) were added to wells of a microtiter plate per predefined plate maps. Test articles (Ab9 or isotype control (D1.3_hIgG1_N297A was used as a negative control)) were added to the effector cells starting at 300 nM to 0.018 nM as a 4-fold dilution and incubated for 30 minutes on ice. Target cells were incubated with Cell Trace Violet (CTV) for 20 minutes at room temperature protected from light. Post incubation, the target cells were incubated for 5 minutes with HI-FBS and then centrifuged. The appropriate target cell (control (K562-GFP cells) or CLEC2D$^+$ (K562-CLEC2D)) was added to the effector cells at a final effector:target ratio of 1:5 and incubated at 37° C./5% $CO_2$ for 4 hours. Cells were washed twice and resuspended in FACS buffer. Phenotyping antibodies (CD3-APC-Cy7, LIVE/DEAD™ Fixable Near-IR, TCRγ 6-APC-Vio770, CD19-APC-Cy7, CD56-BB700, CD107a-PE, IFNγ-FITC) were added and incubated briefly before cells were washed and resuspended in Fix/Perm buffer for 20 minutes. Cells were washed again and left in FACS Buffer overnight. The following day, cells were centrifuged and washed. This was followed by intracellular staining with anti-IFNγ antibody. Cells were centrifuged and resuspended FACS buffer prior to being analyzed on the Symphony Cell Analyzer (BD Biosciences). % CD107$^+$ cells and % IFN-γ cells were measured.

As seen in FIGS. 17A-17H, expression of both CD107a and IFN-γ increased when NK cells were pre-incubated with the anti-CD161 antibody (Ab9) prior to co-culture with K562 cells overexpressing CLEC2D. There was no effect of Ab9 antibody on CD107a expression in NK cells when CLEC2D was not present on the target K562 cells (FIGS. 17B and 17F). Additionally, no effect was seen in the presence of an isotype control antibody. PBMCs from donor RTD165 responded in a dose dependent manner in the degranulation (FIG. 17A) and IFNγ assays (FIG. 17C). $EC_{50}$ values were 0.2 nM for degranulation and 0.3 nM for IFNγ. As seen in FIGS. 17E-17H, degranulation (FIG. 17E) and secretion of IFN-γ (FIG. 17G) from human donor PBMC-030 (MCB117) showed a dose response. The $EC_{50}$ for both degranulation and IFNγ curves was 0.3 nM.

This data suggests that the interaction of CD161$^+$ NK cells with CLEC2D-expressing target cells inhibits the activation of the NK cells. The presence of Ab9 restored cytotoxic degranulation by NK cells, as well as expression of IFN-γ, an effect that was not observed in the presence of an isotype control antibody. Restoration of NK cell activation occurs through inhibition of the CD161/CLEC2D interaction, rather than by directly stimulating CD161 activity.

Example 14—Human NK Cells Display Higher Cytotoxicity of CLEC2D Expressing Target Cells in Presence of An Anti-CD161 Antibody This example assesses the ability of an anti-CD161 antibody (Ab9) to enhance NK cell killing of CLEC2D expressing target cells by blocking the interaction of CD161 on NK cells with CLEC2D on target cells.

The interaction of CD161 on the surface of NK cells with its ligand, CLEC2D, has been previously shown to inhibit the killing function of the NK cells (see Examples 6 and 13) and this can be restored using anti-CD161 antibody.

Direct Killing Assay

Figure 18A:
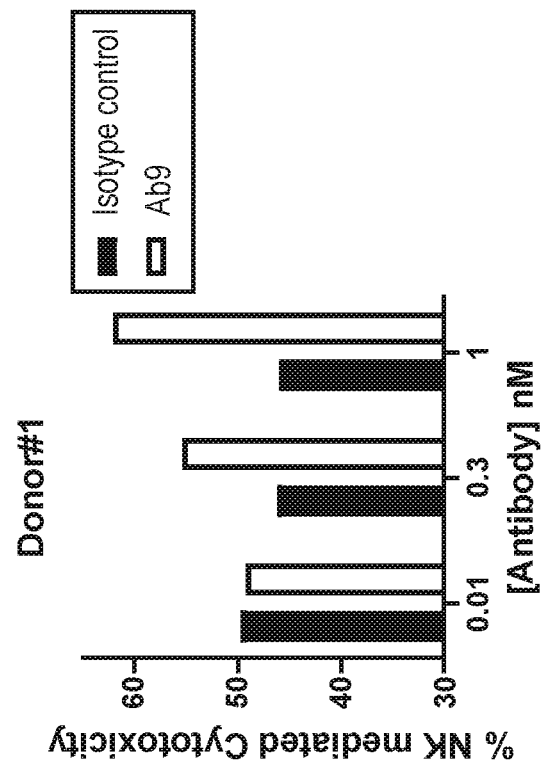
FIGS. 18A-18B are graphs that illustrate killing of Raji target cells by human NK cells isolated from donor #1 (FIG. 18A) or donor #2 (FIG. 18B) in the presence of anti-CD161 antibody (Ab9).
Figure 18B:
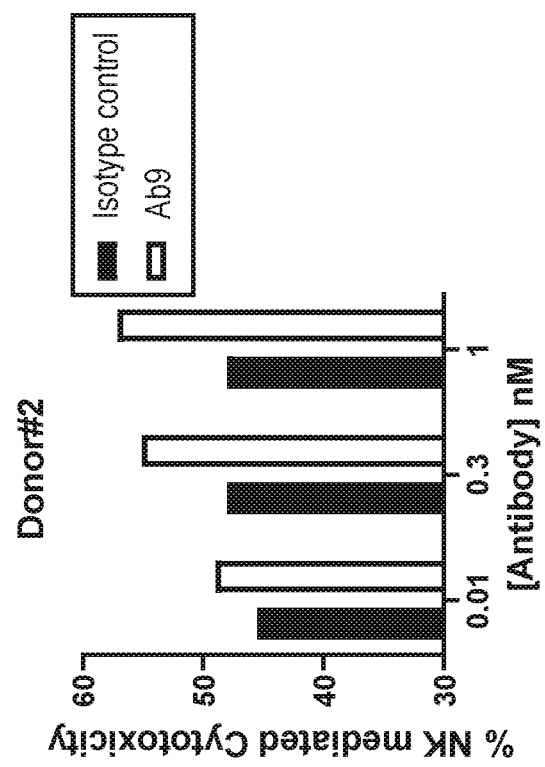

Briefly, NK cells were isolated from frozen human PBMCs of two healthy donors and stimulated with IL-2 overnight. The IL-2 stimulated NK cells (effector cells) were then added to wells of a microtiter plate per pre-defined plate maps. Test articles (Ab9 or isotype control (D1.3_hIgG1_N297A was used as a negative control)) were added to the effector cells starting at 300 nM to 0.02 nM as a 4 fold dilution and incubated for 30 minutes on ice. Burkitt Lymphoma cell line Raji cells (target cell line that endogenously expresses high levels of CLEC2D, CLEC2D$^+$target cells) were stained with Cell Trace Violet (CTV) for 20 minutes at room temperature protected from light. Post staining with CTV, the target cells were incubated for 5 minutes with Heat inactivated-FBS and then centrifuged to remove all unbound CTV. The CLEC2D$^+$target cells were added to the effector cells at a final effector:target ratio of 1:1 and incubated at 37° C./5% $CO_2$ for 4 hours. Cells were washed twice and resuspended in FACS buffer followed by staining with FVD-Near IR. The following day, cells were centrifuged and resuspended in FACS buffer prior to being analyzed on the Symphony™ Cell Analyzer (BD Biosciences) for % dead target cells by gating on CTV$^+$FVD$^+$ cells and analyzed on Flow Jo™, NK cell mediated cytotoxicity was measured by analyzing % CTV$^+$FVD$^+$population. As seen in FIG. 18A (donor #1) and 18B (donor #2), Ab9 shows dose dependent increase in NK cell mediated cytotoxicity, wherein 0.01 nM of Ab9 does not show any efficacy and the cytotoxic activity saturates at 1 nM for both donors showing high potency of the molecule in enhancing NK cell function.

In the presence of Ab9 anti-CD161 antibody, the interaction between CD161 and CLEC2D is efficiently blocked (shown previously in Example 13). This example shows that the blocking activity translates into enhanced cytolytic function of human NK cells expressing CD161 to kill target cells that express endogenously high levels of CLEC2D. The effect occurred at concentrations of Ab9 as low as 0.3 nM with saturation of activity achieved at 1 nM.

Example 15—Enhanced T Cell Activation in Antigenic Peptide Recall Assay in the Presence of an Anti-CD161 Antibody The example assesses the ability of anti-CD161 antibody, Ab9 to enhance re-activation of antigen specific effector memory CD4 T cells by blocking CD161 (expressed on T cells) interaction with CLEC2D (expressed on monocyte-derived DCs).

As shown previously in Examples 7 and 8, anti-CD161 antibodies are able to increase antigen-mediated T cell receptor signaling in engineered Jurkat T cell lines by blocking the interaction of CD161 with CLEC2D expressed on target cells displaying relevant antigen. This example tests whether anti-CD161 antibody (Ab9) treatment enhances the reactivation of an effector memory subset of primary human T cells expanded from human PBMCs.

Infections from a variety of pathogens result in the activation and expansion of antigenic peptide-specific effector T cells. Memory T cells towards these peptides remain in circulation long after the infectious agent is cleared. Peptide reactive memory T cells from human peripheral blood can be re-activated and expanded following presentation with HLA-bound antigenic peptides, termed as antigen specific memory T cell recall response. Peptide pools can be used to expand multiple T cell precursors from a single donor. Recall assays can further expand these precursor frequencies and have been shown to up-regulate immune checkpoint molecules, including PD-1 and TIGIT. Previous work has shown that a subset of effector memory CD4 and CD8 T cells express CD161 (see Truong et al. (2019) NATURE COMM., 10:2263). This example shows that Ab9 treatment leads to enhanced cytokine production and increased proliferation (as measured by Ki-67 expression) by antigen-specific effector memory T (EM) cells.

Antigen-Based T Cell Memory Recall Assay

Briefly, CD14$^+$ monocytes were isolated from donors by negative selection using Miltenyi's Classical Monocyte isolation kit. Monocytes were differentiated into dendritic cells (MoDC) by culturing purified CD14$^+$ monocytes in DC differentiation media supplemented with 100 ng/ml GMCSF and 20 ng/ml IL-4. Purified CD14$^+$ monocytes from donor D10637 (Hemacare) (termed as Donor 6) were plated in 1 ml of media at $1\times10^6$ cells per well in a 12 well plate in the presence of 100 ng/ml GMCSF and 20 ng/ml IL-4. 400 µl of media was removed and discarded every other day (Day2, Day4, and Day6) and replaced with 500 1 new media supplemented with cytokines. On day 6, MoDCs were stimulated with 1 µg/ml LPS and 100 ng/ml IFNγ for 48 hours to induce expression of the CD161 ligand, CLEC2D (see Germain et al. (2011) J. BIOL. CHEM., 286(44):37964-37975). Autologous T cells were expanded from PBMCs by culturing PBMCs in complete media supplemented with 1 µg/ml CEFX peptide (JPT, cat. PM-CEFX-2) for 24 hours. Unbound peptide was removed by washing PBMCs 2× in complete media. Cells were then plated in 4 ml of complete media in one well of a 6 well plate for an additional 48 hours. On Day 3, PBMCs were washed and counted. Cells were plated at $7.5\times10^5$/ml in complete media supplemented with 2.5 ng/ml IL-2, 5 ng/ml IL-7, and 5 ng/ml IL-15. Media was exchanged on Day 5 in complete media supplemented with cytokines. T cell cultures did not exceeded a density of $1.5\times10^6$/ml. On day 7, MoDCs were exposed to CEFX peptide (10 ng/ml) for 2 hours at 37° C. Autologous T cells that had been expanded on CEFX peptide were then plated in 96 well plates at a concentration of $1\times10^5$ cells/well either without the antibody or with either isotype control antibody (D1.3 Isotype Control Human IgG$_1$ (N297A) or anti-CD161 antibody (Ab9) at concentrations ranging from 0.02 nM to 100 nM. Peptide pulsed MoDCs were washed twice with PBS and then resuspended in complete media and added to wells with autologous T cells at a final concentration of $0.5\times10^5$ MoDCs/well. Cells were co-cultured for 24 hours at 37° C. Cells were exposed to Brefeldin A for the final 6 hours of culture to allow for intracellular staining of cytokines (IFNγ) and Ki-67 expression. Cells were harvested from wells and Fc-receptors were blocked prior to surface staining with the following panel of antibodies for flow cytometry:

Cells were washed, and then fixed and permeabilized (Cytofix/Cytoperm kit)
Near IR (Live/Dead stain);
APC-CD8 (Clone HIT8a);
BV605-CD4 (Clone RPA-74);
BV711-CD45RO (Clone UCHL1); and
BV421-CD161 (Clone HP-3G10)

Cells were washed, and then fixed and permeabilized (Cytofix/Cytoperm kit. Cat #BD 554714) following manufacturer recommendations. Intracellular staining was performed with the following antibodies: Alexa-488 K167 (Clone Ki-67) and PE-IFNγ (Clone B27). Cells were washed 3× in FACS staining buffer (PBS+1% FCS) and analyzed on the Symphony™ Cell Analyzer (BD Biosciences). Data was analyzed on Flow Jo™ and plotted using GraphPad PRISM™. Statistics were performed using Graphpad PRISM. P-values were analyzed from replicate datasets using student t-test.

Figure 19B:
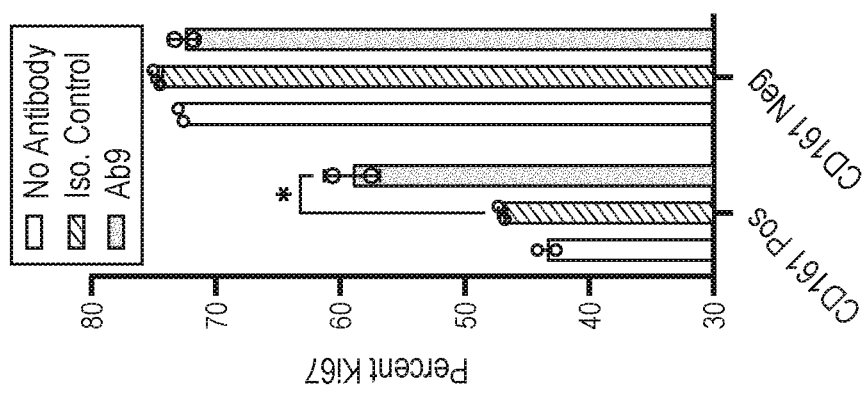
FIG. 19A-19B are graphs that illustrate blocking of CD161-CLEC2D interaction by anti-CD161 antibody (Ab9) leads to enhanced cytokine (as measured by IFNγ, FIG. 19A) and proliferation (as measured by K167, FIG. 19B) responses in memory CD4 T cells. T cells exposed to CEFX peptide in the presence of anti-CD161 antibody (Ab9), isotype control (iso. control) at a concentration of 6.25 nM, or were left untreated (no antibody). Proliferation of CD4 effector memory cells (EM) were determined by gating on CD161 expressing CD4 T cells (CD161 Pos) versus CD4 T cells lacking CD161 expression (CD161 Neg). *P≤0.05 **P≤0.01, (two-tailed Student's t-test).
Figure 19A:
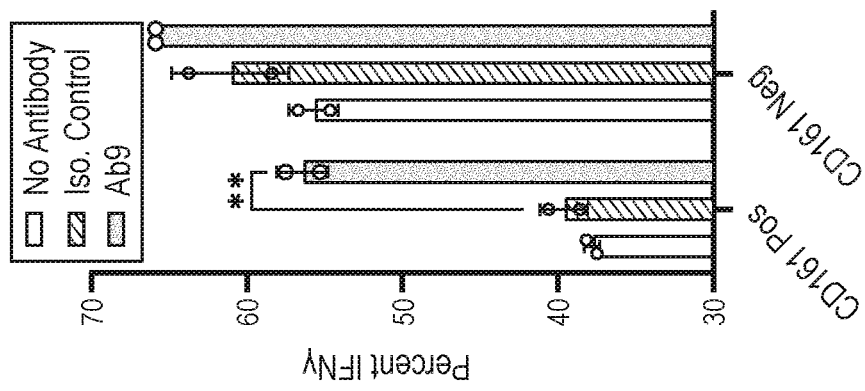

To explore the effect of anti-CD161 antibody (Ab9) in a memory recall assay, PBMCs from a donor who was seropositive for CMV and prior tested to respond to CEFX peptide stimulation were utilized. Monocytes differentiated into dendritic cells (MoDcs) were activated to increase expression of CLEC2D. Simultaneously, autologous T cells were activated and expanded on CEFX peptide for 7 days. Post-activation, MoDCs were pulsed with 10 ng/ml of CEFX peptide and co-cultured with autologous T cells that were previously expanded on CEFX peptide, either in presence of Ab9 or isotype control or absence of any antibody treatment for 24 hours. The co-culture was followed with flow cytometric staining for T cell markers, CD45RO for memory T cells, CD161 using a non-cross-reactive antibody clone and intracellular staining for IFNγ and K167. CD45RO$^+$ EM CD4 T cells expressing CD161 had lower IFNγ production and lower proliferation (as measured by K167 expression) in the presence of CLEC2D expressing MoDCs than CD4 EM cells that did not express CD161, suggesting that CD161 is a negative regulator of T cell activation. However, as shown FIGS. 19A-19B, when Ab9 was used to block CD161 interaction with CLEC2D, both cytokine production and proliferation were significantly increased as compared to the isotype control. Furthermore, treatment with Ab9 increased the cytokine and proliferative response seen in CD161$^+$ T cells to similar levels as T cells that were not expressing CD161 (FIGS. 19A-19B; CD161 Pos, vs CD161 neg) suggesting that Ab9 restores activity of CD161$^+$ cells that was suppressed by presence of CLEC2D on moDCs,

Example 16—Anti-CD161 Antibody (Ab9) Enhances Cytokine Production of Antigen-Specific Human CD8$^+$ T Cells This example assesses the ability of anti CD161 antibody (Ab) to enhance the cytokine production of MART-1-specific T cells in co-culture with Raji target cells through blockade of interaction of CD161 on the T cells with CLEC2D expressed on the target cells.

The production of cytokines from T cells within the tumor microenvironment plays a critical role in anti-tumor immunity. Tumor-infiltrating T cells, however, can express inhibitory molecules which, upon binding to their respective ligands, function to suppress T cell effector functions. The interaction between CD161 on T cells with its ligand, CLEC2D, has been shown to inhibit T cell cytokine production in previous studies (see Mathewson et al. (2021) CELL, 184(5), 1281-1298). The anti CD161 antibody (Ab9) is able to recover IL-2 production by Jurkat T cells in presence of CLEC2D expressing target cells. This example shows that Ab9 reverses this suppressive effect during in vitro co-cultures with CD161-expressing primary human T cells and a CLEC2D-expressing Burkitt lymphoma target cell line (Raji). Administration of Ab9 during the co-culture significantly enhanced the production of interferon gamma (IFNγ), interleukin-2 (IL-2) and tumor necrosis factor alpha (TNFα) from CD8$^+$ T cells in a concentration-dependent manner.

MART-1 Antigen Specific T Cell Cytokine Assay

The T cells utilized in this assay were specific to an antigen called as Melanoma antigen recognized by T cells-1 (MART-1). This antigen is expressed on normal melanocytes and is highly expressed on malignant melanoma samples thus behaving as a Tumor Associated Antigen (TAA). The antigenic peptide of MART-1 (ELAGIGILTV) is presented in context of the HLA-A2 subtype of MHC Class I. Healthy individuals have a high frequency of circulating MART-1 T cells that can display potent anti-tumor lytic activity upon in vitro expansion and reactivation. The experiment leveraged this to develop an antigen specific human T cell functional assay using MART-1 specific CD8$^+$ T cells as effectors and peptide-loaded HLA-A2$^+$ tumor cell lines as target cells. To initially generate the effector cells, MART-1 T cells were primed, activated, and expanded in the presence of autologous antigen-presenting cells that are pulsed with the MART-1 peptide. Post-expansion, these antigen specific T cells were enriched by cell sorting and subsequently reactivated via co-culture with target cells that are peptide pulsed with MART-1 peptide. Upon reactivation, T cell cytokine responses were evaluated.

Briefly, human CD8$^+$ T cells that recognize the MART-1 antigen were expanded and sorted from PBMCs over the course of approximately 3 weeks. 48 hours prior to reactivation, the MART-1-specific T cells were enriched for their expression of CD161 by cell sorting (BD Melody™). Ab9 and the corresponding isotype control antibody were diluted to 400 nM (4× final concentration) in 200 μL of T cell media in the first column of a 96-well polypropylene plate. The antibodies were serially diluted 10-fold across the plate by transferring 20 μL into 180 μL T cell media. MART-1-specific T cells were pre-incubated with antibodies (Ab9 or isotype control) for 30 minutes and then co-cultured with MART-1 peptide-loaded or no-peptide Raji cells overnight (approximately 20 hours). Half of the supernatants from each sample were harvested for cytokine (Granzyme B, IFNγ, IL-2 and TNFα) secretion analysis according to the manufacturer's instructions (Meso Scale Diagnostics or MSD, U-PLEX Immuno-Oncology Group 1 (Cat #K151AEL2)). Brefeldin A was added to the co-cultures, followed by an additional 6 hours of incubation for intracellular detection of IFNγ expression. Co-cultures were transferred to V-bottom assay plates and stained with surface stain master mix containing (diluted in FACS buffer): 1:1000 NEAR-IR Live/Dead stain, 1:20 anti-human CD8a APC, 1:20 anti-human CD161 BV421, and 1:20 anti-human CD19 PE. Following a 30-minute incubation, cells were fixed by incubation with fixation buffer for 30 minutes. Plates were resuspended in FACS buffer, then covered in foil and placed at 4° C. overnight. Plates were spun, supernatant removed, and co-cultures were washed with 1× permeabilization buffer (diluted 10× stock Permeabilization buffer 1:10 in UltraPure water). This step was repeated once more. Co-cultures were then incubated with intracellular stain master mix containing (diluted in 1× permeabilization buffer): 1:20 anti-human IFNγ FITC. Co-cultures were again spun and washed with 1× permeabilization buffer, resuspended in FACS buffer and analyzed on the FACS Symphony™. The data was then analyzed on Flow Jo™ followed with graphing and statistical analyses on GraphPad™ Prism.

To elicit cytokine production, MART-1-specific T cells were expanded in vitro for 23 days and subsequently reactivated via co-culture with peptide-loaded Raji target cells in the presence of Ab9 or an isotype control. Raji is a Burkitt lymphoma cell line which endogenously expresses CLEC2D, the ligand for CD161, and was engineered to overexpress HLA-A0201 to allow for exogenous loading of the MART-1 peptide.

Figure 20B:
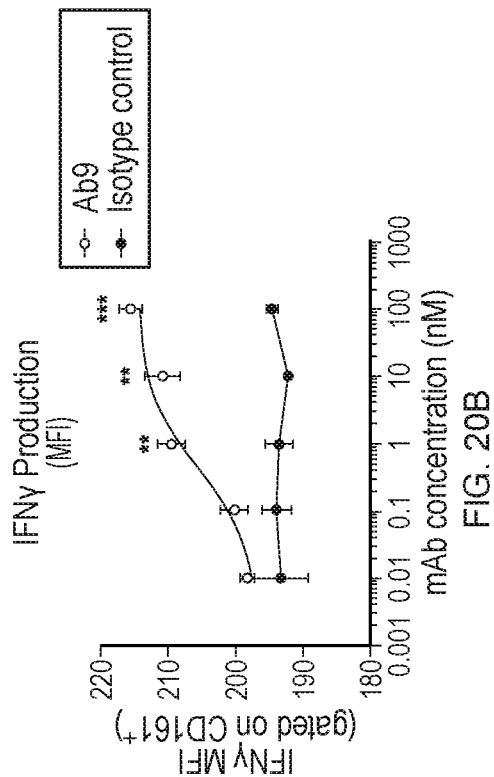
FIGS. 20A-20B are graphs illustrating that anti-CD161 antibody (Ab9) enhanced IFNγ production in CD161+ MART-1-specific T cells upon reactivation as percentage of cytokine-positive cells (FIG. 20A) or as geometric mean fluorescence intensity (MFI) (FIG. 20B). P≤0.01, *P≤0.001 (two-tailed Student's t-test).
Figure 20D:
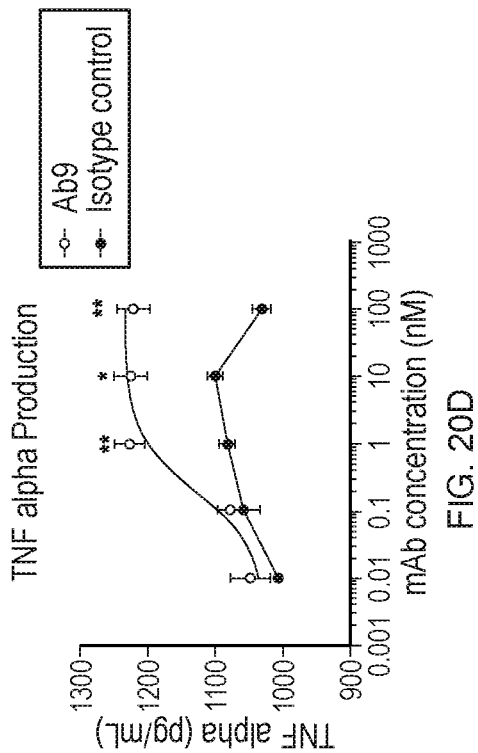
FIGS. 20C-20D are graphs illustrating that anti-CD161 antibody (Ab9) enhanced IL-2 (FIG. 20C) and TNFα (FIG. 20D) production in MART-1-specific T cells upon reactivation. *P≤0.05 P≤0.01, *P≤0.001 (two-tailed Student's t-test).
Figure 20A:
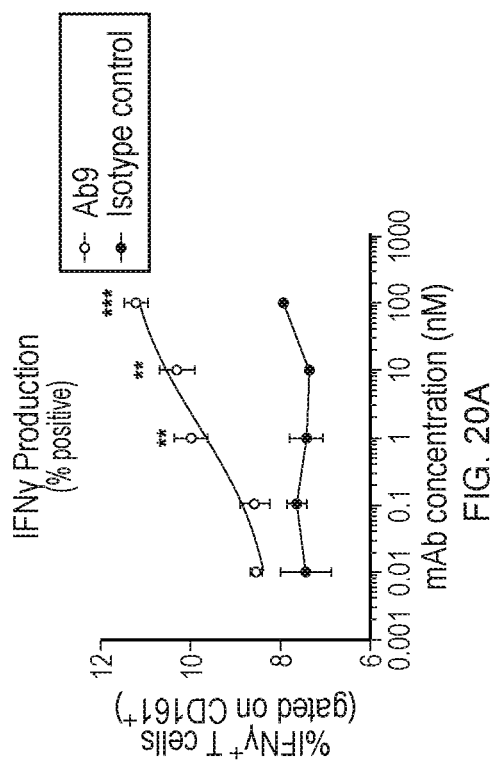
Figure 20C:
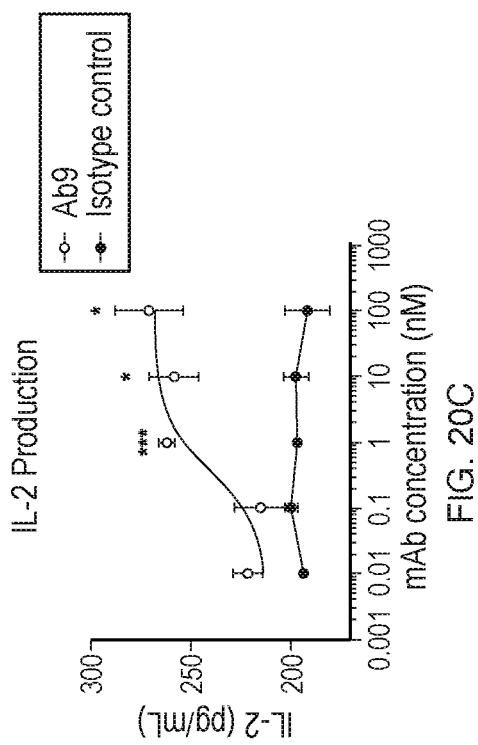

Compared to isotype control, administration of Ab9 resulted in a concentration-dependent increase in the frequency of IFNγ producing T cells (FIG. 20A, $EC_{50}$=1.429 nM or 0.2 μg/ml). Ab9 also augmented the amount of cytokine production as evident by a concentration-dependent increase in the MFI of IFNγ staining (FIG. 20B, $EC_{50}$=0.4363 nM or 0.06 μg/ml and $EC_{90}$ of 8.931 nM or 1.29 μg/ml). Co-cultures containing Ab9 also displayed a concentration-dependent increase in the secretion of IL-2 (FIG. 20C, $EC_{50}$=0.3590 nM or 0.0521 μg/ml and $EC_{90}$ of 3.231 nM or 0.4685 μg/ml) and TNFα (FIG. 20D, $EC_{50}$=0.1966 nM or 0.0285 μg/ml and $EC_{90}$ of 1.769 nM or 0.2565 μg/ml). Granzyme B was undetectable via MSD while secreted IFNγ levels were above the standard curve range. Summary of the cytokine readouts is provided in TABLE 19.

TABLE 19

Summary of the cytokine readouts from MART-1 antigen specific T cell cytokine assay.

| Cytokine Readout | EC50 (nM) | EC50 (μg/ml) | EC90 (nM) | EC90 (μg/ml) |
| --- | --- | --- | --- | --- |
| IFNγ % | 1.429 | 0.2072 | Did not reach | Did not reach |
| IFNγ MFI | 0.4363 | 0.0633 | 8.931 | 1.295 |
| IL-2 | 0.359 | 0.0521 | 3.231 | 0.4685 |
| TNF-α | 0.1966 | 0.0285 | 1.769 | 0.2565 |

The administration of Ab9 to co-culture of MART-1 specific CD161$^+$ CD8$^+$ T cells and CLEC2D-expressing Raji target cells significantly revived T cell cytokine production. This included augmentation of IFNγ positive cells and higher production of IL-2 and TNFα suggesting an increased polyfunctionality of CD161$^+$MART-1 T cells in presence of Ab9 (Table 19). Overall, these studies demonstrate the potential of antibody-mediated CD161 blockade in providing anti-tumor benefit.

Example 17—Blocking of CD161-CLEC2D Interaction by Ab9 Results in Restoration of Anti-Tumor Cytotoxicity of Primary Antigen-Specific Human MART-1 T Cells This example assesses the ability of anti CD161 antibody (Ab9) to enhance the cytotoxicity function of MART-1-specific T cells in co-culture with Raji target cells through blockade of interaction of CD161 on the T cells with CLEC2D expressed on the target cells.

As shown in Examples 13 and 14, anti CD161 antibody (Ab9) is able to restore human NK cell degranulation and cytolytic function. This example shows that Ab9 reverses this suppressive effect during in vitro co-cultures with CD161-expressing primary human T cells and a CLEC2D-expressing Burkitt lymphoma target cell line (Raji). Administration of Ab9 during the co-culture significantly enhanced the production of the cell death-inducing serine protease, Granzyme B, from CD8$^+$ T cells in a concentration-dependent manner and elevated their cytotoxic function.

MART-1 Antigen-Specific T Cell Cytotoxicity Assay

Similar to Example 16, T cells utilized in this assay were specific to MART-1. To initially generate the effector cells, MART-1 T cells are primed, activated and expanded in the presence of autologous antigen-presenting cells that are pulsed with the MART-1 peptide. Post-expansion, these antigen specific T cells are enriched by cell sorting and subsequently reactivated via co-culture with target cells that are peptide pulsed with MART-1 peptide. Upon reactivation, T cell mediated killing of target cells is evaluated as a measure of its cytolytic function.

Briefly, human CD8+ T cells that recognize the MART-1 antigen were expanded and sorted from PBMCs from two donors over the course of approximately 3 weeks. Then, 48 hours prior to reactivation, the MART-1-specific T cells were enriched for their expression of CD161 by cell sorting (BD Melody™). Ab9 and the corresponding isotype control antibody were diluted to 400 nM (4× final concentration) in 200 µL of T cell media in the first column of a 96-well polypropylene plate. The antibodies were serially diluted 10-fold across the plate by transferring 20 µL into 180 µL T cell media. MART-1-specific T cells were pre-incubated with antibodies (Ab9 or isotype control) for 30 minutes and then co-cultured with either MART-1 peptide-loaded or no-peptide Raji cells overnight (approximately 20 hours). Brefeldin A was added to the co-cultures, followed by an additional 6 hours of incubation for intracellular detection of Granzyme B expression. Co-cultures were transferred to V-bottom assay plates and stained with surface stain master mix containing (diluted in FACS buffer): 1:1000 NEAR-IR Live/Dead stain, 1:20 anti-human CD8a APC, 1:20 anti-human CD161 BV421, and 1:20 anti-human CD19 PE. The anti CD19 antibody is used to label the target cell line Raji and the Live/Dead stain is preferentially taken up by dead cells. This staining methodology enables live target cell quantification after co-culture with the MART-1 T cells by flow cytometry. Following a 30-minute incubation, cells were fixed by incubation with fixation buffer for 30 minutes. Plates were resuspended in FACS buffer, then covered in foil and placed at 4° C. overnight. Plates were spun, supernatant removed, and co-cultures were washed with 1× permeabilization buffer (diluted 10× stock Permeabilization buffer 1:10 in UltraPure water). This step was repeated once more. Co-cultures were then incubated with intracellular stain master mix containing (diluted in 1× permeabilization buffer): 1:50 anti-human Granzyme B BV510 for 30 minutes. Co-cultures were again spun and washed with 1× permeabilization buffer, resuspended in FACS buffer and analyzed on the FACS Symphony™. The data was then analyzed on Flow Jo™ followed with graphing and statistical analyses on GraphPad™ Prism.

Figure 21A:
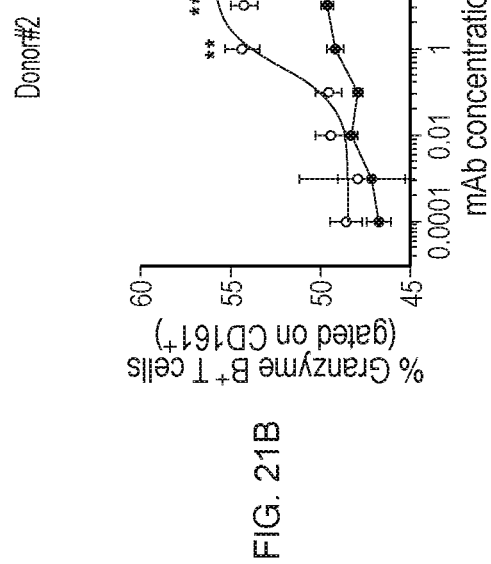
FIGS. 21A-21B are graphs illustrating that anti-CD161 antibody (Ab9) enhances Granzyme B production in CD161+MART-1-specific T cells from two donors upon reactivation.
Figure 21B:
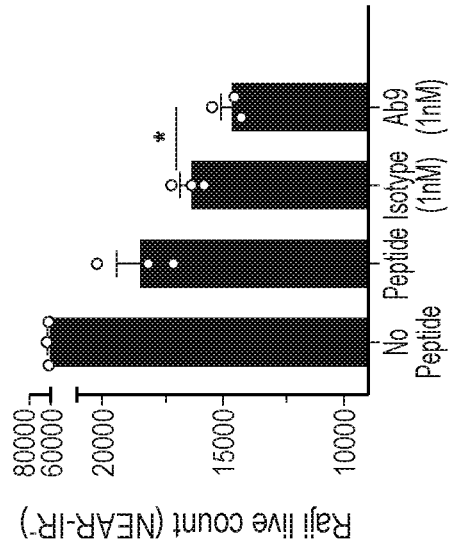

To elicit Granzyme B production and T cell mediated target cell killing, MART-1-specific T cells were expanded in vitro for 23 days and subsequently reactivated via co-culture with peptide-loaded Raji target cells in the presence of Ab9 or an isotype control. Compared to isotype control, administration of Ab9 resulted in a concentration-dependent increase in the frequency of Granzyme B producing T cells from 2 different donors as shown in FIGS. 21A-21B. The $EC_{50}$ and $EC_{90}$ values from these analyses are shown in TABLE 20.

Figure 21C:
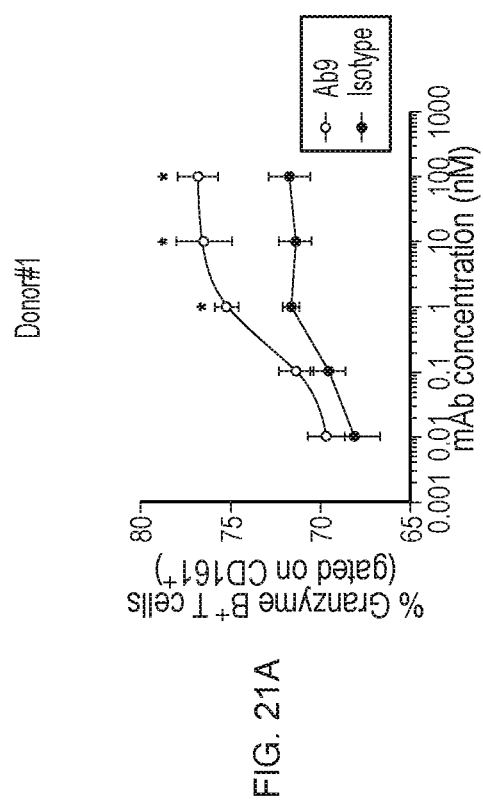
FIGS. 21C-21D are graphs illustrating that Ab9 enhanced antigen specific T cell cytotoxicity of MART-1 specific T cells obtained from two donors. Viable target cells were measured as CD19+, NEAR-IR negative. *P≤0.05, **P≤0.01, (two-tailed Student's t-test).
Figure 21D:
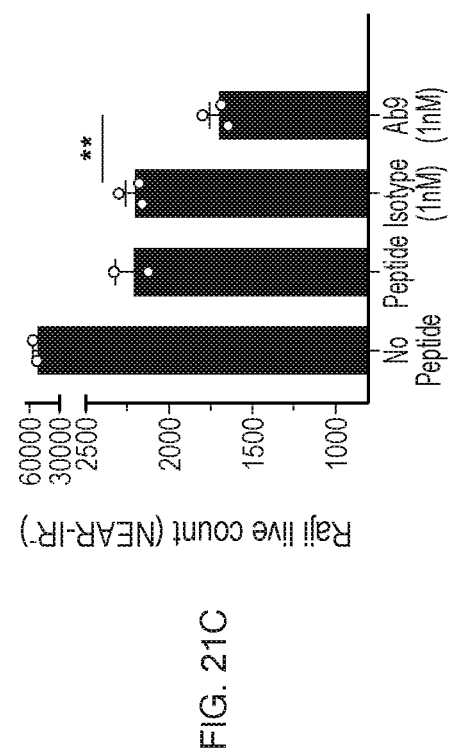
Figure 22A:
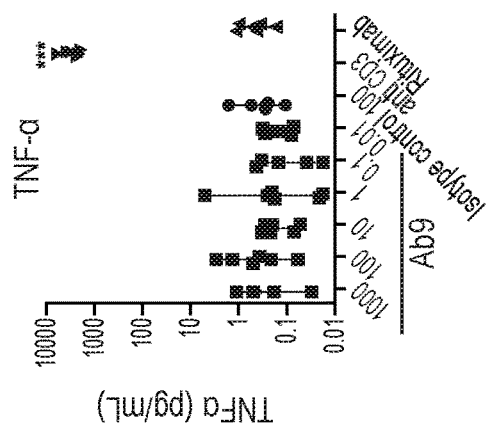
FIGS. 22A-22F are graphs illustrating induction of cytokines from unstimulated healthy human PBMCs following incubation with plate bound Ab9. Treatment of 6 donor human PBMCs with plate bound Ab9, isotype control, anti-CD3 muromonab (anti-CD3), and rituximab treatment (*** p<0.0001). The Y axis is shown in log scale to depict the low concentrations of cytokines elicited by addition of Ab9 and high concentrations released by muromonab treatment. The different points in the plot represent individual PBMC donors.
Figure 22B:
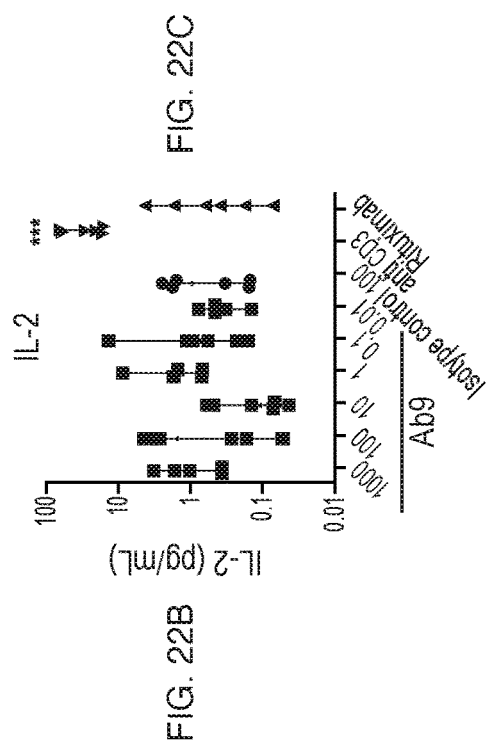
Figure 22C:
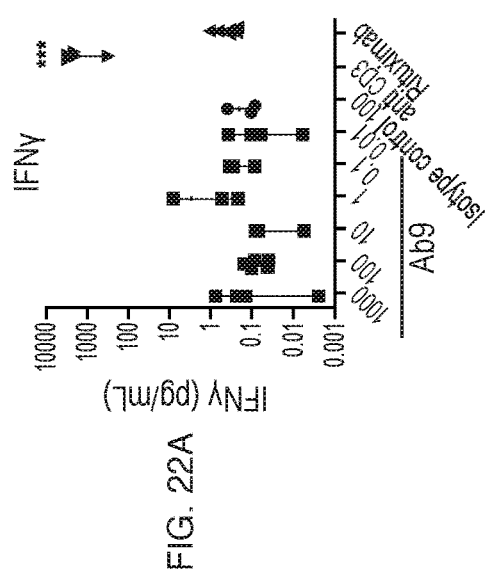
Figure 22D:
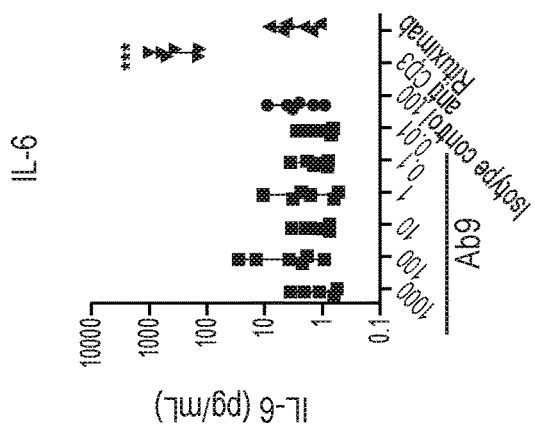
Figure 22E:
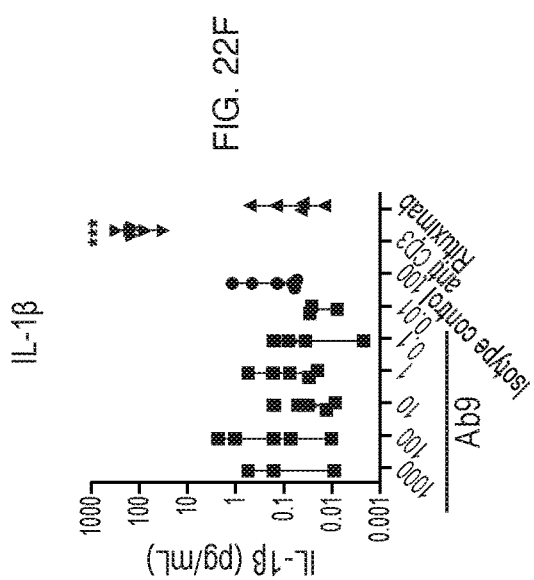
Figure 22F:
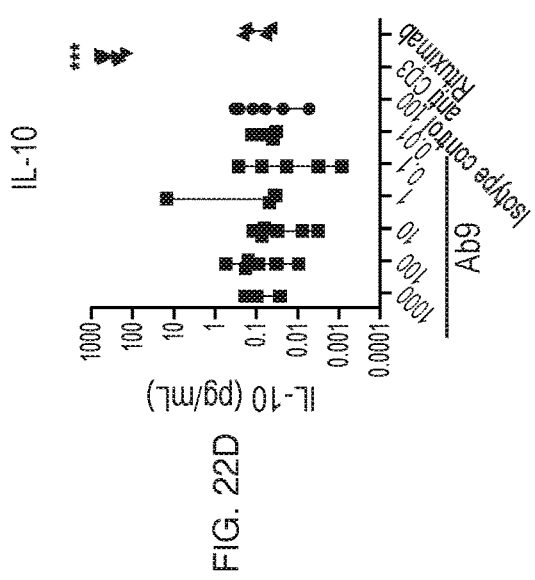

Furthermore, as indicated by a significant decrease in the recovery of live target cells from the co-culture in FIGS. 21C-21D, Ab9 also enhanced the direct cytotoxic function of MART-1 specific T cells compared to isotype control. A cytotoxicity saturation point at 1nM was observed for both donors, showing high potency of the antibody in enhancing T cell mediated target cell killing.

TABLE 20

| | Summary of Granzyme B Readout | | | |
|---|---|---|---|---|
| Donor # | EC50 (nM) | EC50 (µg/ml) | EC90 (nM) | EC90 (µg/ml) |
| Donor 1 | 0.2772 | 0.0402 | 2.535 | 0.3676 |
| Donor 2 | 0.3974 | 0.0576 | 3.991 | 0.5787 |

The administration of Ab9 to co-culture of MART-1 specific CD161$^+$ CD8$^+$ T cells and CLEC2D-expressing Raji target cells significantly revived T cell effector function. This included augmentation of Granzyme B positive cells and evidence of direct T cell-mediated cytotoxicity of CD161$^+$MART-1 T cells in presence of Ab9 resulting in significant decrease in target cell survival. Overall, these studies demonstrate the potential of anti CD161-mediated blockade of CD161-CLEC2D interaction in providing anti-tumor benefit by reviving T cell cytotoxicity.

Example 18—Evaluation of Cytokine Release by Immobilized or Soluble Anti-CD161 Antibody (Ab9) in Human PBMCs From Healthy Donors This example evaluates the potential for Ab9 to induce cytokine release in PBMCs from six healthy donors using two different assay formats: plate bound and soluble form of antibody. Anti-CD20 rituximab (anti-CD20 B-cell depleting antibody and known to stimulate cytokine storm in a subset of cancer patients) and anti-CD3 muromonab (a known CRS inducer) were used as controls along with their corresponding isotype controls. Pro-inflammatory cytokines evaluated included IL-2, IL-10, IL-10, IL-4, IL-6, TNF-α, and IFN-γ.

Cytokine release syndrome (CRS; or cytokine storm) is a rare potential side effect associated with the use of certain therapeutic antibodies and can result in morbidity and mortality. In vitro cytokine release assay using human peripheral blood mononuclear cells (PBMCs) has been shown to be a useful assessment to predict cytokine storm in patients (see Vessillier et al. (2015) J. IMMUNOL. METHODS, 424, 43-52. Key markers include IL-2, IFN-γ, TNF-α, IL-6, IL-13, and IL-10.

Cytokine Release Assay

For plate bound format, test article antibodies (Ab9, isotype control D1.3 with N297A, rituximab, muromonab, mouse $IgG_2A$ isotype control for anti CD3 ("isotype control antibody"), and D1.3 $IgG_1$ WT isotype control) were serially diluted into individual wells of a microtiter plate and incubated at room temperature for 2 hours. Muromonab and rituximab were plated at 1 μg/well and isotype control antibody was plated at 20 μg/well. After 2 hours, the antibody was washed 2 times with 1×PBS to remove any unbound antibody 10 mL ice-cold FACS Buffer was added to 6-50 mL conical labeled with each PBMC donor # to prepare for washing thawed PBMCs. Frozen PBMCs were placed in a 37° C. water bath until partially thawed and were then added to the appropriate tubes prepared with FACS buffer. PBMCs were counted using an automated cell counter, centrifuged, and the supernatant removed. PBMCs were resuspended and plated in the antibody-coated microtiter plates at $2 \times 10^5$ cells in 200 μL per well and then incubated at 37° C. in a $CO_2$ incubator for 48 hours.

For the soluble format, serially diluted antibodies were added to each well mixed with PBMCs at $2 \times 10^5$ cells in 200 μL per well and then incubated at 37° C. in a $CO_2$ incubator for 48 hours. Muromonab and rituximab were added at a final concentration of 5 μg/ml and isotype control antibody (isotype control D1.3 with N297A) was added at a final concentration of 100 μg/ml. After 48 hours, supernatants were collected by centrifugation and stored at −80° C. until analyzed on the Meso Sector S600 instrument (Meso Scale Diagnostics, Rockville, MD). MSD assay was performed according to the manufacturer's instructions (MSD kit for cytokine analyses: U-PLEX Biomarker Group 1 (hu) assays (K15067L-2). This kit includes reagents to detect Human IFN-γ, IL1β, IL-2, IL-4, IL-6, IL-10, IL-17A and TNF-α in a U-PLEX format). Data analyses was done on the Discovery Workbench software from MSD, followed by graphing and statistical analyses on GraphPad™ Prism.

FIGS. 22A-22F and FIGS. 23A-23F show the cytokine release in presence of Ab9 using plate bound format and soluble format, respectively. Ab9 was tested for a range of concentrations from 0.01 μg/ml up to 1000 μg/ml and isotype control (isotype control D1.3 with N297A) was tested at 100 μg/ml. Muromonab and Rituximab and their corresponding isotype controls were tested at a concentration of 5 μg/ml, which has been reported to induce cytokine release in vitro. Data from the respective isotype controls are not shown on the plots since they were very similar to the isotype control (isotype control D1.3 with N297A) and many points were below lower limit of quantification (LLOQ).

As shown in FIGS. 22A-22F and FIGS. 23A-23F, treatment of PBMCs with muromonab significantly stimulated release of all cytokines tested. However, no significant increase in cytokine production was observed when PBMCs were incubated with Ab9 in both solid and aqueous phase formats. Furthermore, treatment with rituximab did not lead to cytokine release in both formats except for a single donor that showed high expression of cytokines in presence of rituximab in the soluble format (FIGS. 23A-23F). Treatment of the unstimulated PBMCs with either anti-CD161 antibody (Ab9) or isotype control (isotype control D1.3 with N297A) did not elicit cytokine release in both plate bound and soluble format. A single point in IL-6 plot (FIG. 23F) that showed higher cytokine production in presence of Ab9 was observed, which was attributed to a single donor and not a concentration-based response. Production of IL-17A and IL-4 were also measured for Ab9 treatment, but most values were below LLOQ (data not shown). This data suggests that there is a low risk of cytokine release in patients treated with Ab9.

Example 19—Pharmacokinetic (PK) and Toxicology Evaluation of Ab9

This example illustrates the PK and toxicology evaluation of Ab9. The toxicokinetics (TK) of Ab9 was evaluated in the non-GLP dose-range finding (DRF) study (3 doses of Ab9 once weekly at 10 mg/kg and 100 mg/kg each) and a 4-week GLP repeat-dose toxicology study (5 doses of Ab9 once weekly at 10 mg/kg, 30 mg/kg, and 100 mg/kg each) conducted in cynomolgus monkeys.

Non-GLP DRF Toxicology Study

A nonterminal, non-GLP, DRF study in cynomolgus monkeys was conducted to evaluate the tolerability and PK of Ab9 after a total of 3 once weekly (days 1, 8, and 15) intravenous (IV) slow bolus injections at 10 mg/kg and 100 mg/kg per dose in female cynomolgus monkeys (3 females/group).

TABLE 22

Study design of non-GLP DRF toxicology study.

| Group | Dose (mg/kg) | Dose Volume (mL/kg) | Concentration (mg/mL) | Females |
| --- | --- | --- | --- | --- |
| 1 | 10 | 5 | 2 | 3 |
| 2 | 100 | 5 | 20 | 3 |

Whole blood samples of approximately 1 mL were collected from a peripheral vein of all animals for determination of Ab9 exposure. Samples were collected at the following target timepoints:

Day 1 at predose, 1-hour, 24 hours, and 96 hours postdose;

Day 8 at predose and 1-hour postdose; and

Day 15 at predose, 1-hour, 24 hours, 96 hours, 168 hours, 336 hours, 528 hours, 672 hours, 840 hours, and 1008 hours postdose.

Quantification of Ab9 in serum from the blood samples was performed using a qualified bioanalytical method (enzyme-linked immunosorbent assay).

A non-compartmental approach using Phoenix® WinNonlin® version 8.0, consistent with the IV slow bolus administration, was used for TK parameter estimation. TK parameters were generated from individual Ab9 serum concentrations and nominal times. Individual concentrations less than the LLOQ were treated as 0 in the TK data analysis.

Figure 24:
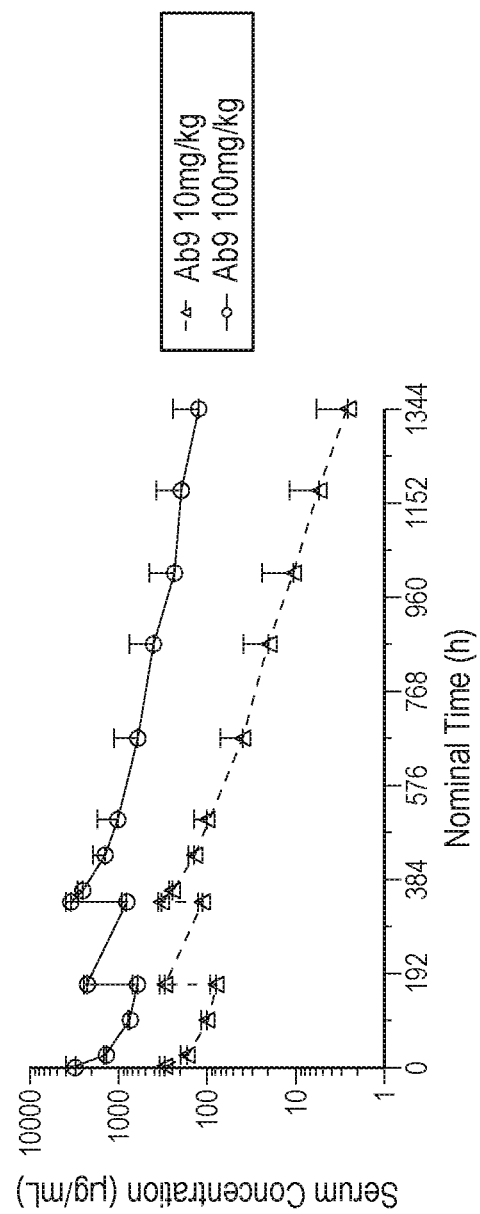
FIG. 24 is a plot of mean Ab9 serum concentrations versus time profiles for each dose group using a semilog scale.

The plots of mean Ab9 serum concentrations versus time profiles for each dose group are presented in FIG. 24 using a semilog scale. After weekly IV slow bolus (over 2-3 minutes) administration of Ab9 at doses of 10 mg/kg and 100 mg/kg per dose for a total of 3 doses, the female monkeys were systemically exposed to Ab9 with concentrations above 0.625 μg/mL (LLOQ) until 1,008 hours for 4 out of 6 animals at both Ab9 dose levels investigated. The time of observed maximum concentration ($T_{max}$) was observed 1 hour after single or multiple weekly dose administrations. There was an approximately dose-proportional increase in exposure (maximum observed concentration ($C_{max}$) and area under the plasma concentration time curve (AUC)) to Ab9 over the 10-fold dose range evaluated following single or multiple weekly administrations. Accumulation ratios ranged between 0.53 and 1.77.

Four-week IV GLP Toxicity and TK Study of Ab9 with a 4-week Recovery Period

A 4-week GLP study in cynomolgus monkeys was conducted to evaluate the potential toxicity and TK profile of Ab9 following 5 once weekly (days 1, 8, 15, 22, and 29) IV slow bolus injections, followed by a 4-week recovery period. Animals were administered Ab9 at doses of 10 mg/kg, 30 mg/kg, or 100 mg/kg per dose or vehicle only.

TABLE 23

Study design of GLP DRF toxicology study

| Group | Dose (mg/kg) | Dose Volume (mL/kg) | Concentration (mg/mL) | Main Study (Day 30) | | Recovery (28 days after last dose) | |
|---|---|---|---|---|---|---|---|
| | | | | Males | Females | Males | Females |
| 1 | 0 (vehicle) | 2 | 0 | 3 | 3 | 2 | 2 |
| 2 | 10 | 2 | 5 | 3 | 3 | — | — |
| 3 | 30 | 2 | 15 | 3 | 3 | — | — |
| 4 | 100 | 2 | 50 | 3 | 3 | 2 | 2 |

Whole blood samples of approximately 1 mL were collected from a peripheral vein of all animals for determination of Ab9 exposure. Samples were collected at the following target timepoints:

Day 1 at pre-dose, 1-hour, 24 hours, and 96 hours post-dose;

Day 8 at pre-dose;

Day 22 at pre-dose, 1-hour, 24 hours, and 96 hours post-dose; and

Day 29 at pre-dose, 1-hour and 24 hours post-dose from all animals; and at 96 hours, 168 hours, 336 hours, 504 hours, and 672 hours post-dose from all recovery animals Serum concentrations of Ab9 were measured using a validated electrochemiluminescence assay. A non-compartmental approach using Phoenix® WinNonlin® version 8.3.4, using an IV bolus model consistent with the route of administration, was used for TK parameter estimation. TK parameters were generated from individual Ab9 serum concentrations and nominal times on days 1, 22, and 29. Individual concentrations less than the LLOQ were treated as 0 in the TK data analysis. For the purpose of TK parameter determination, day 8 pre-dose was used with day 1 data as 168 hours postdose and day 29 pre-dose was used with day 22 data as 168 hours post-dose. To better compare TK results between each study day, area under the plasma concentration-time curve from time 0 to time 24 hours postdose ($AUC_{0-24}$) was estimated for all study days.

Figure 25A:
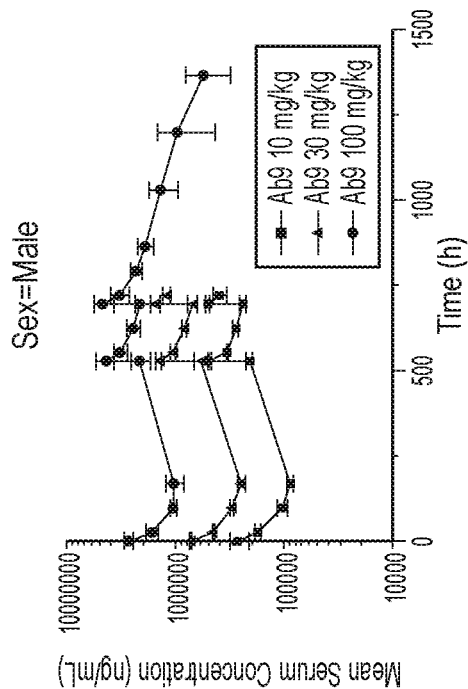
FIGS. 25A-25B are plots of mean Ab9 serum concentrations versus time profiles by treatment and sex using a semilog scale.
Figure 25B:
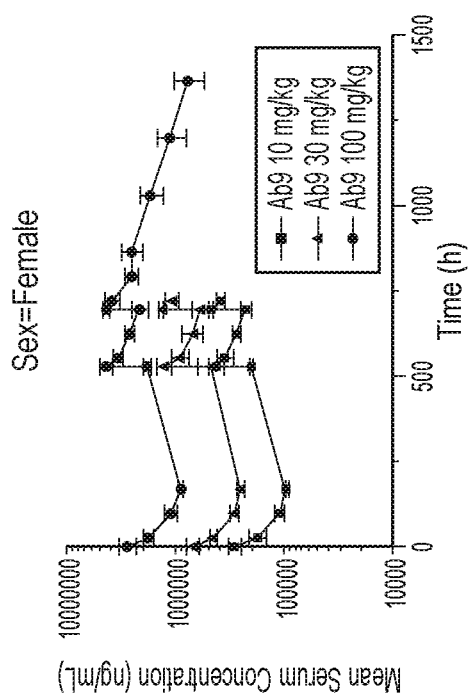

The plots of mean Ab9 serum concentrations versus time profiles by treatment and sex are presented in FIGS. 25A-25B using a semilog scale. No major differences in Ab9 exposure were observed between male and female monkeys. Mean $T_{max}$ was generally observed 1-hour postdose for all treatment groups. Exposure ($C_{max}$ and AUC) to Ab9 increased with increasing Ab9 dose from 10 mg/kg to 100 mg/kg in a dose-proportional manner following one single IV dose (day 1) or following multiple administrations (day 22 and day 29). The mean elimination half-life (T½) ranged between 142 hours and 282 hours post-dose, suggesting expected PK behavior for a mAb. Accumulation ratios on days 22 and 29 ranged between 1.53 and 2.34 for all treatment groups.

Overall, the PK analyses of Ab9 in both the non-GLP DRF study and the 4-week GLP toxicology study showed a dose-proportional increase in exposure ($C_{max}$ and AUC) with increasing Ab9 dose from 10 mg/kg to 100 mg/kg. The mean T½ ranged between 142 hours and 282 hours post-dose for the GLP study, suggesting expected PK behavior for a mAb. As shown above, there were no safety pharmacology findings up to a dose of 100 mg/kg despite evidence of saturating receptor occupancy at doses of 10 mg/kg and 100 mg/kg throughout the dosing periods.

Using data from the toxicology and in vitro functional activity assays described herein, it is contemplated that a dose of 6 mg (0.1 mg/kg based on a 60 kg patient weight) administered IV every 21 days can provide meaningful biological effects at receptor saturation and be well tolerated by a subject in need.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

SEQUENCE LISTING

```
Sequence total quantity: 197
SEQ ID NO: 1            moltype = AA  length = 9
FEATURE                 Location/Qualifiers
source                  1..9
                        mol_type = protein
                        organism = synthetic construct
VARIANT                 2
                        note = T or A
VARIANT                 4
                        note = G or S or E
VARIANT                 5
                        note = Q or T or P or R
```

```
VARIANT                 6
                        note = Y or F
SEQUENCE: 1
FXFXXXAMS                                                                  9

SEQ ID NO: 2            moltype = AA  length = 17
FEATURE                 Location/Qualifiers
source                  1..17
                        mol_type = protein
                        organism = synthetic construct
VARIANT                 4
                        note = A or G
VARIANT                 5
                        note = A or V or S
VARIANT                 8
                        note = T or S
VARIANT                 10
                        note = K or A or Y
SEQUENCE: 2
AISXXGGXTX YADSVKG                                                        17

SEQ ID NO: 3            moltype = AA  length = 14
FEATURE                 Location/Qualifiers
source                  1..14
                        mol_type = protein
                        organism = synthetic construct
VARIANT                 8
                        note = Q or F or L
VARIANT                 13
                        note = D or Q
VARIANT                 14
                        note = L or A
SEQUENCE: 3
AKPLDSSXWA DFXX                                                           14

SEQ ID NO: 4            moltype = AA  length = 11
FEATURE                 Location/Qualifiers
source                  1..11
                        mol_type = protein
                        organism = synthetic construct
VARIANT                 5
                        note = G or D or T
VARIANT                 7
                        note = D or S or Y
SEQUENCE: 4
RASQXIXSWL A                                                              11

SEQ ID NO: 5            moltype = AA  length = 7
FEATURE                 Location/Qualifiers
source                  1..7
                        mol_type = protein
                        organism = synthetic construct
VARIANT                 1
                        note = A or Y or F
VARIANT                 4
                        note = S or A or G or F
VARIANT                 7
                        note = D or S
SEQUENCE: 5
XASXLQX                                                                    7

SEQ ID NO: 6            moltype = AA  length = 9
FEATURE                 Location/Qualifiers
source                  1..9
                        mol_type = protein
                        organism = synthetic construct
VARIANT                 3
                        note = A or H or Q
VARIANT                 4
                        note = S or D or W or L
VARIANT                 5
                        note = V or D or Y or K
SEQUENCE: 6
QQXXXLPIT                                                                  9

SEQ ID NO: 7            moltype = AA  length = 121
FEATURE                 Location/Qualifiers
source                  1..121
                        mol_type = protein
```

```
                                                  organism = synthetic construct
SEQUENCE: 7
EVQLLESGGG LVQPGGSLRL SCAASGFAFS TYAMSWVRQA PGKGLEWVSA ISAAGGTTYY    60
ADSVKGRFTI SRDNSKNTLY LQMNSLRAED TAVYYCAKPL DSSLWADFDL WGRGTLVTVS   120
S                                                                  121

SEQ ID NO: 8              moltype = AA   length = 9
FEATURE                   Location/Qualifiers
source                    1..9
                          mol_type = protein
                          organism = synthetic construct
SEQUENCE: 8
FAFSTYAMS                                                             9

SEQ ID NO: 9              moltype = AA   length = 17
FEATURE                   Location/Qualifiers
source                    1..17
                          mol_type = protein
                          organism = synthetic construct
SEQUENCE: 9
AISAAGGTTY YADSVKG                                                   17

SEQ ID NO: 10             moltype = AA   length = 14
FEATURE                   Location/Qualifiers
source                    1..14
                          mol_type = protein
                          organism = synthetic construct
SEQUENCE: 10
AKPLDSSLWA DFDL                                                      14

SEQ ID NO: 11             moltype = AA   length = 107
FEATURE                   Location/Qualifiers
source                    1..107
                          mol_type = protein
                          organism = synthetic construct
SEQUENCE: 11
DIQMTQSPSS VSASVGDRVT ITCRASQGID SWLAWYQQKP GKAPKLLIYA ASSLQSGVPS    60
RFSGSGSGTD FTLTISSLQP EDFATYYCQQ ASVLPITFGG GTKVEIK                 107

SEQ ID NO: 12             moltype = AA   length = 11
FEATURE                   Location/Qualifiers
source                    1..11
                          mol_type = protein
                          organism = synthetic construct
SEQUENCE: 12
RASQGIDSWL A                                                         11

SEQ ID NO: 13             moltype = AA   length = 7
FEATURE                   Location/Qualifiers
source                    1..7
                          mol_type = protein
                          organism = synthetic construct
SEQUENCE: 13
AASSLQS                                                               7

SEQ ID NO: 14             moltype = AA   length = 9
FEATURE                   Location/Qualifiers
source                    1..9
                          mol_type = protein
                          organism = synthetic construct
SEQUENCE: 14
QQASVLPIT                                                             9

SEQ ID NO: 15             moltype = AA   length = 121
FEATURE                   Location/Qualifiers
source                    1..121
                          mol_type = protein
                          organism = synthetic construct
SEQUENCE: 15
EVQLLESGGG LVQPGGSLRL SCAASGFAFS TYAMSWVRQA PGKGLEWVSA ISGVGGTTYY    60
ADSVKGRFTI SRDNSKNTLY LQMNSLRAED TAVYYCAKPL DSSLWADFDL WGRGTLVTVS   120
S                                                                  121

SEQ ID NO: 16             moltype = AA   length = 9
FEATURE                   Location/Qualifiers
source                    1..9
                          mol_type = protein
                          organism = synthetic construct
SEQUENCE: 16
```

```
FAFSTYAMS                                                                9

SEQ ID NO: 17           moltype = AA   length = 17
FEATURE                 Location/Qualifiers
source                  1..17
                        mol_type = protein
                        organism = synthetic construct
SEQUENCE: 17
AISGVGGTTY YADSVKG                                                       17

SEQ ID NO: 18           moltype = AA   length = 14
FEATURE                 Location/Qualifiers
source                  1..14
                        mol_type = protein
                        organism = synthetic construct
SEQUENCE: 18
AKPLDSSLWA DFDL                                                          14

SEQ ID NO: 19           moltype = AA   length = 107
FEATURE                 Location/Qualifiers
source                  1..107
                        mol_type = protein
                        organism = synthetic construct
SEQUENCE: 19
DIQLTQSPSS VSASVGDRVT ITCRASQGIS SWLAWYQQKP GKAPKLLIYY ASSLQDGVPS         60
RFSGSGSGTD FTLTISSLQP EDFATYYCQQ ASVLPITFGG GTKVEIK                      107

SEQ ID NO: 20           moltype = AA   length = 11
FEATURE                 Location/Qualifiers
source                  1..11
                        mol_type = protein
                        organism = synthetic construct
SEQUENCE: 20
RASQGISSWL A                                                             11

SEQ ID NO: 21           moltype = AA   length = 7
FEATURE                 Location/Qualifiers
source                  1..7
                        mol_type = protein
                        organism = synthetic construct
SEQUENCE: 21
YASSLQD                                                                  7

SEQ ID NO: 22           moltype = AA   length = 9
FEATURE                 Location/Qualifiers
source                  1..9
                        mol_type = protein
                        organism = synthetic construct
SEQUENCE: 22
QQASVLPIT                                                                9

SEQ ID NO: 23           moltype = AA   length = 121
FEATURE                 Location/Qualifiers
source                  1..121
                        mol_type = protein
                        organism = synthetic construct
SEQUENCE: 23
EVQLLESGGG LVQPGGSLRL SCAASGFTFE RYAMSWVRQA PGKGLEWVSA ISAAGGTTYY         60
ADSVKGRFTI SRDNSKNTLY LQMNSLRAED TAVYYCAKPL DSSQWADFDL WGRGTLVTVS         120
S                                                                        121

SEQ ID NO: 24           moltype = AA   length = 9
FEATURE                 Location/Qualifiers
source                  1..9
                        mol_type = protein
                        organism = synthetic construct
SEQUENCE: 24
FTFERYAMS                                                                9

SEQ ID NO: 25           moltype = AA   length = 17
FEATURE                 Location/Qualifiers
source                  1..17
                        mol_type = protein
                        organism = synthetic construct
SEQUENCE: 25
AISAAGGTTY YADSVKG                                                       17

SEQ ID NO: 26           moltype = AA   length = 14
FEATURE                 Location/Qualifiers
```

```
source                   1..14
                         mol_type = protein
                         organism = synthetic construct
SEQUENCE: 26
AKPLDSSQWA DFDL                                                         14

SEQ ID NO: 27            moltype = AA   length = 107
FEATURE                  Location/Qualifiers
source                   1..107
                         mol_type = protein
                         organism = synthetic construct
SEQUENCE: 27
DIQLTQSPSS VSASVGDRVT ITCRASQDIS SWLAWYQQKP GKAPKFLIYA ASALQSGVPS        60
RFSGSGSGTD FTLTISSLQP EDFATYYCQQ ALVLPITFGG GTKVEIK                      107

SEQ ID NO: 28            moltype = AA   length = 11
FEATURE                  Location/Qualifiers
source                   1..11
                         mol_type = protein
                         organism = synthetic construct
SEQUENCE: 28
RASQDISSWL A                                                            11

SEQ ID NO: 29            moltype = AA   length = 7
FEATURE                  Location/Qualifiers
source                   1..7
                         mol_type = protein
                         organism = synthetic construct
SEQUENCE: 29
AASALQS                                                                 7

SEQ ID NO: 30            moltype = AA   length = 9
FEATURE                  Location/Qualifiers
source                   1..9
                         mol_type = protein
                         organism = synthetic construct
SEQUENCE: 30
QQALVLPIT                                                               9

SEQ ID NO: 31            moltype = AA   length = 121
FEATURE                  Location/Qualifiers
source                   1..121
                         mol_type = protein
                         organism = synthetic construct
SEQUENCE: 31
EVQLLESGGG LVQPGGSLRL SCAASGFTFE RYAMSWVRQA PGKGLEWVSA ISAVGGTTKY        60
ADSVKGRFTI SRDNSKNTLY LQMNSLRAED TAVYYCAKPL DSSLWADFDA WGRGTLVTVS        120
S                                                                       121

SEQ ID NO: 32            moltype = AA   length = 9
FEATURE                  Location/Qualifiers
source                   1..9
                         mol_type = protein
                         organism = synthetic construct
SEQUENCE: 32
FTFERYAMS                                                               9

SEQ ID NO: 33            moltype = AA   length = 17
FEATURE                  Location/Qualifiers
source                   1..17
                         mol_type = protein
                         organism = synthetic construct
SEQUENCE: 33
AISAVGGTTK YADSVKG                                                      17

SEQ ID NO: 34            moltype = AA   length = 14
FEATURE                  Location/Qualifiers
source                   1..14
                         mol_type = protein
                         organism = synthetic construct
SEQUENCE: 34
AKPLDSSLWA DFDA                                                         14

SEQ ID NO: 35            moltype = AA   length = 107
FEATURE                  Location/Qualifiers
source                   1..107
                         mol_type = protein
                         organism = synthetic construct
SEQUENCE: 35
```

```
DIQLTQSPSS VSASVGDRVT ITCRASQGIS SWLAWYQQKP GKAPKLLIYA ASGLQSGVPS    60
RFSGSGSGTD FTLTISSLQP EDFATYYCQQ ASYLPITFGG GTKVEIK                107

SEQ ID NO: 36           moltype = AA   length = 11
FEATURE                 Location/Qualifiers
source                  1..11
                        mol_type = protein
                        organism = synthetic construct
SEQUENCE: 36
RASQGISSWL A                                                        11

SEQ ID NO: 37           moltype = AA   length = 7
FEATURE                 Location/Qualifiers
source                  1..7
                        mol_type = protein
                        organism = synthetic construct
SEQUENCE: 37
AASGLQS                                                             7

SEQ ID NO: 38           moltype = AA   length = 9
FEATURE                 Location/Qualifiers
source                  1..9
                        mol_type = protein
                        organism = synthetic construct
SEQUENCE: 38
QQASYLPIT                                                           9

SEQ ID NO: 39           moltype = AA   length = 121
FEATURE                 Location/Qualifiers
source                  1..121
                        mol_type = protein
                        organism = synthetic construct
SEQUENCE: 39
EVQLLESGGG LVQPGGSLRL SCAASGFTFG QYAMSWVRQA PGKGLEWVSA ISAVGGTTAY    60
ADSVKGRFTI SRDNSKNTLY LQMNSLRAED TAVYYCAKPL DSSLWADFQL WGRGTLVTVS   120
S                                                                  121

SEQ ID NO: 40           moltype = AA   length = 9
FEATURE                 Location/Qualifiers
source                  1..9
                        mol_type = protein
                        organism = synthetic construct
SEQUENCE: 40
FTFGQYAMS                                                           9

SEQ ID NO: 41           moltype = AA   length = 17
FEATURE                 Location/Qualifiers
source                  1..17
                        mol_type = protein
                        organism = synthetic construct
SEQUENCE: 41
AISAVGGTTA YADSVKG                                                  17

SEQ ID NO: 42           moltype = AA   length = 14
FEATURE                 Location/Qualifiers
source                  1..14
                        mol_type = protein
                        organism = synthetic construct
SEQUENCE: 42
AKPLDSSLWA DFQL                                                     14

SEQ ID NO: 43           moltype = AA   length = 107
FEATURE                 Location/Qualifiers
source                  1..107
                        mol_type = protein
                        organism = synthetic construct
SEQUENCE: 43
DIQLTQSPSS VSASVGDRVT ITCRASQDIS SWLAWYQQKP GKAPKLLIYF ASSLQSGVPS    60
RFSGSGSGTD FTLTISSLQP EDFATYYCQQ ASKLPITFGG GTKVEIK                107

SEQ ID NO: 44           moltype = AA   length = 11
FEATURE                 Location/Qualifiers
source                  1..11
                        mol_type = protein
                        organism = synthetic construct
SEQUENCE: 44
RASQDISSWL A                                                        11

SEQ ID NO: 45           moltype = AA   length = 7
```

| | | |
|---|---|---|
| FEATURE | Location/Qualifiers | |
| source | 1..7<br>mol_type = protein<br>organism = synthetic construct | |
| SEQUENCE: 45 | | |
| FASSLQS | | 7 |
| | | |
| SEQ ID NO: 46 | moltype = AA length = 9 | |
| FEATURE | Location/Qualifiers | |
| source | 1..9<br>mol_type = protein<br>organism = synthetic construct | |
| SEQUENCE: 46 | | |
| QQASKLPIT | | 9 |
| | | |
| SEQ ID NO: 47 | moltype = AA length = 121 | |
| FEATURE | Location/Qualifiers | |
| source | 1..121<br>mol_type = protein<br>organism = synthetic construct | |
| SEQUENCE: 47 | | |
| EVQLLESGGG LVQPGGSLRL SCAASGFTFG QYAMSWVRQA PGKGLEWVSA ISAAGGTTYY | | 60 |
| ADSVKGRFTI SRDNSKNTLY LQMNSLRAED TAVYYCAKPL DSSQWADFDL WGRGTLVTVS | | 120 |
| S | | 121 |
| | | |
| SEQ ID NO: 48 | moltype = AA length = 9 | |
| FEATURE | Location/Qualifiers | |
| source | 1..9<br>mol_type = protein<br>organism = synthetic construct | |
| SEQUENCE: 48 | | |
| FTFGQYAMS | | 9 |
| | | |
| SEQ ID NO: 49 | moltype = AA length = 17 | |
| FEATURE | Location/Qualifiers | |
| source | 1..17<br>mol_type = protein<br>organism = synthetic construct | |
| SEQUENCE: 49 | | |
| AISAAGGTTY YADSVKG | | 17 |
| | | |
| SEQ ID NO: 50 | moltype = AA length = 14 | |
| FEATURE | Location/Qualifiers | |
| source | 1..14<br>mol_type = protein<br>organism = synthetic construct | |
| SEQUENCE: 50 | | |
| AKPLDSSQWA DFDL | | 14 |
| | | |
| SEQ ID NO: 51 | moltype = AA length = 107 | |
| FEATURE | Location/Qualifiers | |
| source | 1..107<br>mol_type = protein<br>organism = synthetic construct | |
| SEQUENCE: 51 | | |
| DIQLTQSPSS VSASVGDRVT ITCRASQGIS SWLAWYQQKP GKAPKLLIYA ASSLQSGVPS | | 60 |
| RFSGSGSGTD FTLTINSLQP EDFATYYCQQ AWVLPITFGG GTKVEIK | | 107 |
| | | |
| SEQ ID NO: 52 | moltype = AA length = 11 | |
| FEATURE | Location/Qualifiers | |
| source | 1..11<br>mol_type = protein<br>organism = synthetic construct | |
| SEQUENCE: 52 | | |
| RASQGISSWL A | | 11 |
| | | |
| SEQ ID NO: 53 | moltype = AA length = 7 | |
| FEATURE | Location/Qualifiers | |
| source | 1..7<br>mol_type = protein<br>organism = synthetic construct | |
| SEQUENCE: 53 | | |
| AASSLQS | | 7 |
| | | |
| SEQ ID NO: 54 | moltype = AA length = 9 | |
| FEATURE | Location/Qualifiers | |
| source | 1..9<br>mol_type = protein<br>organism = synthetic construct | |

```
SEQUENCE: 54
QQAWVLPIT                                                                             9

SEQ ID NO: 55            moltype = AA  length = 121
FEATURE                  Location/Qualifiers
source                   1..121
                         mol_type = protein
                         organism = synthetic construct
SEQUENCE: 55
EVQLLESGGG LVQPGGSLRL SCAASGFTFG QYAMSWVRQA PGKGLEWVSA ISAAGGTTYY    60
ADSVKGRFTI SRDNSKNTLY LQMNSLRAED TAVYYCAKPL DSSQWADFDL WGRGTLVTVS   120
S                                                                  121

SEQ ID NO: 56            moltype = AA  length = 9
FEATURE                  Location/Qualifiers
source                   1..9
                         mol_type = protein
                         organism = synthetic construct
SEQUENCE: 56
FTFGQYAMS                                                                             9

SEQ ID NO: 57            moltype = AA  length = 17
FEATURE                  Location/Qualifiers
source                   1..17
                         mol_type = protein
                         organism = synthetic construct
SEQUENCE: 57
AISAAGGTTY YADSVKG                                                                   17

SEQ ID NO: 58            moltype = AA  length = 14
FEATURE                  Location/Qualifiers
source                   1..14
                         mol_type = protein
                         organism = synthetic construct
SEQUENCE: 58
AKPLDSSQWA DFDL                                                                      14

SEQ ID NO: 59            moltype = AA  length = 107
FEATURE                  Location/Qualifiers
source                   1..107
                         mol_type = protein
                         organism = synthetic construct
SEQUENCE: 59
DIQLTQSPSS VSASVGDRVT ITCRASQGIS SWLAWYQQKP GKAPKLLIYA ASFLQSGVPS    60
RFSGSGSGTD FTLTISSLQP EDFATYYCQQ ASVLPITFGG GTKVEIK                 107

SEQ ID NO: 60            moltype = AA  length = 11
FEATURE                  Location/Qualifiers
source                   1..11
                         mol_type = protein
                         organism = synthetic construct
SEQUENCE: 60
RASQGISSWL A                                                                         11

SEQ ID NO: 61            moltype = AA  length = 7
FEATURE                  Location/Qualifiers
source                   1..7
                         mol_type = protein
                         organism = synthetic construct
SEQUENCE: 61
AASFLQS                                                                               7

SEQ ID NO: 62            moltype = AA  length = 9
FEATURE                  Location/Qualifiers
source                   1..9
                         mol_type = protein
                         organism = synthetic construct
SEQUENCE: 62
QQASVLPIT                                                                             9

SEQ ID NO: 63            moltype = AA  length = 121
FEATURE                  Location/Qualifiers
source                   1..121
                         mol_type = protein
                         organism = synthetic construct
SEQUENCE: 63
EVQLLESGGG LVQPGGSLRL SCAASGFTFG TFAMSWVRQA PGKGLEWVSA ISGVGGTTYY    60
ADSVKGRFTI SRDNSKNTLY LQMNSLRAED TAVYYCAKPL DSSFWADFDL WGRGTLVTVS   120
S                                                                  121
```

```
SEQ ID NO: 64          moltype = AA  length = 9
FEATURE                Location/Qualifiers
source                 1..9
                       mol_type = protein
                       organism = synthetic construct
SEQUENCE: 64
FTFGTFAMS                                                                  9

SEQ ID NO: 65          moltype = AA  length = 17
FEATURE                Location/Qualifiers
source                 1..17
                       mol_type = protein
                       organism = synthetic construct
SEQUENCE: 65
AISGVGGTTY YADSVKG                                                        17

SEQ ID NO: 66          moltype = AA  length = 14
FEATURE                Location/Qualifiers
source                 1..14
                       mol_type = protein
                       organism = synthetic construct
SEQUENCE: 66
AKPLDSSFWA DFDL                                                           14

SEQ ID NO: 67          moltype = AA  length = 107
FEATURE                Location/Qualifiers
source                 1..107
                       mol_type = protein
                       organism = synthetic construct
SEQUENCE: 67
DIQLTQSPSS VSASVGDRVT ITCRASQTIS SWLAWYQQKP GKAPKLLIYA ASSLQSGVPS         60
RFSGSGSGTD FTLTISSLQP EDFATYYCQQ QSVLPITFGG GTKVEIK                      107

SEQ ID NO: 68          moltype = AA  length = 11
FEATURE                Location/Qualifiers
source                 1..11
                       mol_type = protein
                       organism = synthetic construct
SEQUENCE: 68
RASQTISSWL A                                                              11

SEQ ID NO: 69          moltype = AA  length = 7
FEATURE                Location/Qualifiers
source                 1..7
                       mol_type = protein
                       organism = synthetic construct
SEQUENCE: 69
AASSLQS                                                                    7

SEQ ID NO: 70          moltype = AA  length = 9
FEATURE                Location/Qualifiers
source                 1..9
                       mol_type = protein
                       organism = synthetic construct
SEQUENCE: 70
QQQSVLPIT                                                                  9

SEQ ID NO: 71          moltype = AA  length = 121
FEATURE                Location/Qualifiers
source                 1..121
                       mol_type = protein
                       organism = synthetic construct
SEQUENCE: 71
EVQLLESGGG LVQPGGSLRL SCAASGFTFS PYAMSWVRQA PGKGLEWVSA ISASGGTTYY         60
ADSVKGRFTI SRDNSKNTLY LQMNSLRAED TAVYYCAKPL DSSFWADFDL WGRGTLVTVS        120
S                                                                        121

SEQ ID NO: 72          moltype = AA  length = 9
FEATURE                Location/Qualifiers
source                 1..9
                       mol_type = protein
                       organism = synthetic construct
SEQUENCE: 72
FTFSPYAMS                                                                  9

SEQ ID NO: 73          moltype = AA  length = 17
FEATURE                Location/Qualifiers
source                 1..17
```

```
                        mol_type = protein
                        organism = synthetic construct
SEQUENCE: 73
AISASGGTTY YADSVKG                                                      17

SEQ ID NO: 74           moltype = AA   length = 14
FEATURE                 Location/Qualifiers
source                  1..14
                        mol_type = protein
                        organism = synthetic construct
SEQUENCE: 74
AKPLDSSFWA DFDL                                                         14

SEQ ID NO: 75           moltype = AA   length = 107
FEATURE                 Location/Qualifiers
source                  1..107
                        mol_type = protein
                        organism = synthetic construct
SEQUENCE: 75
DIQLTQSPSS VSASVGDRVT ITCRASQGIS SWLAWYQQKP GKAPKLLIYA ASSLQSGVPS        60
RFSGSGSGTD FTLTISSLQP EDFATYYCQQ HSVLPITFGG GTKVEIK                     107

SEQ ID NO: 76           moltype = AA   length = 11
FEATURE                 Location/Qualifiers
source                  1..11
                        mol_type = protein
                        organism = synthetic construct
SEQUENCE: 76
RASQGISSWL A                                                            11

SEQ ID NO: 77           moltype = AA   length = 7
FEATURE                 Location/Qualifiers
source                  1..7
                        mol_type = protein
                        organism = synthetic construct
SEQUENCE: 77
AASSLQS                                                                 7

SEQ ID NO: 78           moltype = AA   length = 9
FEATURE                 Location/Qualifiers
source                  1..9
                        mol_type = protein
                        organism = synthetic construct
SEQUENCE: 78
QQHSVLPIT                                                               9

SEQ ID NO: 79           moltype = AA   length = 121
FEATURE                 Location/Qualifiers
source                  1..121
                        mol_type = protein
                        organism = synthetic construct
SEQUENCE: 79
EVQLLESGGG LVQPGGSLRL SCAASGFTFS QYAMSWVRQA PGKGLEWVSA ISAVGGSTYY        60
ADSVKGRFTI SRDNSKNTLY LQMNSLRAED TAVYYCAKPL DSSQWADFDL WGRGTLVTVS       120
S                                                                      121

SEQ ID NO: 80           moltype = AA   length = 9
FEATURE                 Location/Qualifiers
source                  1..9
                        mol_type = protein
                        organism = synthetic construct
SEQUENCE: 80
FTFSQYAMS                                                               9

SEQ ID NO: 81           moltype = AA   length = 17
FEATURE                 Location/Qualifiers
source                  1..17
                        mol_type = protein
                        organism = synthetic construct
SEQUENCE: 81
AISAVGGSTY YADSVKG                                                      17

SEQ ID NO: 82           moltype = AA   length = 14
FEATURE                 Location/Qualifiers
source                  1..14
                        mol_type = protein
                        organism = synthetic construct
SEQUENCE: 82
AKPLDSSQWA DFDL                                                         14
```

```
SEQ ID NO: 83            moltype = AA   length = 107
FEATURE                  Location/Qualifiers
source                   1..107
                         mol_type = protein
                         organism = synthetic construct
SEQUENCE: 83
DIQLTQSPSS VSASVGDRVT ITCRASQDIS SWLAWYQQKP GKAPKLLIYA ASALQSGVPS    60
RFSGSGSGTD FTLTISSLQP EDFATYYCQQ ADVLPITFGG GTKVEIK                 107

SEQ ID NO: 84            moltype = AA   length = 11
FEATURE                  Location/Qualifiers
source                   1..11
                         mol_type = protein
                         organism = synthetic construct
SEQUENCE: 84
RASQDISSWL A                                                         11

SEQ ID NO: 85            moltype = AA   length = 7
FEATURE                  Location/Qualifiers
source                   1..7
                         mol_type = protein
                         organism = synthetic construct
SEQUENCE: 85
AASALQS                                                               7

SEQ ID NO: 86            moltype = AA   length = 9
FEATURE                  Location/Qualifiers
source                   1..9
                         mol_type = protein
                         organism = synthetic construct
SEQUENCE: 86
QQADVLPIT                                                             9

SEQ ID NO: 87            moltype = AA   length = 121
FEATURE                  Location/Qualifiers
source                   1..121
                         mol_type = protein
                         organism = synthetic construct
SEQUENCE: 87
EVQLLESGGG LVQPGGSLRL SCAASGFTFS QYAMSWVRQA PGKGLEWVSA ISAAGGTTYY    60
ADSVKGRFTI SRDNSKNTLY LQMNSLRAED TAVYYCAKPL DSSQWADFDL WGRGTLVTVS   120
S                                                                   121

SEQ ID NO: 88            moltype = AA   length = 9
FEATURE                  Location/Qualifiers
source                   1..9
                         mol_type = protein
                         organism = synthetic construct
SEQUENCE: 88
FTFSQYAMS                                                             9

SEQ ID NO: 89            moltype = AA   length = 17
FEATURE                  Location/Qualifiers
source                   1..17
                         mol_type = protein
                         organism = synthetic construct
SEQUENCE: 89
AISAAGGTTY YADSVKG                                                   17

SEQ ID NO: 90            moltype = AA   length = 14
FEATURE                  Location/Qualifiers
source                   1..14
                         mol_type = protein
                         organism = synthetic construct
SEQUENCE: 90
AKPLDSSQWA DFDL                                                      14

SEQ ID NO: 91            moltype = AA   length = 107
FEATURE                  Location/Qualifiers
source                   1..107
                         mol_type = protein
                         organism = synthetic construct
SEQUENCE: 91
DIQLTQSPSS VSASVGDRVT ITCRASQGIY SWLAWYQQKP GKAPKLLIYA ASSLQSGVPS    60
RFSGSGSGTD FTLTISSLQP EDFATYYCQQ ASDLPITFGG GTKVEIK                 107

SEQ ID NO: 92            moltype = AA   length = 11
FEATURE                  Location/Qualifiers
```

```
source                          1..11
                                mol_type = protein
                                organism = synthetic construct
SEQUENCE: 92
RASQGIYSWL A                                                        11

SEQ ID NO: 93                   moltype = AA  length = 7
FEATURE                         Location/Qualifiers
source                          1..7
                                mol_type = protein
                                organism = synthetic construct
SEQUENCE: 93
AASSLQS                                                             7

SEQ ID NO: 94                   moltype = AA  length = 9
FEATURE                         Location/Qualifiers
source                          1..9
                                mol_type = protein
                                organism = synthetic construct
SEQUENCE: 94
QQASDLPIT                                                           9

SEQ ID NO: 95                   moltype = AA  length = 9
FEATURE                         Location/Qualifiers
source                          1..9
                                mol_type = protein
                                organism = synthetic construct
VARIANT                         4
                                note = G or A or P or S
VARIANT                         5
                                note = N or Q or D
SEQUENCE: 95
FTFXXYYMS                                                           9

SEQ ID NO: 96                   moltype = AA  length = 17
FEATURE                         Location/Qualifiers
source                          1..17
                                mol_type = protein
                                organism = synthetic construct
VARIANT                         7
                                note = A or S
VARIANT                         10
                                note = Y or A
SEQUENCE: 96
YISPSGXTIX YADSVKG                                                  17

SEQ ID NO: 97                   moltype = AA  length = 15
FEATURE                         Location/Qualifiers
source                          1..15
                                mol_type = protein
                                organism = synthetic construct
VARIANT                         6
                                note = A or S
SEQUENCE: 97
ARSLMXTGTH LYFDL                                                    15

SEQ ID NO: 98                   moltype = AA  length = 11
FEATURE                         Location/Qualifiers
source                          1..11
                                mol_type = protein
                                organism = synthetic construct
VARIANT                         4
                                note = Q or S
VARIANT                         5
                                note = D or G
VARIANT                         8
                                note = D or S
SEQUENCE: 98
RASXXISXWL A                                                        11

SEQ ID NO: 99                   moltype = AA  length = 7
FEATURE                         Location/Qualifiers
source                          1..7
                                mol_type = protein
                                organism = synthetic construct
VARIANT                         3
                                note = E or S
VARIANT                         4
                                note = S or A or G or V or E
```

```
SEQUENCE: 99
AAXXLQS                                                                    7

SEQ ID NO: 100          moltype = AA  length = 10
FEATURE                 Location/Qualifiers
source                  1..10
                        mol_type = protein
                        organism = synthetic construct
VARIANT                 3
                        note = A or S or V
VARIANT                 6
                        note = F or T or V or Q or A
VARIANT                 7
                        note = L or P
SEQUENCE: 100
QQXTSXXPYT                                                                10

SEQ ID NO: 101          moltype = AA  length = 122
FEATURE                 Location/Qualifiers
source                  1..122
                        mol_type = protein
                        organism = synthetic construct
SEQUENCE: 101
QVQLVESGGG LVKPGGSLRL SCAASGFTFA QYYMSWIRQA PGKGLEWVSY ISPSGSTIAY          60
ADSVKGRFTI SRDNAKNSLY LQMNSLRAED TAVYYCARSL MATGTHLYFD LWGRGTLVTV        120
SS                                                                       122

SEQ ID NO: 102          moltype = AA  length = 9
FEATURE                 Location/Qualifiers
source                  1..9
                        mol_type = protein
                        organism = synthetic construct
SEQUENCE: 102
FTFAQYYMS                                                                  9

SEQ ID NO: 103          moltype = AA  length = 17
FEATURE                 Location/Qualifiers
source                  1..17
                        mol_type = protein
                        organism = synthetic construct
SEQUENCE: 103
YISPSGSTIA YADSVKG                                                        17

SEQ ID NO: 104          moltype = AA  length = 15
FEATURE                 Location/Qualifiers
source                  1..15
                        mol_type = protein
                        organism = synthetic construct
SEQUENCE: 104
ARSLMATGTH LYFDL                                                          15

SEQ ID NO: 105          moltype = AA  length = 108
FEATURE                 Location/Qualifiers
source                  1..108
                        mol_type = protein
                        organism = synthetic construct
SEQUENCE: 105
DIQLTQSPSS VSASVGDRVT ITCRASQDIS SWLAWYQQKP GKAPKLLIYA ASSLQSGVPS          60
RFSGSGSGTD FTLTISSLQP EDFATYYCQQ VTSFPPYTFG GGTKVEIK                     108

SEQ ID NO: 106          moltype = AA  length = 11
FEATURE                 Location/Qualifiers
source                  1..11
                        mol_type = protein
                        organism = synthetic construct
SEQUENCE: 106
RASQDISSWL A                                                              11

SEQ ID NO: 107          moltype = AA  length = 7
FEATURE                 Location/Qualifiers
source                  1..7
                        mol_type = protein
                        organism = synthetic construct
SEQUENCE: 107
AASSLQS                                                                    7

SEQ ID NO: 108          moltype = AA  length = 10
FEATURE                 Location/Qualifiers
source                  1..10
```

```
                        mol_type = protein
                        organism = synthetic construct
SEQUENCE: 108
QQVTSFPPYT                                                              10

SEQ ID NO: 109          moltype = AA   length = 122
FEATURE                 Location/Qualifiers
source                  1..122
                        mol_type = protein
                        organism = synthetic construct
SEQUENCE: 109
QVQLVESGGG LVKPGGSLRL SCAASGFTFA NYYMSWIRQA PGKGLEWVSY ISPSGATIAY        60
ADSVKGRFTI SRDNAKNSLY LQMNSLRAED TAVYYCARSL MATGTHLYFD LWGRGTLVTV       120
SS                                                                     122

SEQ ID NO: 110          moltype = AA   length = 9
FEATURE                 Location/Qualifiers
source                  1..9
                        mol_type = protein
                        organism = synthetic construct
SEQUENCE: 110
FTFANYYMS                                                               9

SEQ ID NO: 111          moltype = AA   length = 17
FEATURE                 Location/Qualifiers
source                  1..17
                        mol_type = protein
                        organism = synthetic construct
SEQUENCE: 111
YISPSGATIA YADSVKG                                                      17

SEQ ID NO: 112          moltype = AA   length = 15
FEATURE                 Location/Qualifiers
source                  1..15
                        mol_type = protein
                        organism = synthetic construct
SEQUENCE: 112
ARSLMATGTH LYFDL                                                        15

SEQ ID NO: 113          moltype = AA   length = 108
FEATURE                 Location/Qualifiers
source                  1..108
                        mol_type = protein
                        organism = synthetic construct
SEQUENCE: 113
DIQLTQSPSS VSASVGDRVT ITCRASSGIS SWLAWYQQKP GKAPKLLIYA ASELQSGVPS        60
RFSGSGSGTD FTLTISSLQP EDFATYYCQQ ATSFPPYTFG GGTKVEIK                    108

SEQ ID NO: 114          moltype = AA   length = 11
FEATURE                 Location/Qualifiers
source                  1..11
                        mol_type = protein
                        organism = synthetic construct
SEQUENCE: 114
RASSGISSWL A                                                            11

SEQ ID NO: 115          moltype = AA   length = 7
FEATURE                 Location/Qualifiers
source                  1..7
                        mol_type = protein
                        organism = synthetic construct
SEQUENCE: 115
AASELQS                                                                 7

SEQ ID NO: 116          moltype = AA   length = 10
FEATURE                 Location/Qualifiers
source                  1..10
                        mol_type = protein
                        organism = synthetic construct
SEQUENCE: 116
QQATSFPPYT                                                              10

SEQ ID NO: 117          moltype = AA   length = 122
FEATURE                 Location/Qualifiers
source                  1..122
                        mol_type = protein
                        organism = synthetic construct
SEQUENCE: 117
QVQLVESGGG LVKPGGSLRL SCAASGFTFG QYYMSWIRQA PGKGLEWVSY ISPSGATIAY        60
```

```
ADSVKGRFTI SRDNAKNSLY LQMNSLRAED TAVYYCARSL MSTGTHLYFD LWGRGTLVTV    120
SS                                                                  122

SEQ ID NO: 118           moltype = AA   length = 9
FEATURE                  Location/Qualifiers
source                   1..9
                         mol_type = protein
                         organism = synthetic construct
SEQUENCE: 118
FTFGQYYMS                                                             9

SEQ ID NO: 119           moltype = AA   length = 17
FEATURE                  Location/Qualifiers
source                   1..17
                         mol_type = protein
                         organism = synthetic construct
SEQUENCE: 119
YISPSGATIA YADSVKG                                                   17

SEQ ID NO: 120           moltype = AA   length = 15
FEATURE                  Location/Qualifiers
source                   1..15
                         mol_type = protein
                         organism = synthetic construct
SEQUENCE: 120
ARSLMSTGTH LYFDL                                                     15

SEQ ID NO: 121           moltype = AA   length = 108
FEATURE                  Location/Qualifiers
source                   1..108
                         mol_type = protein
                         organism = synthetic construct
SEQUENCE: 121
DIQLTQSPSS VSASVGDRVT ITCRASQGIS DWLAWYQQKP GKAPKLLIYA ASSLQSGVPS    60
RFSGSGSGTD FTLTISSLQP EDFATYYCQQ VTSFPPYTFG GGTKVEIK                108

SEQ ID NO: 122           moltype = AA   length = 11
FEATURE                  Location/Qualifiers
source                   1..11
                         mol_type = protein
                         organism = synthetic construct
SEQUENCE: 122
RASQGISDWL A                                                         11

SEQ ID NO: 123           moltype = AA   length = 7
FEATURE                  Location/Qualifiers
source                   1..7
                         mol_type = protein
                         organism = synthetic construct
SEQUENCE: 123
AASSLQS                                                               7

SEQ ID NO: 124           moltype = AA   length = 10
FEATURE                  Location/Qualifiers
source                   1..10
                         mol_type = protein
                         organism = synthetic construct
SEQUENCE: 124
QQVTSFPPYT                                                           10

SEQ ID NO: 125           moltype = AA   length = 122
FEATURE                  Location/Qualifiers
source                   1..122
                         mol_type = protein
                         organism = synthetic construct
SEQUENCE: 125
QVQLVESGGG LVKPGGSLRL SCAASGFTFP QYYMSWIRQA PGKGLEWVSY ISPSGATIYY    60
ADSVKGRFTI SRDNAKNSLY LQMNSLRAED TAVYYCARSL MSTGTHLYFD LWGRGTLVTV   120
SS                                                                  122

SEQ ID NO: 126           moltype = AA   length = 9
FEATURE                  Location/Qualifiers
source                   1..9
                         mol_type = protein
                         organism = synthetic construct
SEQUENCE: 126
FTFPQYYMS                                                             9

SEQ ID NO: 127           moltype = AA   length = 17
```

```
FEATURE              Location/Qualifiers
source               1..17
                     mol_type = protein
                     organism = synthetic construct
SEQUENCE: 127
YISPSGATIY YADSVKG                                                    17

SEQ ID NO: 128       moltype = AA   length = 15
FEATURE              Location/Qualifiers
source               1..15
                     mol_type = protein
                     organism = synthetic construct
SEQUENCE: 128
ARSLMSTGTH LYFDL                                                      15

SEQ ID NO: 129       moltype = AA   length = 108
FEATURE              Location/Qualifiers
source               1..108
                     mol_type = protein
                     organism = synthetic construct
SEQUENCE: 129
DIQLTQSPSS VSASVGDRVT ITCRASQGIS SWLAWYQQKP GKAPKLLIYA ASSLQSGVPS     60
RFSGSGSGTD FTLTISSLQP EDFATYYCQQ VTSTPPYTFG GGTKVEIK                 108

SEQ ID NO: 130       moltype = AA   length = 11
FEATURE              Location/Qualifiers
source               1..11
                     mol_type = protein
                     organism = synthetic construct
SEQUENCE: 130
RASQGISSWL A                                                          11

SEQ ID NO: 131       moltype = AA   length = 7
FEATURE              Location/Qualifiers
source               1..7
                     mol_type = protein
                     organism = synthetic construct
SEQUENCE: 131
AASSLQS                                                                7

SEQ ID NO: 132       moltype = AA   length = 10
FEATURE              Location/Qualifiers
source               1..10
                     mol_type = protein
                     organism = synthetic construct
SEQUENCE: 132
QQVTSTPPYT                                                            10

SEQ ID NO: 133       moltype = AA   length = 122
FEATURE              Location/Qualifiers
source               1..122
                     mol_type = protein
                     organism = synthetic construct
SEQUENCE: 133
QVQLVESGGG LVKPGGSLRL SCAASGFTFS DYYMSWIRQA PGKGLEWVSY ISPSGATIAY     60
ADSVKGRFTI SRDNSKNTLY LQMNSLRAED TAVYYCARSL MATGTHLYFD LWGRGTLVTV    120
SS                                                                   122

SEQ ID NO: 134       moltype = AA   length = 9
FEATURE              Location/Qualifiers
source               1..9
                     mol_type = protein
                     organism = synthetic construct
SEQUENCE: 134
FTFSDYYMS                                                              9

SEQ ID NO: 135       moltype = AA   length = 17
FEATURE              Location/Qualifiers
source               1..17
                     mol_type = protein
                     organism = synthetic construct
SEQUENCE: 135
YISPSGATIA YADSVKG                                                    17

SEQ ID NO: 136       moltype = AA   length = 15
FEATURE              Location/Qualifiers
source               1..15
                     mol_type = protein
                     organism = synthetic construct
```

```
SEQUENCE: 136
ARSLMATGTH LYFDL                                                        15

SEQ ID NO: 137          moltype = AA  length = 108
FEATURE                 Location/Qualifiers
source                  1..108
                        mol_type = protein
                        organism = synthetic construct
SEQUENCE: 137
DIQLTQSPSS VSASVGDRVT ITCRASQGIS SWLAWYQQKP GKAPKLLIYA ASGLQSGVPS        60
RFSGSGSGTD FTLTISSLQP EDFATYYCQQ STSFPPYTFG GGTKVEIK                    108

SEQ ID NO: 138          moltype = AA  length = 11
FEATURE                 Location/Qualifiers
source                  1..11
                        mol_type = protein
                        organism = synthetic construct
SEQUENCE: 138
RASQGISSWL A                                                            11

SEQ ID NO: 139          moltype = AA  length = 7
FEATURE                 Location/Qualifiers
source                  1..7
                        mol_type = protein
                        organism = synthetic construct
SEQUENCE: 139
AASGLQS                                                                 7

SEQ ID NO: 140          moltype = AA  length = 10
FEATURE                 Location/Qualifiers
source                  1..10
                        mol_type = protein
                        organism = synthetic construct
SEQUENCE: 140
QQSTSFPPYT                                                              10

SEQ ID NO: 141          moltype = AA  length = 122
FEATURE                 Location/Qualifiers
source                  1..122
                        mol_type = protein
                        organism = synthetic construct
SEQUENCE: 141
QVQLVESGGG LVKPGGSLRL SCAASGFTFS DYYMSWIRQA PGKGLEWVSY ISPSGATIYY        60
ADSVKGRFTI SRDNAKNSLY LQMNSLRAED TAVYYCARSL MSTGTHLYFD LWGRGTLVTV       120
SS                                                                     122

SEQ ID NO: 142          moltype = AA  length = 9
FEATURE                 Location/Qualifiers
source                  1..9
                        mol_type = protein
                        organism = synthetic construct
SEQUENCE: 142
FTFSDYYMS                                                               9

SEQ ID NO: 143          moltype = AA  length = 17
FEATURE                 Location/Qualifiers
source                  1..17
                        mol_type = protein
                        organism = synthetic construct
SEQUENCE: 143
YISPSGATIY YADSVKG                                                      17

SEQ ID NO: 144          moltype = AA  length = 15
FEATURE                 Location/Qualifiers
source                  1..15
                        mol_type = protein
                        organism = synthetic construct
SEQUENCE: 144
ARSLMSTGTH LYFDL                                                        15

SEQ ID NO: 145          moltype = AA  length = 108
FEATURE                 Location/Qualifiers
source                  1..108
                        mol_type = protein
                        organism = synthetic construct
SEQUENCE: 145
DIQLTQSPSS VSASVGDRVT ITCRASQGIS SWLAWYQQKP GKAPKLLIYA ASSLQSGVPS        60
RFSGSGSGTD FTLTISSLQP EDFATYYCQQ VTSVPPYTFG GGTKVEIK                    108
```

```
SEQ ID NO: 146         moltype = AA  length = 11
FEATURE                Location/Qualifiers
source                 1..11
                       mol_type = protein
                       organism = synthetic construct
SEQUENCE: 146
RASQGISSWL A                                                          11

SEQ ID NO: 147         moltype = AA  length = 7
FEATURE                Location/Qualifiers
source                 1..7
                       mol_type = protein
                       organism = synthetic construct
SEQUENCE: 147
AASSLQS                                                                7

SEQ ID NO: 148         moltype = AA  length = 10
FEATURE                Location/Qualifiers
source                 1..10
                       mol_type = protein
                       organism = synthetic construct
SEQUENCE: 148
QQVTSVPPYT                                                            10

SEQ ID NO: 149         moltype = AA  length = 122
FEATURE                Location/Qualifiers
source                 1..122
                       mol_type = protein
                       organism = synthetic construct
SEQUENCE: 149
QVQLVESGGG LVKPGGSLRL SCAASGFTFS QYYMSWIRQA PGKGLEWVSY ISPSGATIAY      60
ADSVKGRFTI SRDNAKNSLY LQMNSLRAED TAVYYCARSL MATGTHLYFD LWGRGTLVTV     120
SS                                                                   122

SEQ ID NO: 150         moltype = AA  length = 9
FEATURE                Location/Qualifiers
source                 1..9
                       mol_type = protein
                       organism = synthetic construct
SEQUENCE: 150
FTFSQYYMS                                                              9

SEQ ID NO: 151         moltype = AA  length = 17
FEATURE                Location/Qualifiers
source                 1..17
                       mol_type = protein
                       organism = synthetic construct
SEQUENCE: 151
YISPSGATIA YADSVKG                                                    17

SEQ ID NO: 152         moltype = AA  length = 15
FEATURE                Location/Qualifiers
source                 1..15
                       mol_type = protein
                       organism = synthetic construct
SEQUENCE: 152
ARSLMATGTH LYFDL                                                      15

SEQ ID NO: 153         moltype = AA  length = 108
FEATURE                Location/Qualifiers
source                 1..108
                       mol_type = protein
                       organism = synthetic construct
SEQUENCE: 153
DIQLTQSPSS VSASVGDRVT ITCRASQGIS SWLAWYQQKP GKAPKLLIYA AESLQSGVPS      60
RFSGSGSGTD FTLTISSLQP EDFATYYCQQ VTSQPPYTFG GGTKVEIK                  108

SEQ ID NO: 154         moltype = AA  length = 11
FEATURE                Location/Qualifiers
source                 1..11
                       mol_type = protein
                       organism = synthetic construct
SEQUENCE: 154
RASQGISSWL A                                                          11

SEQ ID NO: 155         moltype = AA  length = 7
FEATURE                Location/Qualifiers
source                 1..7
                       mol_type = protein
```

```
                            -continued
                    organism = synthetic construct
SEQUENCE: 155
AAESLQS                                                              7

SEQ ID NO: 156         moltype = AA  length = 10
FEATURE                Location/Qualifiers
source                 1..10
                       mol_type = protein
                       organism = synthetic construct
SEQUENCE: 156
QQVTSQPPYT                                                          10

SEQ ID NO: 157         moltype = AA  length = 122
FEATURE                Location/Qualifiers
source                 1..122
                       mol_type = protein
                       organism = synthetic construct
SEQUENCE: 157
QVQLVESGGG LVKPGGSLRL SCAASGFTFS QYYMSWIRQA PGKGLEWVSY ISPSGATIYY    60
ADSVKGRFTI SRDNAKNSLY LQMNSLRAED TAVYYCARSL MATGTHLYFD LWGRGTLVTV   120
SS                                                                 122

SEQ ID NO: 158         moltype = AA  length = 9
FEATURE                Location/Qualifiers
source                 1..9
                       mol_type = protein
                       organism = synthetic construct
SEQUENCE: 158
FTFSQYYMS                                                            9

SEQ ID NO: 159         moltype = AA  length = 17
FEATURE                Location/Qualifiers
source                 1..17
                       mol_type = protein
                       organism = synthetic construct
SEQUENCE: 159
YISPSGATIY YADSVKG                                                  17

SEQ ID NO: 160         moltype = AA  length = 15
FEATURE                Location/Qualifiers
source                 1..15
                       mol_type = protein
                       organism = synthetic construct
SEQUENCE: 160
ARSLMATGTH LYFDL                                                    15

SEQ ID NO: 161         moltype = AA  length = 108
FEATURE                Location/Qualifiers
source                 1..108
                       mol_type = protein
                       organism = synthetic construct
SEQUENCE: 161
DIQLTQSPSS VSASVGDRVT ITCRASQGIS SWLAWYQQKP GKAPKLLIYA ASALQSGVPS    60
RFSGSGSGTD FTLTISSLQP EDFATYYCQQ VTSAPPYTFG GGTKVEIK                108

SEQ ID NO: 162         moltype = AA  length = 11
FEATURE                Location/Qualifiers
source                 1..11
                       mol_type = protein
                       organism = synthetic construct
SEQUENCE: 162
RASQGISSWL A                                                        11

SEQ ID NO: 163         moltype = AA  length = 7
FEATURE                Location/Qualifiers
source                 1..7
                       mol_type = protein
                       organism = synthetic construct
SEQUENCE: 163
AASALQS                                                              7

SEQ ID NO: 164         moltype = AA  length = 10
FEATURE                Location/Qualifiers
source                 1..10
                       mol_type = protein
                       organism = synthetic construct
SEQUENCE: 164
QQVTSAPPYT                                                          10
```

```
SEQ ID NO: 165          moltype = AA  length = 122
FEATURE                 Location/Qualifiers
source                  1..122
                        mol_type = protein
                        organism = synthetic construct
SEQUENCE: 165
QVQLVESGGG LVQPGGSLRL SCAASGFTFS QYYMSWIRQA PGKGLEWVSY ISPSGATIAY    60
ADSVKGRFTI SRDNAKNSLY LQMNSLRAED TAVYYCARSL MSTGTHLYFD LWGRGTLVTV   120
SS                                                                 122

SEQ ID NO: 166          moltype = AA  length = 9
FEATURE                 Location/Qualifiers
source                  1..9
                        mol_type = protein
                        organism = synthetic construct
SEQUENCE: 166
FTFSQYYMS                                                            9

SEQ ID NO: 167          moltype = AA  length = 17
FEATURE                 Location/Qualifiers
source                  1..17
                        mol_type = protein
                        organism = synthetic construct
SEQUENCE: 167
YISPSGATIA YADSVKG                                                  17

SEQ ID NO: 168          moltype = AA  length = 15
FEATURE                 Location/Qualifiers
source                  1..15
                        mol_type = protein
                        organism = synthetic construct
SEQUENCE: 168
ARSLMSTGTH LYFDL                                                    15

SEQ ID NO: 169          moltype = AA  length = 108
FEATURE                 Location/Qualifiers
source                  1..108
                        mol_type = protein
                        organism = synthetic construct
SEQUENCE: 169
DIQLTQSPSS VSASVGDRVT ITCRASQGIS SWLAWYQQKP GKAPKLLIYA ASVLQSGVPS    60
RFSGSGSGTD FTLTISSLQP EDFATYYCQQ VTSFLPYTFG GGTKVEIK                108

SEQ ID NO: 170          moltype = AA  length = 11
FEATURE                 Location/Qualifiers
source                  1..11
                        mol_type = protein
                        organism = synthetic construct
SEQUENCE: 170
RASQGISSWL A                                                        11

SEQ ID NO: 171          moltype = AA  length = 7
FEATURE                 Location/Qualifiers
source                  1..7
                        mol_type = protein
                        organism = synthetic construct
SEQUENCE: 171
AASVLQS                                                              7

SEQ ID NO: 172          moltype = AA  length = 10
FEATURE                 Location/Qualifiers
source                  1..10
                        mol_type = protein
                        organism = synthetic construct
SEQUENCE: 172
QQVTSFLPYT                                                          10

SEQ ID NO: 173          moltype = AA  length = 390
FEATURE                 Location/Qualifiers
source                  1..390
                        mol_type = protein
                        organism = synthetic construct
SEQUENCE: 173
QKSSIEKCSV DIQQSRNKTT ERPGLLNCPI YWQQLREKCL LFSHTVNPWN NSLADCSTKE    60
SSLLLIRDKD ELIHTQNLIR DKAILFWIGL NFSLSEKNWK WINGSFLNSN DLEIRGDAKE   120
NSCISISQTS VYSEYCSTEI RWICQKELTP VRNKVYPDSG SGSDKTHTCP PCPAPELLGG   180
PSVFLFPPKP KDTLMISRTP EVTCVVVDVS HEDPEVKFNW YVDGVEVHNA KTKPREEQYN   240
STYRVVSVLT VLHQDWLNGK EYKCKVSNKA LPAPIEKTIS KAKGQPREPQ VYTLPPSRDE   300
LTKNQVSLTC LVKGFYPSDI AVEWESNGQP ENNYKTTPPV LDSDGSFFLY SKLTVDKSRW   360
```

```
QQGNVFSCSV MHEALHNHYT QKSLSLSPGK                                  390

SEQ ID NO: 174          moltype = AA   length = 165
FEATURE                 Location/Qualifiers
source                  1..165
                        mol_type = protein
                        organism = synthetic construct
SEQUENCE: 174
QKSSIEKCSV DIQQSRNKTT ERPGLLNCPI YWQQLREKCL LFSHTVNPWN NSLADCSTKE   60
SSLLLIRDKD ELIHTQNLIR DKAILFWIGL NFSLSEKNWK WINGSFLNSN DLEIRGDAKE  120
NSCISISQTS VYSEYCSTEI RWICQKELTP VRNKVYPDSH HHHHH                  165

SEQ ID NO: 175          moltype = AA   length = 358
FEATURE                 Location/Qualifiers
source                  1..358
                        mol_type = protein
                        organism = synthetic construct
SEQUENCE: 175
EPKSCDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GKGGGGSLQA  240
ACPESWIGFQ RKCFYFSDDT KNWTSSQRFC DSQDADLAQV ESFQELNPLL RYKGPSDHWI  300
GLSREQGQPW KWINGTEWTR QFPILGAGEC AYLNDKGASS ARCYTERKWI CSKSDIHV    358

SEQ ID NO: 176          moltype = AA   length = 392
FEATURE                 Location/Qualifiers
source                  1..392
                        mol_type = protein
                        organism = synthetic construct
SEQUENCE: 176
QKPSIGKCSV DIQQNRTKTT ERPDLLNCPI YWQQVQEKCL LFSHTVNPWN NSLADCSTKE   60
SSLLLIQDKD ELTRTQNLIH DKAISFWIGL NFSLSEKNWK WINGSFLSSN DLKITGDAKE  120
NSCVYISQTS VYSEYCSTEM KWICQKELTL VRNKVSPDSW HHHHHHDKTHT CPPCPAPELL  180
GGPSVFLFPP KPKDTLMISR TPEVTCVVVD VSHEDPEVKF NWYVDGVEVH NAKTKPREEQ  240
YNSTYRVVSV LTVLHQDWLN GKEYKCKVSN KALPAPIEKT ISKAKGQPRE PQVYTLPPSR  300
DELTKNQVSL TCLVKGFYPS DIAVEWESNG QPENNYKTTP PVLDSDGSFF LYSKLTVDKS  360
RWQQGNVFSC SVMHEALHNH YTQKSLSLSP GK                               392

SEQ ID NO: 177          moltype = AA   length = 395
FEATURE                 Location/Qualifiers
source                  1..395
                        mol_type = protein
                        organism = synthetic construct
SEQUENCE: 177
EPKSCDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GKGGGGSKPS  240
IGKCSVDIQQ NRTKTTERPD LLNCPIYWQQ VQEKCLLFSH TVNPWNNSLA DCSTKESSLL  300
LIQDKDELTR TQNLIHDKAI SFWIGLNFSL SEKNWKWING SFLSSNDLKI TGDAKENSCV  360
YISQTSVYSE YCSTEMKWIC QKELTLVRNK VSPDS                            395

SEQ ID NO: 178          moltype = AA   length = 240
FEATURE                 Location/Qualifiers
source                  1..240
                        mol_type = protein
                        organism = synthetic construct
SEQUENCE: 178
DYKDDDDKEP KSCDKTHTCP PCPAPELLGG PSVFLFPPKP KDTLMISRTP EVTCVVVDVS   60
HEDPEVKFNW YVDGVEVHNA KTKPREEQYN STYRVVSVLT VLHQDWLNGK EYKCKVSNKA  120
LPAPIEKTIS KAKGQPREPQ VYTLPPSRDE LTKNQVSLTC LVKGFYPSDI AVEWESNGQP  180
ENNYKTTPPV LDSDGSFFLY SKLTVDKSRW QQGNVFSCSV MHEALHNHYT QKSLSLSPGK  240

SEQ ID NO: 179          moltype = AA   length = 225
FEATURE                 Location/Qualifiers
source                  1..225
                        mol_type = protein
                        organism = Homo sapiens
SEQUENCE: 179
MDQQAIYAEL NLPTDSGPES SSPSSLPRDV CQGSPWHQFA LKLSCAGIIL LVLVVTGLSV   60
SVTSLIQKSS IEKCSVDIQQ SRNKTTERPG LLNCPIYWQQ LREKCLLFSH TVNPWNNSLA  120
DCSTKESSLL LIRDKDELIH TQNLIRDKAI LFWIGLNFSL SEKNWKWING SFLNSNDLEI  180
RGDAKENSCI SISQTSVYSE YCSTEIRWIC QKELTPVRNK VYPDS                 225

SEQ ID NO: 180          moltype = AA   length = 227
FEATURE                 Location/Qualifiers
source                  1..227
                        mol_type = protein
```

```
                            organism = Macaca fascicularis
SEQUENCE: 180
MDQQMMYAEL TLPKDSGPES SSPSSLPRDV CQGSPWHQFA LKLSCAGIIL LVLVVTGLSL   60
SVASLLQKPS IGKCSVDIQQ NRTKTTERPD LLNCPIYWQQ VQEKCLLFSH TVNPWNNSLA  120
DCSTKESSLL LIQDKDELTR TQNLIHDKAI SFWIGLNFSL SEKNWKWING SFLSSNDLKI  180
TGDAKENSCV YISQTSVYSE YCSTEMKWIC QKELTLVRNK VSPDSWL               227

SEQ ID NO: 181          moltype = AA  length = 223
FEATURE                 Location/Qualifiers
source                  1..223
                        mol_type = protein
                        organism = Mus musculus
SEQUENCE: 181
MDSTTLVYAD LNLARIQEPK HDSPPSLSPD TCRCPRWHRL ALKFGCAGLI LLVLVVIGLC   60
VLVLSVQKSS VQKICADVQE NRTHTTGCSA KLECPQDWLS HRDKCFHVSQ VSNTWKECRI  120
DCDKKGATLL LIQDQEELRF LLDSIKEKYN SFWIGLSYTL TDMNWKWING TAFNSDVLKI  180
TGVTENGSCA AISGEKVTSE GCSSDNRWIC QKELNHETPC NDS                   223

SEQ ID NO: 182          moltype = AA  length = 223
FEATURE                 Location/Qualifiers
source                  1..223
                        mol_type = protein
                        organism = Rattus norvegicus
SEQUENCE: 182
MDTAVVYADL HLARTGEPKH KSPPSLSPDT CQCPRWHRLA LKLGCACLIL LVLSVIGLGV   60
LVLTLLQKPL IQNSPADVQE NRTKTTDSPT KLKCPDWHS HQDKCFHVSQ APNTWNKSLA  120
DCGGKGATLL LIQDQEELRF LRNLTKGKDR SFWIGLNYTL PDKNWKWINS STLNSDVLSI  180
FGDTKQNSCA SISQDKVLSE SCDSDNLWIC QKELKCECMC NGS                   223

SEQ ID NO: 183          moltype = AA  length = 231
FEATURE                 Location/Qualifiers
source                  1..231
                        mol_type = protein
                        organism = Homo sapiens
SEQUENCE: 183
MQDEERYMTL NVQSKKRSSA QTSQLTFKDY SVTLHWYKIL LGISGTVNGI LTLTLISLIL   60
LVSQGVLLKC QKGSCSNATQ YEDTGDLKVN NGTRRNISNK DLCASRSDQ TVLCQSEWLK  120
YQGKCYWFSN EMKSWSDSYV YCLERKSHLL IIHDQLEMAF IQKNLRQLNY VWIGLNFTSL  180
KMTWTWVDGS PIDSKIFFIK GPAKENSCAA IKESKIFSET CSSVFKWICQ Y          231

SEQ ID NO: 184          moltype = AA  length = 207
FEATURE                 Location/Qualifiers
source                  1..207
                        mol_type = protein
                        organism = Homo sapiens
SEQUENCE: 184
MENEDGYMTL SFKNRCKSKQ KSKDFSLYPQ YYCLLLIFGC IVILIFIMTG IDLKFWHKKM   60
DFSQNVNVSS LSGHNYLCPN DWLLNEGKCY WFSTSFKTWK ESQRDCTQLQ AHLLVIQNLD  120
ELEFIQNSLK PGHFGWIGLY VTFQGNLWMW IDEHFLVPEL FSVIGPTDDR SCAVITGNWV  180
YSEDCSSTFK GICQRDAILT HNGTSGV                                     207

SEQ ID NO: 185          moltype = AA  length = 276
FEATURE                 Location/Qualifiers
source                  1..276
                        mol_type = protein
                        organism = Homo sapiens
SEQUENCE: 185
MSEEVTYATL TFQDSAGARN NRDGNNLRKR GHPAPSPIWR HAALGLVTLC LMLLIGLVTL   60
GMMFLQISND INSDSEKLSQ LQKTIQQQQD NLSQQLGNSN NLSMEEEFLK SQISSVLKRQ  120
EQMAIKLCQE LIIHTSDHRC NPCPKMWQWY QNSCYYFTTN EEKTWANSRK DCIDKNSTLV  180
KIDSLEEKDF LMSQPLLMFS FFWLGLSWDS SGRSWFWEDG SVPSPSLFST KELDQINGSK  240
GCAYFQKGNI YISRCSAEIF WICEKTAAPV KTEDLD                           276

SEQ ID NO: 186          moltype = AA  length = 191
FEATURE                 Location/Qualifiers
source                  1..191
                        mol_type = protein
                        organism = Homo sapiens
SEQUENCE: 186
MHDSNNVEKD ITPSELPANP GCLHSKEHSI KATLIWRLFF LIMFLTIIVC GMVAALSAIR   60
ANCHQEPSVC LQAACPESWI GFQRKCFYFS DDTKNWTSSQ RFCDSQDADL AQVESFQELN  120
FLLRYKGPSD HWIGLSREQG QPWKWINGTE WTRQFPILGA GECAYLNDKG ASSARHYTER  180
KWICSKSDIH V                                                      191

SEQ ID NO: 187          moltype = AA  length = 30
FEATURE                 Location/Qualifiers
source                  1..30
                        mol_type = protein
                        organism = synthetic construct
```

```
SITE                       1..30
                           note = This sequence may be 1-6 GGGGS repeats
SEQUENCE: 187
GGGGSGGGGS GGGGSGGGGS GGGGSGGGGS                                      30

SEQ ID NO: 188             moltype = AA  length = 121
FEATURE                    Location/Qualifiers
source                     1..121
                           mol_type = protein
                           organism = synthetic construct
VARIANT                    28
                           note = T or A
VARIANT                    30
                           note = G or S or E
VARIANT                    31
                           note = Q or T or P or R
VARIANT                    32
                           note = Y or F
VARIANT                    53
                           note = A or G
VARIANT                    54
                           note = A or V or S
VARIANT                    57
                           note = T or S
VARIANT                    59
                           note = K or A or Y
VARIANT                    104
                           note = Q or F or L
VARIANT                    109
                           note = D or Q
VARIANT                    110
                           note = L or A
SEQUENCE: 188
EVQLLESGGG LVQPGGSLRL SCAASGFXFX XXAMSWVRQA PGKGLEWVSA ISXXGGXTXY      60
ADSVKGRFTI SRDNSKNTLY LQMNSLRAED TAVYYCAKPL DSSXWADFXX WGRGTLVTVS     120
S                                                                    121

SEQ ID NO: 189             moltype = AA  length = 110
FEATURE                    Location/Qualifiers
source                     1..110
                           mol_type = protein
                           organism = synthetic construct
VARIANT                    4
                           note = M or L
VARIANT                    29
                           note = G or D or T
VARIANT                    31
                           note = D or S or Y
VARIANT                    47
                           note = L or F
VARIANT                    52
                           note = A or Y or F
VARIANT                    55
                           note = S or A or G or F
VARIANT                    58
                           note = D or S
VARIANT                    78
                           note = S or N
VARIANT                    94
                           note = A or H or Q
VARIANT                    95
                           note = S or D or W or L
VARIANT                    96
                           note = V or D or Y or K
SEQUENCE: 189
DIQXATQSPS SVSASVGDRV TITCRASQXI XSWLAWYQQK PGKAPKXBLI YXASXLQXGV      60
PSRFSGSGSG TDFTLTIXCS LQPEDFATYY CQQXXXLPIT FGGGTKVEIK                110

SEQ ID NO: 190             moltype = AA  length = 125
FEATURE                    Location/Qualifiers
source                     1..125
                           mol_type = protein
                           organism = synthetic construct
VARIANT                    13
                           note = K or Q
VARIANT                    31
                           note = G or A or P or S
VARIANT                    32
                           note = N or Q or D
```

```
VARIANT             57
                    note = A or S
VARIANT             60
                    note = Y or A
VARIANT             76
                    note = A or S
VARIANT             80
                    note = S or T
VARIANT             105
                    note = A or S
SEQUENCE: 190
QVQLVESGGG LVXAPGGSLR LSCAASGFTF XXYYMSWIRQ APGKGLEWVS YISPSGXTIX   60
YADSVKGRFT ISRDNXBKNX CLYLQMNSLR AEDTAVYYCA RSLMXTGTHL YFDLWGRGTL  120
VTVSS                                                              125

SEQ ID NO: 191      moltype = AA  length = 108
FEATURE             Location/Qualifiers
source              1..108
                    mol_type = protein
                    organism = synthetic construct
VARIANT             27
                    note = Q or S
VARIANT             28
                    note = D or G
VARIANT             31
                    note = D or S
VARIANT             52
                    note = E or S
VARIANT             53
                    note = S or A or G or V or E
VARIANT             91
                    note = A or S or V
VARIANT             94
                    note = F or T or V or Q or A
VARIANT             95
                    note = L or P
SEQUENCE: 191
DIQLTQSPSS VSASVGDRVT ITCRASXXIS XWLAWYQQKP GKAPKLLIYA AXXLQSGVPS   60
RFSGSGSGTD FTLTISSLQP EDFATYYCQQ XTSXXPYTFG GGTKVEIK               108

SEQ ID NO: 192      moltype = AA  length = 9
FEATURE             Location/Qualifiers
source              1..9
                    mol_type = protein
                    organism = synthetic construct
SEQUENCE: 192
SLLMWITQV                                                            9

SEQ ID NO: 193      moltype = AA  length = 352
FEATURE             Location/Qualifiers
source              1..352
                    mol_type = protein
                    organism = synthetic construct
SEQUENCE: 193
LQAACPESWI GFQRKCFYFS DDTKNWTSSQ RFCDSQDADL AQVESFQELN FLLRYKGPSD   60
HWIGLSREQG QPWKWINGTE WTRQFPILGA GECAYLNDKG ASSARHYTER KWICSKSDIH  120
VGSGSDKTHT CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR DELTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 194      moltype = AA  length = 396
FEATURE             Location/Qualifiers
source              1..396
                    mol_type = protein
                    organism = synthetic construct
SEQUENCE: 194
EPKSCDKTHT CPPCPAPELL GGPSVFLFPP KPKDTLMISR TPEVTCVVVD VSHEDPEVKF   60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GKGGGGSQKS  240
SIEKCSVDIQ QSRNKTTERP GLLNCPIYWQ QLREKCLLFS HTVNPWNNSL ADCSTKESSL  300
LLIRDKKDELI HTQNLIRDKA ILFWIGLNFS LSEKNWKWIN GSFLNSNDLE IRGDAKENSC  360
ISISIQTSVYS EYCSTEIRWI CQKELTPVRN KVYPDS                          396

SEQ ID NO: 195      moltype = AA  length = 4
FEATURE             Location/Qualifiers
source              1..4
                    mol_type = protein
```

```
                    organism = Homo sapiens
SEQUENCE: 195
ELLG                                                                 4

SEQ ID NO: 196      moltype = AA   length = 4
FEATURE             Location/Qualifiers
source              1..4
                    mol_type = protein
                    organism = Homo sapiens
SEQUENCE: 196
EFLG                                                                 4

SEQ ID NO: 197      moltype = AA   length = 6
FEATURE             Location/Qualifiers
source              1..6
                    mol_type = protein
                    organism = synthetic construct
SEQUENCE: 197
HHHHHH                                                               6
```

What is claimed is:

1. An isolated anti-CD161 antibody comprising:
   a heavy chain variable region comprising CDR-H1, CDR-H2, and CDR-H3 sequences, wherein:
   (a) the amino acid sequence of CDR-H1 comprises the amino acid sequence set forth in SEQ ID NO: 72;
   (b) the amino acid sequence of CDR-H2 comprises the amino acid sequence set forth in SEQ ID NO: 73;
   (c) the amino acid sequence of CDR-H3 comprises the amino acid sequence set forth in SEQ ID NO: 74; and
   a light chain variable region comprising CDR-L1, CDR-L2 and CDR-L3 sequences, wherein:
   (d) the amino acid sequence of CDR-L1 comprises the amino acid sequence set forth in SEQ ID NO: 76;
   (e) the amino acid sequence of CDR-L2 comprises the amino acid sequence set forth in SEQ ID NO: 77; and
   (f) the amino acid sequence of CDR-L3 comprises the amino acid sequence set forth in SEQ ID NO: 78.

2. The isolated anti-CD161 antibody of claim 1, wherein the amino acid sequence of the heavy chain variable region comprises an amino acid sequence at least 85%, 90%, 95%, 96%, 97%, 98%, 99%, or 100% identical to the amino acid sequence set forth in SEQ ID NO: 71; and the amino acid sequence of the light chain variable region comprises an amino acid sequence at least 85%, 90%, 95%, 96%, 97%, 98%, 99%, or 100% identical to the amino acid sequence set forth in SEQ ID NO: 75.

3. The isolated anti-CD161 antibody of claim 1, wherein the amino acid sequence of the heavy chain variable region comprises the amino acid sequence set forth in SEQ ID NO: 71; and the amino acid sequence of the light chain variable region comprises the amino acid sequence set forth in SEQ ID NO: 75.

4. The isolated anti-CD161 antibody of claim 1, wherein the antibody is a full length antibody.

5. The isolated anti-CD161 antibody of claim 4, wherein the antibody is aglycosylated.

6. The isolated anti-CD161 antibody of claim 5, wherein the antibody comprises an IgG1 Fc region comprising a modification at amino acid position N297 according to EU numbering.

7. The isolated anti-CD161 antibody of claim 1, wherein the amino acid sequence of the heavy chain variable region comprises an amino acid sequence at least 90% identical to the amino acid sequence set forth in SEQ ID NO: 71; and the amino acid sequence of the light chain variable region comprises an amino acid sequence at least 90% identical to the amino acid sequence set forth in SEQ ID NO: 75.

8. The isolated anti-CD161 antibody of claim 1, wherein the amino acid sequence of the heavy chain variable region comprises an amino acid sequence at least 95% identical to the amino acid sequence set forth in SEQ ID NO: 71; and the amino acid sequence of the light chain variable region comprises an amino acid sequence at least 95% identical to the amino acid sequence set forth in SEQ ID NO: 75.

9. The isolated anti-CD161 antibody of claim 1, wherein the amino acid sequence of the heavy chain variable region comprises an amino acid sequence at least 99% identical to the amino acid sequence set forth in SEQ ID NO: 71; and the amino acid sequence of the light chain variable region comprises an amino acid sequence at least 99% identical to the amino acid sequence set forth in SEQ ID NO: 75.

10. The isolated anti-CD161 antibody of claim 6, wherein the antibody comprises an alanine at amino acid position N297 according to EU numbering.

11. The isolated anti-CD161 antibody of claim 2, wherein the antibody is a full length antibody.

12. The isolated anti-CD161 antibody of claim 11, wherein the antibody is aglycosylated.

13. The isolated anti-CD161 antibody of claim 12, wherein the antibody comprises an IgG1 Fc region comprising a modification at amino acid position N297 according to EU numbering.

14. The isolated anti-CD161 antibody of claim 13, wherein the antibody comprises an alanine at amino acid position N297 according to EU numbering.

15. The isolated anti-CD161 antibody of claim 3, wherein the antibody is a full length antibody.

16. The isolated anti-CD161 antibody of claim 15, wherein the antibody is aglycosylated.

17. The isolated anti-CD161 antibody of claim 16, wherein the antibody comprises an IgG1 Fc region comprising a modification at amino acid position N297 according to EU numbering.

18. The isolated anti-CD161 antibody of claim 17, wherein the antibody comprises an alanine at amino acid position N297 according to EU numbering.

19. The isolated anti-CD161 antibody of claim 1, wherein the amino acid sequence of the heavy chain variable region comprises an amino acid sequence at least 85% identical to the amino acid sequence set forth in SEQ ID NO: 71; and the amino acid sequence of the light chain variable region comprises an amino acid sequence at least 85% identical to the amino acid sequence set forth in SEQ ID NO: 75.

20. The isolated anti-CD161 antibody of claim 19, wherein the antibody is a full length antibody.

21. The isolated anti-CD161 antibody of claim 20, wherein the antibody is aglycosylated.

22. The isolated anti-CD161 antibody of claim 21, wherein the antibody comprises an IgG1 Fc region comprising a modification at amino acid position N297 according to EU numbering.

23. The isolated anti-CD161 antibody of claim 22, wherein the antibody comprises an alanine at amino acid position N297 according to EU numbering.

24. The isolated anti-CD161 antibody of claim 1, wherein the amino acid sequence of the heavy chain variable region comprises an amino acid sequence at least 96% identical to the amino acid sequence set forth in SEQ ID NO: 71; and the amino acid sequence of the light chain variable region comprises an amino acid sequence at least 96% identical to the amino acid sequence set forth in SEQ ID NO: 75.

25. The isolated anti-CD161 antibody of claim 1, wherein the amino acid sequence of the heavy chain variable region comprises an amino acid sequence at least 97% identical to the amino acid sequence set forth in SEQ ID NO: 71; and the amino acid sequence of the light chain variable region comprises an amino acid sequence at least 97% identical to the amino acid sequence set forth in SEQ ID NO: 75.

26. The isolated anti-CD161 antibody of claim 1, wherein the amino acid sequence of the heavy chain variable region comprises an amino acid sequence at least 98% identical to the amino acid sequence set forth in SEQ ID NO: 71; and the amino acid sequence of the light chain variable region comprises an amino acid sequence at least 98% identical to the amino acid sequence set forth in SEQ ID NO: 75.

27. The isolated anti-CD161 antibody of claim 26, wherein the antibody is a full length antibody.

28. The isolated anti-CD161 antibody of claim 27, wherein the antibody is aglycosylated.

29. The isolated anti-CD161 antibody of claim 28, wherein the antibody comprises an IgG1 Fc region comprising a modification at amino acid position N297 according to EU numbering.

30. The isolated anti-CD161 antibody of claim 29, wherein the antibody comprises an alanine at amino acid position N297 according to EU numbering.

* * * * *